US012624382B2

(12) United States Patent
Yang et al.

(10) Patent No.: US 12,624,382 B2
(45) Date of Patent: May 12, 2026

(54) BETA-LACTAM COMPOUNDS AND METHODS OF USE THEREOF

(71) Applicant: THE UNIVERSITY OF HONG KONG, Hong Kong (HK)

(72) Inventors: Dan Yang, Hong Kong (HK); Chi-Wang Ma, Hong Kong (HK)

(73) Assignee: THE UNIVERSITY OF HONG KONG, Hong Kong (HK)

( * ) Notice: Subject to any disclaimer, the term of this patent is extended or adjusted under 35 U.S.C. 154(b) by 1367 days.

(21) Appl. No.: 17/273,791

(22) PCT Filed: Sep. 19, 2019

(86) PCT No.: PCT/CN2019/106645
§ 371 (c)(1),
(2) Date: Mar. 5, 2021

(87) PCT Pub. No.: WO2020/057592
PCT Pub. Date: Mar. 26, 2020

(65) Prior Publication Data

US 2021/0207188 A1 Jul. 8, 2021

Related U.S. Application Data

(60) Provisional application No. 62/734,009, filed on Sep. 20, 2018.

(51) Int. Cl.

| | |
|---|---|
| ***C12Q 1/34*** | (2006.01) |
| ***C07B 43/00*** | (2006.01) |
| ***C07D 477/04*** | (2006.01) |
| ***C07D 477/14*** | (2006.01) |
| ***C07D 499/06*** | (2006.01) |
| ***C07D 499/883*** | (2006.01) |
| ***C12Q 1/02*** | (2006.01) |
| ***G01N 21/64*** | (2006.01) |

(52) U.S. Cl.
CPC ................ *C12Q 1/34* (2013.01); *C07B 43/00* (2013.01); *C07D 477/04* (2013.01); *C07D 477/14* (2013.01); *C07D 499/06* (2013.01); *C07D 499/883* (2013.01); *C12Q 1/025* (2013.01); *G01N 21/6428* (2013.01); *C12Q 2334/10* (2013.01); *G01N 2021/6432* (2013.01); *G01N 2333/986* (2013.01)

(58) Field of Classification Search
CPC ........................................................ C12Q 1/34
See application file for complete search history.

(56) References Cited

U.S. PATENT DOCUMENTS

| | | | | |
|---|---|---|---|---|
| 6,310,055 | B2 * | 10/2001 | Dininno | C07D 477/14 514/210.09 |
| 7,427,680 | B2 | 9/2008 | Tsien et al. | |
| 7,868,147 | B2 | 1/2011 | Nagano et al. | |
| 2016/0311858 | A1 * | 10/2016 | Kariyuki | C07K 1/113 |

FOREIGN PATENT DOCUMENTS

| | | | | |
|---|---|---|---|---|
| CN | 106279178 A | * | 1/2017 | C07D 487/04 |
| CN | 106279178 | * | 4/2018 | |
| WO | WO-2018143145 A1 | * | 8/2018 | C07H 21/02 |

OTHER PUBLICATIONS

Proquest translation of Chinese patent CN-106279178A (Year: 2017).*
Sherman et al.(Biorganic & Medicinal Chemistry letters 16, 2006, p. 1506-1509) (Year: 2006).*
Brakel et.al. (Bioconjugate Chem. 2008, 19, 714â718) (Year: 2008).*
Tanaka, et al. Synthesis of a Sialic Acid Containing Complex-Type N-Glycan on a Solid Support. Chemistry (2009) An Asian Journal, 4: 574-580 (Year: 2009).*
International Search Report and Written Opinion for International Application No. PCT/CN2019/106645 mailed on Dec. 18, 2019, 12 pages.

* cited by examiner

*Primary Examiner* — John S Kenyon
*Assistant Examiner* — Rehana Ismail
(74) *Attorney, Agent, or Firm* — Amin, Turocy & Watson, LLP

(57) ABSTRACT

Beta-lactam compounds to detect carbapenemases or microbial carbapenem resistance are disclosed. The compounds contain a chemical probe. Upon hydrolysis by carbapenemases, the compounds undergo intramolecular rearrangement and release the chemical probe. Detection of the released chemical probe indicates the presence of carbapenemases and the presence of microbial carbapenem resistance.

44 Claims, 11 Drawing Sheets

BETA-LACTAM COMPOUNDS AND METHODS OF USE THEREOF

FIELD OF THE INVENTION

The invention is generally directed to beta-lactam compounds that are useful in detecting microbial antibiotic resistance, more particularly to beta-lactam compounds that are useful in detecting carbapenemases or microbial carbapenem resistance.

BACKGROUND OF THE INVENTION

Beta-lactam antibiotics, such as the penam series, have been widely used for treating different kinds of bacterial infections. They contain a beta-lactam ring in their molecular structures and work by inhibiting cell wall biosynthesis in bacterial organisms. However, misuse of beta-lactam antibiotics in human and livestock has led to serious antibiotic resistance. In particular, beta-lactamases are enzymes produced by bacteria that cause antibiotic resistance via hydrolyzing the antibiotics' beta-lactam ring, thereby deactivating their antibacterial properties. In recent decades, the carbapenem series of beta-lactam antibiotics were developed and known to be one of the last resort antibiotics. However, bacterial carbapenemases are capable of hydrolyzing them.

To mitigate outbreaks of antibiotic-resistant bacteria, clinicians are advised to prescribe antibiotics only when necessary. They are also advised to start the treatment with narrow spectrum and first-line antibiotics unless patients are not responding to medication. Unfortunately, patients infected with antibiotic-resistant bacteria usually do not exhibit distinctive symptoms. Oftentimes, clinicians have to make rapid decisions on the prescription of antibiotics without knowing whether antibiotic resistance is present.

Prescribing carbapenem antibiotics to patients infected with bacteria that have already developed resistance against such antibiotics is ineffective and may even lead to life threatening conditions such as sepsis (Hampton, *JAMA,* 2016, 315, p. 19; Shorr et al., *Critical Care Medicine,* 2011, 39, p. 46). The existing methods for identifying carbapenemases or microbial carbapenem resistance, such as agar plate diffusion, are time-consuming and may delay proper treatment. Although compounds with carbapenem-like structures have been designed and synthesized as chromogenic or fluorescence probes for carbapenemases or microbial carbapenem resistance, they frequently suffer from slow kinetics and narrow carbapenemase specificity (Mao et al., *ChemBioChem,* 2018, doi: 10.1002/cbic.201800126 (epub. ahead of print); Xie et al., CN Patent Application No. 106279178; Mao et al., *Angewandte Chemie International Edition,* 2017, 56, p. 4468; Xie et al., CN Patent Application No. 106811192; Pfaendler et al., U.S. Pat. No. 9,296,752).

There is an urgent need to develop a rapid test for detecting antibiotic resistance, especially carbapenem resistance. There is also a tremendous demand to develop a method for quickly evaluating the efficacy of carbapenem inhibitors for drug development.

SUMMARY OF THE INVENTION

Therefore, it is an object of the present invention to provide compounds to detect carbapenemases or microbial carbapenem resistance.

It is another object of the present invention to provide methods of making such compounds.

It is another object of the present invention to provide methods for detecting carbapenemases or microbial carbapenem resistance.

It is another object of the present invention to provide methods for testing the efficacy of carbapenemase inhibitors.

It is yet another object of the present invention to develop kits for detecting carbapenemases or microbial carbapenem resistance.

Throughout the description and claims of this specification, the word "comprise" and variations of the word, such as "comprising" and "comprises," mean "including but not limited to," and are not intended to exclude, for example, other additives, components, integers or steps.

Any discussion of documents, acts, materials, articles or the like which has been included in the present specification is not to be taken as an admission that any or all of these matters form part of the prior art base or were common general knowledge in the field relevant to the present disclosure as it existed before the priority date of each claim of this application.

Disclosed are compounds and methods for detecting carbapenemases or microbial carbapenem resistance.

Generally, the compound of the present invention has the structure of CP-A-D, wherein CP is an azabicyclo moiety composed of a beta-lactam ring and an unsaturated five-membered hetero-ring having a C—C double bond; A is a conjugated system attached to the unsaturated five-membered hetero-ring at a carbon atom of the double bond and is at meta-position relative to the nitrogen atom; and D is connected to A via a methylene bridge and comprises a chemical probe, wherein the beta-lactam ring of the compound can be hydrolyzed by one or more carbapenemases, thereby triggering intramolecular rearrangement to release D from the compounds.

For example, in some forms, the disclosed compounds have the structure of Formulas Ia, Ib, Ic, Id or Ie, or salts thereof, Formula Ia

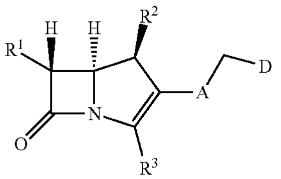

Formula Ib

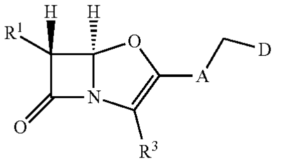

Formula Ic

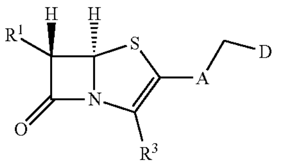

-continued

Formula Id

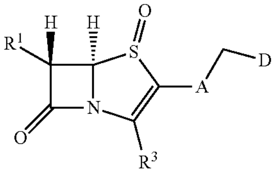

Formula Ie

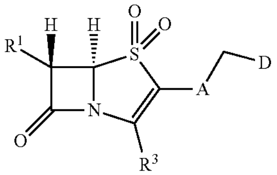

(a) wherein A is a selected from —$(CR^4{=}CR^5)_m$—, —$(C{\equiv}C)_n$—, optionally substituted arylenes, optionally substituted heteroarylenes, and covalent adducts thereof, wherein the covalent adducts are conjugated systems and wherein m and n are positive integers;

(b) wherein D is connected to A via a methylene bridge and comprises a chemical probe;

(c) wherein the beta-lactam ring of the compound can be hydrolyzed by one or more carbapenemases, thereby triggering intramolecular rearrangement to release D from the compound;

(d) wherein $R^1$, $R^2$, $R^4$, and $R^5$ are independently:

a hydrogen atom, a halogen atom, a sulfonic acid, an azide group, a cyanate group, an isocyanate group, a nitrate group, a nitrile group, an isonitrile group, a nitrosooxy group, a nitroso group, a nitro group, an aldehyde group, an acyl halide group, a carboxylic acid group, a carboxylate group, an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, an optionally substituted heteroaryl group;

a hydroxyl group optionally containing one substituent at the hydroxyl oxygen, wherein the substituent is an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

a thiol group optionally containing one substituent at the thiol sulfur, wherein the substituent is an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

a sulfonyl group containing an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

an amino group optionally containing one or two substituents at the amino nitrogen, wherein the substituents are optionally substituted alkyl groups, optionally substituted heteroalkyl groups, optionally substituted alkenyl groups, optionally substituted heteroalkenyl groups, optionally substituted alkynyl groups, optionally substituted heteroalkynyl groups, optionally substituted aryl groups, optionally substituted heteroaryl groups, or combinations thereof;

an amide group optionally containing one or two substituents at the amide nitrogen, wherein the substituents are optionally substituted alkyl groups, optionally substituted heteroalkyl groups, optionally substituted alkenyl groups, optionally substituted heteroalkenyl groups, optionally substituted alkynyl groups, optionally substituted heteroalkynyl groups, optionally substituted aryl groups, optionally substituted heteroaryl groups, or combinations thereof;

an azo group containing an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

an acyl group containing an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

an ester group containing an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

a carbonate ester group containing an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

an ether group containing an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

an aminooxy group optionally containing one or two substituents at the amino nitrogen, wherein the substituents are optionally substituted alkyl groups, optionally substituted heteroalkyl groups, optionally substituted alkenyl groups, optionally substituted heteroalkenyl groups, optionally substituted alkynyl groups, optionally substituted heteroalkynyl groups, optionally substituted aryl groups, optionally substituted heteroaryl groups, or combinations thereof; or a hydroxyamino group optionally containing one or two substituents, wherein the substituents are optionally substituted alkyl groups, optionally substituted heteroalkyl groups, optionally substituted alkenyl groups, optionally substituted heteroalkenyl groups, optionally substituted alkynyl groups, optionally substituted heteroalkynyl groups, optionally substituted aryl groups, optionally substituted heteroaryl groups, or combinations thereof;

(e) wherein $R^3$ is:

a carboxylic acid or carboxylate;

an ester group containing an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

an amide group optionally containing one or two substituents at the amide nitrogen, wherein the substituents are optionally substituted alkyl groups, optionally substituted heteroalkyl groups, optionally substituted alkenyl groups, optionally substituted heteroalkenyl groups, optionally substituted alkynyl groups, optionally substituted heteroalkynyl groups, optionally substituted aryl groups, optionally substituted heteroaryl groups, or combinations thereof; or a hydroxamate group optionally containing one or two substituents, wherein the substituents are optionally substituted alkyl groups, optionally substituted heteroalkyl groups, optionally substituted alkenyl groups, optionally substituted heteroalkenyl groups, optionally substituted alkynyl groups, optionally substituted heteroalkynyl groups, optionally substituted aryl groups, optionally substituted heteroaryl groups, or combinations thereof;

(f) wherein $R^1$, $R^2$, $R^3$, $R^4$, and $R^5$, and their substituents are optionally and independently substituted with one or more chemical groups, wherein each chemical group is independently:

a halogen atom, an alkyl group, a heteroalkyl group, an alkenyl group, a heteroalkenyl group, an alkynyl group, a heteroalkynyl group, an aryl group, a heteroaryl group, —OH, —SH, —$NH_2$, —$N_3$, —OCN, —NCO, —$ONO_2$, —CN, —NC, —ONO, —$CONH_2$, —NO, —$NO_2$, —$ONH_2$, —SCN, —SNCS, —$CF_3$, —$CH_2CF_3$, —$CH_2Cl$, —$CHCl_2$, —$CH_2NH_2$, —NHCOH, —CHO, —COCl, —COF, —COBr, —COOH, —$SO_3H$, —$CH_2SO_2CH_3$, —$PO_3H_2$, —$OPO_3H_2$, —P(═O)($OR^{G1}$)($OR^{G2}$), —OP(═O)($OR^{G1}$)($OR^{G2}$), —$BR^{G1}$($OR^{G2}$), —B($OR^{G1}$)($OR^{G2}$), or -$GR^{G1}$ in which -G is —O—, —S—, —$NR^{G2}$—, —C(═O)—, —S(═O)—, —$SO_2$—, —C(═O)O—, —C(═O)$NR^{G2}$—, —OC(═O)—, —$NR^{G2}$C(═O)—, —OC(═O)O—, —OC(═O)$NR^{G2}$—, —$NR^{G2}$C(═O)O—, —$NR^{G2}$C(═O)$NR^{G3}$—, —C(═S)—, —C(═S)S—, —SC(═S)—, —SC(═S)S—, —C(═$NR^{G2}$)—, —C(═$NR^{G2}$)O—, —C(═$NR^{G2}$)$NR^{G3}$—, —OC(═$NR^{G2}$)—, —$NR^{G2}$C(═$NR^{G3}$)—, —$NR^{G2}SO_2$—, —C(═$NR^{G2}$)$NR^{G3}$—, —OC(═$NR^{G2}$)—, —$NR^{G2}$C(═$NR^{G3}$)—, —$NR^{G2}SO_2$—, —$NR^{G2}SO_2NR^{G3}$—, —$NR^{G2}$C(═S)—, —SC(═S)$NR^{G2}$—, —$NR^{G2}$C(═S)S—, —$NR^{G2}$C(═S)$NR^{G3}$—, —SC(═$NR^{G2}$)—, —C(═S)$NR^{G2}$—, —OC(═S)$NR^{G2}$—, —$NR^{G2}$C(═S)O—, —SC(═O)$NR^{G2}$—, —$NR^{G2}$C(═O)S—, —C(═O)S—, —SC(═O)—, —SC(═O)S—, —C(═S)O—, —OC(═S)—, —OC(═S)O—, —$SO_2NR^{G2}$—, —$BR^{G2}$—, or —$PR^{G2}$— wherein each occurrence of $R^{G1}$, $R^{G2}$, and $R^{G3}$ is, independently, a hydrogen atom, a halogen atom, an alkyl group, a heteroalkyl group, an alkenyl group, a heteroalkenyl group, an alkynyl group, a heteroalkynyl group, an aryl group, or a heteroaryl group.

In some embodiments, D contains a self-immolative linker interposed between the methylene bridge and the rest of D. The self-immolative linker is spontaneously separated from the rest of D following the release of D from the compounds.

In some embodiments, D is or contains a luminescence probe. The luminescence probe may be non-luminescent or luminescence-quenched prior to carbapenemase-catalyzed hydrolysis of the compounds and become luminescent or luminescence-enhanced after being released from the compounds. Optionally, the luminescence probe may contain a donor chromophore and an acceptor chromophore which enable Förster resonance energy transfer (FRET) after the luminescence probe is released from the compounds.

In some embodiments, D is or contains a colorimetric probe. The colorimetric probe may undergo a colorimetric change after being released from the compounds.

In some embodiments, D is or contains an oligonucleotide. The oligonucleotide may be amplified by PCR or RT-PCR after being released from the compounds.

Methods of making the disclosed compounds are disclosed. The methods are compatible with a wide variety of functional groups, and thus a wide variety of analogs and derivatives are obtainable from the disclosed methods.

Methods of detecting carbapenemases or microbial carbapenem resistance using the disclosed compounds are disclosed. The methods include (a) contacting a sample containing one or more populations of bacteria with one or more of the disclosed compounds and (b) detecting the release of D from the disclosed compounds. Detection of the release of D indicates the presence of carbapenemases, and the presence of carbapenemases indicates the presence of carbapenem resistance. In some embodiments, the bacteria in the sample include enterobacteriaceae, such as *Escherichia coli, Enterobacter aerogenes, Enterobacter cloacae, Klebsiella pneumoniae, Klebsiella oxytoca*, and combinations thereof. In some embodiments, the sample contains a human or non-human animal bodily fluid, a human or non-human animal tissue, or both. In some embodiments, the methods have an additional step, involving contacting the sample with one or more additional compounds that can trigger colorimetric change, luminescence change, or both, of the chemical probe of D after D is released from the disclosed compounds. In some embodiments, the one or more additional compounds include an enzyme, such as peroxidase, luciferase, and beta-galactosidase.

Methods of testing the efficacy of a carbapenemase inhibitor using the disclosed compounds are disclosed. The methods include (a) contacting a solution or suspension containing an isolated carbapenemase, a bacterial cell lysate, one or more populations of bacteria, or combinations thereof with one or more of the disclosed compounds in the absence of the carbapenemase inhibitor and, separately, in the presence of the carbapenemase inhibitor and (b) detecting the release of D from the disclosed compounds. The magnitude of the difference in the release of D in the absence of the carbapenemase inhibitor and in the presence of the carbapenemase inhibitor indicates the efficacy of the carbapenemase inhibitor. In some embodiments, the methods contain an additional step, involving contacting the solution or suspension with one or more additional compounds that can trigger colorimetric change, luminescence change, or both, of the chemical probe of D after D is released from the disclosed compounds. In some embodiments, the one or more additional compounds include an enzyme, such as peroxidase, luciferase, and beta-galactosidase.

Kits for detecting carbapenemases or microbial carbapenem resistance are also disclosed. The kits contain, in one or more containers, one or more of the disclosed compounds, a pharmaceutical carrier, instructions for use, and, optionally, an ionic or non-ionic detergent.

Additional advantages of the disclosed compounds, mixtures, compositions, kits, and methods will be set forth in part in the description which follows, and in part will be understood from the description, or may be learned by practice of the disclosed compounds, mixtures, compositions, kits, and methods. The advantages of the disclosed compounds, mixtures, compositions, kits, and methods will be realized and attained by means of the elements and combinations particularly pointed out in the appended claims.

It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed compounds, mixtures, compositions, kits, and methods, and together with the description, serve to explain the principles of the disclosed compounds, mixtures, compositions, kits, and methods.

DETAILED DESCRIPTION OF THE INVENTION

Figure 1:
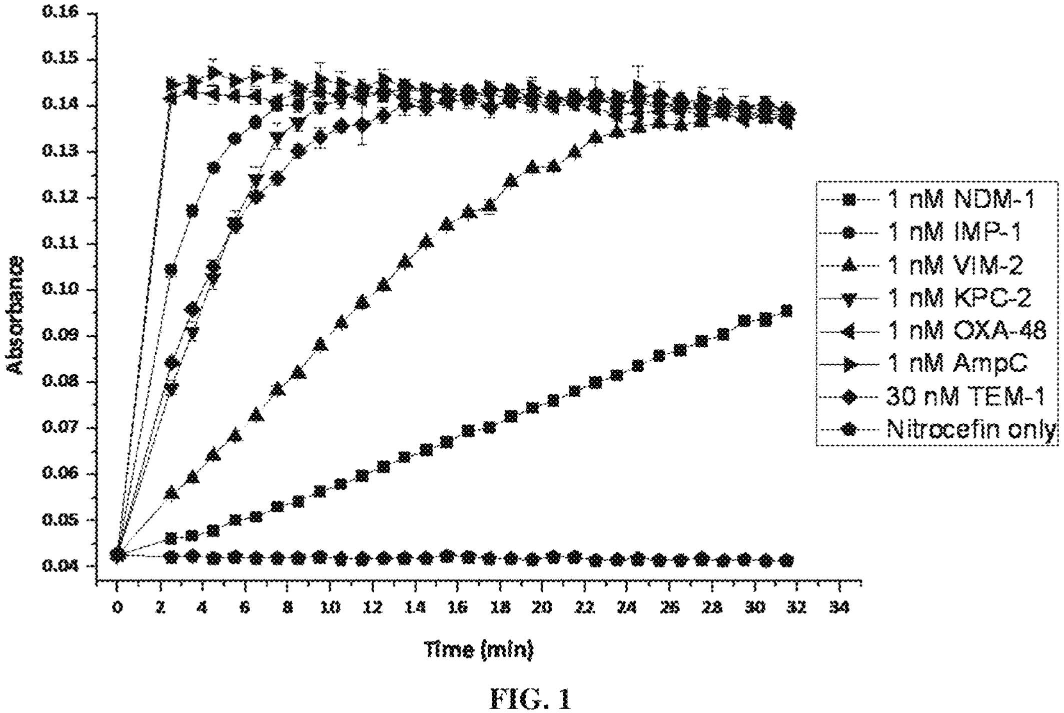
FIG. 1 is a graph showing the hydrolysis of nitrocefin (50 μM) by various beta-lactamases over time (min). The formation of the hydrolysis product of nitrocefin was monitored at 485 nm.

The disclosed compounds, mixtures, compositions, kits, and methods may be understood more readily by reference to the following detailed description of particular embodiments and the Examples included therein and to the Figures and their previous and following description.

All methods described herein can be performed in any suitable order unless otherwise indicated herein or otherwise clearly contradicted by context. The use of any and all examples or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The disclosed compounds, mixtures, compositions, and kits, can be used for, can be used in conjunction with, can be used in preparation for, or are products of the disclosed methods. It is understood that when combinations, subsets, interactions, groups, etc. of these compounds, mixtures, compositions, and kits are disclosed, while specific reference of each various individual and collective combinations of these materials may not be explicitly disclosed, each is specifically contemplated and described herein. For example, if a compound is disclosed and discussed and a number of modifications that can be made to a number of molecules including the compound are discussed, each and every combination and permutation of the compound and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B—F, and C-E are specifically contemplated and should be considered disclosed from disclosure of A, B, and C; D, E, and F; and the example combination A-D. Further, each of the compounds, mixtures, compositions, kits, components, etc. contemplated and disclosed as above can also be specifically and independently included or excluded from any group, subgroup, list, set, etc. of such materials. These concepts apply to all aspects of this application including, but not limited to, steps in methods of making and using the disclosed compounds, compositions, mixtures, and kits. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

The singular forms "a," "an," and "the" include plural reference unless the context clearly dictates otherwise. For example, reference to "a compound" includes a plurality of compounds and reference to "the compound" is a reference to one or more compounds and equivalents thereof known to those skilled in the art.

The terms "may," "may be," "can," and "can be," and related terms are intended to convey that the subject matter involved is optional (that is, the subject matter is present in some embodiments and is not present in other embodiments), not a reference to a capability of the subject matter or to a probability, unless the context clearly indicates otherwise.

The terms "optional" and "optionally" mean that the subsequently described event, circumstance, or material may or may not occur or be present, and that the description includes instances where the event, circumstance, or material occurs or is present and instances where it does not occur or is not present.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied.

As used herein, the term "analog" refers to a compound with a structure similar to that of another (reference compound) but differing from it in respect to a particular component, functional group, atom, etc. As used herein, the term "derivative" refers to a compound which is formed from a parent compound by chemical reaction(s). The differences between suitable analogues and derivatives and their reference or parent compounds include, but are not limited to, replacement of one or more functional groups with one or more different functional groups or reacting one or more functional groups to introduce one or more substituents.

Numerical ranges disclosed in the present application of any type, disclose individually each possible number that such a range could reasonably encompass, as well as any sub-ranges and combinations of sub-ranges encompassed therein. A carbon range (e.g., $C_1$-$C_{10}$), is intended to disclose individually every possible carbon value and/or sub-range encompassed within. For example, a carbon length range of $C_1$-$C_{10}$ discloses $C_1$, $C_2$, $C_3$, $C_4$, $C_5$, $C_6$, $C_7$, $C_8$, $C_9$, and $C_{10}$, as well as discloses sub-ranges encompassed therein, such as $C_2$-$C_9$, $C_3$-$C_8$, $C_1$-$C_5$, etc.

"Halogen" or "halide," as used herein, refers to fluorine, chlorine, bromine, or iodine.

The term "alkyl" refers to univalent groups derived from alkanes by removal of a hydrogen atom from any carbon atom. Alkanes represent saturated hydrocarbons, including those that are cyclic (either monocyclic or polycyclic). Alkyl groups can be linear, branched, or cyclic. Preferred alkyl groups have one to 30 carbon atoms, i.e., $C_1$-$C_{30}$ alkyl. In some forms, a $C_1$-$C_{30}$ alkyl can be a linear $C_1$-$C_{30}$ alkyl, a branched $C_1$-$C_{30}$ alkyl, a cyclic $C_1$-$C_{30}$ alkyl, a linear or branched $C_1$-$C_{30}$ alkyl, a linear or cyclic $C_1$-$C_{30}$ alkyl, a branched or cyclic $C_1$-$C_{30}$ alkyl, or a linear, branched, or cyclic $C_1$-$C_{30}$ alkyl. More preferred alkyl groups have one to 20 carbon atoms, i.e., $C_1$-$C_{20}$ alkyl, and especially have one to 10 carbon atoms, i.e., $C_1$-$C_{10}$ alkyl. Most preferred alkyl groups have one to 6 carbon atoms, i.e., $C_1$-$C_6$ alkyl, for example $C_1$-$C_4$ alkyl.

The term "heteroalkyl" refers to alkyl groups where one or more carbon atoms are replaced with a heteroatom, such as, O, N, or S. Heteroalkyl groups can be linear, branched, or cyclic. Preferred heteroalkyl groups have one to 30 carbon atoms, i.e., $C_1$-$C_{30}$ heteroalkyl. In some forms, a $C_1$-$C_{30}$ heteroalkyl can be a linear $C_1$-$C_{30}$ heteroalkyl, a branched $C_1$-$C_{30}$ heteroalkyl, a cyclic $C_1$-$C_{30}$ heteroalkyl, a linear or branched $C_1$-$C_{30}$ heteroalkyl, a linear or cyclic $C_1$-$C_{30}$ heteroalkyl, a branched or cyclic $C_1$-$C_{30}$ heteroalkyl, or a linear, branched, or cyclic $C_1$-$C_{30}$ heteroalkyl. More preferred heteroalkyl groups have one to 20 carbon atoms, i.e., $C_1$-$C_{20}$ heteroalkyl, and especially have one to 10 carbon atoms, i.e., $C_1$-$C_{10}$ heteroalkyl. Most preferred heteroalkyl groups have one to 5 carbon atoms, i.e., $C_1$-$C_5$ heteroalkyl, for example $C_1$-$C_4$ heteroalkyl.

The term "alkenyl" refers to univalent groups derived from alkenes by removal of a hydrogen atom from any carbon atom. Alkenes are unsaturated hydrocarbons that contain at least one carbon-carbon double bond. Alkenyl groups can be linear, branched, or cyclic. Preferred alkenyl groups have two to 30 carbon atoms, i.e., $C_2$-$C_{30}$ alkenyl. In some forms, a $C_2$-$C_{30}$ alkenyl can be a linear $C_2$-$C_{30}$ alkenyl, a branched $C_2$-$C_{30}$ alkenyl, a cyclic $C_2$-$C_{30}$ alkenyl, a linear or branched $C_2$-$C_{30}$ alkenyl, a linear or cyclic $C_2$-$C_{30}$ alkenyl, a branched or cyclic $C_2$-$C_{30}$ alkenyl, or a linear, branched, or cyclic $C_2$-$C_{30}$ alkenyl. More preferred alkenyl groups have two to 20 carbon atoms, i.e., $C_2$-$C_{20}$ alkenyl, and especially have two to 10 carbon atoms, i.e., $C_2$-$C_{10}$ alkenyl. Most preferred alkenyl groups have two to 6 carbon atoms, i.e., $C_2$-$C_6$ alkenyl, for example $C_2$-$C_4$ alkenyl.

The term "heteroalkenyl" refers to alkenyl groups in which one or more doubly bonded carbon atoms are replaced by a heteroatom. Heteroalkenyl groups can be linear, branched, or cyclic. Preferred heteroalkenyl groups have one to 30 carbon atoms, i.e., $C_1$-$C_{30}$ heteroalkenyl. In some forms, a $C_1$-$C_{30}$ heteroalkenyl can be a linear $C_1$-$C_{30}$ heteroalkenyl, a branched $C_1$-$C_{30}$ heteroalkenyl, a cyclic $C_1$-$C_{30}$ heteroalkenyl, a linear or branched $C_1$-$C_{30}$ heteroalkenyl, a linear or cyclic $C_1$-$C_{30}$ heteroalkenyl, a branched or cyclic $C_1$-$C_{30}$ heteroalkenyl, or a linear, branched, or cyclic $C_1$-$C_{30}$ heteroalkenyl. More preferred heteroalkenyl groups have one to 20 carbon atoms, i.e., $C_1$-$C_{20}$ heteroalkenyl, and especially have one to 10 carbon atoms, i.e., $C_1$-$C_{10}$ heteroalkenyl. Most preferred heteroalkenyl groups have one to 5 carbon atoms, i.e., $C_1$-$C_5$ heteroalkenyl, for example $C_1$-$C_4$ heteroalkenyl.

The term "alkynyl" refers to univalent groups derived from alkynes by removal of a hydrogen atom from any carbon atom. Alkynes are unsaturated hydrocarbons that contain at least one carbon-carbon triple bond. Alkynyl groups can be linear, branched, or cyclic. Preferred alkynyl groups have two to 30 carbon atoms, i.e., $C_2$-$C_{30}$ alkynyl. In some forms, a $C_2$-$C_{30}$ alkynyl can be a linear $C_2$-$C_{30}$ alkynyl, a branched $C_2$-$C_{30}$ alkynyl, a cyclic $C_2$-$C_{30}$ alkynyl, a linear or branched $C_2$-$C_{30}$ alkynyl, a linear or cyclic $C_2$-$C_{30}$ alkynyl, a branched or cyclic $C_2$-$C_{30}$ alkynyl, or a linear, branched, or cyclic $C_2$-$C_{30}$ alkynyl. More preferred alkynyl groups have two to 20 carbon atoms, i.e., $C_2$-$C_{20}$ alkynyl, and especially have two to 10 carbon atoms, i.e., $C_2$-$C_{10}$ alkynyl. Most preferred alkynyl groups have one to 5 carbon atoms, i.e., $C_2$-$C_5$ alkynyl, for example $C_2$-$C_4$ alkynyl.

The term "heteroalkynyl" refers to alkynyl groups in which one or more triply bonded carbon atoms are replaced by a heteroatom. Heteroalkynyl groups can be linear, branched, or cyclic. Preferred heteroalkynyl groups have one to 30 carbon atoms, i.e., $C_1$-$C_{30}$ heteroalkynyl. In some forms, a $C_1$-$C_{30}$ heteroalkynyl can be a linear $C_1$-$C_{30}$ heteroalkynyl, a branched $C_1$-$C_{30}$ heteroalkynyl, a cyclic $C_1$-$C_{30}$ heteroalkynyl, a linear or branched $C_1$-$C_{30}$ heteroalkynyl, a linear or cyclic $C_1$-$C_{30}$ heteroalkynyl, a branched or cyclic $C_1$-$C_{30}$ heteroalkynyl, or a linear, branched, or cyclic $C_1$-$C_{30}$ heteroalkynyl. More preferred heteroalkynyl groups have one to 20 carbon atoms, i.e., $C_1$-$C_{20}$ heteroalkynyl, and especially have one to 10 carbon atoms, i.e., $C_1$-$C_{10}$ heteroalkynyl. Most preferred heteroalkynyl groups have one to 5 carbon atoms, i.e., $C_1$-$C_5$ heteroalkynyl, for example $C_1$-$C_4$ heteroalkynyl.

The term "aryl" refers to univalent groups derived from arenes by removal of a hydrogen atom from a ring atom. Arenes are monocyclic and polycyclic aromatic hydrocarbons. In polycyclic aryl groups, the rings may be attached together in a pendant manner or may be fused. Preferred aryl groups have six to 50 carbon atoms, i.e., $C_6$-$C_{50}$ aryl. In some forms, a $C_6$-$C_{50}$ aryl can be a branched $C_6$-$C_{50}$ aryl, a monocyclic $C_6$-$C_{50}$ aryl, a polycyclic $C_6$-$C_{50}$ aryl, a branched polycyclic $C_6$-$C_{50}$ aryl, a fused polycyclic $C_6$-$C_{50}$ aryl, or a branched fused polycyclic $C_6$-$C_{50}$ aryl. More preferred aryl groups have six to 30 carbon atoms, i.e., $C_6$-$C_{30}$ aryl, and especially have six to 20 carbon atoms, i.e., $C_6$-$C_{20}$ aryl. Most preferred aryl groups have six to 10 carbon atoms, i.e., $C_6$-$C_{10}$ aryl.

The term "heteroaryl" refers to univalent groups derived from heteroarenes by removal of a hydrogen atom from a ring atom. Heteroarenes are heterocyclic compounds derived from arenes by replacement of one or more methine (—C=) and/or vinylene (—CH=CH—) groups by trivalent or divalent heteroatoms, respectively, in such a way as to maintain the continuous π-electron system characteristic of aromatic systems and a number of out-of-plane π-electrons corresponding to the Hückel rule (4n+2). In polycyclic heteroaryl groups, the rings may be attached together in a pendant manner or may be fused. Preferred heteroaryl groups have three to 50 carbon atoms, i.e., $C_3$-$C_{50}$ heteroaryl. In some forms, a $C_3$-$C_{50}$ heteroaryl can be a branched $C_3$-$C_{50}$ heteroaryl, a monocyclic $C_3$-$C_{50}$ heteroaryl, a polycyclic $C_3$-$C_{50}$ heteroaryl, a branched polycyclic $C_3$-$C_{50}$ heteroaryl, a fused polycyclic $C_3$-$C_{50}$ heteroaryl, or a branched fused polycyclic $C_3$-$C_{50}$ heteroaryl. More preferred heteroaryl groups have three to 30 carbon atoms, i.e., $C_3$-$C_{30}$ heteroaryl, and especially have three to 20 carbon atoms, i.e., $C_3$-$C_{20}$ heteroaryl. Most preferred heteroaryl groups have three to 10 carbon atoms, i.e., $C_3$-$C_{10}$ heteroaryl.

The term "arylene" refers to divalent groups derived from arenes by removal of a hydrogen atom from two ring carbon atoms. In polycyclic arylene groups, the rings may be attached together in a pendant manner or may be fused. Preferred arylenes groups have six to 50 carbon atoms, i.e., $C_6$-$C_{50}$ arylene. In some forms, a $C_6$-$C_{50}$ arylene can be a branched $C_6$-$C_{50}$ arylene, a monocyclic $C_6$-$C_{50}$ arylene, a polycyclic $C_6$-$C_{50}$ arylene, a branched polycyclic $C_6$-$C_{50}$ arylene, a fused polycyclic $C_6$-$C_{50}$ arylene, or a branched fused polycyclic $C_6$-$C_{50}$ arylene. More preferred arylene groups have six to 30 carbon atoms, i.e., $C_6$-$C_{30}$ arylene, and especially have six to 20 carbon atoms, i.e., $C_6$-$C_{20}$ arylene. Most preferred arylene groups have six to 10 carbon atoms, i.e., $C_6$-$C_{10}$ arylene.

The term "heteroarylene" refers to divalent groups derived from heteroarenes by removal of a hydrogen atom from two ring atoms. In polycyclic heteroarylene groups, the rings may be attached together in a pendant manner or may be fused. Preferred heteroarylene groups have three to 50 carbon atoms, i.e., $C_3$-$C_{50}$ heteroalkenyl. In some forms, a $C_3$-$C_{50}$ heteroarylene can be a branched $C_3$-$C_{50}$ heteroarylene, a monocyclic $C_3$-$C_{50}$ heteroarylene, a polycyclic $C_3$-$C_{50}$ heteroarylene, a branched polycyclic $C_3$-$C_{50}$ heteroarylene, a fused polycyclic $C_3$-$C_{50}$ heteroarylene, or a branched fused polycyclic $C_3$-$C_{50}$ heteroarylene. More preferred heteroarylene groups have three to 30 carbon atoms, i.e., $C_3$-$C_{30}$ heteroarylene, and especially have three to 20 carbon atoms, i.e., $C_3$-$C_{20}$ heteroarylene. Most preferred heteroarylene groups have three to 10 carbon atoms, i.e., $C_3$-$C_{10}$ heteroarylene.

The term "aminooxy" refers to —O—$NH_2$, wherein the hydrogen atoms can be substituted with substituents.

The term "hydroxyamino" refers to —NH—OH, wherein the hydrogen atoms can be substituted with substituents.

The term "hydroxamate" refers to —C(=O)NH—OH, wherein the hydrogen atoms can be substituted with substituents.

The term "conjugated system" refers to a molecular entity whose structure may be represented as a system of alternating single and multiple bonds, e.g., $CH_2$=CH—CH=$CH_2$, $CH_2$=CH—C≡N. In such systems, conjugation is the interaction of one p-orbital with another across an intervening σ-bond in such structures. Conjugated systems may be or contain arene and/or heteroarene moieties.

The term "substituted," as used herein, means that the chemical group or moiety contains one or more substituents replacing the hydrogen atoms in the chemical group or moiety. The substituents include, but not limited to:

a halogen atom, an alkyl group, a heteroalkyl group, an alkenyl group, a heteroalkenyl group, an alkynyl group, a heteroalkynyl group, an aryl group, a heteroaryl group, —OH, —SH, —$NH_2$, —$N_3$, —OCN, —NCO, —$ONO_2$, —CN, —NC, —ONO, —$CONH_2$, —NO, —$NO_2$, —$ONH_2$, —SCN, —SNCS, —$CF_3$, —$CH_2CF_3$, —$CH_2Cl$, —$CHCl_2$, —$CH_2NH_2$, —NHCOH, —CHO, —COCl, —COF, —COBr, —COOH, —$SO_3H$, —$CH_2SO_2CH_3$, —$PO_3H_2$, —$OPO_3H_2$, —P(═O)($OR^{G1'}$)($OR^{G2'}$), —OP(═O)($OR^{G1'}$)($OR^{G2'}$), —$BR^{G1'}$($OR^{G2'}$), —B($OR^{G1'}$)($OR^{G2'}$), or -G'$R^{G1'}$ in which -G' is —O—, —S—, —$NR^{G2'}$—, —C(═O)—, —S(═O)—, —$SO_2$—, —C(═O)O—, —C(═O)$NR^{G2'}$—, —OC(═O)—, —$NR^{G2'}$C(═O)—, —OC(═O)O—, —OC(═O)$NR^{G2'}$—, —$NR^{G2'}$C(═O)O—, —$NR^{G2'}$C(═O)$NR^{G3'}$—, —C(═S)—, —C(═S)S—, —SC(═S)—, —SC(═S)S—, —C(═$NR^{G2'}$)—, —C(═$NR^{G2'}$)O—, —C(═$NR^{G2'}$)$NR^{G3'}$—, —OC(═$NR^{G2'}$)—, —$NR^{G2'}$C(═$NR^{G3'}$)—, —$NR^{G2'}SO_2$—, —C(═$NR^{G2'}$)$NR^{G3'}$—, —OC(═$NR^{G2'}$)—, —$NR^{G2'}$C(═$NR^{G3'}$)—, —$NR^{G2'}SO_2$—, —$NR^{G2'}SO_2NR^{G3'}$—, —$NR^{G2'}$C(═S)—, —SC(═S)$NR^{G2'}$—, —$NR^{G2'}$C(═S)S—, —$NR^{G2'}$ C(═S)$NR^{G3'}$—, —SC(═$NR^{G2'}$)—, —C(═S)$NR^{G2'}$—, —OC(═S)$NR^{G2'}$—, —$NR^{G2'}$C(═S)O—, —SC(═O)$NR^{G2'}$—, —$NR^{G2'}$C(═O)S—, —C(═O)S—, —SC(═O)S—, SC(═O)S—, —C(═S)O, —OC(═S), —OC(═S)O—, —$SO_2NR^{G2'}$—, —$BR^{G2'}$—, or —$PR^{G2'}$—; wherein each occurrence of $R^{G1'}$, $R^{G2'}$, and $R^{G3'}$ is, independently, a hydrogen atom, a halogen atom, an alkyl group, a heteroalkyl group, an alkenyl group, a heteroalkenyl group, an alkynyl group, a heteroalkynyl group, an aryl group, or a heteroaryl group.

In some instances, "substituted" also refers to one or more substitutions of one or more of the carbon atoms in a carbon chain (e.g., alkyl, alkenyl, alkynyl, and aryl groups) by a heteroatom, such as, but not limited to, nitrogen, oxygen, and sulfur.

It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

The term "protecting group" refers to a chemical fragment which can be used to deactivate a reactive functional group. The protecting group forms one or more covalent bonds with the reactive functional group. The protecting group can be removed under specific conditions to regenerate the reactive functional group. Such process is herein referred to as "deprotection" or "deprotecting." Exemplary oxygen protecting groups include silyl ethers such as trimethylsilyl, tertbutyldimethylsilyl, triisopropylsilyl, and tertbutyldiphenylsilyl; esters such as acetate and benzoate; and ethers such as benzyl, methoxybenzyl, tetrahydropyranyl, triphenylmethyl, and methoxymethyl. Exemplary nitrogen protecting groups include carbamates such as tert-butoxycarbonyl, benzyloxycarbonyl, and 9-fluorenylmethyloxycarbonyl; amides such as acetamide, benzamide, trifluoroacetamide, and trichloroacetamide; phthalimides; amines such as benzyl and methoxybenzyl; and sulfonamides such as 4-methylphenylsulfonamide and nitrophenylsulfonamides.

"Oligonucleotide" refers to short nucleic acid (i.e., DNA and RNA) molecules. They contain less than 100 nucleotides. Preferably, they contain less than 50 nucleotides. More preferably, they contain 25 or less nucleotides. Most preferably, they contain 13-25 nucleotides.

"Luminescence" refers to emission of light by a substance not resulting from heat. It can be caused by chemical reactions, electrical energy, subatomic motions or stress on a crystal, which all are ultimately caused by spontaneous emission. It may refer to chemiluminescence, i.e., the emission of light as a result of a chemical reaction. It may also refer to photoluminescence, i.e., the emission of light as a result of absorption of photons. The photoluminescence may include fluorescence and phosphorescence.

"Self-immolative linker" refers to a class of organic spacers connecting a cleavable moiety to an output cargo moiety. Upon an input reaction that cleaves the cleavable moiety from the rest of the molecule, the self-immolative linker spontaneously disintegrate from the output cargo moiety via end-to-end decomposition or cyclization mechanisms, thereby releasing the output cargo moiety.

The terms "carrier" or "carriers" refer to all components present in a formulation other than the active ingredient or ingredients. They may include but are not limited to diluents, binders, lubricants, desintegrators, fillers, plasticizers, pigments, colorants, stabilizing agents, and glidants.

B. Compounds

Disclosed herein are compounds useful for detecting carbapenemases or microbial carbapenem resistance.

Generally, the compounds of the present invention have the structure of CP-A-D or salts thereof, wherein CP is an azabicyclo moiety composed of a beta-lactam ring and a five-element hetero-unsaturated ring having a double bond between two carbon atoms; A is a conjugated system; D is connected to A via a methylene bridge and comprises a chemical probe, wherein the beta-lactam ring of the compound can be hydrolyzed by one or more carbapenemases, thereby triggering intramolecular rearrangement to release D from the compound.

For example, in some forms, the disclosed compounds have the structure of Formulas Ia, Ib, Ic, Id or Ie, or salts thereof Formula Ia

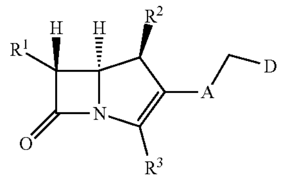

Formula Ib

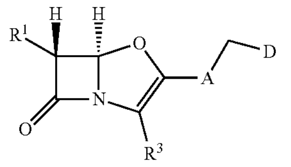

Formula Ic

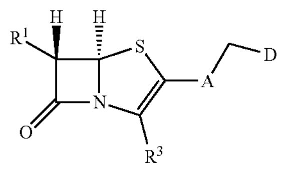

-continued

Formula Id

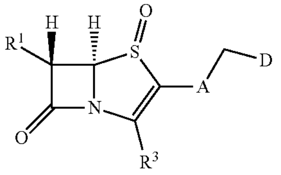

Formula Ie

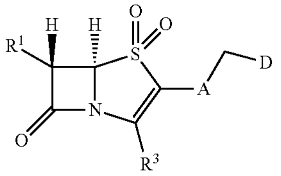

where $R^1$, $R^2$, and $R^3$ are organic moieties, A is an unsaturated chemical moiety, and D is or contains a chemical probe.

In preferred forms of the compounds:

(a) A is a divalent group selected from $-(CR^4=CR^5)_m-$, $-(C\equiv C)_n-$, optionally substituted arylenes, optionally substituted heteroarylenes, and covalent adducts thereof, wherein the covalent adducts are conjugated systems and wherein m and n are positive integers;

(b) D is connected to A via a methylene bridge and comprises a chemical probe;

(c) The beta-lactam ring of the compound can be hydrolyzed by one or more carbapenemases, thereby triggering intramolecular rearrangement to release D from the compound;

(d) $R^1$, $R^2$, $R^4$, and $R^5$ are independently:

a hydrogen atom, a halogen atom, a sulfonic acid, an azide group, a cyanate group, an isocyanate group, a nitrate group, a nitrile group, an isonitrile group, a nitrosooxy group, a nitroso group, a nitro group, an aldehyde group, an acyl halide group, a carboxylic acid group, a carboxylate group, an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, an optionally substituted heteroaryl group;

a hydroxyl group optionally containing one substituent at the hydroxyl oxygen, wherein the substituent is an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

a thiol group optionally containing one substituent at the thiol sulfur, wherein the substituent is an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

a sulfonyl group containing an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

an amino group optionally containing one or two substituents at the amino nitrogen, wherein the substituents are optionally substituted alkyl groups, optionally substituted heteroalkyl groups, optionally substituted alkenyl groups, optionally substituted heteroalkenyl groups, optionally substituted alkynyl groups, optionally substituted heteroalkynyl groups, optionally substituted aryl groups, optionally substituted heteroaryl groups, or combinations thereof;

an amide group optionally containing one or two substituents at the amide nitrogen, wherein the substituents are optionally substituted alkyl groups, optionally substituted heteroalkyl groups, optionally substituted alkenyl groups, optionally substituted heteroalkenyl groups, optionally substituted alkynyl groups, optionally substituted heteroalkynyl groups, optionally substituted aryl groups, optionally substituted heteroaryl groups, or combinations thereof;

an azo group containing an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

an acyl group containing an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

an ester group containing an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

a carbonate ester group containing an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

an ether group containing an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

an aminooxy group optionally containing one or two substituents at the amino nitrogen, wherein the substituents are optionally substituted alkyl groups, optionally substituted heteroalkyl groups, optionally substituted alkenyl groups, optionally substituted heteroalkenyl groups, optionally substituted alkynyl groups, optionally substituted heteroalkynyl groups, optionally substituted aryl groups, optionally substituted heteroaryl groups, or combinations thereof; or a hydroxyamino group optionally containing one or two substituents, wherein the substituents are optionally substituted alkyl groups, optionally substituted heteroalkyl groups, optionally substituted alkenyl groups, optionally substituted heteroalkenyl groups, optionally substituted alkynyl groups, optionally substituted heteroalkynyl groups, optionally substituted aryl groups, optionally substituted heteroaryl groups, or combinations thereof;

(e) $R^3$ is:

a carboxylic acid or carboxylate;

an ester group containing an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

an amide group optionally containing one or two substituents at the amide nitrogen, wherein the substituents are optionally substituted alkyl groups, optionally substituted heteroalkyl groups, optionally substituted alkenyl groups, optionally substituted heteroalkenyl groups, optionally substituted alkynyl groups, optionally substituted heteroalkynyl groups, optionally substituted aryl groups, optionally substituted heteroaryl groups, or combinations thereof; or a hydroxamate group optionally containing one or two substituents, wherein the substituents are optionally substituted alkyl groups, optionally substituted heteroalkyl groups, optionally substituted alkenyl groups, optionally substituted heteroalkenyl groups, optionally substituted alkynyl groups, optionally substituted heteroalkynyl groups, optionally substituted aryl groups, optionally substituted heteroaryl groups, or combinations thereof;

(f) $R^1$, $R^2$, $R^3$, $R^4$, and $R^5$, and their substituents are optionally and independently substituted with one or more chemical groups, wherein each chemical group is independently:

a halogen atom, an alkyl group, a heteroalkyl group, an alkenyl group, a heteroalkenyl group, an alkynyl group, a heteroalkynyl group, an aryl group, a heteroaryl group, —OH, —SH, $—NH_2$, $—N_3$, —OCN, —NCO, $—ONO_2$, —CN, —NC, —ONO, $—CONH_2$, —NO, $—NO_2$, $—ONH_2$, —SCN, —SNCS, $—CF_3$, $—CH_2CF_3$, $—CH_2Cl$, $—CHCl_2$, $—CH_2NH_2$, —NHCOH, —CHO, —COCl, —COF, —COBr, —COOH, $—SO_3H$, $—CH_2SO_2CH_3$, $—PO_3H_2$, $—OPO_3H_2$, $—P(=O)(OR^{G1})(OR^{G2})$, $—OP(=O)(OR^{G1})(OR^{G2})$, $—BR^{G1}(OR^{G2})$, $—B(OR^{G1})(OR^{G2})$, or $-GR^{G1}$ in which -G is —O—, —S—, $—NR^{G2}—$, —C(=O)—, —S(=O)—, $—SO_2—$, —C(=O)O—, $—C(=O)NR^{G2}—$, $—OC(=O)—$-$NR^{G2}C(=O)—$, —OC(=O)O—, $—OC(=O)NR^{G2}—$, $—NR^{G2}C(=O)O—$, $—NR^{G2}C(=O)NR^{G3}—$, —C(=S)—, —C(=S)S—, —SC(=S)—, —SC(=S)S—, $—C(=NR^{G2})—$, $—C(=NR^{G2})O—$, $—C(=NR^{G2})NR^{G3}—$, $—OC(=NR^{G2})—$, $—NR^{G2}C(=NR^{G3})—$, $—NR^{G2}SO_2—$, $—C(=NR^{G2})NR^{G3}—$, $—OC(=NR^{G2})—$, $—NR^{G2}C(=NR^{G3})—$, $—NR^{G2}SO_2—$, $—NR^{G2}SO_2NR^{G3}—$, $—NR^{G2}C(=S)—$, $—SC(=S)NR^{G2}—$, $—NR^{G2}C(=S)S—$, $—NR^{G2}C(=S)NR^{G3}—$, $—SC(=NR^{G2})—$, $—C(=S)NR^{G2}—$, $—OC(=S)NR^{G2}—$, $—NR^{G2}C(=S)O—$, $—SC(=O)NR^{G2}—$, $—NR^{G2}C(=O)S—$, —C(=O)S—, —SC(=O)—, —SC(=O)S—, —C(=S)O—, —OC(=S)—, —OC(=S)O—, $—SO_2NR^{G2}—$, $—BR^{G2}—$, or $—PR^{G2}—$ wherein each occurrence of $R^{G1}$, $R^{G2}$, and $R^{G3}$ is, independently, a hydrogen atom, a halogen atom, an alkyl group, a heteroalkyl group, an alkenyl group, a heteroalkenyl group, an alkynyl group, a heteroalkynyl group, an aryl group, or a heteroaryl group.

Specific examples of A include optionally substituted vinylene groups, e.g., —CH=CH—, and optionally substituted phenylene group, e.g.,

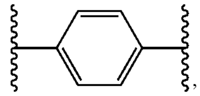
,
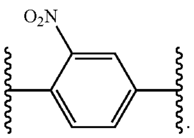
.

Other specific examples of A include optionally substituted five-membered-ring hetercycles, optionally substituted six-membered-ring hetercycles, e.g.,

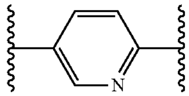
,
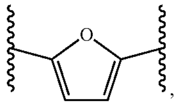
,
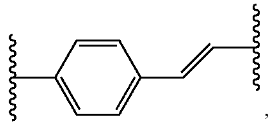
,

—CH=CH—CH=CH—, and —C≡C—.

In some forms, D can be:

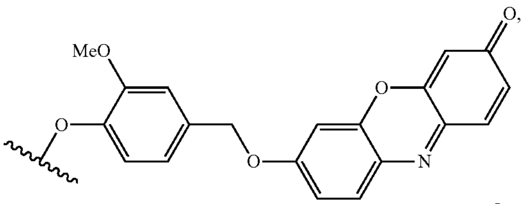
,
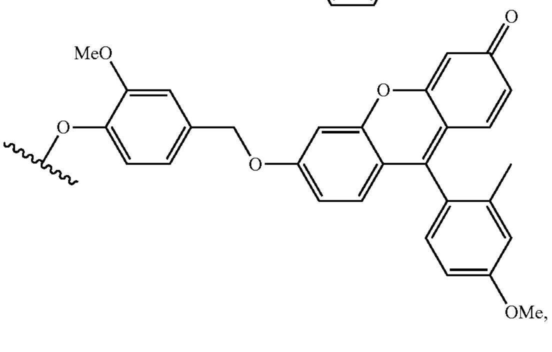
,

-continued
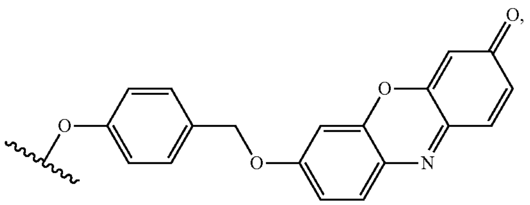
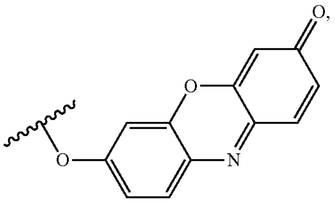
and
-continued
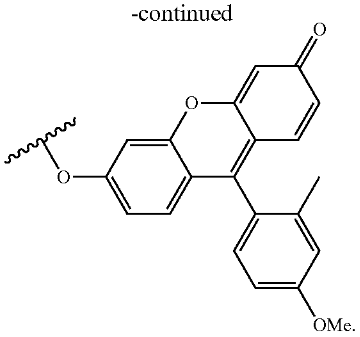
Exemplary compounds with the structure of Formula Ia include compounds MCW-001, MCW-002, MCW-003, MCW-004, MCW-005, MCW-006, MCW-007, MCW-008, MCW-009, MCW-010, and MCW-013. Exemplary compounds with the structure of Formula Ic include compounds MCW-011 and MCW-012. The structure of the exemplary compounds are shown below and in Table 1.
MCW-001
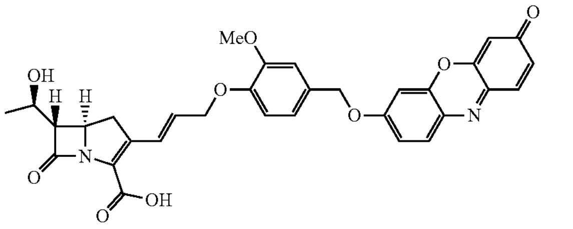
MCW-002
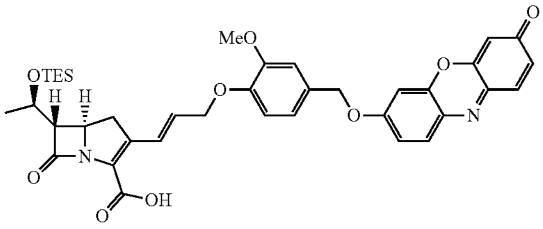
MCW-003
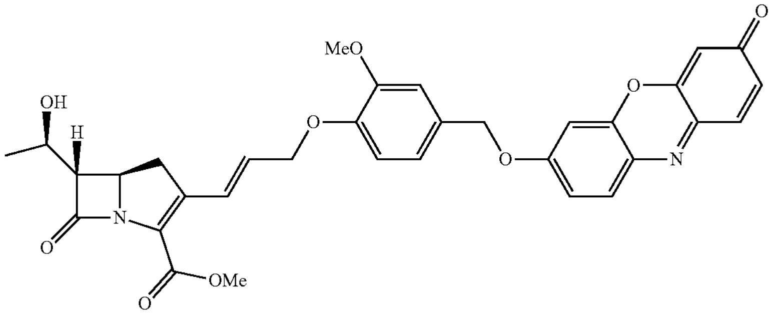
MCW-004
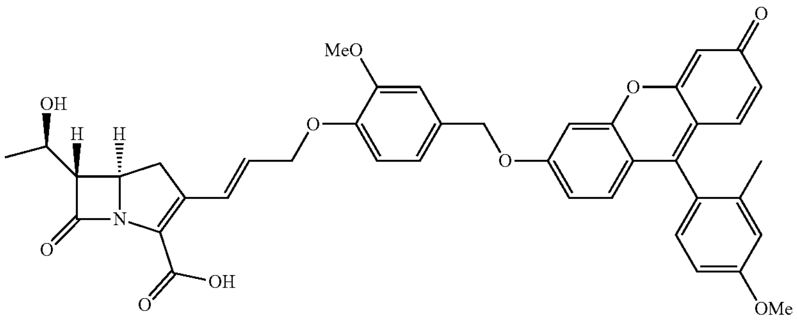

-continued
MCW-005
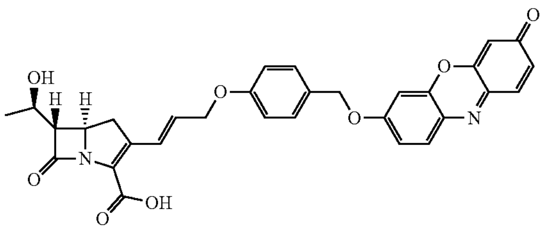
MCW-006
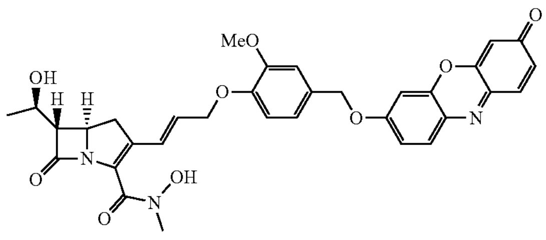
MCW-007
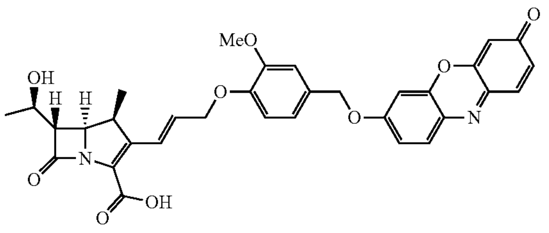
MCW-008
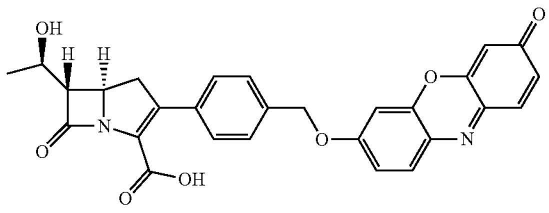
MCW-009
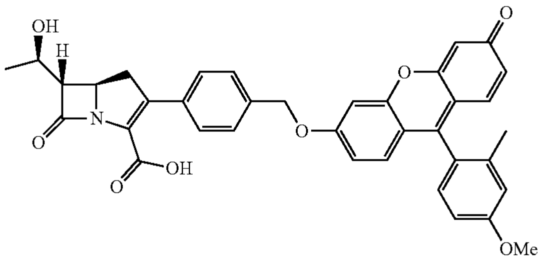
MCW-010
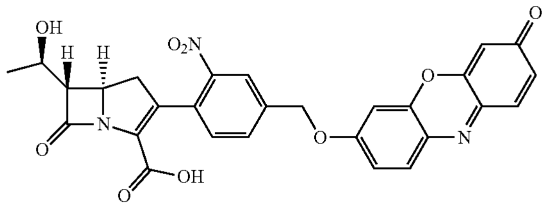
MCW-011
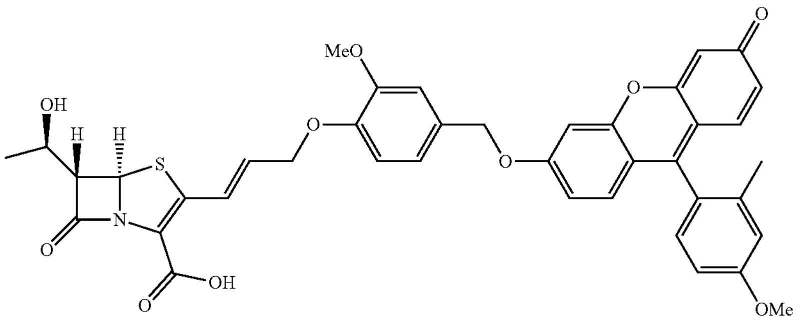
MCW-012
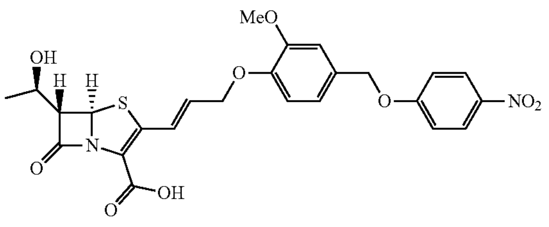
MCW-013
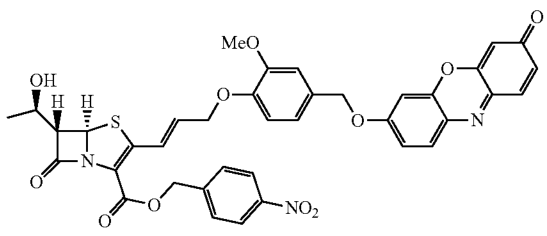

Additional exemplary compounds with the structure of Formula Ia are shown below.

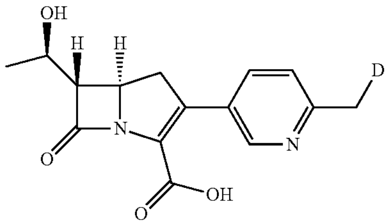

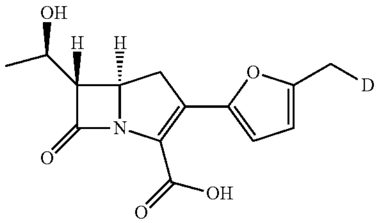

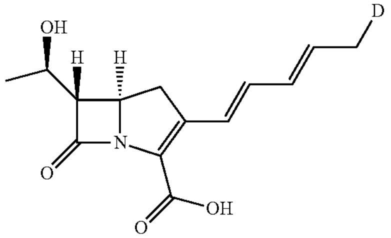

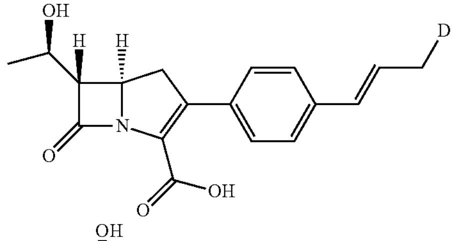

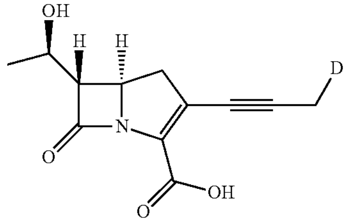

The salts of Formulas Ia, Ib, Ic, Id, and Ie can be prepared by treating the free acid form of the compounds with an appropriate amount of a base. Exemplary bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature between about 0° C. and about 100° C. such as at room temperature. The molar ratio of the free acid form of the compounds to the base used is chosen to provide the ratio desired for any particular salts. For preparing, for example, the ammonium salts of the free acid starting material, the starting material can be treated with approximately one equivalent, two equivalents, or up to five equivalents of the base to yield a neutral salt.

The beta-lactam ring of the disclosed compounds can be hydrolyzed by beta-lactamases, such as enzymes in the CTX-M family, the TEM family, the SHV family, and the AmpC family (e.g., LAT series, ACT series, MIR series, FOX series, MOX series, DHA series, ACC series). In a preferred embodiment, the compounds can be hydrolyzed by carbapenemases. In a more preferred embodiment, the compounds can have higher specificity for carbapenemases than for any other beta-lactamases. In the most preferred embodiments, the compounds can be only hydrolyzed by carbapenemases but not by any other beta-lactamases.

Exemplary carbapenemases include Class A carbapenemases, such as the SME family (e.g., SME-1, SME-2, SME-3), the NMC family (e.g., NMC-A), the IMI family (e.g., IMI-1, IMI-2), the KPC family (e.g., KPC-1, KPC-2, KPC-3, KPC-4), and the GES family (e.g., GES-1, GES-2, GES-3, GES-4, GES-5, GES-6), Class B carbapenemases, such as the IMP family (e.g., IMP-1, IMP-2, IMP-3, IMP-4, IMP-5, IMP-6), the VIM family (VIM-1, VIM-2, VIM-3, VIM-4, VIM-5), the SPM family (e.g., SPM-1), the GIM family (e.g., GIM-1), and the NDM family (e.g., NDM-1), Class C carbapenemases, such as the CMY family, and Class D carbapenemases, such as the OXA family (e.g., OXA-23, OXA-24, OXA-48, OXA-51, and OXA-181).

The compounds can have different specificity towards different carbapenemases.

In some embodiments, the compounds can have higher specificity for one class or sub-class of carbapenemases than for another class or sub-class of carbapenemases. In some embodiments, the compounds can be only hydrolyzed by one class or sub-class of carbapenemases but not by another class or sub-class of carbapenemases.

As exemplified by the scheme below, hydrolysis of the disclosed compounds by carbapenemases can trigger intramolecular rearrangement of the compounds, thereby causing the release of D from the compounds. $A^1$ represent the product of A after rearrangements of electrons.

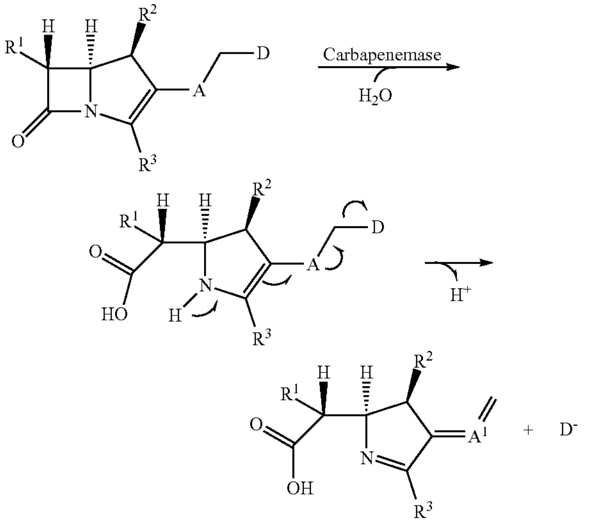

In some embodiments, the rate of the overall reaction, i.e., carbapenemase-catalyzed hydrolysis+intramolecular rearrangement, is within the range between about 0.01 and about 5 nmol compound per minute per nmol carbapenemases.

Example ranges include between about 0.010 and about 5 nmol compound per minute per nmol carbapenemase, between about 0.011 and about 5 nmol compound per minute per nmol carbapenemase, between about 0.012 and about 5 nmol compound per minute per nmol carbapenemase, between about 0.013 and about 5 nmol compound per minute per nmol carbapenemase, between about 0.014 and about 5 nmol compound per minute per nmol carbapenemase, between about 0.015 and about 5 nmol compound per minute per nmol carbapenemase, between about 0.016 and about 5 nmol compound per minute per nmol carbapenemase, between about 0.017 and about 5 nmol compound per minute per nmol carbapenemase, between about 0.018 and about 5 nmol compound per minute per nmol carbapenemase, between about 0.019 and about 5 nmol compound per minute per nmol carbapenemase, between about 0.020 and about 5 nmol compound per minute per nmol carbapenemase, between about 0.021 and about 5 nmol compound per minute per nmol carbapenemase, between about 0.022 and about 5 nmol compound per minute per nmol carbapenemase, between about 0.023 and about 5 nmol compound per minute per nmol carbapenemase, between about 0.024 and about 5 nmol compound per minute per nmol carbapenemase, between about 0.025 and about 5 nmol compound per minute per nmol carbapenemase, between about 0.026 and about 5 nmol compound per minute per nmol carbapenemase, between about 0.027 and about 5 nmol compound per minute per nmol carbapenemase, between about 0.028 and about 5 nmol compound per minute per nmol carbapenemase, between about 0.029 and about 5 nmol compound per minute per nmol carbapenemase, between about 0.030 and about 5 nmol compound per minute per nmol carbapenemase, between about 0.031 and about 5 nmol compound per minute per nmol carbapenemase, between about 0.032 and about 5 nmol compound per minute per nmol carbapenemase, between about 0.033 and about 5 nmol compound per minute per nmol carbapenemase, between about 0.034 and about 5 nmol compound per minute per nmol carbapenemase, between about 0.035 and about 5 nmol compound per minute per nmol carbapenemase, between about 0.036 and about 5 nmol compound per minute per nmol carbapenemase, between about 0.037 and about 5 nmol compound per minute per nmol carbapenemase, between about 0.038 and about 5 nmol compound per minute per nmol carbapenemase, between about 0.039 and about 5 nmol compound per minute per nmol carbapenemase, between about 0.04 and about 5 nmol compound per minute per nmol carbapenemase, between about 0.05 and about 5 nmol compound per minute per nmol carbapenemase, between about 0.06 and about 5 nmol compound per minute per nmol carbapenemase, between about 0.07 and about 5 nmol compound per minute per nmol carbapenemase, between about 0.08 and about 5 nmol compound per minute per nmol carbapenemase, between about 0.09 and about 5 nmol compound per minute per nmol carbapenemase, between about 0.1 and about 5 nmol compound per minute per nmol carbapenemase, between about 0.2 and about 5 nmol compound per minute per nmol carbapenemase, between about 0.3 and about 5 nmol compound per minute per nmol carbapenemase, between about 0.4 and about 5 nmol compound per minute per nmol carbapenemase, between about 0.5 and about 5 nmol compound per minute per nmol carbapenemase, between about 0.6 and about 5 nmol compound per minute per nmol carbapenemase, between about 0.7 and about 5 nmol compound per minute per nmol carbapenemase, between about 0.8 and about 5 nmol compound per minute per nmol carbapenemase, between about 0.9 and about 5 nmol compound per minute per nmol carbapenemase, and between about 1.0 and about 5 nmol compound per minute per nmol carbapenemase.

Example ranges also include between about 0.03 and about 5.0 nmol compound per minute per nmol carbapenemase, between about 0.03 and about 4.9 nmol compound per minute per nmol carbapenemase, between about 0.03 and about 4.8 nmol compound per minute per nmol carbapenemase, between about 0.03 and about 4.7 nmol compound per minute per nmol carbapenemase, between about 0.03 and about 4.6 nmol compound per minute per nmol carbapenemase, between about 0.03 and about 4.5 nmol compound per minute per nmol carbapenemase, between about 0.03 and about 4.0 nmol compound per minute per nmol carbapenemase, between about 0.03 and about 3.5 nmol compound per minute per nmol carbapenemase, between about 0.03 and about 3.0 nmol compound per minute per nmol carbapenemase, between about 0.03 and about 2.5 nmol compound per minute per nmol carbapenemase, between about 0.03 and about 2.0 nmol compound per minute per nmol carbapenemase, between about 0.03 and about 1.5 nmol compound per minute per nmol carbapenemase, between about 0.03 and about 1.0 nmol compound per minute per nmol carbapenemase, between about 0.03 and about 0.9 nmol compound per minute per nmol carbapenemase, between about 0.03 and about 0.8 nmol compound per minute per nmol carbapenemase, between about 0.03 and about 0.7 nmol compound per minute per nmol carbapenemase, between about 0.03 and about 0.5 nmol compound per minute per nmol carbapenemase, between about 0.03 and about 0.5 nmol compound per minute per nmol carbapenemase, between about 0.03 and about 0.4 nmol compound per minute per nmol carbapenemase, between about 0.03 and about 0.3 nmol compound per minute per nmol carbapenemase, between about 0.03 and about 0.2 nmol compound per minute per nmol carbapenemase, between about 0.03 and about 0.1 nmol compound per minute per nmol carbapenemase, between about 0.03 and about 0.09 nmol compound per minute per nmol carbapenemase, between about 0.03 and about 0.08 nmol compound per minute per nmol carbapenemase, between about 0.03 and about 0.07 nmol compound per minute per nmol carbapenemase, between about 0.03 and about 0.06 nmol compound per minute per nmol carbapenemase, between about 0.03 and about 0.05 nmol compound per minute per nmol carbapenemase, between about 0.03 and about 0.04 nmol compound per minute per nmol carbapenemase, between about 0.030 and about 0.039 nmol compound per minute per nmol carbapenemase, between about 0.030 and about 0.038 nmol compound per minute per nmol carbapenemase, between about 0.030 and about 0.037 nmol compound per minute per nmol carbapenemase, between about 0.030 and about 0.036 nmol compound per minute per nmol carbapenemase, between about 0.030 and about 0.035 nmol compound per minute per nmol carbapenemase, between about 0.030 and about 0.034 nmol compound per minute per nmol carbapenemase, between about 0.030 and about 0.033 nmol compound per minute per nmol carbapenemase, between about 0.030 and about 0.032 nmol compound per minute per nmol carbapenemase, and between about 0.030 and about 0.031 nmol compound per minute per nmol carbapenemase.

Example ranges also include between about 0.030 and about 4.6 nmol compound per minute per nmol carbapenemase, between about 0.031 and about 4.6 nmol compound per minute per nmol carbapenemase, between about 0.032 and about 4.6 nmol compound per minute per nmol carbapenemase, between about 0.033 and about 4.6 nmol compound per minute per nmol carbapenemase, between about 0.034 and about 4.6 nmol compound per minute per nmol carbapenemase, between about 0.035 and about 4.6 nmol compound per minute per nmol carbapenemase, between about 0.036 and about 4.6 nmol compound per minute per nmol carbapenemase, between about 0.037 and about 4.6 nmol compound per minute per nmol carbapenemase, between about 0.038 and about 4.6 nmol compound per minute per nmol carbapenemase, between about 0.039 and about 4.6 nmol compound per minute per nmol carbapenemase, between about 0.04 and about 4.6 nmol compound per minute per nmol carbapenemase, between about 0.05 and about 4.6 nmol compound per minute per nmol carbapenemase, between about 0.06 and about 4.6 nmol compound per minute per nmol carbapenemase, between about 0.07 and about 4.6 nmol compound per minute per nmol carbapenemase, between about 0.08 and about 4.6 nmol compound per minute per nmol carbapenemase, between about 0.09 and about 4.6 nmol compound per minute per nmol carbapenemase, between about 0.1 and about 4.6 nmol compound per minute per nmol carbapenemase, between about 0.2 and about 4.6 nmol compound per minute per nmol carbapenemase, between about 0.3 and about 4.6 nmol compound per minute per nmol carbapenemase, between about 0.4 and about 4.6 nmol compound per minute per nmol carbapenemase, between about 0.5 and about 4.6 nmol compound per minute per nmol carbapenemase, between about 0.6 and about 4.6 nmol compound per minute per nmol carbapenemase, between about 0.7 and about 4.6 nmol compound per minute per nmol carbapenemase, between about 0.8 and about 4.6 nmol compound per minute per nmol carbapenemase, between about 0.9 and about 4.6 nmol compound per minute per nmol carbapenemase, and between about 1.0 and about 4.6 nmol compound per minute per nmol carbapenemase.

Example ranges also include between about 0.030 and about 0.40 nmol compound per minute per nmol carbapenemase, between about 0.031 and about 0.39 nmol compound per minute per nmol carbapenemase, between about 0.032 and about 0.38 nmol compound per minute per nmol carbapenemase, between about 0.033 and about 0.37 nmol compound per minute per nmol carbapenemase, between about 0.034 and about 0.36 nmol compound per minute per nmol carbapenemase, between about 0.035 and about 0.35 nmol compound per minute per nmol carbapenemase, between about 0.036 and about 0.34 nmol compound per minute per nmol carbapenemase, between about 0.037 and about 0.33 nmol compound per minute per nmol carbapenemase, between about 0.038 and about 0.32 nmol compound per minute per nmol carbapenemase, between about 0.039 and about 0.31 nmol compound per minute per nmol carbapenemase, between about 0.04 and about 0.30 nmol compound per minute per nmol carbapenemase, between about 0.05 and about 0.29 nmol compound per minute per nmol carbapenemase, between about 0.06 and about 0.28 nmol compound per minute per nmol carbapenemase, between about 0.07 and about 0.27 nmol compound per minute per nmol carbapenemase, between about 0.08 and about 0.26 nmol compound per minute per nmol carbapenemase, between about 0.09 and about 0.25 nmol compound per minute per nmol carbapenemase, between about 0.1 and about 0.24 nmol compound per minute per nmol carbapenemase, and between about 0.2 and about 0.23 nmol compound per minute per nmol carbapenemase.

In some specific examples, the range can be between about 0.0381 and about 4.586 nmol compound per minute per nmol carbapenemase, or between about 0.0381 and about 0.3273 nmol compound per minute per nmol carbapenemase.

In some embodiments, the relative specificity of the compounds, calculated as the ratio of the activity of the compounds to the activity of nitrocefin, towards the same carbapenemase, is larger than 0.05, larger than 0.068, or larger than 1.

TABLE 1

| Example Compounds | | |
|---|---|---|
| Example number | Description | Compound number |
| 1 | (E)-7-((3-methoxy-4-((3-(4,4,5,5-tetramethyl-1,3,2-dioxaborolan-2-yl)allyl)oxy)benzyl)oxy)-3H-phenoxazin-3-one 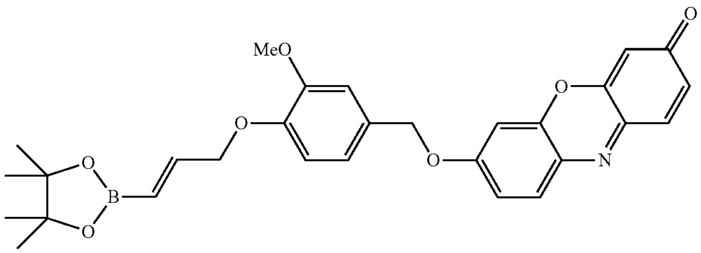 [SMILES: COc1cc(COc2ccc3nc4ccc(=O)cc-4oc3c2)ccc1OC/C=C/B1OC(C)(C)C(C)(C)O1] | 6 |
| 2 | 4-azidobenzyl 2-diazo-3-oxo-4-((2R,3S)-4-oxo-3-((R)-1-((triethylsilyl)oxy)ethyl)azetidin-2-yl)butanoate 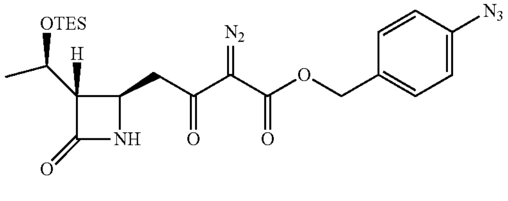 | 12 |

TABLE 1-continued

| Example Compounds | | |
|---|---|---|
| Example number | Description | Compound number |
| 3 | (5R,6S)-6-((R)-1-hydroxyethyl)-3-((E)-3-(2-methoxy-4-(((3-oxo-3H-phenoxazin-7-yl)oxy)methyl)phenoxy)prop-1-en-1-yl)-7-oxo-1-azabicyclo[3.2.0]hept-2-ene-2-carboxylic acid 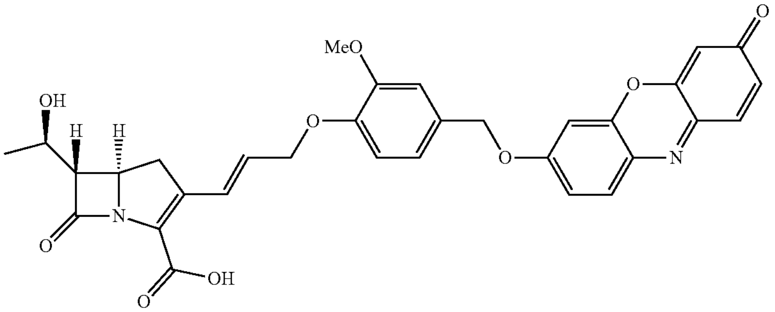 [SMILES: COc1cc(COc2ccc3nc4ccc(=O)cc-4oc3c2)ccc1OC/C=C/C1=C(C(=O)O)N2C(=O)[C@H]([C@@H](C)O)[C@H]2C1] | MCW-001 |
| 4 | (5R,6S)-3-((E)-3-(2-methoxy-4-(((3-oxo-3H-phenoxazin-7-yl)oxy)methyl)phenoxy)prop-1-en-1-yl)-7-oxo-6-((R)-1-((triethylsilyl)oxy)ethyl)-1-azabicyclo[3.2.0]hept-2-ene-2-carboxylic acid 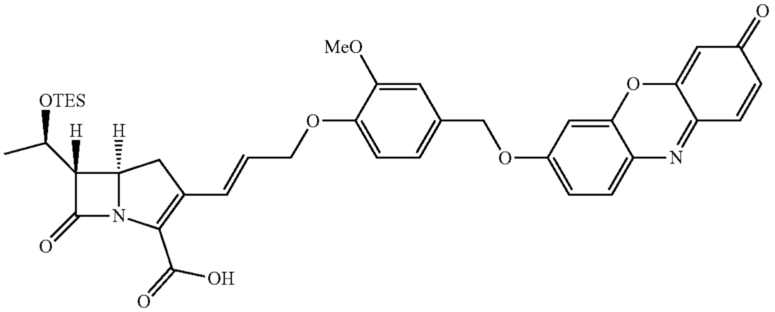 | MCW-002 |
| 5 | Methyl (5R,6S)-6-((R)-1-hydroxyethyl)-3-((E)-3-(2-methoxy-4-(((3-oxo-3H-phenoxazin-7-yl)oxy)methyl)phenoxy)prop-1-en-1-yl)-7-oxo-1-azabicyclo[3.2.0]hept-2-ene-2-carboxylate 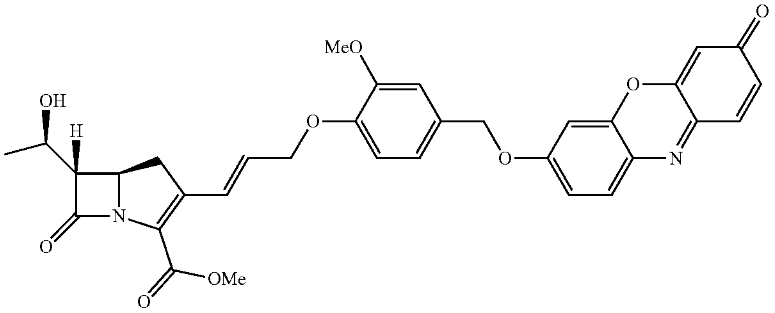 [SMILES: COC(=O)C1=C(/C=C/COc2ccc(COc3ccc4nc5ccc(=O)cc-5oc4c3)cc2OC)C[C@@H]2[C@@H]([C@@H](C)O)C(=O)N12] | MCW-003 |

TABLE 1-continued

| Example Compounds | | |
|---|---|---|
| Example number | Description | Compound number |
| 6 | (E)-9-(4-methoxy-2-methylphenyl)-6-((3-methoxy-4-((3-(4,4,5,5-tetramethyl-1,3,2-dioxaborolan-2-yl)allyl)oxy)benzyl)oxy)-3H-xanthen-3-one 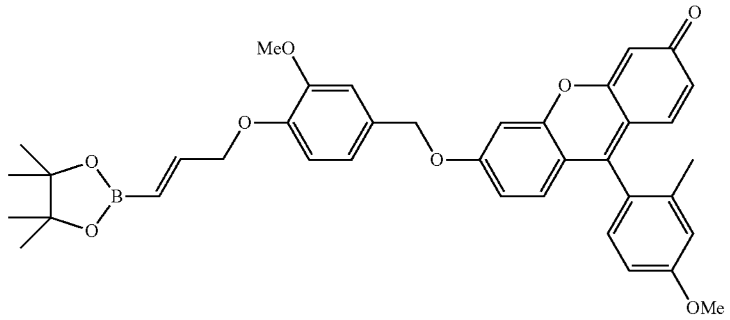 [SMILES: COc1ccc(-c2c3ccc(=O)cc-3oc3cc(OCc4ccc(OC/C=C/B5OC(C)(C)C(C)(C)O5)c(OC)c4)ccc23)c(C)c1] | 15 |
| 7 | (5R,6S)-6-((R)-1-hydroxyethyl)-3-((E)-3-(2-methoxy-4-(((9-(4-methoxy-2-methylphenyl)-3-oxo-3H-xanthen-6-yl)oxy)methyl)phenoxy)prop-1-en-1-yl)-7-oxo-1-azabicyclo[3.2.0]hept-2-ene-2-carboxylic acid 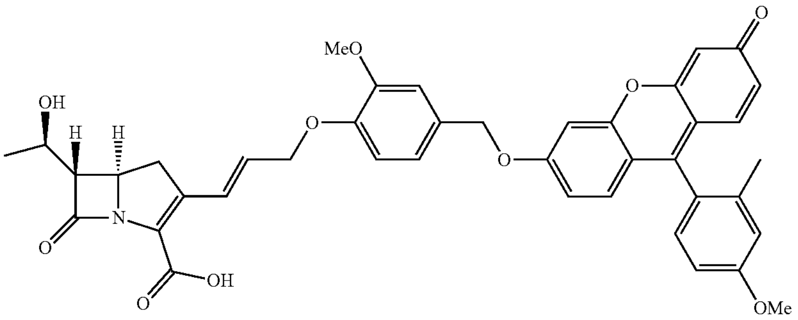 [SMILES: COc1ccc(-c2c3ccc(=O)cc-3oc3cc(OCc4ccc(OC/C=C/C5=C(C(=O)O)N6C(=O)[C@H]([C@@H](C)O)[C@H]6C5)c(OC)c4)ccc23)c(C)c1] | MCW-004 |
| 8 | (E)-7-((4-((3-(4,4,5,5-tetramethyl-1,3,2-dioxaborolan-2-yl)allyl)oxy)benzyl)oxy)-3H-phenoxazin-3-one 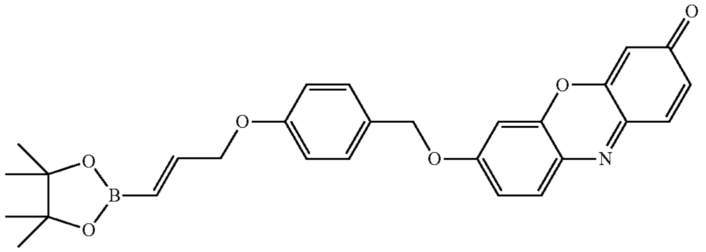 [SMILES: CC1(C)OB(/C=C/COc2ccc(COc3ccc4nc5ccc(=O)cc-5oc4c3)cc2)OC1(C)C] | 20 |
| 9 | (5R,6S)-6-((R)-1-hydroxyethyl)-7-oxo-3-((E)-3-(4-(((3-oxo-3H-phenoxazin-7-yl)oxy)methyl)phenoxy)prop-1-en-1-yl)-1-azabicyclo[3.2.0]hept-2-ene-2-carboxylic acid 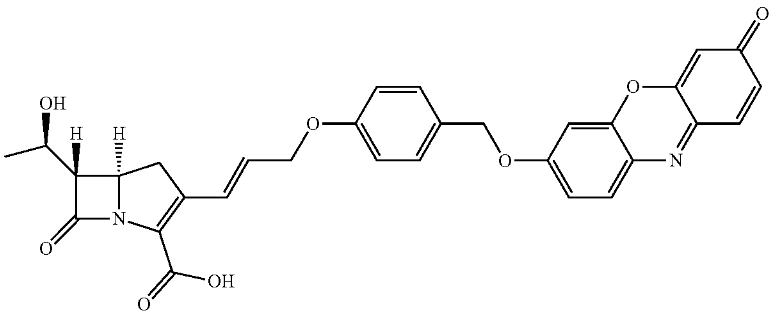 [SMILES: C[C@@H](O)[C@H]1C(=O)N2C(C(=O)O)=C(/C=C/COc3ccc(COc4ccc5nc6ccc(=O)cc-6oc5c4)cc3)C[C@H]12] | MCW-005 |

TABLE 1-continued

| Example Compounds | | |
|---|---|---|
| Example number | Description | Compound number |
| 10 | N-((4-azidobenzyl)oxy)-2-diazo-N-methyl-3-oxo-4-((2R,3S)-4-oxo-3-((R)-1-((triethylsilyl)oxy)ethyl)azetidin-2-yl)butanamide 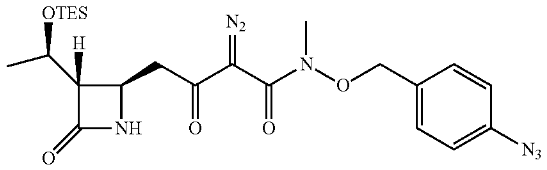 | 31 |
| 11 | (5R,6S)-N-hydroxy-6-((R)-1-hydroxyethyl)-3-((E)-3-(2-methoxy-4-(((3-oxo-3H-phenoxazin-7-yl)oxy)methyl)phenoxy)prop-1-en-1-yl)-N-methyl-7-oxo-1-azabicyclo[3.2.0]hept-2-ene-2-carboxamide 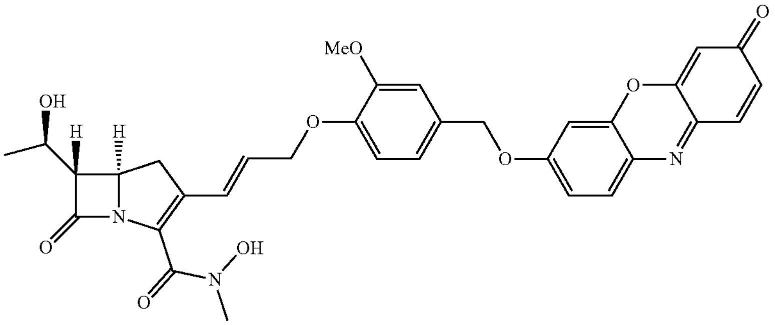 [SMILES: COc1cc(COc2ccc3nc4ccc(=O)cc-4oc3c2)ccc1OC/C=C/C1=C(C(=O)N(C)O)N2C(=O)[C@H]([C@@H](C)O)[C@H]2C1] | MCW-006 |
| 12 | 4-azidobenzyl (R)-2-diazo-3-oxo-4-((2R,3S)-4-oxo-3-((R)-1-((triethylsilyl)oxy)ethyl)azetidin-2-yl)pentanoate 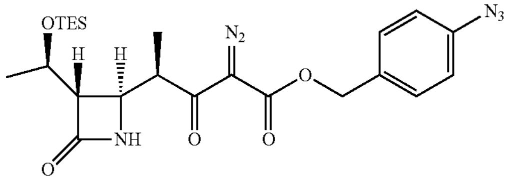 | 38 |
| 13 | (4S,5R,6S)-6-((R)-1-hydroxyethyl)-3-((E)-3-(2-methoxy-4-(((3-oxo-3H-phenoxazin-7-yl)oxy)methyl)phenoxy)prop-1-en-1-yl)-4-methyl-7-oxo-1-azabicyclo[3.2.0]hept-2-ene-2-carboxylic acid 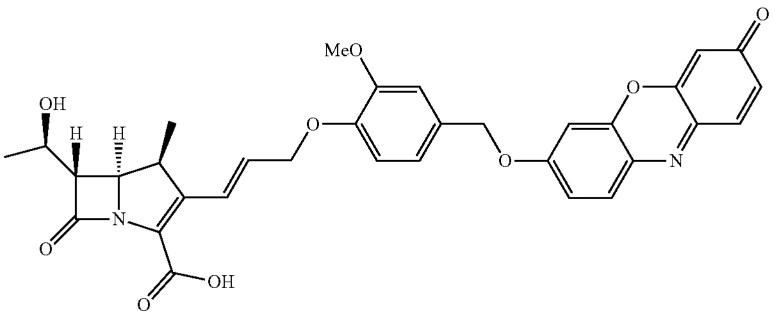 [SMILES: COc1cc(COc2ccc3nc4ccc(=O)cc-4oc3c2)ccc1OC/C=C/C1=C(C(=O)O)N2C(=O)[C@H]([C@@H](C)O)[C@H]2[C@H]1C] | MCW-007 |

TABLE 1-continued

| Example Compounds | | |
|---|---|---|
| Example number | Description | Compound number |
| 14 | 7-((4-(4,4,5,5-tetramethyl-1,3,2-dioxaborolan-2-yl) benzyl)oxy)-3H-phenoxazin-3-one<br>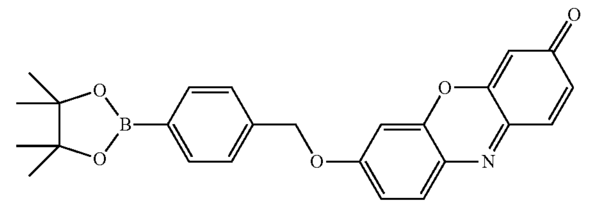 [SMILES: CC1(C)OB(c2ccc(COc3ccc4nc5ccc(=O)cc-5oc4c3)cc2)OC1(C)C] | 43 |
| 15 | (5R,6S)-6-((R)-1-hydroxyethyl)-7-oxo-3-(4-(((3-oxo-3H-phenoxazin-7-yl)oxy)methyl)phenyl)-1-azabicyclo[3.2.0]hept-2-ene-2-carboxylic acid<br>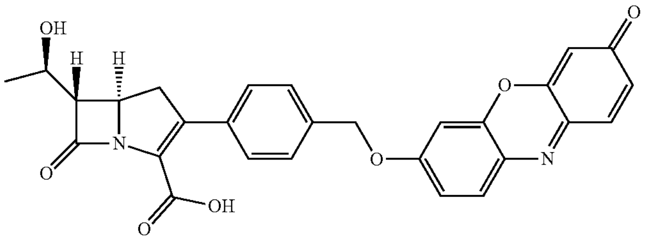 [SMILES: C[C@@H](O)[C@H]1C(=O)N2C(C(=O)O)=C(c3ccc(COc4ccc5nc6ccc(=O)cc-6oc5c4)cc3)C[C@H]12] | MCW-008 |
| 16 | 9-(4-methoxy-2-methylphenyl)-6-((4-(4,4,5,5-tetramethyl-1,3,2-dioxaborolan-2-yl)benzyl)oxy)-3H-xanthen-3-one<br>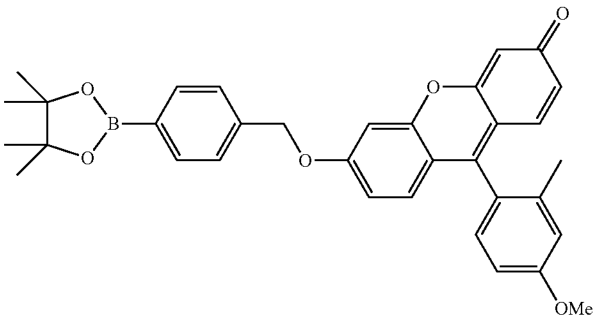 [SMILES: COc1ccc(-c2c3ccc(=O)cc-3oc3cc(OCc4ccc(B5OC(C)(C)C(C)(C)O5)cc4)ccc23)c(C)c1] | 46 |
| 17 | (5R,6S)-6-((R)-1-hydroxyethyl)-3-(4-(((9-(4-methoxy-2-methylphenyl)-3-oxo-3H-xanthen-6-yl)oxy)methyl)phenyl)-7-oxo-1-azabicyclo[3.2.0]hept-2-ene-2-carboxylic acid<br>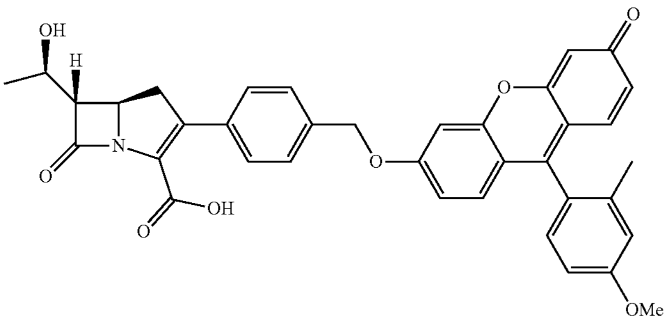 [SMILES: COc1ccc(-c2c3ccc(=O)cc-3oc3cc(OCc4ccc(C5=C(C(=O)O)N6C(=O)[C@H]([C@@H](C)O)[C@H]6C5)cc4)ccc23)c(C)c1] | MCW-009 |

TABLE 1-continued

| Example Compounds | | |
|---|---|---|
| Example number | Description | Compound number |
| 18 | 7-((3-nitro-4-(4,4,5,5-tetramethyl-1,3,2-dioxaborolan-2-yl)benzyl)oxy)-3H-phenoxazin-3-one<br>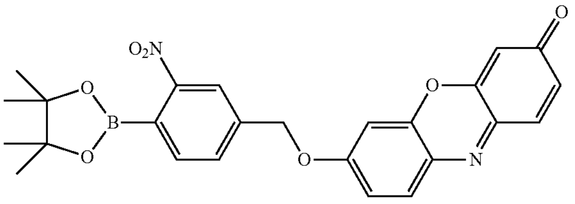 [SMILES: CC1(C)OB(c2ccc(COc3ccc4nc5ccc(=O)cc-5oc4c3)cc2[N+](=O)[O-])OC1(C)C] | 52 |
| 19 | (5R,6S)-6-((R)-1-hydroxyethyl)-3-(2-nitro-4-(((3-oxo-3H-phenoxazin-7-yl)oxy)methyl)phenyl)-7-oxo-1-azabicyclo[3.2.0]hept-2-ene-2-carboxylic acid<br>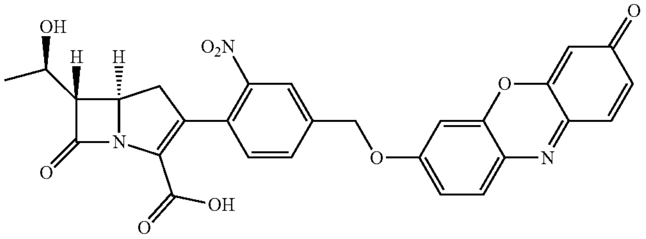 [SMILES: C[C@@H](O)[C@H]1C(=O)N2C(C(=O)O)=C(c3ccc(COc4ccc5nc6ccc(=O)cc-6oc5c4)cc3[N+](=O)[O-])C[C@H]12] | MCW-010 |
| 20 | (5R,6S)-6-((R)-1-hydroxyethyl)-3-((E)-3-(2-methoxy-4-(((9-(4-methoxy-2-methylphenyl)-3-oxo-3H-xanthen-6-yl)oxy)methyl)phenoxy)prop-1-en-1-yl)-7-oxo-4-thia-1-azabicyclo[3.2.0]hept-2-ene-2-carboxylic acid<br>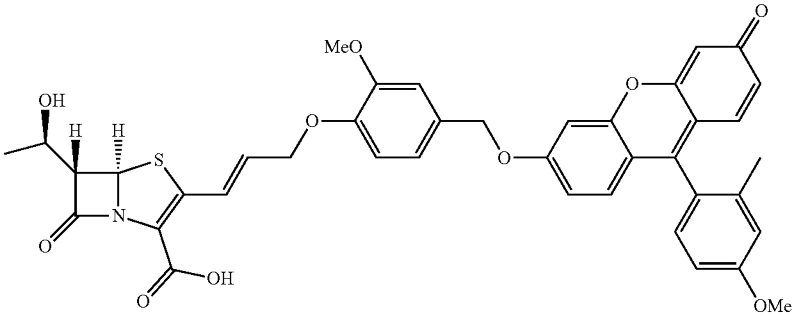 | MCW-011 |
| 21 | (5R,6S)-6-((R)-1-hydroxyethyl)-3-((E)-3-(2-methoxy-4-((4-nitrophenoxy)methyl)phenoxy)prop-1-en-1-yl)-7-oxo-4-thia-1-azabicyclo[3.2.0]hept-2-ene-2-carboxylic acid<br>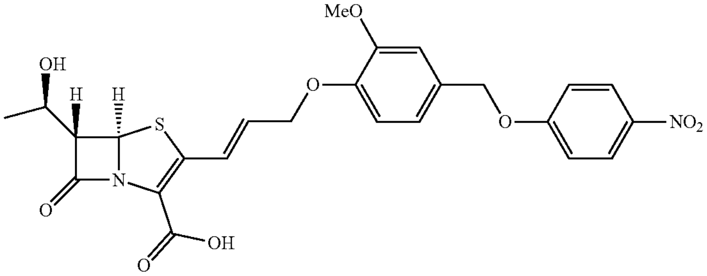 [SMILES: COc1cc(COc2ccc([N+](=O)[O-])cc2)ccc1OC/C=C/C1=C(C(=O)O)N2C(=O)[C@H]([C@@H](C)O)[C@H]2S1] | MCW-012 |

TABLE 1-continued

| Example number | Description | Compound number |
|---|---|---|
| | Example Compounds | |
| 22 | 4-nitrobenzyl (5R,6S)-6-((R)-1-hydroxyethyl)-3-((E)-3-(2-methoxy-4-(((3-oxo-3H-phenoxazin-7-yl)oxy)methyl)phenoxy)prop-1-en-1-yl)-7-oxo-1-azabicyclo[3.2.0]hept-2-ene-2-carboxylate<br>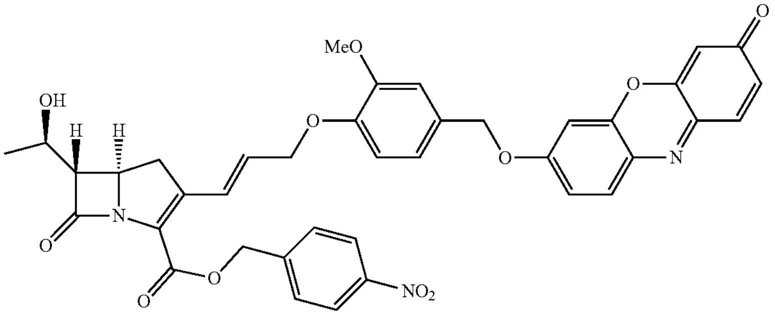 [SMILES: COc1cc(COc2ccc3nc4ccc(=O)cc-4oc3c2)ccc1OC/C=C/C1=C(C(=O)OCc2ccc([N+](=O)[O-])cc2)N2C(=O)[C@H]([C@@H](C)O)[C@H]2C1] | MCW-013 |

1. Leaving Group D

As exemplified in the aforementioned scheme, D is a leaving group that can be released from the compounds following the hydrolysis reactions catalyzed by carbapenemases. D is or contains a chemical probe that can be detected after being released from the compounds.

i. Chemical Probes

The chemical probe of D may be a luminescence probe. The luminescence probe may be non-luminescent or luminescence-quenched prior to carbapenemase-catalyzed hydrolysis of the compounds and becomes luminescent or luminescence-enhanced after being released from the compounds. Exemplary luminescence probes include resorufin, fluorescein, Tokyo Green, coumarin, luciferin, and derivatives thereof.

In some embodiments, the luminescence probe is a fluorescence probe. The fluorescence probe may be non-fluorescent or fluorescence-quenched prior to carbapenemase-catalyzed hydrolysis of the compounds and becomes fluorescent or fluorescence-enhanced after being released from the compounds. Such a fluorescence probe are herein referred to as a fluorescence turn-on probe. An exemplary fluorescence turn-on probe is resorufin, the fluorescence of which can be easily quenched via substitution on its 7-hydroxyl group.

In some embodiments, the luminescence probe contains a donor chromophore and an acceptor chromophore which enable Förster resonance energy transfer (FRET) after the luminescence probe is released from the compounds.

The chemical probe of D may be a colorimetric probe. The colorimetric probe may undergo a colorimetric change after being released from the compounds. The colorimetric change may include a shift in the absorption maxima, a variation in the absorption extinction coefficients, or both. Exemplary colorimetric probes include p-nitrophenol, p-thio-nitrobenzoic acid, and derivatives thereof.

The chemical probe of D may be both a luminescence probe and a colorimetric probe. They may exhibit both a luminescence change and a colorimetric change after being released from the compounds.

The chemical probe of D may be an oligonucleotide. The oligonucleotide may be amplified by PCR or reverse-transcription PCR after being released from the compounds. The amount of the oligonucleotide released from the compounds may be quantified by quantitative real-time PCR or reverse-transcription quantitative real-time PCR.

ii. Self-Immolative Linker

D may contain a self-immolative linker interposed between the methylene bridge and the rest of D. The self-immolative linker is spontaneously separated from the rest of D following the release of D from the compounds. Exemplary self-immolative linkers include 4-methanediyl-2-methoxyphenoxy and derivatives thereof, such as

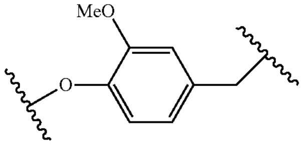

and

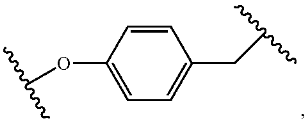

, wherein the phenoxy oxygen of the self-immolative linker is connected to the methylene bridge and the methanediyl group of the self-immolative linker is connected to the rest of D.

The presence of the self-immolative linker may place the chemical probe away from the carbapenemase active site, thereby facilitating the enzymatic hydrolysis. The self-immolative linker may also facilitate the release of D from the compounds by altering the kinetics of the cleavage reaction. The self-immolative linker may also improve the stability of the chemical probe, D, and/or the compounds.

B. Mixtures and Compositions

Disclosed are mixtures and compositions formed by performing or preparing to perform the disclosed methods.

For example, disclosed are mixtures containing multiple compounds with the structure of Formulas Ia, Ib, Ic, Id, or Ie, or salts thereof. The compounds in the mixtures may have different specificity towards different carbapenemases. The compounds in the mixtures may contain different chemical probes.

In another example, disclosed are compositions containing one or more compounds with the structure of Formulas Ia, Ib, Ic, Id, or Ie, or salts thereof as well as one or more other compounds, solvents, or materials. The composition may be in the form of solutions, suspensions, emulsions, powders, and solid cakes.

C. Samples

The sample containing one or more populations of bacteria may be or contain a human or non-human animal bodily fluid, a human or non-human animal tissue, or both. Exemplary bodily fluids include saliva, sputum, blood serum, blood, urine, mucus, vaginal lubrication, pus, and wound exudate.

The one or more populations of bacteria may include enterobacteriaceae, such as *Escherichia coli, Enterobacter aerogenes, Enterobacter cloacae, Klebsiella pneumoniae, Klebsiella oxytoca*, and combinations thereof. In some embodiments, the enterobacteriaceae are carbapenem-resistant enterobacteriaceae, such as carbapenem-resistant *Escherichia coli*, carbapenem-resistant *Enterobacter aerogenes*, carbapenem-resistant *Enterobacter cloacae*, carbapenem-resistant *Klebsiella pneumoniae*, carbapenem-resistant *Klebsiella oxytoca*, and combinations thereof.

D. Kits

The compounds, mixtures, and compositions described above can be packaged together with other components in any suitable combination as a kit useful for performing, or aiding in the performance of, the disclosed methods. It is useful if the components in a given kit are designed and adapted for use together in the disclosed methods.

In one aspect disclosed are kits for detecting microbial carbapenem resistance. The kits contains, in one or more containers, one or more of the disclosed compounds, mixtures, and compositions as well as one or more other components, such as compounds, solvents, and materials, as carriers. The carriers do not interfere with the effectiveness of the disclosed compounds in detecting microbial carbapenem resistance.

The kits may also contain an ionic or non-ionic detergent. The kits may also include instructions to use.

E. Methods of Making the Compounds

Disclosed are methods to make the disclosed compounds. In one aspect, methods of making the compounds of Formula Ia involve:

(a) forming a compound of Formula IV from a compound of Formula II and a compound of Formula III, wherein $R^{1'}$, $R^{2'}$, $R^{3'}$, A', and D' in the compounds of Formulas II, III, and IV represent $R^1$, $R^2$, $R^3$, A, and D, respectively, in the compound of Formula Ia with protecting groups over hydroxyl, amine, carbonyl, carboxylic acid, carboxylate, and/or phosphate groups; and Formula II

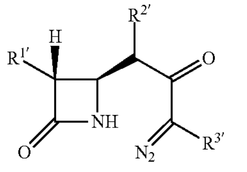

Formula III

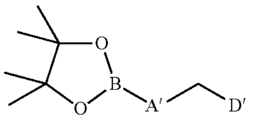

-continued

Formula IV

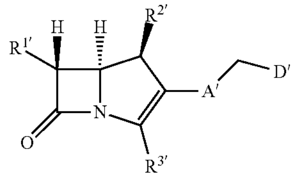

(b) deprotecting $R^{1'}$, $R^{2'}$, $R^{3'}$, A', and/or D' in the compound of Formula IV to form the compound of Formula Ia.

In some embodiments, step (a) of the methods include sub-steps, including:

(a1) performing a cyclization reaction of the compound of Formula II to form a compound of Formula IIa, wherein the reaction is catalyzed by a rhodium catalyst;

Formula IIa

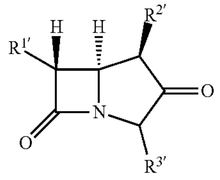

(a2) performing a reaction to convert the compound of Formula IIa to an enolate in the presence of a base and then convert the enolate to a compound of Formula IIb, wherein $OR^6$ is selected from perfluoroalkyl sulfonate, tosylate, mesylate, and derivatives thereof as well as halides;

Formula IIb

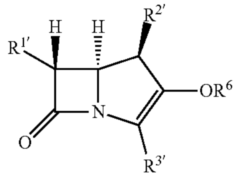

(a3) performing a carbon-carbon coupling reaction between the compound of Formula IIb and the compound of Formula III to form the compound of Formula IV, wherein the reaction is catalyzed by a palladium catalyst.

In some embodiments, the rhodium catalyst in step (a1) is rhodium(II) octanoate and/or its dimer. In some embodiments, the base in step (a2) is diisopropylamine. In some embodiments, the reaction of step (a2) is performed at a temperature at or below 0° C., preferably at or below −40° C., more preferably at or below −78° C. In some embodiments, $R^6$ in Formula IIb is triflyl. In some embodiments, the palladium catalyst in step (a3) is a mixture of palladium(0) and palladium(II), preferably at a 1:1 ratio. In some embodiments, the palladium catalyst is a mixture of $Pd_2dba_3$ and $PdCl_2dppf$. In some embodiments, a mildly basic condition is maintained in step (a3) by using a mixture of $H_2O$ and triethylamine ($NEt_3$) as solvent in the reaction.

In some embodiments, compounds MCW-001, MCW-002, MCW-003, MCW-004, MCW-005, MCW-006, MCW- 007, MCW-008, MCW-009, MCW-010, MCW-011, MCW-012 and MCW-013 are synthesized using the disclosed methods.

The compounds of Formulas II and III can be readily synthesized using techniques generally known to synthetic organic chemists. Exemplary methods to synthesize the specific compounds of Formulas II and III, for making MCW-001, MCW-002, MCW-003, MCW-004, MCW-005, MCW-006, MCW-007, MCW-008, MCW-009, MCW-010, MCW-011, MCW-012 and MCW-013 are described in the disclosed Examples.

In some embodiments, the carboxylic acid and/or carboxylate groups from $R^1$, $R^2$, $R^3$, A, and D can be protected in $R^{1'}$, $R^{2'}$, $R^{3'}$, A', and D' via being or forming an ester containing ap-azido-benzyl group or a derivative thereof. This protection method allows for rapid deprotection of the carboxylic acid or carboxylate groups by using a phosphine, such as triethylphosphine, as illustrated in the scheme below. In some embodiments, the deprotection reactions medicated by the phosphine can reach completion within about 10 min, about 5 min, about 4 min, about 3 min, about 2 min, or about min after the reactions start.

In some embodiments, the carboxylic acid and/or carboxylate groups from the organic compounds can be protected via being or forming an ester containing ap-azido-benzyl group or a derivative thereof.

An example of the ester is shown below. Other examples of the ester may contain one or more substituents on the benzyl moiety.

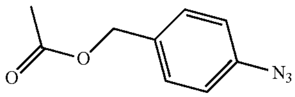

Deprotection of the carboxylic acid and/or carboxylate groups can be performed via hydrolysis of the ester in the presence of a phosphine, such as triethylphosphine. In some embodiments, the deprotection reactions medicated by the phosphine can reach completion within about 10 min, about 5 min, about 4 min, about 3 min, about 2 min, or about min after the reactions start.

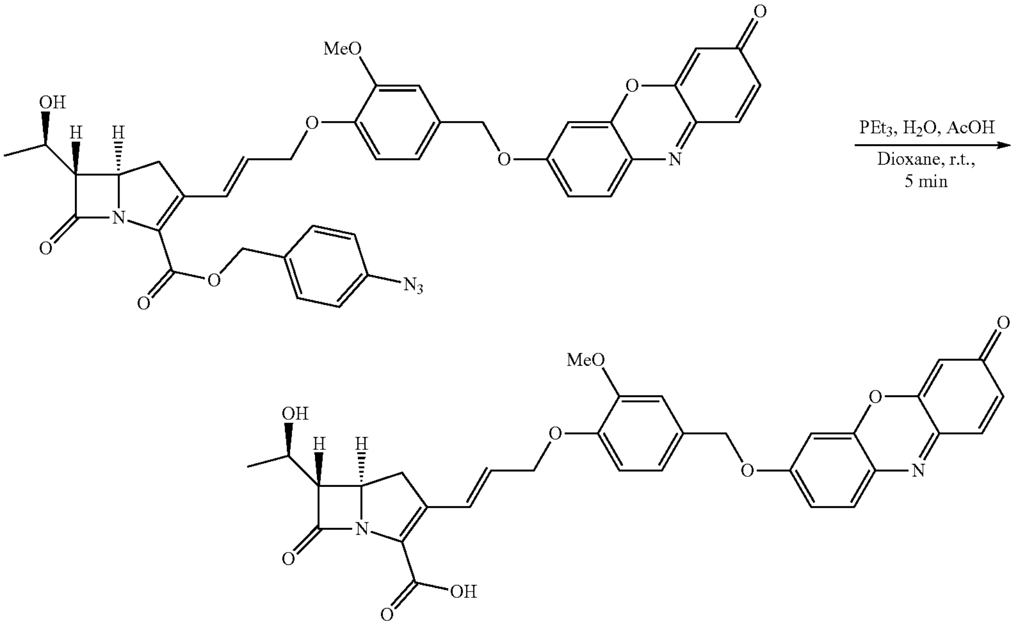

MCW-001

To avoid decomposition or degradation of the disclosed compounds, step (b) may be performed right before using the compounds to detect carbapenemases or evaluate the efficacy of carbapenemase inhibitors. Optionally, step (b) may be partially completed prior to using the compounds, thereby allowing some functional groups being deprotected and the rest remaining protected. In some embodiments, on-site deprotection may be performed and the crude mixture from the deprotection reaction may be directly used for detecting carbapenemases or evaluating the efficacy of carbapenemase inhibitors.

F. Methods of Protecting Carboxylate or Carboxylic Acid Groups

Disclosed are methods of protecting carboxylate or carboxylic acid groups of organic compounds, especially during organic synthesis.

In-situ deprotection of carboxylic acid and/or carboxylate groups can be achieved via hydrolysis of the ester in the presence of a cellular esterase or nitroreductase.

G. Methods of Using the Compounds

1. Detecting Carbapenemases or Microbial Carbapenem Resistance

Disclosed are methods to detect carbapenemases or microbial carbapenem resistance. The methods include (a) contacting a sample containing one or more populations of bacteria with one or more of the disclosed compounds and (b) detecting the release of D from the compounds. Detection of the release of D indicates the presence of carbapenemases and the presence of carbapenemases indicates the presence of carbapenem resistance.

In some embodiments, D is or contains a luminescence probe that remains non-luminescent or luminescence-quenched prior to carbapenemase-catalyzed hydrolysis of the compounds and becomes luminescent or luminescence-enhanced after being released from the compounds. The release of D can be detected by detecting the luminescence signal of the luminescence probe. The luminescence signal of the luminescence probe may reach between about 80 and about 100% of its maximum value within about 5 minutes, about 10 minutes, about 15 minutes, about 20 minutes, about 25 minutes, or about 30 minutes, following the contact of the sample with the compounds. The luminescence signal of the luminescence probe, detected at about 5 minutes, about 10 minutes, about 15 minutes, about 20 minutes, about 25 minutes, or about 30 minutes following the contact of the sample with the compounds, may be positively correlated with the total concentration of carbapenemases, the total population of bacteria with carbapenem resistance, or both.

The disclosed methods may include an additional step before step (a)—lysing the sample to release carbapenemases from the bacteria.

The disclosed methods may also include another additional step before, during, or after step (a)—contacting the sample with one or more additional compounds that can trigger colorimetric change, luminescence change, or both, of the chemical probe of D after D is released. In some embodiments, the one or more additional compounds may be or include an enzyme. Exemplary enzymes include peroxidase, such as horseradish peroxidase, luciferase, or beta-galactosidase. These enzymes may catalyze chemical modifications on the chemical probe of D after D is released, thereby generating colorimetric change, bioluminescence, or fluorescence.

Traditional diagnosis methods for microbial carbapenemase producing bacteria, such as the Hodge Test and carbapenem inactivation method (mCIM), are usually time-consuming and require processes of in vitro bacterial culturing. Detection of microbial carbapenem resistance using the disclosed compounds and methods can be performed without any additional bacterial culturing processes, thereby minimizing the time required to obtain the diagnosis results. CarbaNP is to date the only CLSI recommended colorimetric test for carbapenemases. However, it still required 2 hour incubation. Moreover, it suffered from poor sensitivity towards OXA-48 like carbapenemase. The sensitivity could be as low as 11%, making it to be not recommended to use routinely (CLSI M100 Ed29).

By incubating one or more of the disclosed compounds containing a colorimetric or luminescence probe, such as a fluorescence probe, with a patient sample containing bacteria, such as a sputum sample, only bacteria with carbapenem resistance will show a luminescence signal. The luminescence signal can be detected by eye via light irradiation, by fluorescence spectrometer or fluorescence imaging under a fluorescence microscope. Methods of detecting bacteria at a single cell level via fluorescence imaging are reported in Kamariza et al., *Science Translational Medicine,* 2018, 10, eaam6310 and Cheng et al., *Science Translational Medicine,* 2018, 10, eaam4470. These fluorescence imaging methods can be adapted for the detection of carbapenem resistance using the disclosed compounds.

In some embodiments, detection of microbial carbapenem resistance using the disclosed compounds can be performed on a microfluidic chip or apparatus, thereby allow for rapid diagnosis with a small sample volume.

2. Evaluating the Efficacy of Carbapenemase Inhibitors

Disclosed are methods to test the efficacy of carbapenemase inhibitors. The methods include (a) contacting a solution or suspension comprising an isolated carbapenemase, a bacterial cell lysate, one or more populations of bacteria, or combinations thereof, with one of more of the disclosed compounds in the absence of any carbapenemase inhibitor and, separately, in the presence of a carbapenemase inhibitor; and (b) detecting the release of D from the compounds. The magnitude of the difference in the release of D detected in the absence of the carbapenemase inhibitor and in the presence of the carbapenemase inhibitor within the same time frame indicates the efficacy of the carbapenemase inhibitor.

In certain embodiments, the compounds and the carbapenemase inhibitor are simultaneously added to the solution or suspension. Optionally, the compounds and the carbapenemase inhibitor are mixed together before being simultaneously added to the solution or suspension.

In certain embodiments, the compound is added after the addition of the carbapenemase inhibitor to the solution or suspension.

In certain embodiments, the carbapenemase inhibitor is added after the addition of the compound to the solution or suspension.

The disclosed methods may include an additional step before, during, or after step (a)—adding one or more additional compounds that can trigger colorimetric change, luminescence change, or both, of the chemical probe of D after D is released. In some embodiments, the one or more additional compounds may be or include an enzyme.

Exemplary enzymes include peroxidase, such as horseradish peroxidase, luciferase, or beta-galactosidase. These enzymes may catalyze chemical modifications on the chemical probe of D after D is released, thereby generating colorimetric change, bioluminescence, or fluorescence.

3. Combinational Uses

The disclosed methods also include combinational use of multiple compounds having the structure of Formula Ia, Ib, Ic, Id or Ie, or salts thereof. The compounds may be combined to form mixtures or compositions as described previously.

The compounds in the mixtures or compositions may have different specificity towards different carbapenemases, allowing for the coverage of a wide range of carbapenemases. In some embodiments, the compounds in the mixtures or combinations may contain different chemical probes so that each class or sub-class of carbapenemases can be selectively recognized or detected.

EXAMPLES

Example 1. Preparation of (E)-7-((3-methoxy-4-((3-(4,4,5,5-tetramethyl-1,3,2-dioxaborolan-2-yl)allyl)oxy)benzyl)oxy)-3H-phenoxazin-3-one (6)

Overall Synthesis Scheme:

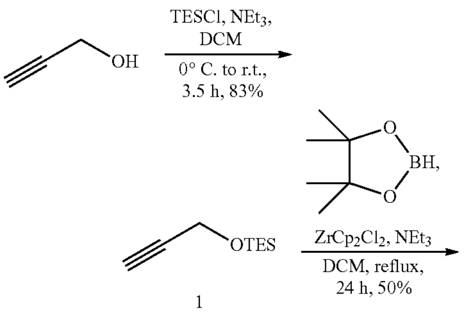

1

-continued

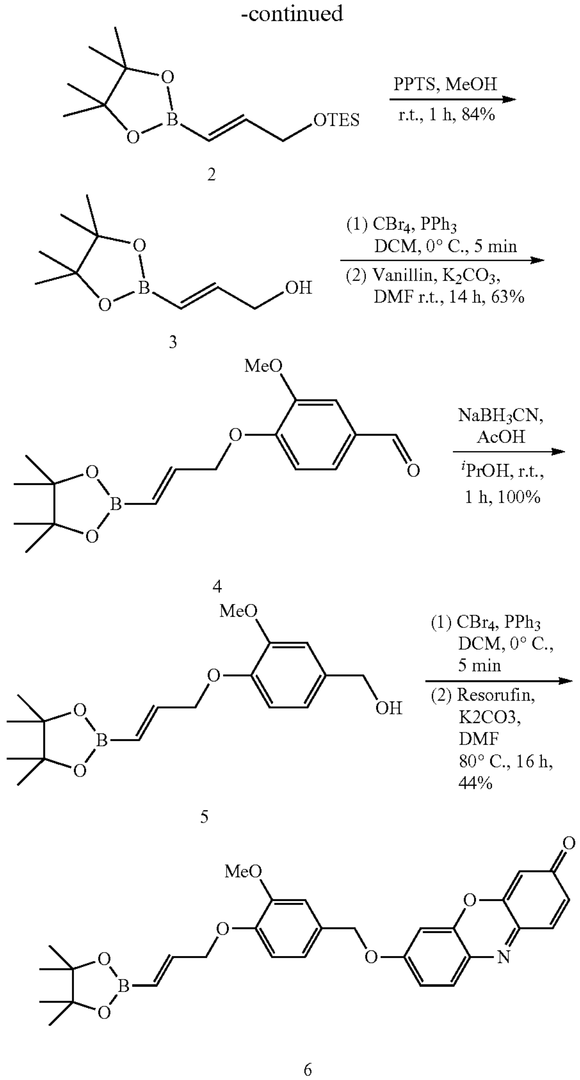

Step 1:

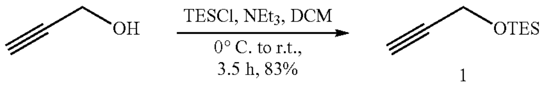

To a round bottom flask were added propargyl alcohol (1.00 g, 17.8 mmol) and DCM (20 mL). $NEt_3$ (3.34 mL, 35.7 mmol) and TESCl (4.50 mL, 26.7 mmol) were then added at 0° C. The resulting reaction mixture was warmed up to room temperature and stirred for 3.5 h. When TLC indicated that the reaction was complete, the reaction was quenched with water (10 mL). The mixture was partitioned with DCM (80 mL) and then washed with brine (10 mL). The aqueous layer was further extracted with DCM (3×10 mL). The combined organic extract was dried over anhydrous sodium sulphate, filtered, and concentrated in vacuo. The crude product was purified by flash column chromatography with pentane to afford 1 (2.52 g, 83%) in a mixture of pentane (0.63 g) and $TES_2O$ (0.81 g) as a volatile colorless liquid (Total 3.96 g). All weights and yield were estimated according to NMR integration. Analytical TLC (100% n-pentane), $R_f$=0.3; $^1$H NMR (300 MHz, $CDCl_3$) δ 4.31 (d, J=2.4 Hz, 2H), 2.39 (t, J=2.4 Hz, 1H), 1.00 (t, J=8.0 Hz, 9H), 0.66 (q, J=8.0 Hz, 6H). The characterization data are consistent with the reported data (*Chem Ber,* 1995, 128, 1267).

Step 2:

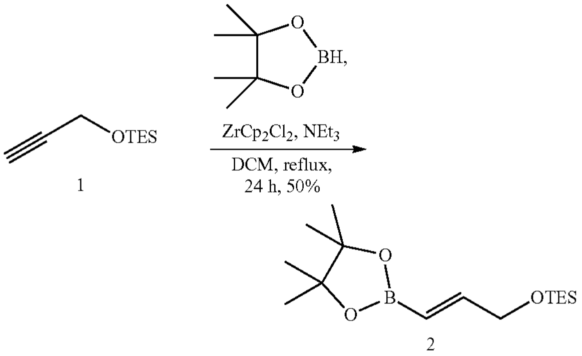

To a round bottom flask were added TES-protected propargyl alcohol 1 (1.00 g, 5.87 mmol) and DCM (20 mL). Pinacolborane (1.70 mL, 11.7 mmol), $ZrCp_2Cl_2$ (0.340 g, 0.587 mmol), and $NEt_3$ (0.11 mL, 0.587 mmol) were then added. The resulting mixture was stirred under reflux for 24 h. When TLC indicated that the reaction was complete, the reaction was quenched with water (10 mL). The mixture was partitioned with DCM (80 mL) and then washed with brine (10 mL). The aqueous layer was further extracted with DCM (3×10 mL). The combined organic extract was dried over anhydrous sodium sulphate, filtered, and concentrated in vacuo. The crude product was purified by flash column chromatography to afford 2 (0.430 g, 50%) as a colorless liquid.

Analytical TLC (20% EtOAc in n-hexane), $R_f$=0.7; $^1$H NMR (300 MHz, $CDCl_3$) δ 6.68 (dt, J=18.0, 3.7 Hz, 1H), 5.76 (dt, J=18.0, 2.0 Hz, 1H), 4.24 (dd, J=3.7, 2.1 Hz, 2H), 1.27 (s, 12H), 0.95 (t, J=7.7 Hz, 9H), 0.61 (q, J=7.9 Hz, 6H). The characterization data are consistent with the reported data (*J. Am. Chem. Soc.,* 2008, 130, 16864).

Step 3:

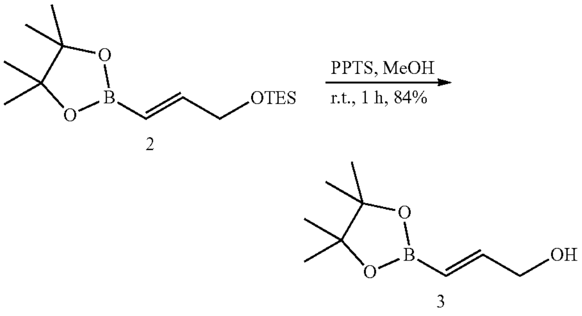

To a round bottom flask were added TES-protected alcohol 2 (0.842 g, 2.83 mmol) and MeOH (8 mL). PPTS (70.9 mg, 0.283 mmol) was then added. The resulting mixture was stirred at room temperature for 1 h. When TLC indicated that the reaction was complete, the reaction was quenched with water (10 mL). The mixture was partitioned with ethyl acetate (30 mL) and then washed with brine (10 mL). The aqueous layer was further extracted with ethyl acetate (3×10 mL). The combined organic extract was dried over anhydrous sodium sulphate, filtered, and concentrated in vacuo. The crude product was purified by flash column chromatography to afford 3 (439 mg, 84%) as a colorless liquid.

Analytical TLC (50% EtOAc in n-hexane), $R_f$=0.6; $^1H$ NMR (400 MHz, $CDCl_3$) δ 6.73 (d, J=18.1 Hz, 1H), 5.70 (d, J=18.2 Hz, 1H), 4.22 (br s, 2H), 2.30 (br s, 1H), 1.27 (s, 12H). The characterization data are consistent with the reported data (*Chem Eur J,* 2011, 17, 6469).

Step 4:

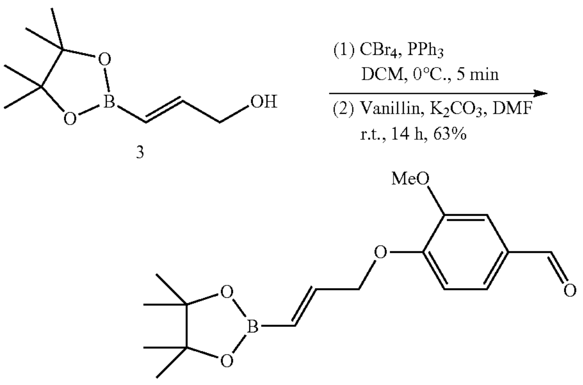

3

4

To a round bottom flask were added alcohol 3 (2.00 g, 10.9 mmol), DCM (25 mL), and $PPh_3$ (5.13 g, 19.6 mmol) at 0° C. $CBr_4$ (6.50 g, 19.6 mmol) was then added. The reaction mixture was stirred at 0° C. for 5 min. When TLC indicated that the reaction was complete, water (5 mL) was added. The mixture was partitioned with ethyl acetate (15 mL) and then washed with brine (5 mL). The aqueous layer was further extracted with ethyl acetate (3×5 mL). The combined organic extract was dried over anhydrous sodium sulphate, filtered, and concentrated in vacuo. The crude product was quickly purified by flash column chromatography to afford the bromide intermediate.

To a round bottom flask were added anhydrous DMF (10 mL) and the semi-purified bromide. Vanillin (3.31 g, 21.7 mmol) and $K_2CO_3$ (3.00 g, 21.7 mmol) were then added. The reaction mixture was stirred at room temperature for 14 h. When TLC indicated that the reaction was complete, the reaction was quenched with water (30 mL). The mixture was partitioned with ethyl acetate (90 mL) and then washed with brine (30 mL). The aqueous layer was further extracted with ethyl acetate (3×30 mL). The combined organic extract was dried over anhydrous sodium sulphate, filtered, and concentrated in vacuo. The crude product was purified by flash column chromatography to afford 4 (2.19 g, 63%) as a colorless oil.

Analytical TLC (40% ethyl acetate in n-hexane), $R_f$=0.5; $^1H$ NMR (300 MHz, $CDCl_3$) δ 9.84 (s, 1H), 7.42-7.29 (m, 2H), 6.93 (d, J=8.6 Hz, 1H), 6.76 (dt, J=18.2, 4.4 Hz, 1H), 5.82 (dt, J=18.2, 1.6 Hz, 1H), 4.79 (dd, J=4.4, 1.6 Hz, 2H), 3.98 (s, 3H), 1.27 (s, 12H); $^{13}C$ NMR (75 MHz, $CDCl_3$) δ 190.9, 153.3, 149.8, 145.7, 130.2, 126.6, 111.8, 109.3, 83.5, 70.1, 56.0, 24.7; HRMS (ESI) calcd. for $C_{17}H_{23}{}^{11}BO_5Na$ ($[M+Na]^+$) 341.1534, found 341.1514.

The $^{13}C$ NMR signal corresponding to the carbon directly attached to the boron atom was not reported due to quadrupolar broadening.

Step 5:

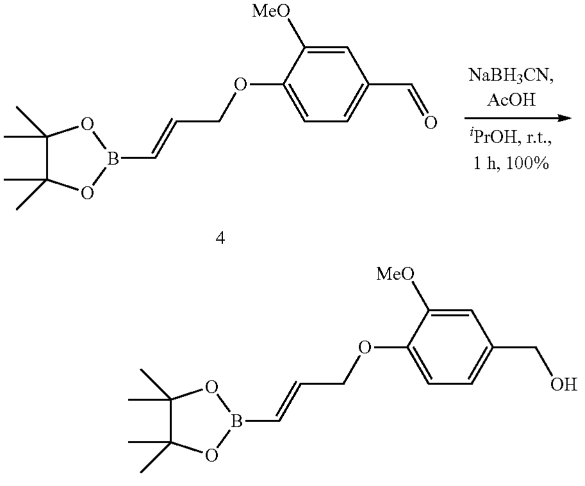

4

5

To a round bottom flask were added aldehyde 4 (1.85 g, 5.80 mmol), $^i$PrOH (20 mL), AcOH (1.66 mL, 29.0 mmol), and $NaBH_3CN$ (0.474 g, 7.54 mmol) at room temperature and the reaction mixture was stirred for 1 h. When TLC indicated that the reaction was complete, the reaction was quenched with water (5 mL). The mixture was partitioned with ethyl acetate (15 mL) and then washed with brine (5 mL). The aqueous layer was further extracted with ethyl acetate (3×5 mL). The combined organic extract was dried over anhydrous sodium sulphate, filtered, and concentrated in vacuo. The crude product was purified by flash column chromatography to afford 5 (1.93 g, 100%) as a colorless oil.

Analytical TLC (50% ethyl acetate in n-hexane), $R_f$=0.2; $^1H$ NMR (400 MHz, $CDCl_3$) δ 6.93 (d, J=1.7 Hz, 1H), 6.88-6.71 (m, 3H), 5.80 (dt, J=18.1, 1.6 Hz, 1H), 4.69 (dd, J=4.5, 1.8 Hz, 2H), 4.62 (d, J=4.0 Hz, 2H), 3.88 (s, 3H), 1.26 (s, 12H); $^{13}C$ NMR (100 MHz, $CDCl_3$) δ 149.4, 147.2, 133.9, 119.2, 113.0, 110.8, 83.3, 70.2, 65.1, 65.0, 55.8, 24.7; HRMS (ESI) calcd. for $C_{17}H_{25}{}^{11}BO_5Na$ ($[M+Na]^+$) 343.1690, found 343.1668.

The OH peak was not observed in $^1H$ NMR due to rapid exchange with signal from residual water. The $^{13}C$ NMR signal corresponding to the carbon directly attached to the boron atom was not reported due to quadrupolar broadening.

Step 6:

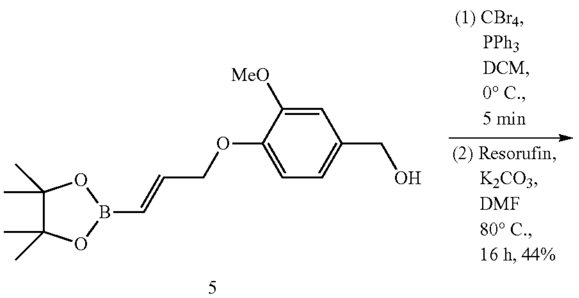

5

-continued

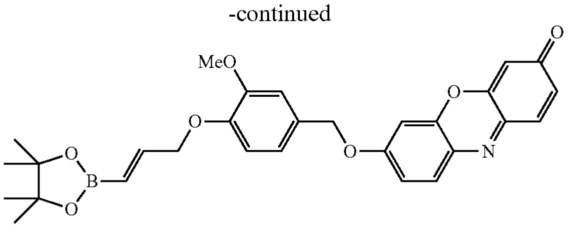

6

To a round bottom flask were added alcohol 5 (140 mg, 0.43 mmol), DCM (2.5 mL), and DMF (68 μL, 0.88 mmol) at 0° C. $SOCl_2$ (57.4.4 μL, 0.79 mmol) was then added and the reaction mixture was stirred for 5 min. When TLC indicated that the reaction was complete, the reaction was quenched with saturated $NaHCO_3$ (2×5 mL). The mixture was partitioned with ethyl acetate (15 mL) and then washed with water (5 mL) and brine (5 mL). The aqueous layer was further extracted with ethyl acetate (3×5 mL). The combined organic extract was dried over anhydrous sodium sulphate, filtered, and concentrated in vacuo. The crude product was semi-purified by flash column chromatography and eluted with 10% ethyl acetate in n-hexane to remove triphenylphosphine oxide.

To a round bottom flask were added the crude product and anhydrous DMF (1.3 mL). Resorufin (186 mg, 0.88 mmol) and $K_2CO_3$ (121 mg, 0.87 mmol) were then added. The reaction mixture was stirred at 80° C. for 16 h. When TLC indicated that the reaction was complete, the reaction mixture was diluted with DCM (50 mL), filtered through a short pad of silica gel to remove unreacted resorufin and $K_2CO_3$, and then concentrated. The crude product was purified by flash column chromatography to afford 6 (99.8 mg, 44%) as an orange solid.

Analytical TLC (50% ethyl acetate in n-hexane), $R_f$=0.5; $^1$H NMR (400 MHz, $CDCl_3$) δ 7.69 (d, J=8.9 Hz, 1H), 7.39 (d, J=9.8 Hz, 1H), 7.00 (dd, J=8.9, 2.6 Hz, 1H), 6.98-6.91 (m, 2H), 6.90-6.72 (m, 4H), 6.29 (d, J=2.0 Hz, 1H), 5.81 (d, J=18.2 Hz, 1H), 5.07 (s, 2H), 4.71 (dd, J=4.3, 1.5 Hz, 2H), 3.89 (s, 3H), 1.26 (s, 12H); $^{13}$C NMR (100 MHz, $CDCl_3$) δ 186.1, 162.6, 149.7, 149.5, 148.2, 146.8, 145.5, 145.4, 134.6, 134.0, 131.5, 128.3, 127.9, 120.3, 114.2, 112.9, 111.3, 106.6, 100.9, 83.3, 70.9, 70.1, 55.9, 24.7; LRMS (ESI) 516.3 ($[M+H]^+$); HRMS (ESI) calcd. for $C_{29}H_{31}O_7{}^{11}BN$ ($[M+H]^+$) 516.2193, found 516.2179.

The $^{13}$C NMR signal corresponding to the carbon directly attached to the boron atom was not reported due to quadrupolar broadening.

Example 2. Preparation of 4-azidobenzyl 2-diazo-3-oxo-4-((2R,3S)-4-oxo-3-((R)-1-((triethylsilyl)oxy)ethyl)azetidin-2-yl)butanoate (12)

Overall Synthesis Scheme:

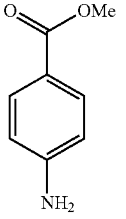

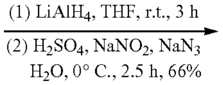

-continued

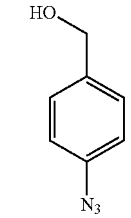

7

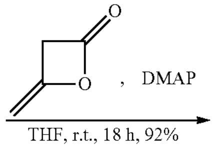

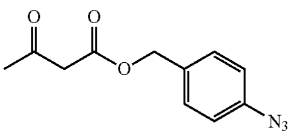

8

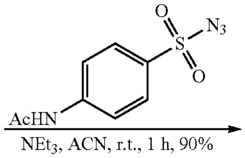

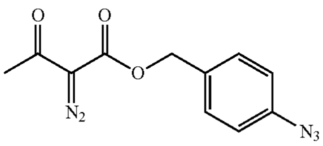

9

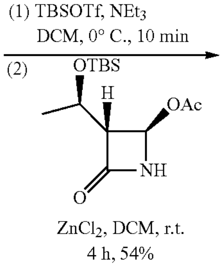

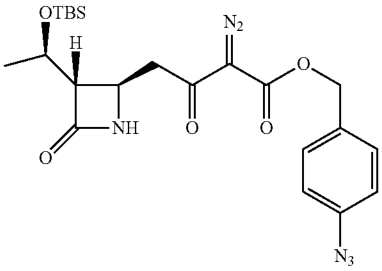

10

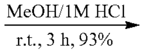

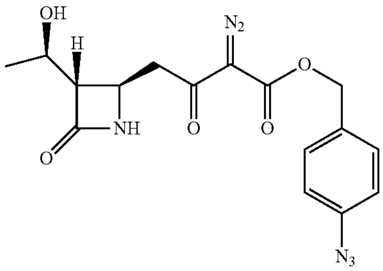

11

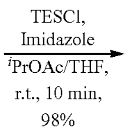

-continued

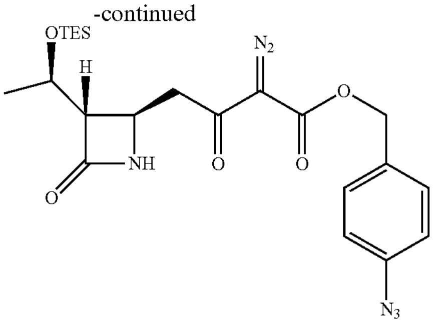

12

Step 1:

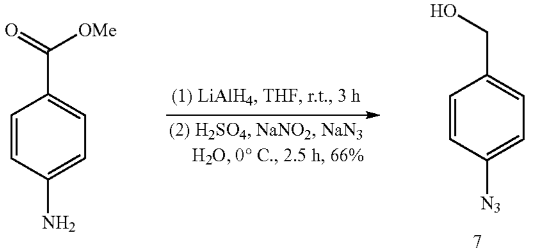 [SMILES: COC(=O)c1ccc(N)cc1 ; [N-]=[N+]=Nc1ccc(CO)cc1]

7

To a round bottom flask were added $LiAlH_4$ (0.760 g, 19.9 mmol) and THF (40 mL). Methyl 4-aminobenzoate (2.00 g, 13.3 mmol) was dissolved in THF (5 mL) and the resulting solution was added dropwise to the $LiAlH_4$ solution at 0° C. The reaction mixture was then warmed up to room temperature and stirred for 3 h. When TLC indicated that the reaction was complete, the reaction was quenched with ethyl acetate (5 mL) and water (5 mL). HCl (3 M aq) was added until pH=7 was achieved. The precipitate was filtered and washed with ethyl acetate. The liquid was combined, concentrated, further diluted with ethyl acetate (90 mL), and then washed with saturated $NaHCO_3$ (30 mL) solution and brine (30 mL). The aqueous layer was further extracted with ethyl acetate (2×30 mL). The combined organic extract was dried over anhydrous sodium sulphate, filtered, and concentrated in vacuo.

The crude alcohol was added to a round bottom flask and dissolved in $H_2SO_4$ (15 mL, 4 M aq) to form a deep red solution. $NaNO_2$ (1.37 g, 19.9 mmol) dissolved in water (10 mL) was added dropwise to the reaction flask at 0° C. The reaction mixture was stirred for 15 min. $NaN_3$ (1.29 g, 19.9 mmol) dissolved in water (10 mL) was added dropwise to the reaction mixture at 0° C. with evolution of gas bubbles. The final reaction mixture was then stirred at 0° C. for 2.5 h. When TLC indicated that the reaction was complete, the reaction mixture was partitioned with water (30 mL). The mixture was further diluted with ethyl acetate (90 mL) and then washed with saturated $NaHCO_3$ solution (30 mL) and brine (30 mL). The aqueous layer was further extracted with ethyl acetate (2×30 mL). The combined organic extract was dried over anhydrous sodium sulphate, filtered, and concentrated in vacuo. The crude product was purified by flash column chromatography to afford 7 (1.30 g, 66%) as a brown oil.

Analytical TLC (40% ethyl acetate in n-hexane), $R_f$=0.5; $^1$H NMR (400 MHz, $CDCl_3$) δ 7.35 (d, J=8.7 Hz, 2H), 7.02 (d, J=8.5 Hz, 2H), 4.66 (s, 2H), 1.87 (s, 1H). The characterization data are consistent with the reported data (*J Med Chem,* 2004, 47, 6459)

Step 2:

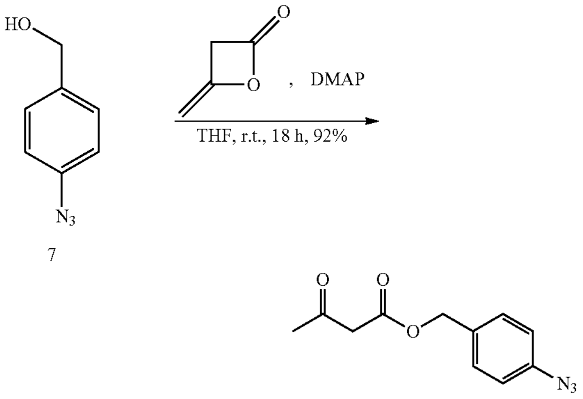

7

8

To a round bottom flask were added alcohol 7 (1.21 g, 8.11 mmol), DMAP (50.0 mg, 0.405 mmol) and THF (15 mL). Diketene (0.75 mL, 9.73 mmol) was added dropwise at room temperature and the reaction mixture was stirred for 18 h. When TLC indicated that the reaction was complete, the reaction was quenched with water (30 mL). The mixture was partitioned with ethyl acetate (90 mL) and then washed with brine (30 mL). The aqueous layer was further extracted with ethyl acetate (2×30 mL). The combined organic extract was dried over anhydrous sodium sulphate, filtered, and concentrated in vacuo. The crude product was purified by flash column chromatography to afford 8 (1.74 g, 92%) as a yellow oil.

Analytical TLC (40% ethyl acetate in n-hexane), $R_f$=0.5; $^1$H NMR (400 MHz, $CDCl_3$) δ 7.43-7.30 (m, 2H), 7.09-6.95 (m, 2H), 5.13 (s, 2H), 3.49 (s, 2H), 2.24 (s, 3H); $^{13}$C NMR (100 MHz, $CDCl_3$) δ 200.1, 166.7, 140.1, 131.9, 129.9, (129.7), 119.0, (119.0), (89.4), 66.3, (64.9), 49.8, 30.0, (21.1); HRMS (ESI) calcd. for $C_{11}H_{11}N_3O_3Na$ ($[M+Na]^+$) 256.0693, found 256.0697.

Note: the NMR spectra show an equilibrium mixture of keto and enol tautomers in a ratio of 95:5. Observable signals corresponding to the minor species are shown in parentheses.

Step 3:

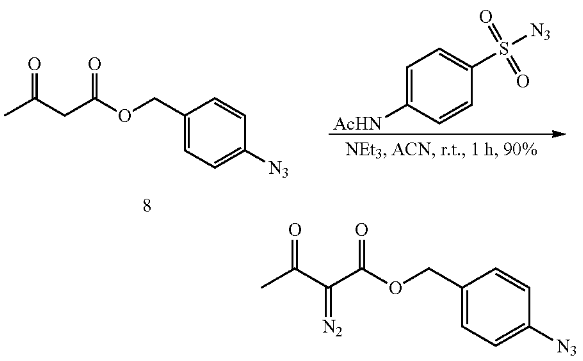

8

9

To a round bottom flask were added β-ketoester 8 (1.71 g, 7.35 mmol) and $CH_3CN$ (15 mL) at 0° C. $NEt_3$ (1.05 mL, 9.56 mmol) and 4-acetamidobenzenesulfonyl azide (1.77 g, 7.35 mmol) were then added slowly. The mixture was then warmed up to room temperature and stirred for 1 h. When TLC indicated that the reaction was complete, the reaction mixture was partitioned with n-hexane:ethyl acetate=1:1 (50 mL). The organic layer was then filtered and concentrated in vacuo. The crude product was purified by flash column chromatography to afford 9 (1.72 g, 90%) as a pale yellow solid, which was slightly light sensitive.

Analytical TLC (40% ethyl acetate in n-hexane), $R_f$=0.7; $^1H$ NMR (300 MHz, $CDCl_3$) δ 7.33 (d, J=8.5 Hz, 2H), 6.99 (d, J=8.5 Hz, 2H), 5.19 (s, 2H), 2.43 (s, 3H); $^{13}C$ NMR (75 MHz, $CDCl_3$) δ 189.6, 161.0, 140.3, 131.7, 130.0, 119.1, 66.2, 28.0; HRMS (ESI) calcd. for $C_{11}H_{10}N_5O_3$ ($[M+H]^+$) 260.0778, found 260.0784.

The $^{13}C$ NMR signal corresponding to the diazo carbon was not observed.

Step 4:

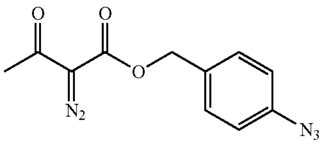

9

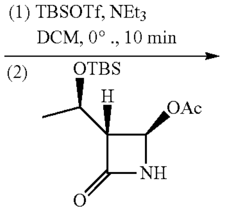

ZnCl2, DCM, r.t.
4 h, 54%

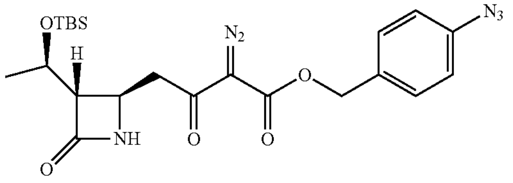

10

To a round bottom flask were added β-ketoester 9 (4.70 g, 18.1 mmol) and DCM (50 mL) at 0° C. $NEt_3$ (5.10 mL, 54.3 mmol) and TBSOTf (6.33 mL, 27.2 mmol) were then added slowly. The mixture was stirred for 10 min at 0° C. The reaction was quenched with water (30 mL). The mixture was partitioned with ethyl acetate (90 mL) and then washed with brine (30 mL). The aqueous layer was further extracted with ethyl acetate (2×30 mL). The combined organic extract was dried over anhydrous sodium sulphate, filtered, and concentrated in vacuo. Chloroform (30 mL) was added and insoluble suspension was filtered, and the filtrate was concentrated in vacuo.

The azetidinone (4.01 g, 14.0 mmol) was dissolved in DCM (50 mL) at 0° C. Freshly fused $ZnCl_2$ (0.953 g, 6.97 mmol) was added and the resulting mixture was stirred for 30 min. Crude silylenol ether in DCM (10 mL) was added dropwise over 20 min, and the reaction mixture was stirred at room temperature for 4 h. The reaction was then quenched with water (30 mL). The final mixture was partitioned with ethyl acetate (90 mL) and then washed with brine (30 mL). The aqueous layer was further extracted with ethyl acetate (2×30 mL). The combined organic extract was dried over anhydrous sodium sulphate, filtered, and concentrated in vacuo. The crude product was purified by flash column chromatography to afford 10 (4.70 g, 54%) as a pale yellow oil.

Analytical TLC (40% ethyl acetate in n-hexane), $R_f$=0.4; $^1H$ NMR (400 MHz, $CDCl_3$) δ 7.33 (dd, J=8.4, 1.9 Hz, 2H), 7.00 (dd, J=8.4, 2.5 Hz, 2H), 6.28 (d, J=11.4 Hz, 1H), 5.19 (s, 2H), 4.18-4.14 (m, 1H), 4.02-3.88 (m, 1H), 3.34 (dd, J=17.7, 3.1 Hz, 1H), 2.96 (dd, J=17.7, 9.8 Hz, 1H), 2.81 (dd, J=4.6, 2.1 Hz, 1H), 1.17 (d, J=6.2 Hz, 3H), 0.83 (s, 9H), 0.03 (s, 3H), 0.02 (s, 3H); $^{13}C$ NMR (100 MHz, $CDCl_3$) δ 190.2, 168.0, 160.8, 140.5, 131.5, 130.1, 119.2, 76.0, 66.4, 65.3, 63.7, 46.2, 45.2, 25.6, 22.4, 17.8, −4.4, −5.1; LRMS (ESI) 486.6 ($[M+H]^+$); HRMS (ESI) calcd. for $C_{22}H_{31}N_6O_5Si$ ($[M+H]^+$) 487.2120, found 487.2129.

Step 5:

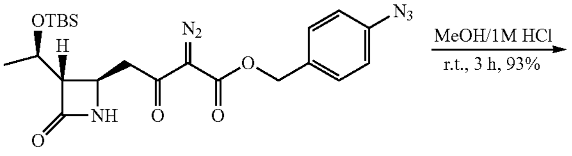

10

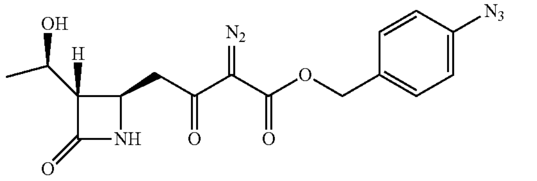

11

To a round bottom flask were added azetidinone 10 (1.11 g, 2.29 mmol) and MeOH (9 mL). HCl (3 mL, 1 M aq). The mixture was stirred at room temperature for 3 h. When TLC indicated that the reaction was complete, the reaction was quenched with water (30 mL). The mixture was partitioned with ethyl acetate (90 mL) and then washed with a saturated $NaHCO_3$ solution (30 mL) and brine (30 mL). The aqueous layer was further extracted with ethyl acetate (3×30 mL). The combined organic extract was dried over anhydrous sodium sulphate, filtered, and concentrated in vacuo. The crude product was purified by flash column chromatography to afford 11 (793 mg, 93%) as a yellow liquid.

Analytical TLC (80% ethyl acetate in n-hexane), $R_f$=0.3; $^1H$ NMR (300 MHz, $CDCl_3$) δ 7.37 (d, J=8.4 Hz, 2H), 7.03 (d, J=8.4 Hz, 2H), 6.75 (br s, 1H), 5.23 (s, 2H), 4.23-4.04 (m, 1H), 3.97 (dt, J=6.5, 5.7 Hz, 1H), 3.63 (br s, 1H), 3.31 (dd, J=18.2, 5.7 Hz, 1H), 3.18 (dd, J=18.2, 7.6 Hz, 1H), 2.86 (dd, J=6.7, 1.7 Hz, 1H), 1.28 (d, J=6.2 Hz, 3H); $^{13}C$ NMR (75 MHz, $CDCl_3$) δ 190.7, 168.2, 160.7, 140.5, 131.4, 130.1, 119.2, 76.2, 66.5, 65.3, 63.9, 47.3, 45.1, 21.1; LRMS (ESI) 373.4 ($[M+H]^+$); HRMS (ESI) calcd. for $C_{16}H_{17}N_6O_5$ ($[M+H]^+$) 373.1255, found 373.1263.

Step 6:

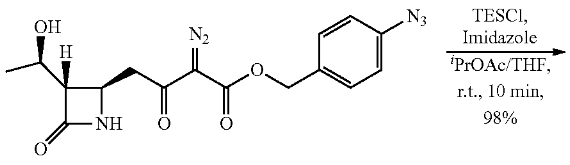

11

-continued

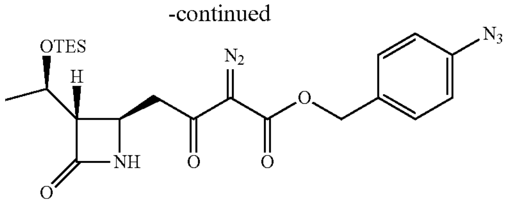

12

To a round bottom flask were added azetidinone 11 (786 mg, 2.11 mmol), $^{i}$PrOAc (6 mL), and THF (1.5 mL). Imidazole (258 mg, 3.80 mmol) and TESCl (0.500 mL, 2.96 mmol) were added at room temperature and the reaction mixture was stirred for 10 min. The reaction was quenched with water (15 mL). The mixture was partitioned with ethyl acetate (60 mL) and then washed with brine (15 mL). The aqueous layer was further extracted with ethyl acetate (2×15 mL). The combined organic extract was dried over anhydrous sodium sulphate, filtered, and concentrated in vacuo. The crude product was purified by flash column chromatography to afford 12 (1.01 g, 98%) as a colorless oil.

Analytical TLC (80% ethyl acetate in n-hexane), $R_f$=0.7; $^{1}$H NMR (400 MHz, $CDCl_3$) δ 7.37 (dd, J=8.3, 1.4 Hz, 2H), 7.04 (dd, J=8.5, 2.0 Hz, 2H), 6.30 (s, 1H), 5.24 (s, 2H), 4.19 (dq, J=6.1, 5.6 Hz, 1H), 4.00 (dd, J=9.2, 2.1 Hz, 1H), 3.38 (d, J=17.6 Hz, 1H), 3.00 (dd, J=17.8, 9.8 Hz, 1H), 2.85 (dd, J=5.3, 2.3 Hz, 1H), 1.23 (d, J=6.2 Hz, 3H), 0.95 (t, J=7.9 Hz, 9H), 0.60 (q, J=8.1 Hz, 6H); $^{13}$C NMR (100 MHz, $CDCl_3$) δ 190.3, 167.9, 160.8, 140.6, 131.5, 130.1, 119.2, 76.0, 66.4, 65.5, 63.8, 46.5, 45.3, 22.5, 6.7, 4.8; HRMS (ESI) calcd. for $C_{22}H_{31}N_6O_5Si$ ($[M+H]^+$) 487.2120, found 487.2131.

Example 3. Preparation of (5R,6S)-6-((R)-1-hydroxyethyl)-3-((E)-3-(2-methoxy-4-(((3-oxo-3H-phenoxazin-7-yl)oxy)methyl)phenoxy)prop-1-en-1-yl)-7-oxo-1-azabicyclo[3.2.0]hept-2-ene-2-carboxylic acid (MCW-001)

Overall Synthesis Scheme:

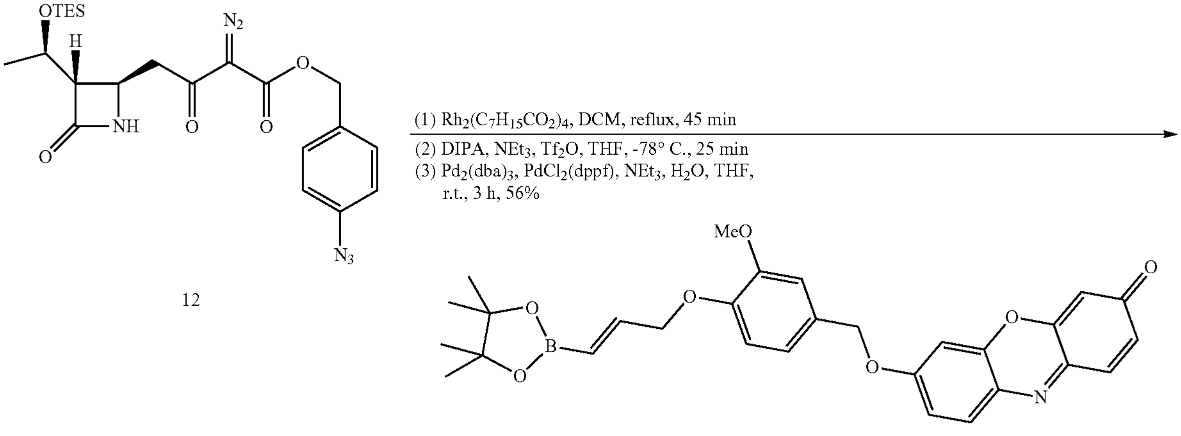

12

6

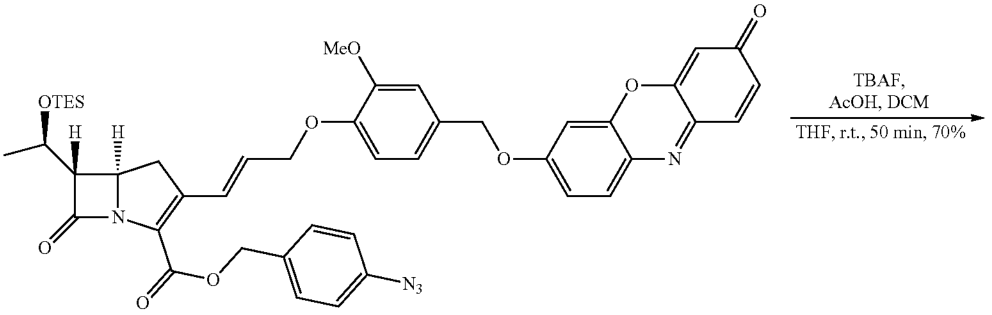

13

-continued
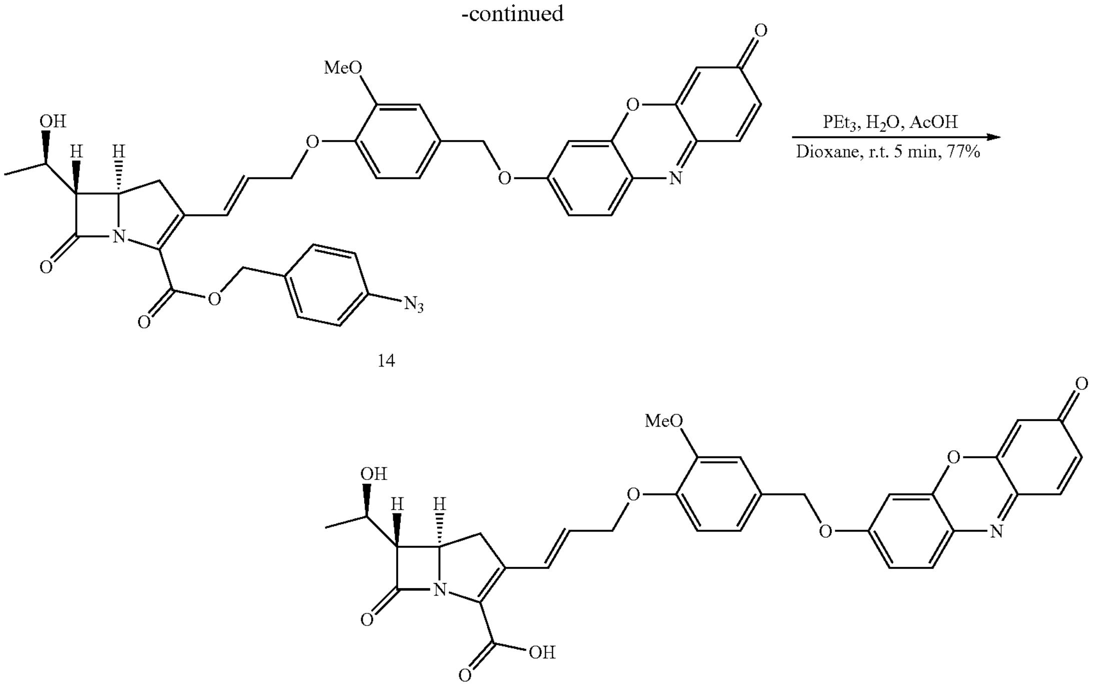
14
MCW-001
Step 1:
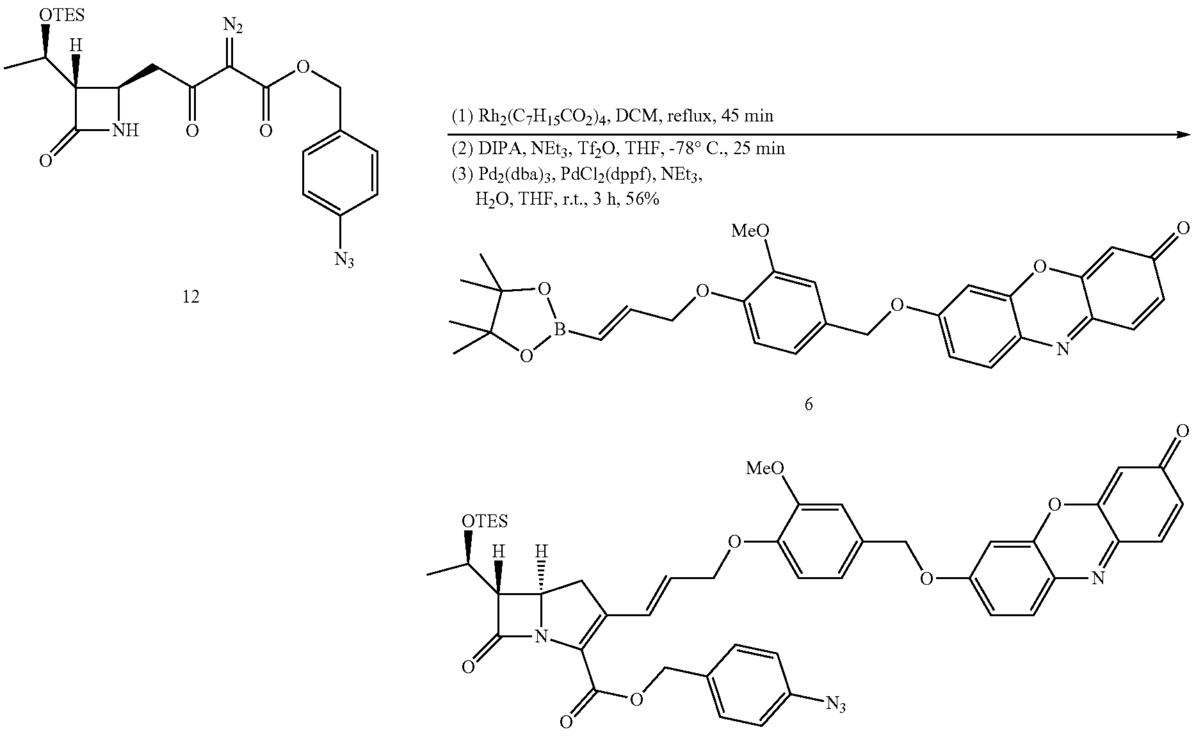
12
6
13
To a round bottom flask were added TES protected azetidinone 12 (105 mg, 0.216 mmol) and DCM (1.5 mL). $Rh_2(C_7H_{15}CO_2)_4$ (0.8 mg, 1 μmol) was then added and the reaction mixture was stirred under reflux for 45 min. When TLC indicated that the reaction was complete, the reaction mixture was concentrated and used directly for next step. To a round bottom flask were added the crude ketone and THF (1.2 mL) at −78° C. DIPA (40 μL, 0.28 mmol) and $NEt_3$ (8.0 μL, 86 μmol) were then added dropwise and the resulting solution was stirred for 10 min. $Tf_2O$ (47 μL, 0.28 mmol) was then added dropwise and the resulting mixture was stirred at −78° C. for 15 min. When TLC indicated that the reaction was complete, $NEt_3$ (52 μL, 0.57 mmol), $H_2O$ (10 μL, 0.56 mmol), boronic ester 6 (71.6 mg, 0.139 mmol), $Pd_2(dba)_3$ (9.5 mg, 10 μmol) and $PdCl_2dppf$ (7.6 mg, 10 μmol) were added. The resulting solution was warmed up to room temperature and stirred for 3 h. When TLC indicated that the reaction was complete, the reaction was quenched with water (5 mL). The mixture was partitioned with ethyl acetate (15 mL) and then washed with brine (5 mL). The aqueous layer was further extracted with ethyl acetate (3×5 mL). The combined organic extract was dried over anhydrous sodium sulphate, filtered, and concentrated in vacuo. The crude product was purified by flash column chromatography to afford 13 (64.1 mg, 56%) as an orange solid, which was inseparable from boronic ester 2.456 (12.9 mg). All weights and yield were estimated according to NMR integration.

Analytical TLC (40% ethyl acetate in n-hexane), $R_f$=0.2; HRMS (ESI) calcd. for $C_{45}H_{48}N_5O_9Si$ ([M+H]$^+$) 830.3216, found 830.3183.

Step 2:

To a round bottom flask were added β-lactam 13 (64.1 mg, 77.2 μmol), THF (1.2 mL), and DCM (0.7 mL). AcOH (44.2 μL, 722 μmol) and TBAF (772 μL, 722 μmol, 1 M in THF) were added at room temperature and the reaction mixture was stirred for 50 min. When TLC indicated that the reaction was complete, the reaction was quenched with water (5 mL). The mixture was partitioned with ethyl acetate (15 mL) and then washed with brine (5 mL). The aqueous layer was further extracted with ethyl acetate (2×5 mL). The combined organic extract was dried over anhydrous sodium sulphate, filtered, and concentrated in vacuo. The crude product was purified by flash column chromatography to afford 14 (38.7 mg, 70%) as an orange solid.

Analytical TLC (80% ethyl acetate in n-hexane), $R_f$=0.3; $^1$H NMR (600 MHz, 10% $CD_3OD$ in $CDCl_3$) δ 7.77 (d, J=8.9 Hz, 1H), 7.50 (d, J=9.7 Hz, 1H), 7.49-7.41 (m, 3H), 7.08 (dd, J=8.9, 2.6 Hz, 1H), 7.01 (dd, J=9.3, 3.3 Hz, 4H), 6.97 (d, J=2.5 Hz, 1H), 6.91 (d, J=8.0 Hz, 1H), 6.88 (dd, J=9.8, 2.0 Hz, 1H), 6.38 (d, J=2.0 Hz, 1H), 6.13 (dt, J=16.0, 5.9 Hz, 1H), 5.31 (d, J=12.5 Hz, 1H), 5.21 (d, J=12.5 Hz, 1H), 5.14 (s, 2H), 4.75 (d, J=5.8 Hz, 2H), 4.24-4.11 (m, 2H), 3.91 (s, 3H), 3.19-3.10 (m, 2H), 3.03 (dd, J=17.8, 8.6 Hz, 1H), 1.32 (d, J=6.3 Hz, 3H); $^{13}$C NMR (150 MHz, $CDCl_3$) δ 187.1, 176.7, 163.3, 161.2, 150.4, 149.8, 148.1, 145.9, 145.2, 143.1, 140.1, 135.1, 134.0, 133.3, 132.3, 131.8, 129.9, 128.7, 128.6, 127.8, 126.1, 120.7, 119.2, 115.0, 113.5, 111.5, 106.5, 101.1, 71.1, 69.6, 66.6, 66.5, 65.4, 56.1, 53.0, 36.9, 21.5; LRMS (ESI) 716.2 ([M+H]$^+$); HRMS (ESI) calcd. for $C_{39}H_{34}N_5O_9$ ([M+H]$^+$) 716.2351, found 716.2331.

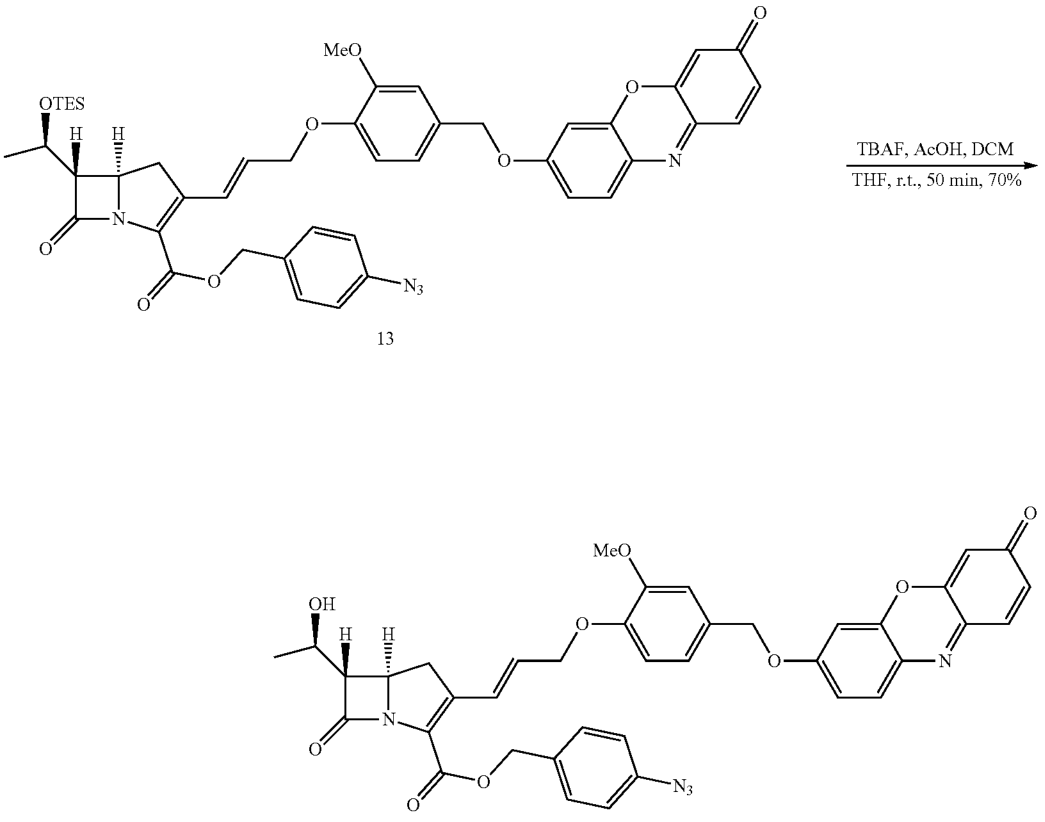

13

14

Step 3:

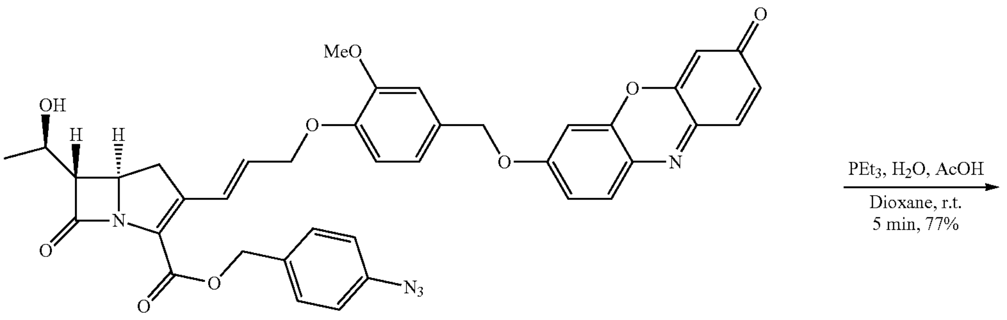

14

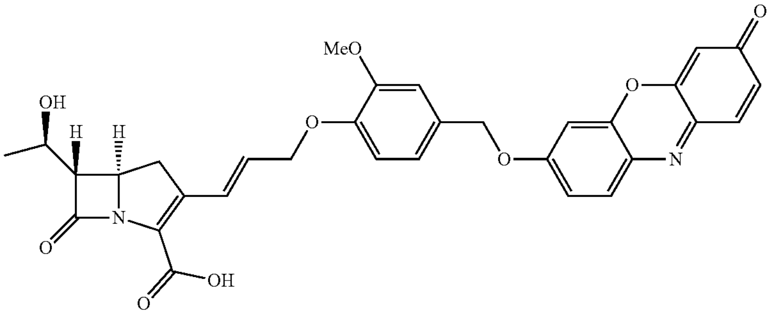

MCW-001

To a round bottom flask were added β-lactam 14 (4.0 mg, 5.6 μmol), dioxane (0.4 mL), and $H_2O$ (40 μL). AcOH (4 μL) and $PEt_3$ (13.1 μL, 7.3 μmol, 10% in n-hexane) were added at room temperature and the reaction mixture was stirred for 5 min. The crude mixture was subjected to preparative C18 reverse phase HPLC purification using 0.01% TFA in water and $CH_3CN$ as eluent, and used directly for fluorescence assay. Alternatively, the eluent was partitioned between PBS pH 7.4 buffer (2 mL), DCM (50 mL) with AcOH (50 μL). The organic extract was concentrated to afford MCW-001 (2.5 mg, 77%) as a red solid.

$^1H$ NMR (500 MHz, 5% $CD_3OD$ in $CDCl_3$) δ 7.73 (d, J=8.9 Hz, 1H), 7.48 (d, J=15.9 Hz, 1H), 7.44 (d, J=9.9 Hz, 1H), 7.03 (dd, J=9.0, 2.6 Hz, 1H), 7.00-6.87 (m, 5H), 6.85 (dd, J=9.8, 2.1 Hz, 1H), 6.34 (d, J=2.1 Hz, 1H), 6.08 (dt, J=16.1, 6.1 Hz, 1H), 5.11 (s, 2H), 4.76 (d, J=5.5 Hz, 2H), 4.27-4.12 (m, 2H), 3.90 (s, 3H), 3.18 (dd, J=6.4, 2.8 Hz, 1H), 3.12 (dd, J=17.6, 10.0 Hz, 1H), 3.01 (dd, J=17.6, 8.6 Hz, 1H), 1.33 (d, J=6.3 Hz, 3H). LRMS (ESI) 585.3 ($[M+H]^+$); HRMS (ESI) calcd. for $C_{32}H_{29}N_2O_9$ ($[M+H]^+$) 585.1868, found 585.1860.

Example 4. Preparation of (5R,6S)-3-((E)-3-(2-methoxy-4-(((3-oxo-3H-phenoxazin-7-yl)oxy)methyl)phenoxy)prop-1-en-1-yl)-7-oxo-6-((R)-1-((triethylsilyl)oxy)ethyl)-1-azabicyclo[3.2.0]hept-2-ene-2-carboxylic acid (MCW-002)

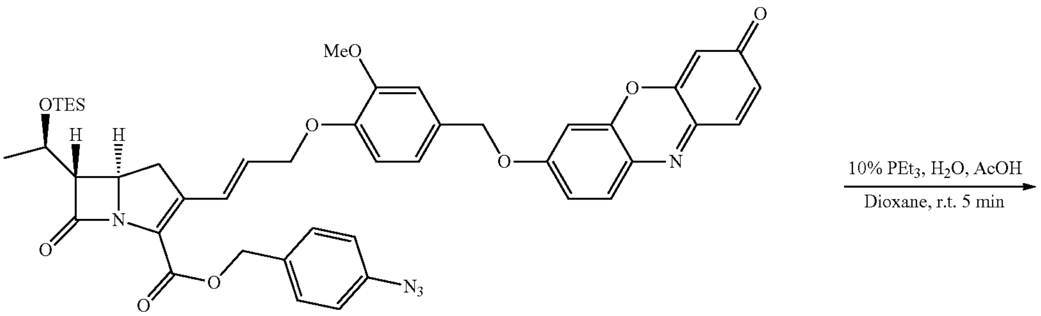

13

-continued

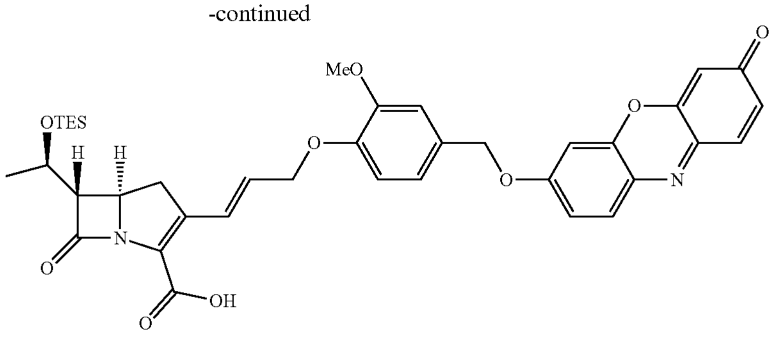

MCW-002

To a 10 mL round bottom flask were added β-lactam 13 (4.0 mg, 5.6 μmol), dioxane (0.2 mL), and $H_2O$ (20 μL). AcOH (2 μL) and $PEt_3$ (13.1 μL, 7.7 μmol, 10% in n-hexane) were added at room temperature and the reaction mixture was stirred for 5 minutes. The crude mixture was subjected to preparative C18 reverse phase HPLC purification using 0.01% TFA in water and $CH_3CN$ as eluent, and used directly for fluorescence assay.

To the above freshly purified carboxylic acid was added TMS-diazomethane (1.3 mL, 2.60 mmol, 2 M in hexane). A persistent yellow color was observed upon completion of addition. The reaction was quenched by addition of acetic acid until a colorless solution was observed. The mixture was diluted with chloroform (15 mL) and then washed with brine (5 mL). The aqueous layer was further extracted with chloroform (2x5 mL). The combined organic extract was dried over anhydrous sodium sulphate, filtered, and concentrated in vacuo. The crude product was purified by preparative $C_{18}$ reverse phase HPLC to afford MCW-003 (2.0 mg, 67%) as an orange solid.

Example 5. Preparation of methyl (5R,6S)-6-((R)-1-hydroxyethyl)-3-((E)-3-(2-methoxy-4-(((3-oxo-3H-phenoxazin-7-yl)oxy)methyl)phenoxy)prop-1-en-1-yl)-7-oxo-1-azabicyclo[3.2.0]hept-2-ene-2-carboxylate (MCW-003)

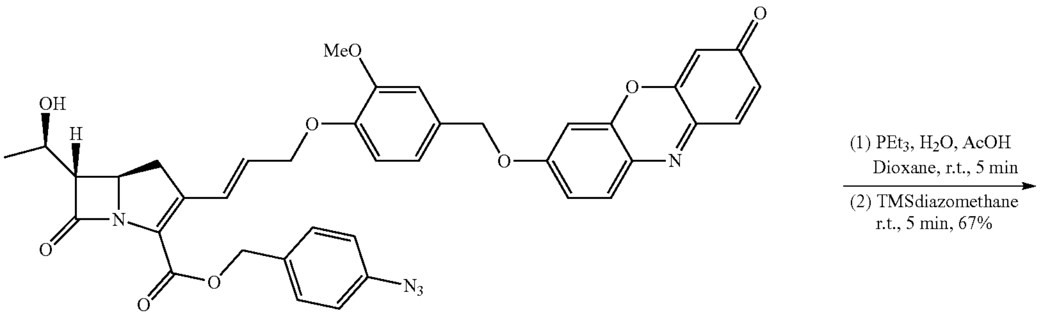

14

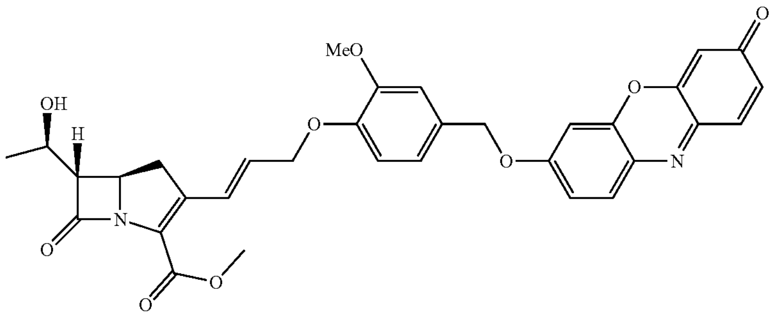

MCW-003

To a round bottom flask were added 14 (4.3 mg, 6.0 μmol), dioxane (0.43 mL), and $H_2O$ (43 μL). AcOH (4.3 μL) and $PEt_3$ (13.1 μL, 16.7 μmol, 10% in n-hexane) were added. The reaction mixture was stirred for 5 min at room temperature, and subjected to preparative C18 reverse phase HPLC purification using 0.01% TFA in water and $CH_3CN$ as eluent.

$^1H$ NMR (500 MHz, $CDCl_3$) δ 7.72 (d, J=8.9 Hz, 1H), 7.48 (d, J=16.1 Hz, 1H), 7.43 (d, J=9.8 Hz, 1H), 7.02 (dd, J=8.9, 2.6 Hz, 1H), 7.00-6.95 (m, 2H), 6.93-6.89 (m, 1H), 6.88 (d, J=2.6 Hz, 1H), 6.84 (dd, J=9.8, 2.0 Hz, 1H), 6.33 (d, J=2.0 Hz, 1H), 6.10 (dt, J=16.0, 6.0 Hz, 1H), 5.11 (s, 2H), 4.77 (d, J=6.0 Hz, 2H), 4.25 (dq, J=7.1, 6.2 Hz, 1H), 4.19 (td, J=9.6, 3.3 Hz, 1H), 3.91 (s, 3H), 3.86 (s, 3H), 3.17 (dd, J=6.8, 2.8 Hz, 1H), 3.12 (dd, J=17.6, 10.0 Hz, 1H), 3.00 (dd, J=17.6, 8.6 Hz, 1H), 1.87 (s, 1H), 1.36 (d, J=6.3 Hz, 3H);

$^{13}C$ NMR (125 MHz, $CDCl_3$) δ 186.3, 175.6, 162.7, 161.6, 149.9 (×2, overlapping), 148.1, 145.7, 145.6, 142.1, 134.7, 134.3, 132.8, 131.6, 128.6, 128.5, 128.1, 126.2, 120.4, 114.3, 113.5, 111.4, 106.8, 101.1, 71.0, 69.5, 66.4, 66.0, 56.1, 52.7, 52.3, 36.8, 21.9; HRMS (ESI) calcd. for $C_{33}H_{31}O_9N_2$ ($[M+H]^+$) 599.2024, found 599.2001.

Example 6. Preparation of (E)-9-(4-methoxy-2-methylphenyl)-6-((3-methoxy-4-((3-(4,4,5,5-tetramethyl-1,3,2-dioxaborolan-2-yl)allyl)oxy)benzyl)oxy)-3H-xanthen-3-one (15)

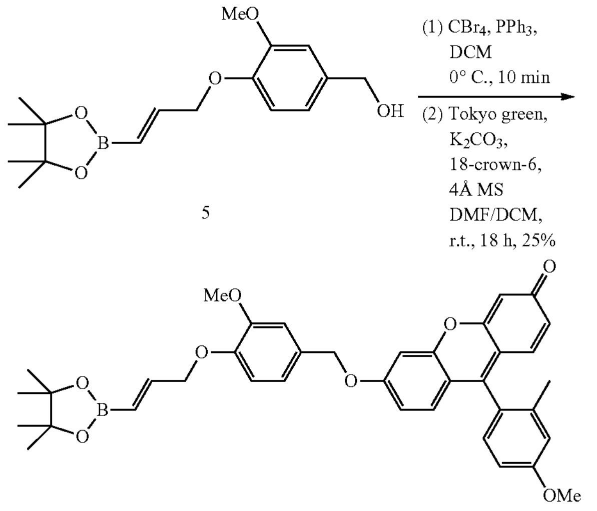

5

15

To a round bottom flask were added alcohol 5 (155 mg, 0.484 mmol), DCM (3 mL), and $PPh_3$ (229 mg, 0.873 mmol) at 0° C. $CBr_4$ (290 mg, 0.873 mmol) was then added and the reaction mixture was stirred for 10 min. When TLC indicated the reaction was complete, the reaction was quenched with water (5 mL). The resulting mixture was partitioned with ethyl acetate (15 mL) and washed with brine (5 mL). The aqueous layer was further extracted with ethyl acetate (3×5 mL). The combined organic extract was dried over anhydrous sodium sulphate, filtered, and concentrated in vacuo. The crude product was semi-purified by flash column chromatography with 10% ethyl acetate in n-hexane as eluent to remove triphenylphosphine oxide.

To a round bottom flask were added the crude product and anhydrous DMF (2 mL). TokyoGreen (188 mg, 0.565 mmol) and $KHCO_3$ (97.0 mg, 0.970 mmol) were then added and the reaction mixture was stirred at room temperature for 18 h. When TLC indicated the reaction was complete, the reaction mixture was diluted with DCM (40 mL), filtered through silica gel to remove unreacted TokyoGreen and $KHCO_3$, and concentrated in vacuo. The crude product was purified by flash column chromatography to afford 15 (104 mg, 25%) as an orange solid.

Analytical TLC (80% ethyl acetate in n-hexane), $R_f$=0.5; $^1H$ NMR (400 MHz, $CDCl_3$) δ 7.09-7.01 (m, 4H), 6.96-6.84 (m, 6H), 6.77 (dt, J=18.2, 4.4 Hz, 1H), 6.62 (dd, J=9.7, 1.9 Hz, 1H), 6.51 (d, J=1.9 Hz, 1H), 5.81 (dt, J=18.0, 1.5 Hz, 1H), 5.10 (s, 2H), 4.71 (dd, J=4.4, 1.6 Hz, 2H), 3.89 (s, 6H), 2.04 (s, 3H), 1.26 (s, 12H); $^{13}C$ NMR (151 MHz, $CDCl_3$) δ 185.8, 163.4, 160.4, 159.1, 154.6, 150.1, 149.6, 148.2, 146.9, 137.8, 130.8, 130.4, 129.8, 129.6, 128.0, 124.5, 120.4, 118.6, 116.0, 114.9, 114.1, 113.0, 111.5, 111.4, 105.6, 101.3, 83.4, 70.8, 70.1, 56.0, 55.3, 24.8, 20.0; HRMS (ESI) calcd. for $C_{38}H_{40}O_8{}^{11}B$ ($[M+H]^+$) 634.3847, found 634.2826.

The $^{13}C$ NMR signal corresponding to the carbon directly attached to the boron atom was not reported due to quadrupolar broadening.

Example 7. Preparation of (5R,6S)-6-((R)-1-hydroxyethyl)-3-((E)-3-(2-methoxy-4-(((9-(4-methoxy-2-methylphenyl)-3-oxo-3H-xanthen-6-yl)oxy)methyl)phenoxy)prop-1-en-1-yl)-7-oxo-1-azabicyclo[3.2.0]hept-2-ene-2-carboxylic acid (MCW-004)

Overall Synthesis Scheme:

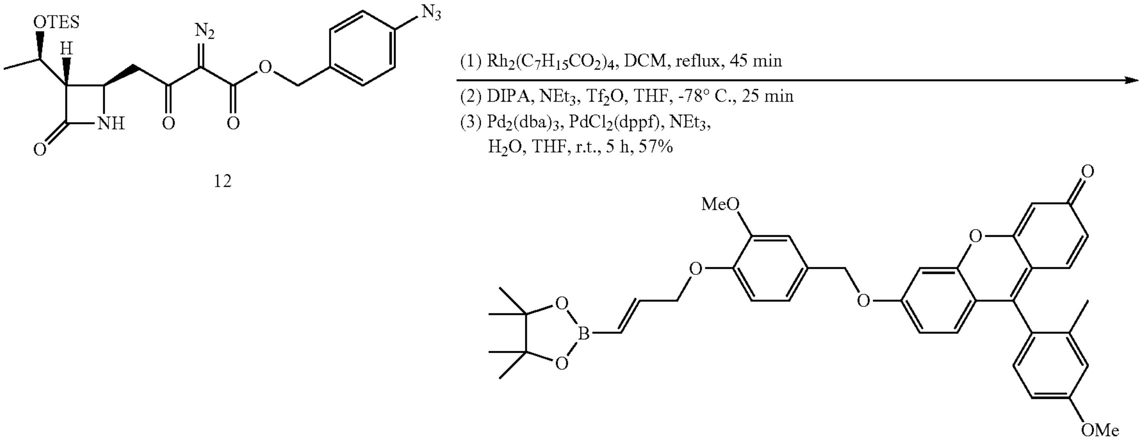

12

15

-continued
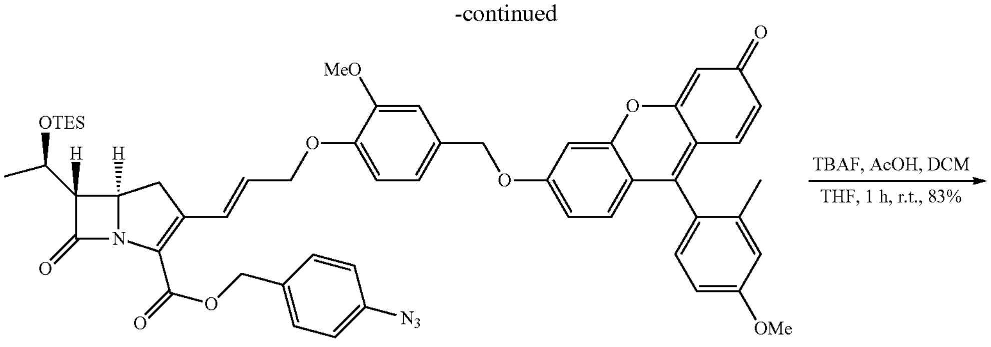
16
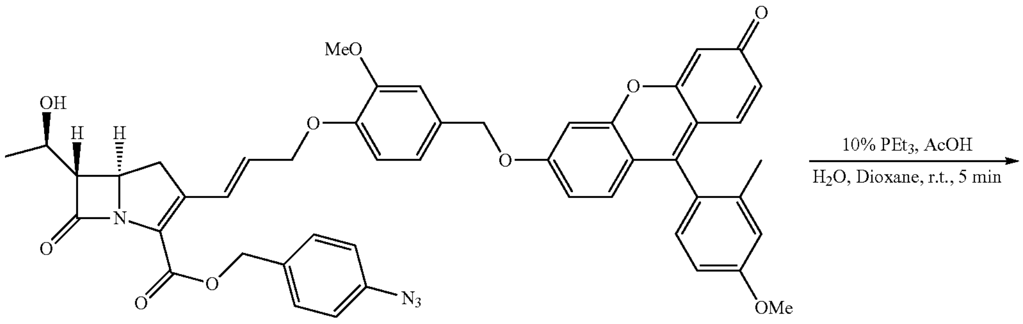
17
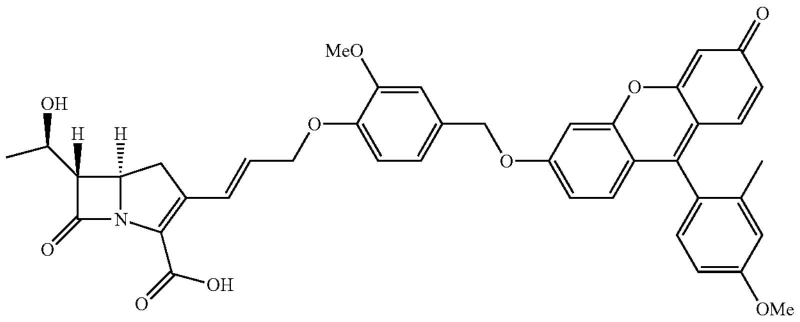
MCW-004
Step 1:
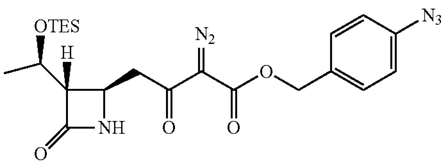
12
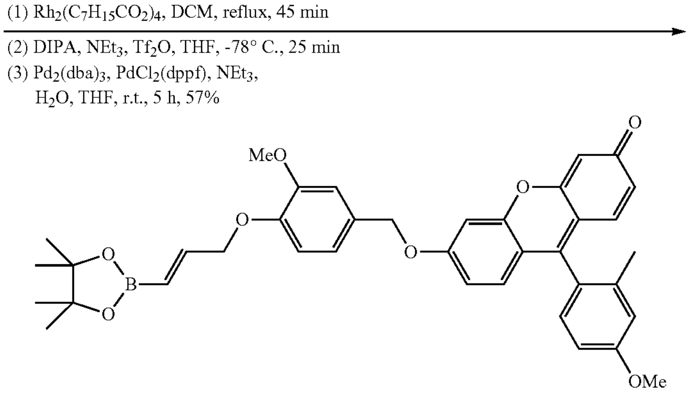
15

-continued

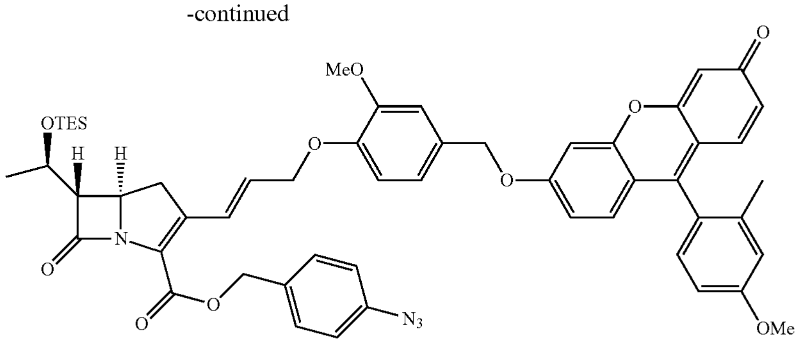

16

To a round bottom flask were added azetidinone 12 (114 mg, 0.233 mmol) and DCM (1.5 mL). $Rh_2(C_7H_{15}CO_2)_4$ (0.9 mg, 1 μmol) was then added and the reaction mixture was stirred under reflux for 45 min. When TLC indicated the reaction was complete, the reaction mixture was concentrated and used directly for the next step.

The above crude product was dissolved in THF (1.2 mL) at −78° C. DIPA (43 μL, 0.303 mmol) and $NEt_3$ (9 μL, 90 μmol) were then added dropwise and the resulting solution was stirred for 10 min. $Tf_2O$ (51 μL, 0.303 mmol) was then added dropwise and the resulting mixture was stirred at −78° C. for 15 min. When TLC indicated the reaction was complete, $NEt_3$ (38 μL, 0.401 mmol), $H_2O$ (7 μL, 0.401 mmol), boronic ester 15 (63.6 mg, 0.100 mmol), $Pd_2(dba)_3$ (6.9 mg, 8 μmol) and $PdCl_2dppf$ (5.5 mg, 8 μmol) were added. The resulting solution was warmed up to room temperature and stirred for 2.5 h. $Pd_2(dba)_3$ (6.9 mg, 8 μmol) and $PdCl_2dppf$ (5.5 mg, 8 μmol) were added and stirred for another 2.5 h. When TLC indicated the reaction was complete, the reaction was quenched with water (5 mL). The mixture was partitioned with ethyl acetate (15 mL) and then washed with brine (5 mL). The aqueous layer was further extracted with ethyl acetate (3×5 mL). The combined organic extract was dried over anhydrous sodium sulphate, filtered, and concentrated in vacuo. The crude product was purified by flash column chromatography to afford 16 (54.2 mg, 57%) as an orange solid.

Analytical TLC (80% ethyl acetate in n-hexane), $R_f$=0.6; $^1H$ NMR (500 MHz, $CDCl_3$) δ 7.52-7.38 (m, 3H), 7.10-6.95 (m, 8H), 6.94-6.87 (m, 3H), 6.85 (dd, J=8.9, 2.3 Hz, 1H), 6.58 (dd, J=9.7, 1.5 Hz, 1H), 6.45 (d, J=1.4 Hz, 1H), 6.08 (dt, J=16.0, 6.0 Hz, 1H), 5.29 (d, J=12.6 Hz, 1H), 5.19 (d, J=12.6 Hz, 1H), 5.10 (s, 2H), 4.73 (d, J=6.0 Hz, 2H), 4.22 (dq, J=12.5, 6.1 Hz, 1H), 4.14 (td, J=9.5, 2.8 Hz, 1H), 3.89 (d, J=1.7 Hz, 6H), 3.13 (dd, J=6.4, 2.9 Hz, 1H), 3.07 (dd, J=17.7, 10.1 Hz, 1H), 2.98 (dd, J=17.6, 8.7 Hz, 1H), 2.05 (s, 3H), 1.28 (d, J=6.2 Hz, 3H), 0.95 (t, J=7.9 Hz, 9H), 0.60 (q, J=7.7 Hz, 6H); $^{13}C$ NMR (125 MHz, $CDCl_3$) δ 185.8, 175.8, 163.3, 160.9, 160.4, 159.0, 154.6, 149.8, 149.7, 148.1, 142.2, 139.8, 137.8, 132.7, 132.3, 130.7, 130.4, 130.0, 129.6, 129.6, 128.6, 128.0, 126.2, 124.6, 120.5, 119.0, 118.7, 116.0, 114.9, 113.9, 113.5, 111.5, 111.4, 105.7, 101.3, 70.8, 69.6, 67.1, 66.2, 66.2, 56.0, 55.3, 52.6, 36.7, 22.6, 20.0, 6.7, 4.9; HRMS (ESI) calcd. for $C_{54}H_{57}O_{10}N_4Si$ ($[M+H]^+$) 949.3838, found 949.3803.

Step 2:

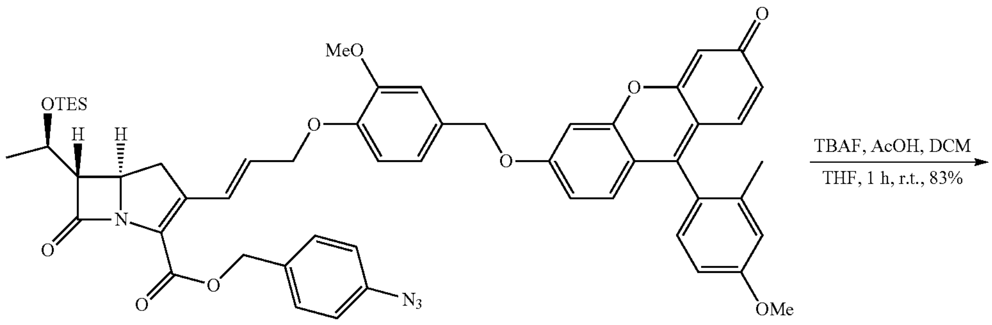

16

-continued

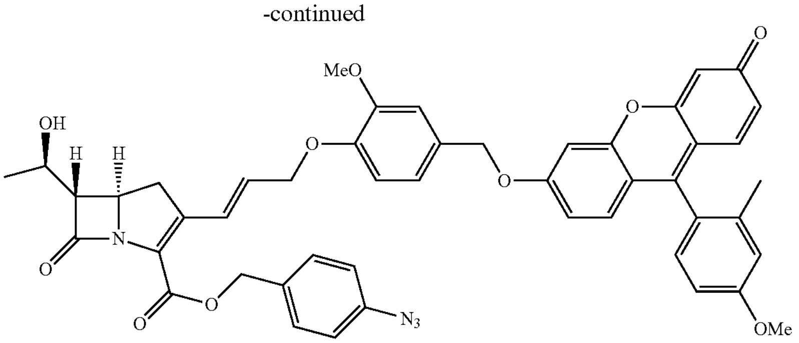

17

To a round bottom flask were added β-lactam 16 (31.6 mg, 33 μmol), THF (0.6 mL), and DCM (0.3 mL). AcOH (21 μL, 0.366 mmol) and TBAF (333 μL, 0.333 mmol, 1 M in THF) were added and the reaction mixture was stirred for 1 h at room temperature When TLC indicated the reaction was complete, the reaction was quenched with water (5 mL). The resulting mixture was partitioned with ethyl acetate (15 mL) and then washed with brine (5 mL). The aqueous layer was further extracted with ethyl acetate (2×5 mL). The combined organic extract was dried over anhydrous sodium sulphate, filtered, and concentrated in vacuo. The crude product was purified by flash column chromatography to afford 17 (23 mg, 83%) as an orange solid.

Analytical TLC (80% ethyl acetate in n-hexane), $R_f$=0.6; $^1$H NMR (500 MHz, $CDCl_3$) δ 7.51-7.40 (m, 3H), 7.08-7.04 (m, 2H), 7.03-6.87 (m, 10H), 6.85 (dd, J=8.9, 2.4 Hz, 1H), 6.58 (dd, J=9.7, 1.8 Hz, 1H), 6.44 (d, J=1.8 Hz, 1H), 6.08 (dt, J=16.0, 6.0 Hz, 1H), 5.32 (d, J=12.6 Hz, 1H), 5.18 (d, J=12.6 Hz, 1H), 5.12 (s, 2H), 4.75 (d, J=5.9 Hz, 2H), 4.27-4.16 (m, 2H), 3.89 (d, J=5.6 Hz, 6H), 3.17 (dd, J=7.1, 2.8 Hz, 1H), 3.10 (dd, J=17.7, 10.0 Hz, 1H), 2.99 (dd, J=17.7, 8.6 Hz, 1H), 2.04 (s, 3H), 1.37 (d, J=6.3 Hz, 3H); $^{13}$C NMR (125 MHz, $CDCl_3$) δ 185.8, 175.7, 163.4, 160.9, 160.4, 159.1, 154.6, 150.0, 149.9, 147.9, 142.5, 139.9, 137.8, 132.9, 132.3, 130.8, 130.4, 129.9, 129.7, 129.6, 128.7, 127.9, 126.2, 124.5, 120.4, 119.1, 118.7, 116.1, 115.0, 114.2, 113.6, 111.6, 111.3, 105.6, 101.4, 70.8, 69.5, 66.7, 66.3, 65.9, 56.0, 55.4, 52.8, 36.8, 21.9, 20.0; HRMS (ESI) calcd. for $C_{48}H_{43}O_{10}N_4$ ($[M+H]^+$) 835.2973, found 835.2941.

Step 3:

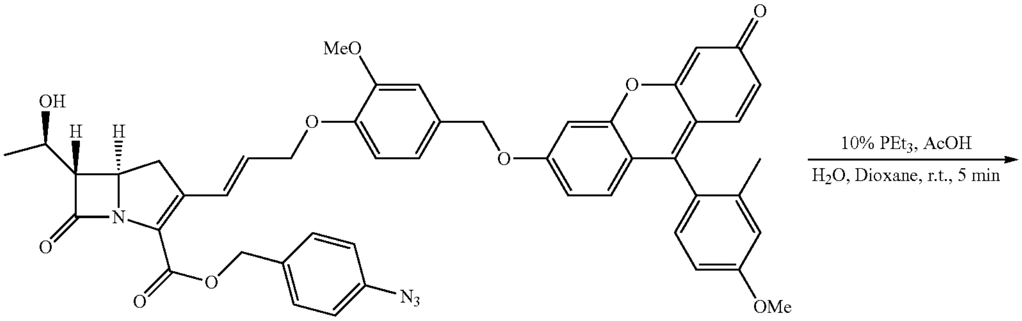

17

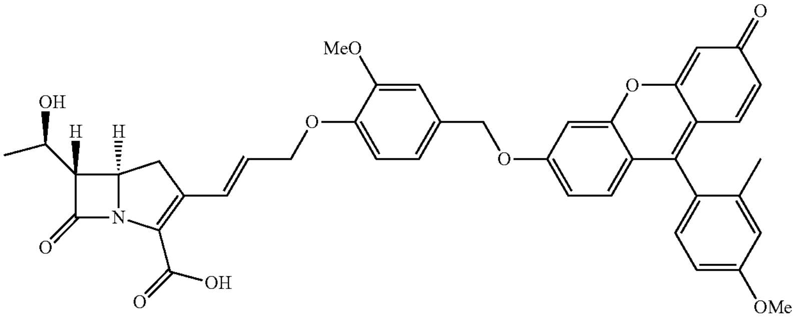

MCW-004

To a round bottom flask were added β-lactam 17 (4.8 mg, 5.7 μmol), dioxane (0.4 mL), and $H_2O$ (40 μL). AcOH (4 μL) and $PEt_3$ (13.5 μL, 7.5 μmol, 10% in n-hexane) were added at room temperature and the reaction mixture was stirred for 5 min. The crude mixture was subjected to preparative C18 reverse phase HPLC purification using 0.01% TFA in water and $CH_3CN$ as eluent, and used directly for fluorescence assay. HRMS (ESI) calcd. for $C_{41}H_{38}NO_{10}$ ([M+H]$^+$) 704.2490, found 704.2475.

Example 8. Preparation of (E)-7-((4-((3-(4,4,5,5-tetramethyl-1,3,2-dioxaborolan-2-yl)allyl)oxy)benzyl)oxy)-3H-phenoxazin-3-one (20)

Overall Synthesis Scheme:

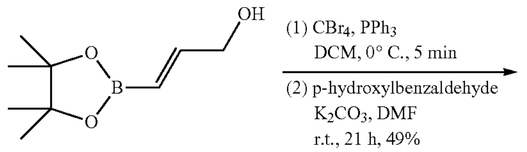

3

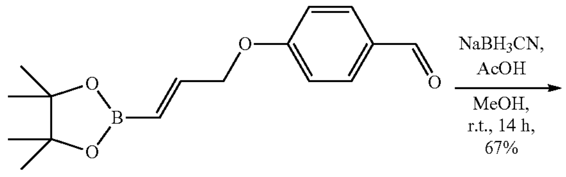

18

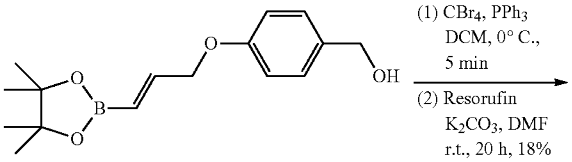

19

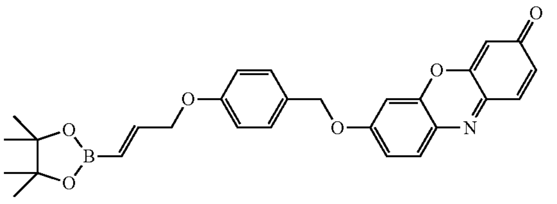

20

Step 1:

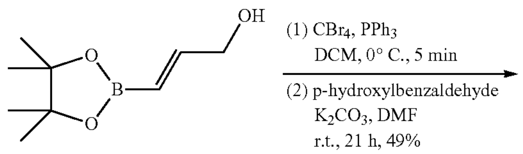

3

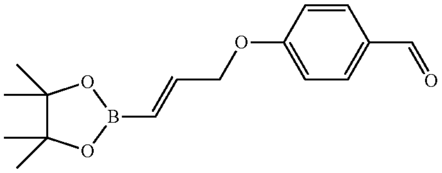

18

To a round bottom flask were added alcohol 3 (504 mg, 2.74 mmol), DCM (13 mL), and $PPh_3$ (1.29 g, 4.93 mmol) at 0° C. $CBr_4$ (1.63 g, 4.93 mmol) was then added and the reaction mixture was stirred at 0° C. for 5 min. When TLC indicated the reaction was complete, the reaction was quenched with water (5 mL). The resulting mixture was partitioned with ethyl acetate (15 mL) and then washed with brine (5 mL). The aqueous layer was further extracted with ethyl acetate (3x5 mL). The combined organic extract was dried over anhydrous sodium sulphate, filtered, and concentrated in vacuo. The crude product was semi-purified by flash column chromatography with 10% ethyl acetate in n-hexane as eluent to remove triphenylphosphine oxide.

The crude product in anhydrous DMF (4 mL) was added to a round bottom flask. p-Hydroxybenzaldehyde (669 mg, 5.48 mmol) and $K_2CO_3$ (756 mg, 5.48 mmol) were then added and the reaction mixture was stirred at room temperature for 21 h. When TLC indicated the reaction was complete, the reaction was quenched with water (5 mL). The mixture was partitioned with ethyl acetate (15 mL) and then washed with brine (5 mL).

The aqueous layer was further extracted with ethyl acetate (3x5 mL). The combined organic extract was dried over anhydrous sodium sulphate, filtered, and concentrated in vacuo. The crude product was purified by flash column chromatography to afford 18 (390 mg, 49%) as colorless oil.

Analytical TLC (50% ethyl acetate in n-hexane), $R_f$=0.7; $^1$H NMR (400 MHz, $CDCl_3$) δ 9.82 (s, 1H), 7.77 (d, J=8.6 Hz, 2H), 6.95 (d, J=8.7 Hz, 2H), 6.69 (dt, J=18.2, 4.4 Hz, 1H), 5.77 (dt, J=18.2, 1.7 Hz, 1H), 4.66 (dd, J=4.3, 1.7 Hz, 2H), 1.23 (s, 12H); $^{13}$C NMR (100 MHz, $CDCl_3$) δ 190.6, 163.3, 145.7, 131.8, 129.9, 114.8, 83.3, 69.2, 24.6; LRMS (EI) 288.1 ([M]$^+$, 28), 167.0 (14), 83.1 (100); HRMS (EI) calcd. for $C_{16}H_{21}{}^{11}BO_4$ ([M]$^+$) 288.1527, found 288.1530.

The $^{13}$C NMR signal corresponding to the carbon directly attached to the boron atom was not reported due to quadrupolar broadening.

Step 2:

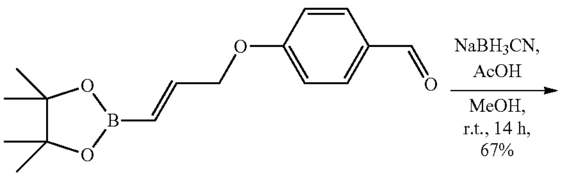

18

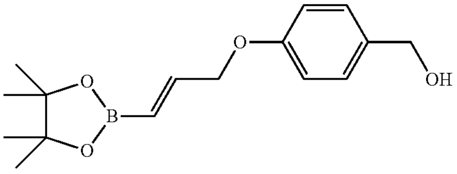

19

To a round bottom flask were added aldehyde 18 (384 mg, 1.33 mmol), MeOH (3.5 mL), AcOH (0.8 mL, 13.3 mmol), and $NaBH_3CN$ (167 mg, 2.66 mmol). The reaction mixture was stirred at room temperature for 14 h. When TLC indicated the reaction was complete, the reaction was quenched with water (5 mL). The resulting mixture was partitioned with ethyl acetate (15 mL) and then washed with brine (5 mL). The aqueous layer was further extracted with ethyl acetate (3x5 mL). The combined organic extract was dried over anhydrous sodium sulphate, filtered, and concentrated in vacuo. The crude product was purified by flash column chromatography to afford 19 (261 mg, 67%) as a colorless oil.

Analytical TLC (50% ethyl acetate in n-hexane), $R_f$=0.5; $^1$H NMR (400 MHz, $CDCl_3$) δ 7.26 (d, J=9.2 Hz, 2H), 6.87

(d, J=7.7 Hz, 2H), 6.74 (dt, J=18.2, 4.3 Hz, 1H), 5.87-5.74 (m, 1H), 4.64-4.53 (m, 4H), 2.14 (s, 1H), 1.27 (s, 12H); $^{13}C$ NMR (100 MHz, $CDCl_3$) δ 158.1, 147.2, 133.3, 128.6, 114.7, 83.4, 69.2, 64.9, 24.7; HRMS (ESI) calcd. for $C_{16}H_{24}{}^{11}BO_4$ ($[M+H]^+$) 291.1711, found 291.1765.

The $^{13}C$ NMR signal corresponding to the carbon directly attached to the boron atom was not reported due to quadrupolar broadening.

Step 3:

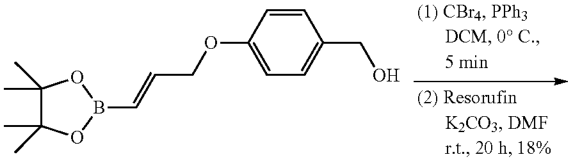

19

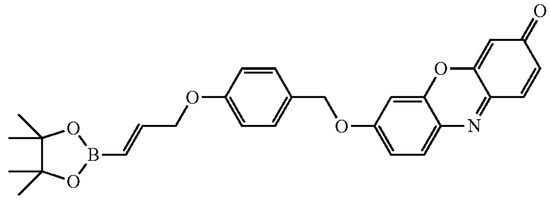

20

To a round bottom flask were added alcohol 19 (117 mg, 0.403 mmol), DCM (2.5 mL), and $PPh_3$ (190 mg, 0.724 mmol) at 0° C. $CBr_4$ (240 mg, 0.724 mmol) was then added and the reaction mixture was stirred for 5 min. When TLC indicated the reaction was complete, the reaction was quenched with water (5 mL). The resulting mixture was partitioned with ethyl acetate (15 mL) and washed with brine (5 mL). The aqueous layer was further extracted with ethyl acetate (3×5 mL). The combined organic extract was dried over anhydrous sodium sulphate, filtered, and concentrated in vacuo. The crude product was quickly purified by flash column chromatography and eluted with 10% ethyl acetate in n-hexane to remove triphenylphosphine oxide.

To a round bottom flask were added the crude product and anhydrous DMF. Resorufin (172 mg, 0.805 mmol) and $K_2CO_3$ (111 mg, 0.805 mmol) were then added and the reaction mixture was stirred at room temperature for 20 h. When TLC indicated the reaction was complete, the reaction mixture was partitioned with DCM (40 mL), filtered through silica gel to remove unreacted resorufin and $K_2CO_3$, and concentrated in vacuo. The crude product was purified by flash column chromatography to afford 20 (30.5 mg, 18%) as an orange solid.

Analytical TLC (50% ethyl acetate in n-hexane), $R_f$=0.5; $^1H$ NMR (400 MHz, $CDCl_3$) δ 7.72 (d, J=8.9 Hz, 1H), 7.43 (d, J=9.8 Hz, 1H), 7.36 (d, J=8.6 Hz, 2H), 7.01 (dd, J=8.9, 2.5 Hz, 1H), 6.95 (d, J=8.6 Hz, 2H), 6.89 (d, J=2.5 Hz, 1H), 6.85 (dd, J=9.8, 1.9 Hz, 1H), 6.76 (dt, J=18.2, 4.3 Hz, 1H), 6.34 (d, J=1.8 Hz, 1H), 5.83 (dt, J=18.2, 1.5 Hz, 1H), 5.10 (s, 2H), 4.65 (dd, J=4.3, 1.6 Hz, 2H), 1.29 (s, 12H); $^{13}C$ NMR (100 MHz, $CDCl_3$) δ 186.3, 162.8, 158.8, 149.8, 146.9, 145.6, 145.5, 134.7, 134.2, 131.6, 129.3, 128.4, 127.5, 115.0, 114.4, 106.7, 101.0, 83.4, 70.7, 69.3, 24.8; LRMS (ESI) 486.3 ($[M+H]^+$); HRMS (ESI) calcd. for $C_{28}H_{2911}BO_6N$ ($[M+H]^+$) 486.2098, found 486.2077.

The $^{13}C$ NMR signal corresponding to the carbon directly attached to the boron atom was not reported due to quadrupolar broadening.

Example 9. Preparation of (5R,6S)-6-((R)-1-hydroxyethyl)-7-oxo-3-((E)-3-(4-(((3-oxo-3H-phenoxazin-7-yl)oxy)methyl)phenoxy)prop-1-en-1-yl)-1-azabicyclo[3.2.0]hept-2-ene-2-carboxylic acid (MCW-005)

Overall synthesis scheme:

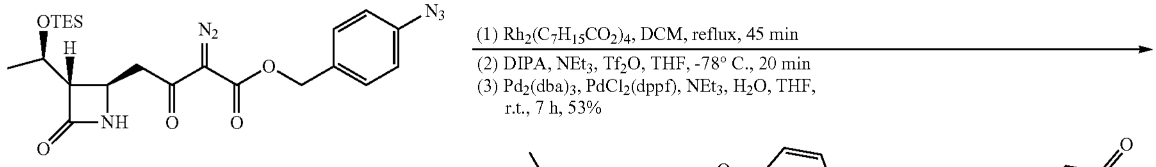

12

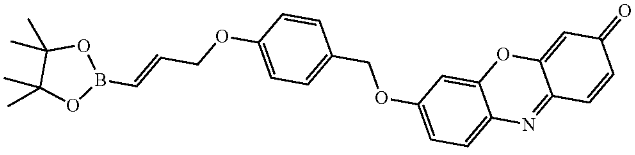

18

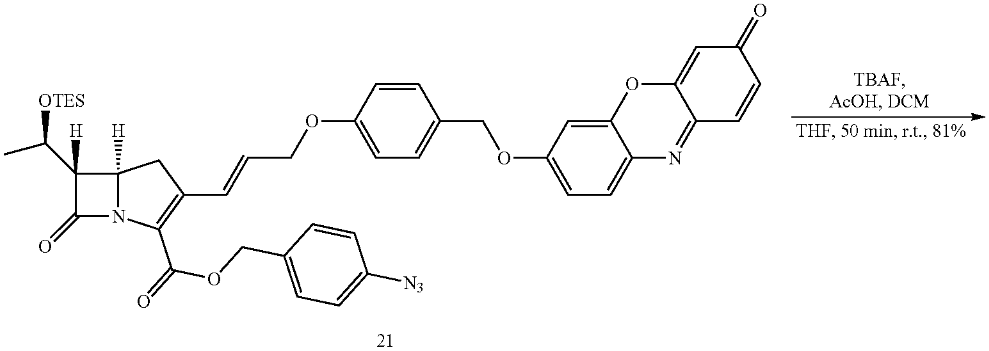

21

-continued

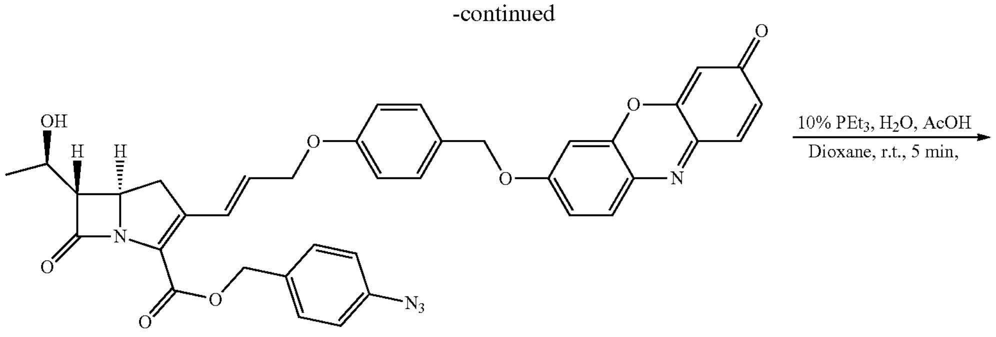

22

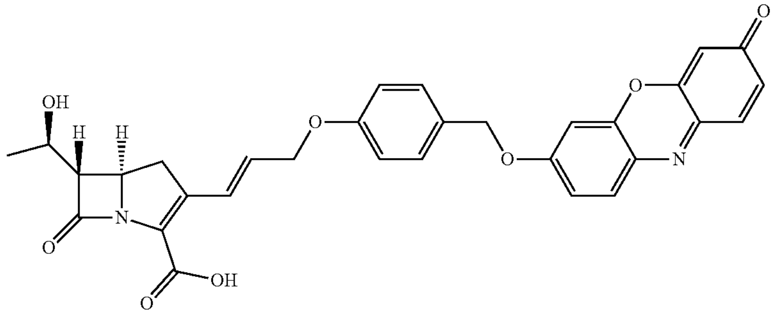

MCW-005

Step 1:

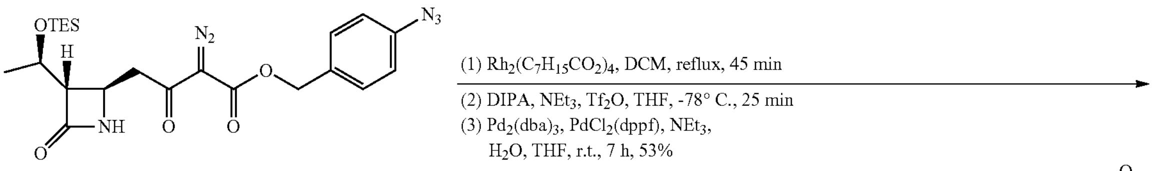

12

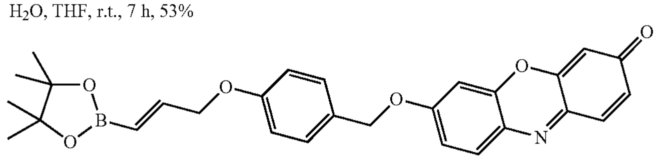

18

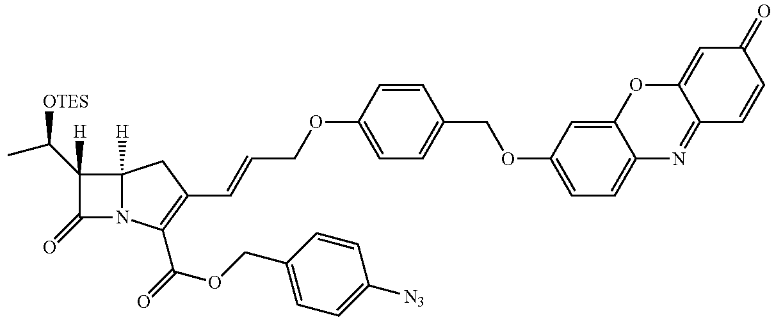

21

To a round bottom flask were added azetidinone 12 (80.1 mg, 0.165 mmol) and DCM (1 mL). Rhodium octanoate dimer (0.7 mg, 0.8 μmol) was then added and the reaction mixture was stirred under reflux for 45 min. When TLC indicated the reaction was complete, the reaction mixture was concentrated and used directly for the next step.

To a 10 mL round bottom flask were added the crude ketone and THF (0.9 mL) at −78° C. DIPA (30.1 μL, 0.214 mmol) and $NEt_3$ (5.6 μL, 66 μmol) were then added dropwise and the resulting solution was stirred for 10 min. $Tf_2O$ (36.0 μL, 0.214 mmol) was then added dropwise and the resulting mixture was stirred for 15 min. When TLC indicated the reaction was complete, $NEt_3$ (56.0 μL, 0.599 mmol), $H_2O$ (10.8 μL, 0.599 mmol), boronic ester 18 (72.7 mg, 0.150 mmol), $Pd_2(dba)_3$ (10.3 mg, 22 μmol) and $PdCl_2dppf$ (8.2 mg, 22 μmol) were added. The resulting solution was warmed up to room temperature and stirred for 7 h. When TLC indicated the reaction was complete, the reaction was quenched with water (5 mL). The mixture was partitioned with ethyl acetate (15 mL) and then washed with brine (5 mL). The aqueous layer was further extracted with ethyl acetate (3×5 mL). The combined organic extract was dried over anhydrous sodium sulphate, filtered and concentrated in vacuo. The crude product was purified by flash column chromatography to afford 21 (63.9 mg, 53%) as an orange solid which was inseparable from boronic ester 18 (17.7 mg). All weights and yield were estimated according to NMR integration.

Analytical TLC (40% ethyl acetate in n-hexane), $R_f$=0.5.

Step 2:

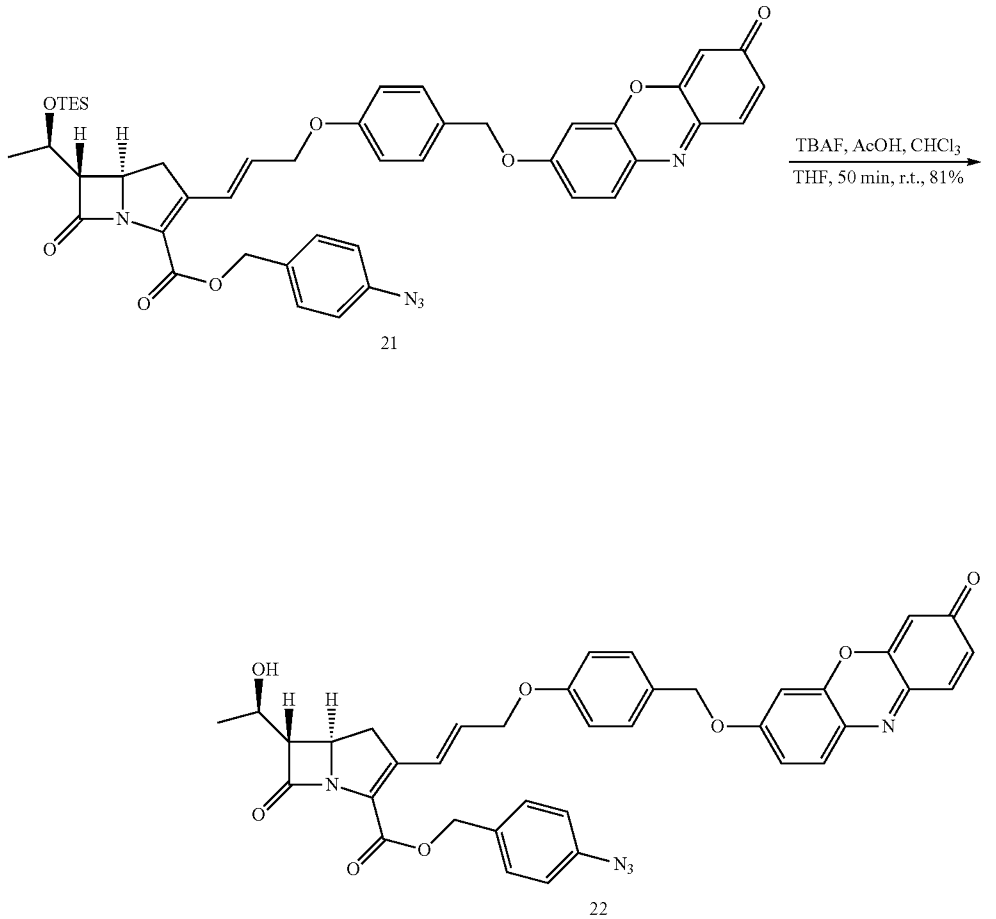

21

22

To a round bottom flask were added β-lactam 21 (63.9 mg, 80.0 μmol), THF (0.3 mL) and $CHCl_3$ (1 mL). AcOH (50.3 μL, 0.800 mmol) and TBAF (800 μL, 0.800 mmol, 1 M in THF) were added at room temperature and the reaction mixture was stirred for 50 min. When TLC indicated the reaction was complete, the reaction was quenched with water (5 mL). The mixture was partitioned with ethyl acetate (15 mL) and then washed with brine (5 mL). The aqueous layer was further extracted with ethyl acetate (2×5 mL). The combined organic extract was dried over anhydrous sodium sulphate, filtered, and concentrated in vacuo. The crude product was purified by flash column chromatography to afford 22 (44.4 mg, 81%) as an orange solid.

Analytical TLC (80% ethyl acetate in n-hexane), $R_f$=0.3; $^1H$ NMR (500 MHz, 20% $CD_3OD$ in $CDCl_3$) δ 7.76 (d, J=8.9 Hz, 1H), 7.50 (d, J=9.8 Hz, 1H), 7.48-7.41 (m, 3H), 7.39 (d, J=8.6 Hz, 2H), 7.07 (dd, J=8.9, 2.7 Hz, 1H), 7.02 (d, J=8.5 Hz, 2H), 6.96 (d, J=2.6 Hz, 1H), 6.94 (d, J=8.6 Hz, 2H), 6.87 (dd, J=9.8, 2.1 Hz, 1H), 6.37 (d, J=2.1 Hz, 1H), 6.09 (dt, J=16.0, 5.5 Hz, 1H), 5.31 (d, J=12.5 Hz, 1H), 5.21 (d, J=12.5 Hz, 1H), 5.14 (s, 2H), 4.70 (d, J=5.5 Hz, 2H), 4.26-4.11 (m, 2H), 3.71 (s, 1H), 3.22-3.09 (m, 2H), 3.04 (dd, J=17.7, 8.7 Hz, 1H), 1.32 (d, J=6.4 Hz, 3H); $^{13}C$ NMR (125 MHz, 20% $CD_3OD$ in $CDCl_3$) δ 186.7, 176.3, 163.0, 160.9, 158.4, 150.1, 145.6, 144.8, 142.6, 139.8, 134.7, 133.6, 132.8, 132.0, 131.5, 129.6, 129.2, 128.3, 127.7, 127.5, 125.2, 118.9, 114.8, 114.6, 106.1, 100.8, 70.5, 68.0, 66.3, 66.2, 65.1, 52.6, 36.6, 21.1; LRMS (ESI) 686.1 ($[M+H]^+$); HRMS (ESI) calcd. for $C_{38}H_{32}O_8N_5$ ($[M+H]^+$) 686.2256, found 686.2224.

Step 3:

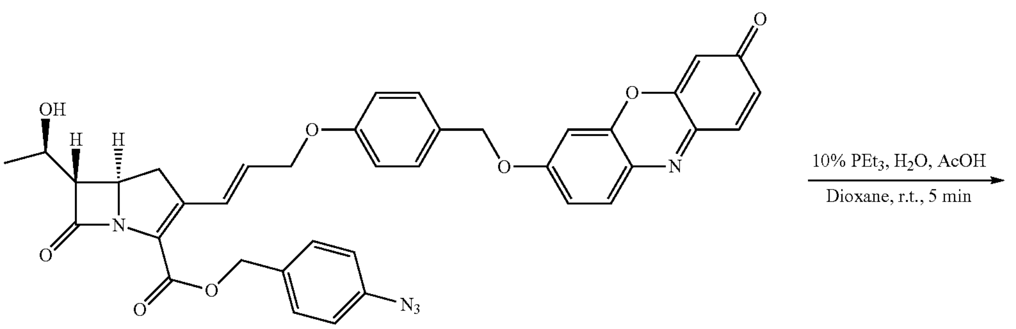

22

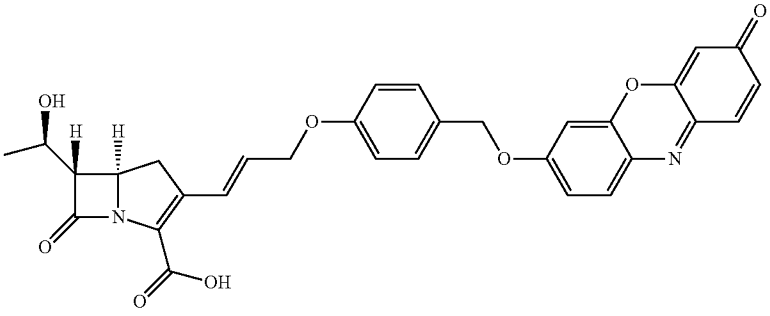

MCW-005

To a round bottom flask were added β-lactam 22 (1.9 mg, 2.8 μmol), dioxane (0.1 mL) and $H_2O$ (10 μL). AcOH (1 μL) and $PEt_3$ (6.5 μL, 5.0 μmol, 10% in n-hexane) were added at room temperature and the reaction mixture was stirred for 5 min. The crude mixture was subjected to preparative C18 reverse phase HPLC purification using 0.01% TFA in water and $CH_3CN$ as eluent, and used directly for fluorescence assay.

HRMS (ESI) calcd. for $C_{31}H_{27}N_2O_8$ ($[M+H]^+$) 555.1762, found 555.1743.

Example 10. Preparation of N-((4-azidobenzyl)oxy)-2-diazo-N-methyl-3-oxo-4-((2R,3S)-4-oxo-3-((R)-1-((triethylsilyl)oxy)ethyl)azetidin-2-yl)butanamide (31)

Overall synthesis scheme:

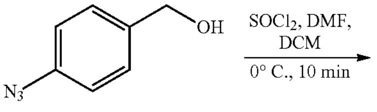

7

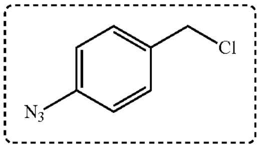

23

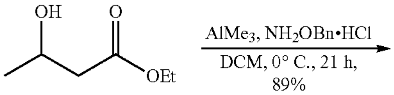

-continued

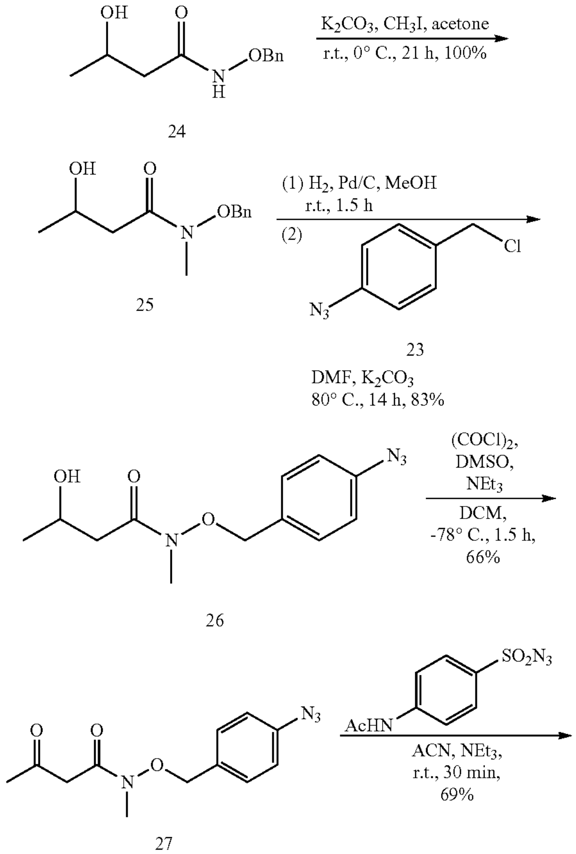

24

25

23

26

27

-continued

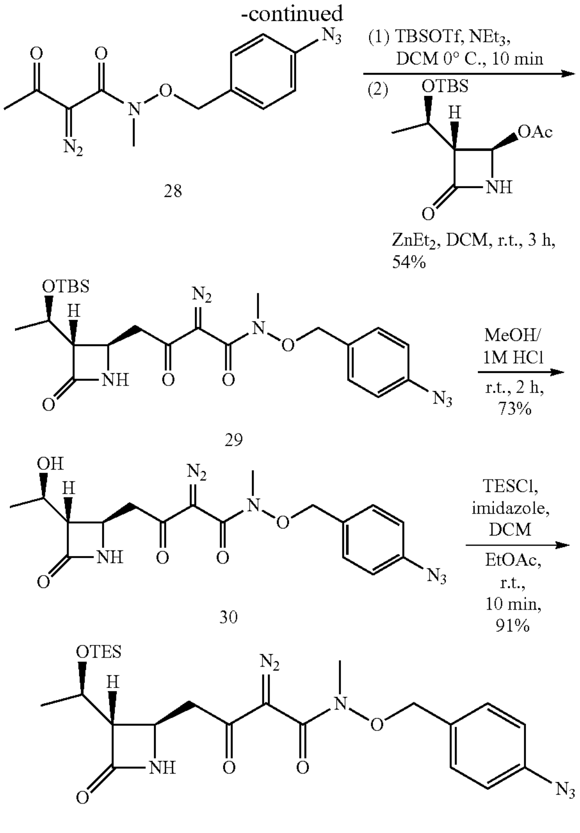

28

29

30

31

Step 1:

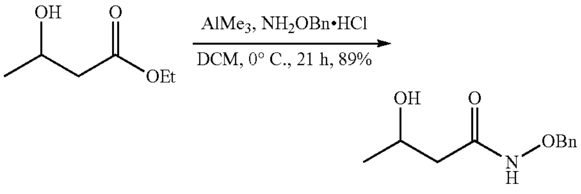

24

To a round bottom flask were added the O-benzylhydroxylamine HCl salt (7.98 g, 50.0 mmol) and DCM (25 mL). $AlMe_3$ (25 mL, 50.0 mmol, 2 M in toluene) was added at 0° C. and the resulting mixture was stirred for 10 min. Ethyl 3-hydroxybutyrate (3.30 g, 25.0 mmol) in DCM (25 mL) was added and the reaction mixture was warmed up to room temperature and stirred for 21 h. When TLC indicated the reaction was complete, the reaction was quenched with excess HCl (30 mL, 1 M aq) and mixture was partitioned with ethyl acetate (80 mL). The resulting mixture was washed with brine (20 mL). The aqueous layer was further extracted with ethyl acetate (3×20 mL). The combined organic extract was dried over anhydrous sodium sulphate, filtered, and concentrated in vacuo. The crude product was recrystallized with hot ethyl acetate to afford 24 (4.64 g, 89%).

Analytical TLC (60% ethyl acetate in n-hexane), $R_f$=0.1; $^1$H NMR (400 MHz, $CDCl_3$) δ 7.38-7.33 (m, 6H), 4.85 (s, 2H), 4.09 (br s, 1H), 3.70 (br s, 1H), 2.18-2.15 (m, 2H), 1.15 (d, J=6.4 Hz, 3H); $^{13}$C NMR (100 MHz, $CDCl_3$) δ 169.6, 135.0, 128.9, 128.4, 128.2, 77.8, 64.3, 41.3, 22.5; HRMS (ESI) calcd. for $C_{11}H_{16}NO_3$ ($[M+H]^+$) 210.1125, found 210.1117.

Step 2:

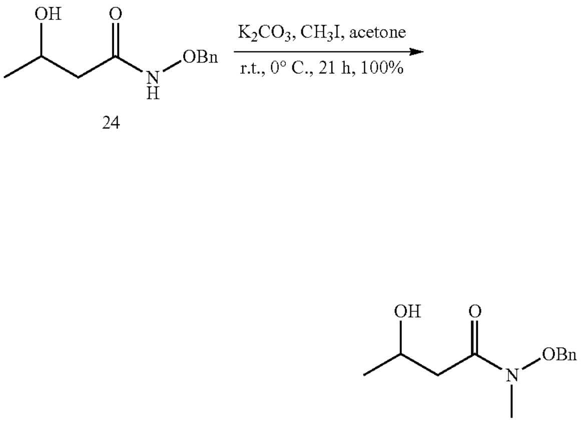

24

25

To a round bottom flask were added the hydroxamate 24 (3.40 g, 16.3 mmol), acetone (25 mL), and $K_2CO_3$ (4.49 g, 32.5 mmol). $CH_3I$ (1.52 mL, 24.4 mmol) was added and the resulting solution was stirred at room temperature for 21 h. When TLC indicated the reaction was complete, the reaction mixture was concentrated in vacuo and suspension was filtered off. The filtrate was concentrated in vacuo. The crude product was purified by flash column chromatography to afford 25 (4.12 g, 100%) as a white solid.

Analytical TLC (silica gel 60), 60% ethyl acetate in n-hexane, $R_f$=0.3; $^1$H NMR (400 MHz, $CDCl_3$) δ 7.48-7.33 (m, 5H), 4.83 (s, 2H), 4.10 (br s, 1H), 3.89 (s, 1H), 3.21 (s, 3H), 2.58 (d, J=16.6 Hz, 1H), 2.34 (dd, J=16.8, 9.5 Hz, 1H), 1.17 (d, J=6.3 Hz, 3H); $^{13}$C NMR (100 MHz, $CDCl_3$) δ 174.6, 134.1, 129.3, 129.1, 128.7, 76.2, 64.1, 39.9, 33.1, 22.3. HRMS (ESI) calcd. for $C_{12}H_{17}NO_3$ ($[M+H]^+$) 224.1281, found 224.1273.

Step 3:

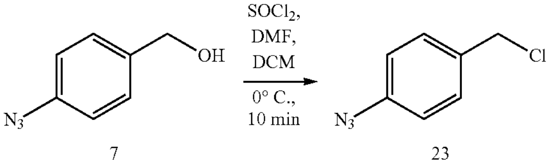 [SMILES: [N-]=[N+]=Nc1ccc(CO)cc1 ; [N-]=[N+]=Nc1ccc(CCl)cc1]

7

23

To a round bottom flask were added benzyl alcohol 7 (3.47 g, 23.3 mmol), DCM (50 mL), and DMF (3.60 mL, 46.6 mmol). $SOCl_2$ (3.06 mL, 41.9 mmol) was added at 0° C. and the resulting solution was stirred for 10 min. When TLC indicated the reaction was complete, the reaction was quenched with water (50 mL) and the reaction mixture was partitioned with ethyl acetate (150 mL). The resulting mixture was washed with saturated $NaHCO_3$ solution (2×50 mL) and then brine (50 mL). The aqueous layer was further extracted with ethyl acetate (2×50 mL). The combined organic extract was dried over anhydrous sodium sulphate, filtered, concentrated and the crude product was used directly for the next step.

Step 4:

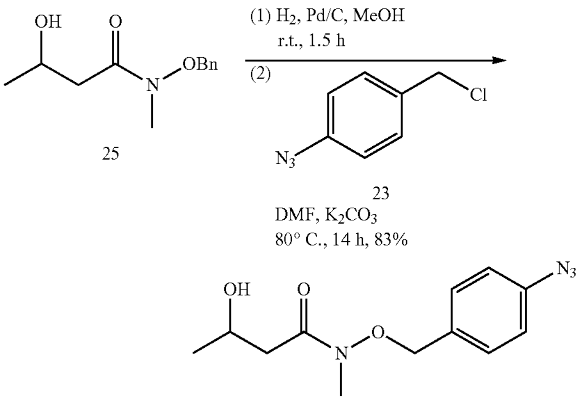

25

23

26

To a round bottom flask were added hydroxylamide 25 (3.96 g, 17.8 mmol), palladium on charcoal (0.954 g, 0.897 mmol, 10% Pd/C), and degassed methanol (40 mL). Hydrogen balloon was attached and the resulting solution was stirred for 1.5 h. When TLC indicated the reaction was complete, the reaction mixture was filtered through Celite®, concentrated, and used directly for the next step.

To a round bottom flask were added the crude mixture hydroxamate, 23, DMF (15 mL), and $K_2CO_3$ (2.98 g, 35.5 mmol) at room temperature. The reaction mixture was stirred at 80° C. for 14 h. When TLC indicated the reaction was complete, the reaction mixture was diluted in DCM (100 mL) and the resulting mixture was filtered through silica gel. The crude product was concentrated and purified by flash column chromatography to afford 26 (3.90 g, 83%) as a brown oil.

Analytical TLC (60% ethyl acetate in n-hexane), $R_f$=0.3; $^1$H NMR (400 MHz, $CD_3OD$) δ 7.45 (d, J=8.4 Hz, 2H), 7.06 (d, J=8.3 Hz, 2H), 4.87 (s, 2H), 4.2-4.13 (m, 1H), 3.20 (s, 3H), 2.62 (dd, J=14.7, 7.4 Hz, 1H), 2.42 (dd, J=15.4, 4.9 Hz, 1H), 1.18 (d, J=6.2 Hz, 3H); $^{13}$C NMR (100 MHz, $CD_3OD$) δ 174.7, 142.0, 132.7, 132.4, 120.1, 76.4, 65.3, 42.0, 33.5, 23.4; HRMS (ESI) calcd. for $C_{12}H_{17}N_4O_3$ ([M+H]$^+$) 265.1295, found 265.1285.

Step 5:

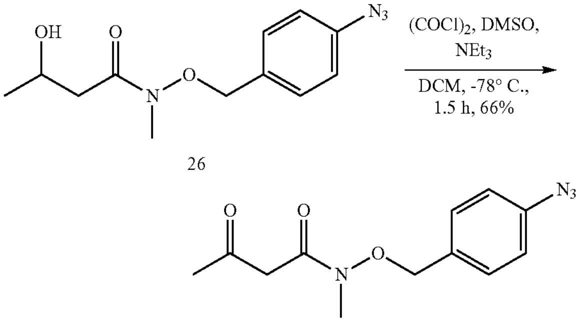

26

27

To a round bottom flask was added DCM (30 mL). $(COCl)_2$ (0.470 mL, 5.59 mmol) and DMSO (0.790 mL, 11.2 mmol) were added at −78° C. and the resulting mixture was stirred for 20 min. Hydroxylamide 26 (0.983 g, 3.72 mmol) in DCM (20 mL) was then added dropwise and the resulting mixture was stirred for 20 min. $NEt_3$ (3.37 mL, 2.23 mmol) were then added and the reaction mixture was stirred for 20 min at −78° C. The reaction mixture was warmed up to room temperature and stirred for 20 min. When TLC indicated the reaction was complete, the reaction was quenched with water (30 mL). The mixture was partitioned with ethyl acetate (90 mL) and washed with brine (30 mL). The aqueous layer was further extracted with ethyl acetate (3×30 mL). The combined organic extract was dried over anhydrous sodium sulphate, filtered, and concentrated in vacuo. The crude product was purified by flash column chromatography to afford 27 (641 mg, 66%) as a pale yellow oil.

Analytical TLC (60% ethyl acetate in n-hexane), $R_f$=0.4; $^1$H NMR (400 MHz, $CD_3OD$) δ 7.35 (d, J=8.0 Hz, 2H), 7.05 (d, J=8.0 Hz, 2H), 4.80 (s, 2H), 3.50 (s, 2H), 3.24 (s, 3H), 2.19 (s, 3H); $^{13}$C NMR (100 MHz, $CD_3OD$) δ 201.6, 175.5, (173.2), 168.7, 141.0, (140.8), 131.0, (130.8), 119.3, (87.0), (75.8), 75.7, 48.9, 33.5, 30.1, (21.9); HRMS (ESI) calcd. for $C_{12}H_{15}N_4O_3$ ([M+H]$^+$) 263.1139, found 263.1129.

Note: the NMR spectra show an equilibrium mixture of keto and enol tautomers in a ratio of 85:15. Observable signals corresponding to the minor species are shown in parentheses.

Step 6:

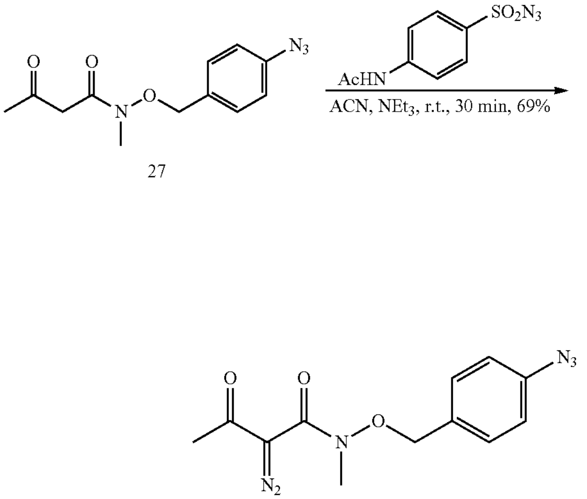

27

28

To a round bottom flask were added ketone 27 (2.05 g, 7.82 mmol), $CH_3CN$ (20 mL), and 4-acetamidobenzenesulfonyl azide (1.88 g, 7.82 mmol) at room temperature. $NEt_3$ (1.53 mL, 10.2 mmol) was then added and the reaction mixture was stirred for 30 min. When TLC indicated the reaction was complete, the reaction mixture was concentrated and filtered through silica gel. The resulting solution was concentrated in vacuo and purified by flash column chromatography to afford 28 (1.55 g, 69%) as a pale yellow solid.

Analytical TLC (60% ethyl acetate in n-hexane), $R_f$=0.6; $^1$H NMR (500 MHz, $CDCl_3$) δ 7.34 (d, J=8.2 Hz, 2H), 7.04 (d, J=8.2 Hz, 2H), 4.83 (s, 2H), 3.30 (s, 3H), 2.38 (s, 3H); $^{13}$C NMR (125 MHz, $CDCl_3$) δ 191.5, 162.1, 141.4, 131.1, 129.8, 119.3, 75.8, 72.4, 34.4, 28.3; HRMS (ESI) calcd. for $C_{12}H_{13}N_6O_3$ ([M+H]$^+$) 289.1044, found 289.1033.

Step 7:

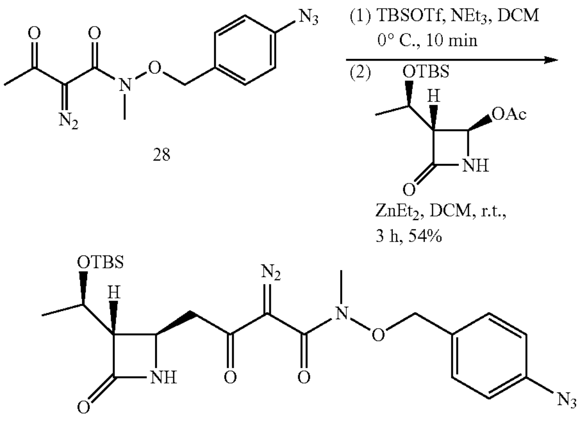

28

29

To a round bottom flask were added β-ketoester 28 (1.14 g, 3.96 mmol) and DCM (15 mL) at 0° C. $NEt_3$ (1.90 mL, 11.9 mmol) and TBSOTf (1.36 mL, 5.94 mmol) were then added slowly. The mixture was stirred for 10 min at 0° C. The reaction was then quenched with water (30 mL). The mixture was partitioned with ethyl acetate (90 mL) and then washed with brine (30×5 mL). The aqueous layer was further extracted with ethyl acetate (2×30 mL). The combined organic extract was dried over anhydrous sodium sulphate, filtered, and concentrated in vacuo to afford the crude silylenol ether.

The azetidinone (3.41 g, 11.9 mmol) was dissolved in DCM (20 mL) at 0° C. $ZnEt_2$ (13.1 mL, 13.1 mmol, 1 M in hexane) was added and the resulting mixture was stirred for 10 min. Crude silylenol ether was dissolved in DCM (5 mL) and the solution was added dropwise to the reaction mixture over 10 min. The reaction mixture was stirred at room temperature for 3 h. The reaction was quenched with water (30 mL), partitioned with ethyl acetate (90 mL) and washed with brine (30×5 mL). The aqueous layer was further extracted with ethyl acetate (2×30 mL). The combined organic extract was dried over anhydrous sodium sulphate, filtered, and concentrated in vacuo. The crude product was purified by flash column chromatography to afford 29 (1.09 g, 54%) as a pale yellow oil.

Analytical TLC (60% ethyl acetate in n-hexane), $R_f$=0.4; $^1$H NMR (500 MHz, $CDCl_3$) δ 7.34 (d, J=8.5 Hz, 2H), 7.05 (d, J=8.3 Hz, 2H), 6.12 (s, 1H), 4.84 (s, 2H), 4.20 (qd, J=6.3, 4.3 Hz, 1H), 4.00 (dt, J=10.0, 2.9 Hz, 1H), 3.33 (dd, J=17.8, 3.2 Hz, 1H), 3.30 (s, 3H), 2.92-2.81 (m, 2H), 1.20 (d, J=6.3 Hz, 3H), 0.87 (s, 9H), 0.07 (s, 6H). $^{13}$C NMR (125 MHz, $CDCl_3$) δ 192.0, 168.1, 161.6, 141.5, 131.1, 129.6, 119.3, 75.9, 72.5, 65.1, 63.6, 46.3, 45.5, 34.4, 25.7, 22.4, 17.9, −4.4, −5.1; HRMS (ESI) calcd. for $C_{23}H_{34}N_7O_5Si$ ([M+H]$^+$) 516.2385, found 516.2364.

Step 8:

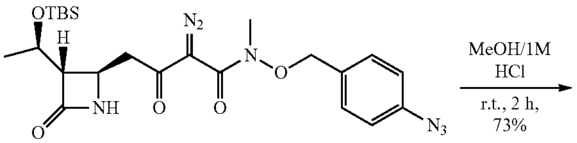

29

-continued

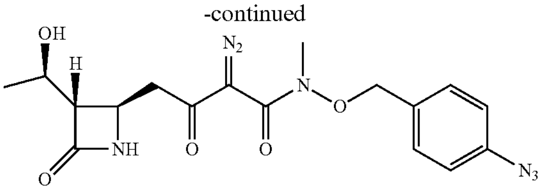

30

To a round bottom flask were added azetidinone 29 (1.09 g, 2.12 mmol) and MeOH (9 mL). HCl (3 mL, 1 M, aq) was then added. The mixture was stirred at room temperature for 4 h. When TLC indicated the reaction was complete, the reaction was quenched with water (30 mL). The resulting mixture was partitioned with ethyl acetate (90 mL), washed with saturated $NaHCO_3$ solution (30 mL) and brine (30 mL). The aqueous layer was further extracted with ethyl acetate (3×30 mL). The combined organic extract was dried over anhydrous sodium sulphate, filtered, and concentrated in vacuo. The crude product was purified by flash column chromatography to afford 30 (621 mg, 73%) as a yellow viscous liquid.

Analytical TLC (60% ethyl acetate in n-hexane), $R_f$=0.6; $^1$H NMR (400 MHz, $CDCl_3$) δ 7.36 (d, J=8.2 Hz, 2H), 7.05 (d, J=8.2 Hz, 2H), 6.80 (s, 1H), 4.85 (s, 2H), 4.02 (dq, J=5.9, 7.3 Hz, 2H), 3.86 (s, 1H), 3.30 (s, 3H), 3.18 (dd, J=18.2, 6.0 Hz, 1H), 3.10 (dd, J=18.1, 7.2 Hz, 1H), 2.83 (d, J=6.3 Hz, 1H), 1.29 (d, J=6.2 Hz, 3H); $^{13}$C NMR (100 MHz, $CDCl_3$) δ 192.3, 168.0, 161.1, 141.2, 131.1, 129.4, 119.2, 75.7, 72.6, 65.4, 63.7, 47.7, 45.1, 34.1, 21.0; HRMS (ESI) calcd. for $C_{17}H_{20}N_7O_5$ ([M+H]$^+$) 402.1520, found 402.1502.

Step 9:

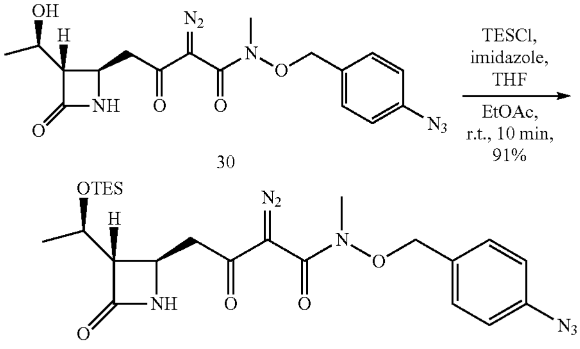

30

31

To a round bottom flask were added azetidinone 30 (570 mg, 1.42 mmol), ethyl acetate (6 mL), and THF (1.5 mL). Imidazole (174 mg, 2.56 mmol) and TESCl (0.34 mL, 1.99 mmol) were added at room temperature and the reaction mixture was stirred for 10 min. The reaction was quenched with water (15 mL). The mixture was partitioned with ethyl acetate (60 mL) and then washed with brine (15×5 mL). The aqueous layer was further extracted with ethyl acetate (2×15 mL). The combined organic extract was dried over anhydrous sodium sulphate, filtered, and concentrated in vacuo. The crude product was purified by flash column chromatography to afford 31 (670 mg, 91%) as a colorless viscous liquid.

Analytical TLC (60% ethyl acetate in n-hexane), $R_f$=0.4; $^1$H NMR (400 MHz, $CDCl_3$) δ 7.34 (d, J=8.3 Hz, 2H), 7.05 (d, J=8.4 Hz, 2H), 6.02 (s, 1H), 4.83 (s, 2H), 4.20 (dq, J=6.0, 5.7 Hz, 1H), 3.99 (dt, J=10.0, 2.4 Hz, 1H), 3.35 (dd, J=17.9, 3.0 Hz, 1H), 3.30 (s, 3H), 2.94-2.79 (m, 2H), 1.22 (d, J=6.2 Hz, 3H), 0.94 (t, J=7.9 Hz, 9H), 0.59 (q, J=8.0 Hz, 6H); $^{13}C$ NMR (100 MHz, $CDCl_3$) δ 192.1, 168.1, 161.7, 141.6, 131.2, 129.6, 119.4, 76.0, 72.6, 65.3, 63.6, 46.6, 45.7, 34.4, 22.7, 6.8, 4.9; HRMS (ESI) calcd. for $C_{23}H_{34}N_7O_5Si$ ([M+H]$^+$) 516.2385, found 516.2361.
Example 11. Preparation of (5R,6S)—N-hydroxy-6-((R)-1-hydroxyethyl)-3-((E)-3-(2-methoxy-4-(((3-oxo-3H-phenoxazin-7-yl)oxy)methyl)phenoxy)prop-1-en-1-yl)-N-methyl-7-oxo-1-azabicyclo[3.2.0]hept-2-ene-2-carboxamide (MCW-006)
Overall Synthesis Scheme:
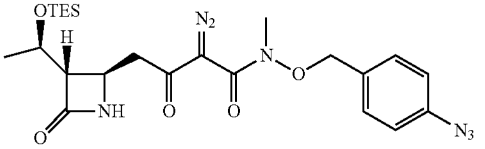
31
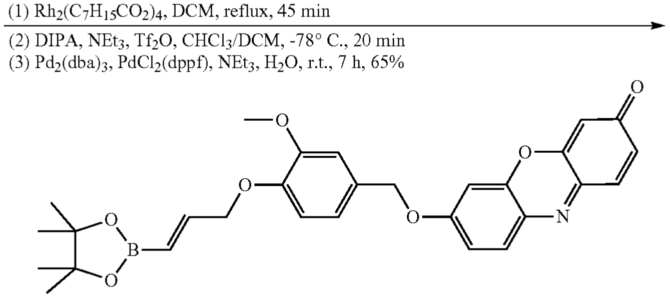
6
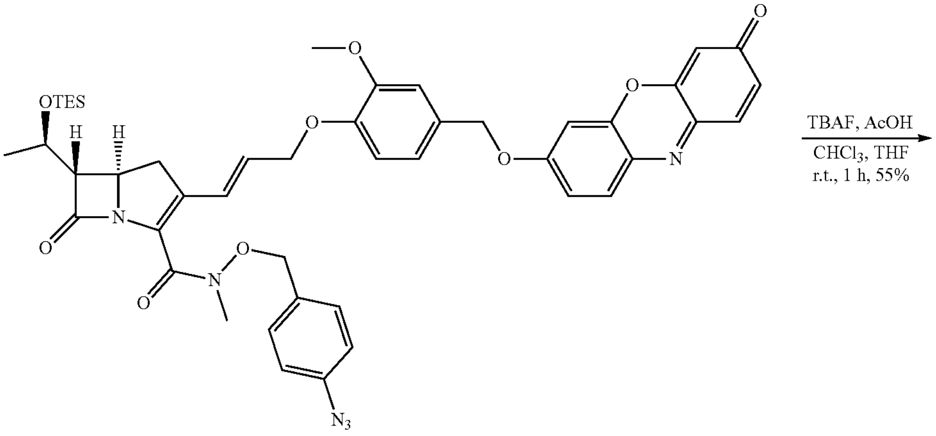
32
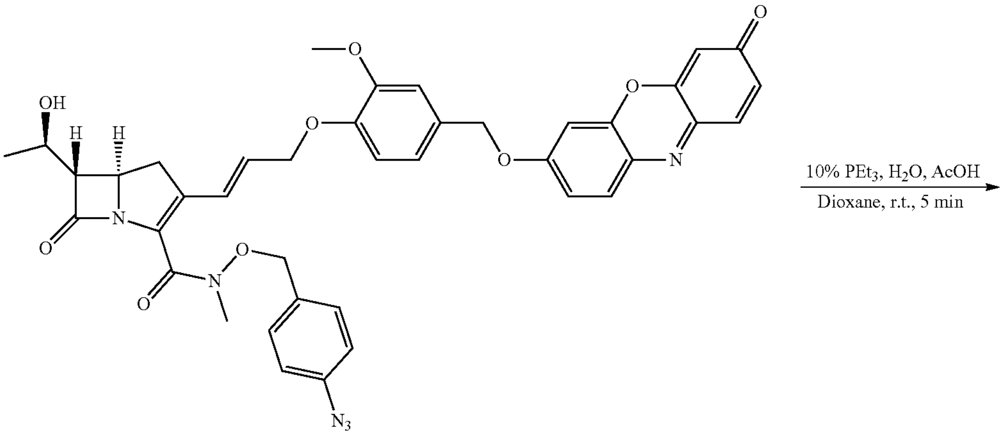
33

-continued

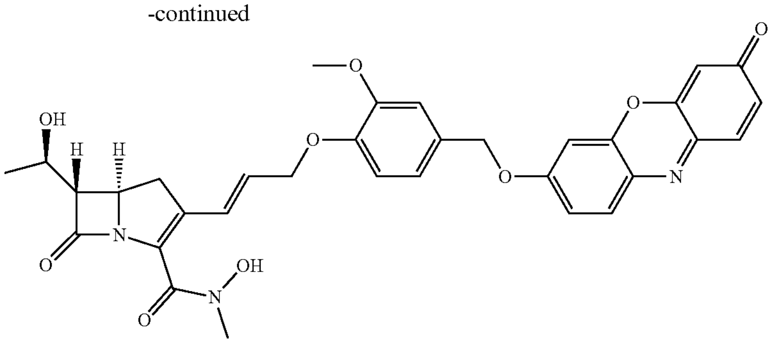

MCW-006

Step 1:

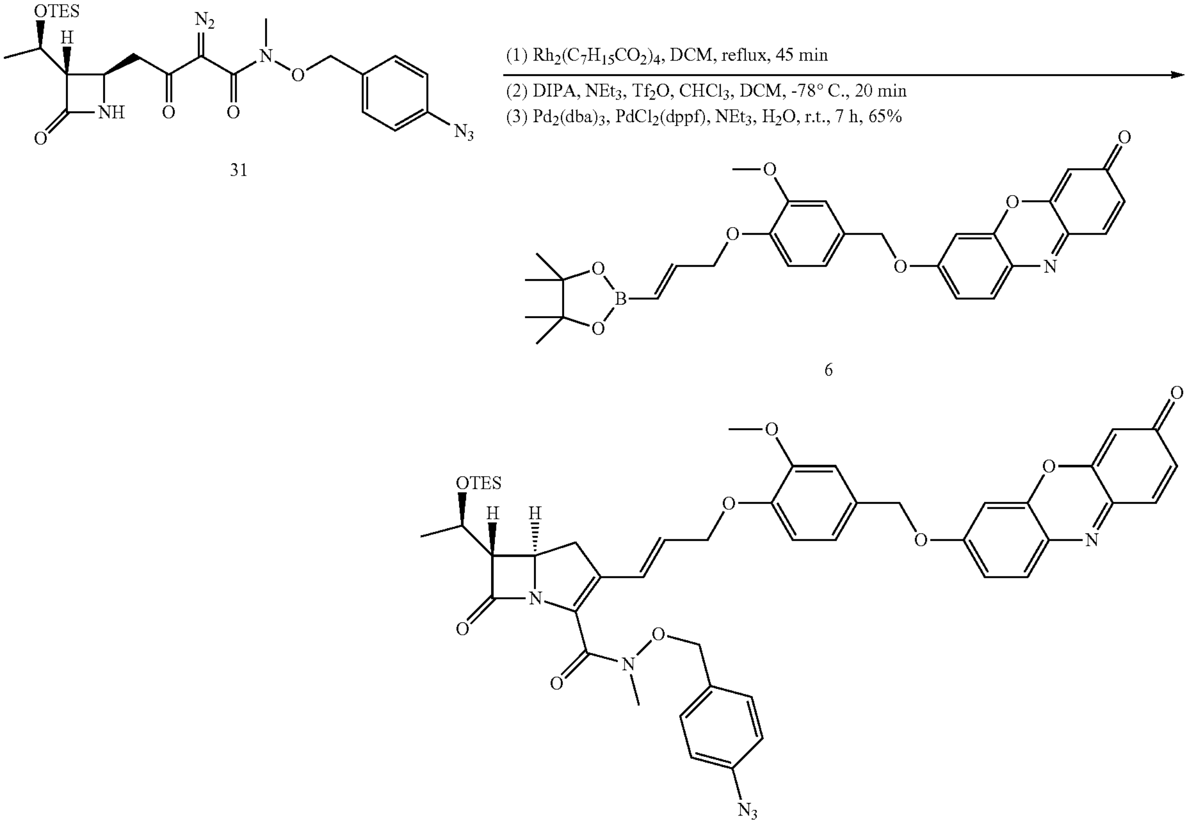

31

6

32

To a round bottom flask were added azetidinone 31 (108 mg, 0.210 mmol) and DCM (2 mL). $Rh_2(C_7H_{15}CO_2)_4$ (0.8 mg, 1 μmol) was then added and the resulting mixture was stirred under reflux for 45 min. When TLC indicated the reaction was complete, the mixture was concentrated in vacuo and used directly for the next step. To a 10 mL round bottom flask were added the crude β-ketoester, $CHCl_3$ (1 mL) and DCM (0.35 mL) at −78° C. DIPA (38 μL, 0.27 mmol) and $NEt_3$ (13 μL, 84 μmol) were then added dropwise and the resulting solution was stirred for 10 min. $Tf_2O$ (45.8 μL, 0.273 mmol) was then added dropwise and the reaction mixture was stirred at −78° C. for 15 min and warmed up to room temperature. When TLC indicated the reaction was complete, the crude triflate was quickly purified by flash column chromatography using silica gel pre-neutralized with $NEt_3$ (0.5% in n-hexane). To the triflate were added $CHCl_3$ (1 mL), $NEt_3$ (44.0 μL, 76 μmol), $H_2O$ (5.0 μL, 0.76 mmol), boronic ester 6 (35.4 mg, 69 μmol), $Pd_2(dba)_3$ (4.7 mg, 5.2 μmol) and $PdCl_2dppf$ (3.8 mg, 5.2 μmol). The resulting solution stirred for 7 h at room temperature. When TLC indicated the reaction was complete, the reaction was quenched with water (5 mL). The mixture was partitioned with ethyl acetate (15 mL) and washed with brine (5 mL). The aqueous layer was further extracted with ethyl acetate (3×5 mL). The combined organic extract was dried over anhydrous sodium sulphate, filtered, and concentrated in vacuo. The crude product was purified by flash column chromatography to afford 32 (38.8 mg, 65%) as an orange solid which was inseparable with boronic ester 6 (3.5 mg). All weights and yield were estimated according to NMR integration.

Analytical TLC (60% ethyl acetate in n-hexane), $R_f$=0.4.

Step 2:

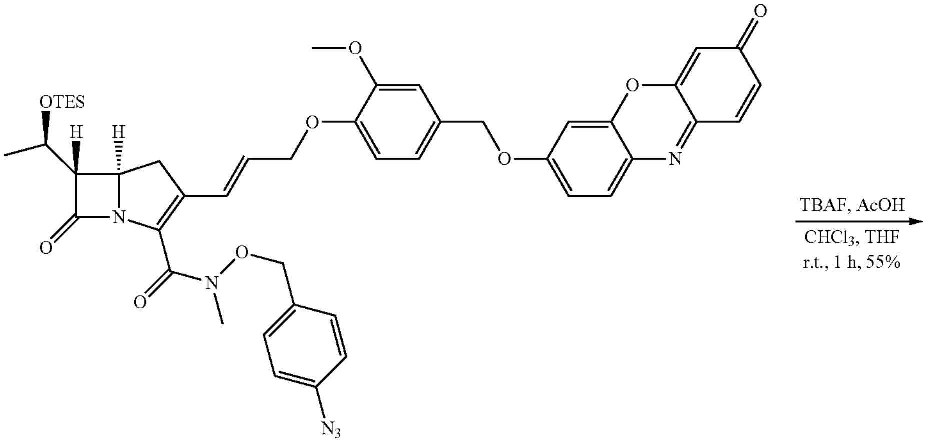

32

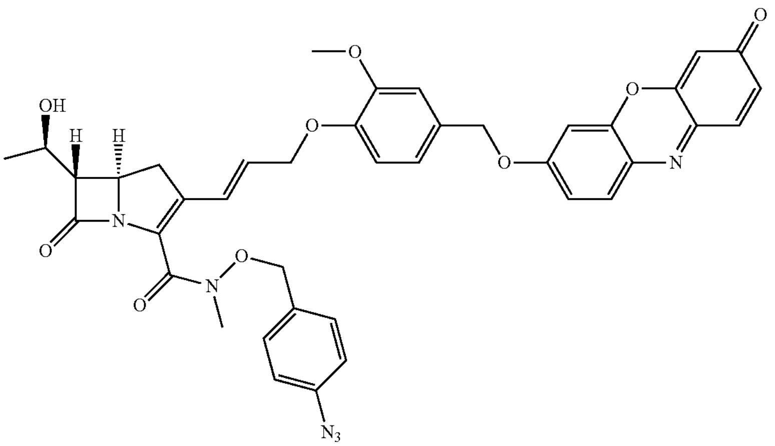

33

To a round bottom flask were added β-lactam 32 (42.3 mg, 49.2 μmol), THF (0.25 mL), and $CHCl_3$ (0.8 mL). AcOH (32.5 μL, 0.542 mmol) and TBAF (492 μL, 0.492 mmol, 1 M in THF) were then added. The reaction mixture was stirred for 1 h at room temperature. When TLC indicated the reaction was complete, the reaction was quenched with water (5 mL). The resulting mixture was partitioned with ethyl acetate (15 mL) and then washed with brine (5 mL). The aqueous layer was further extracted with ethyl acetate (2×5 mL). The combined organic extract was dried over anhydrous sodium sulphate, filtered, and concentrated in vacuo. The crude product was purified by flash column chromatography to afford 33 (20.3 mg, 55%) as an orange solid.

Analytical TLC (10% MeOH in DCM), $R_f$=0.3; $^1$H NMR (500 MHz, $CDCl_3$) δ 7.71 (d, J=8.9 Hz, 1H), 7.43-7.39 (m, 3H), 7.02-6.99 (m, 3H), 6.96-6.95 (m, 2H), 6.89-6.86 (m, 3H), 6.83 (dd, J=9.8, 1.8 Hz, 1H), 6.32 (d, J=1.8 Hz, 1H), 5.93 (dt, J=15.9, 6.1 Hz, 1H), 5.09 (s, 2H), 4.95 (d, J=10.1 Hz, 1H), 4.88 (d, J=10.1 Hz, 1H), 4.69 (dddd, J=13.3, 13.1, 6.8, 5.8 Hz, 2H), 4.28-4.24 (m, 2H), 3.89 (s, 3H), 3.32-3.18 (m, 4H), 3.01 (dd, J=17.0, 10.1 Hz, 1H), 2.94 (dd, J=17.0, 8.1 Hz, 1H), 2.37 (s, 1H), 1.33 (d, J=6.3 Hz, 3H); $^{13}$C NMR (125 MHz, $CDCl_3$) δ 186.3, 176.5, 162.7 (×2, overlapping), 149.8, 149.7, 148.1, 145.6 (×2, overlapping), 140.5, 136.4, 134.7, 134.2, 131.6, 131.5, 131.0, 130.6, 129.8, 128.5, 128.3, 126.2, 120.4, 119.1, 114.3, 113.4, 111.3, 106.7, 101.0, 75.7, 70.9, 69.5, 66.7, 65.2, 56.0, 52.9, 35.8 (×2, overlapping), 21.8; HRMS (ESI) calcd. for $C_{40}H_{37}N_6O_9$ ($[M+H]^+$) 745.2617, found 745.2586.

Step 3:

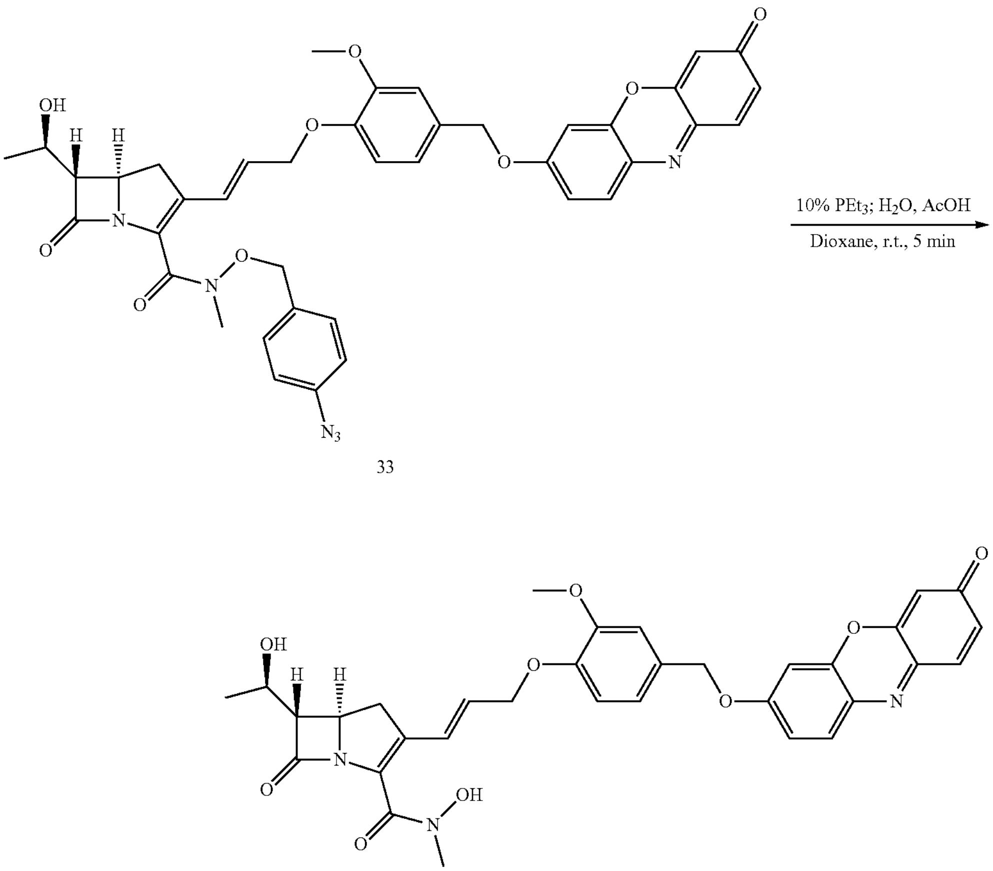

33

MCW-006

To a round bottom flask were added β-lactam 33 (2.9 mg, 3.9 μmol), dioxane (0.3 mL) and $H_2O$ (30 μL). AcOH (3 μL) and $PEt_3$ (15.1 μL, 8.4 μmol, 10% in n-hexane) were added at room temperature and the reaction mixture was stirred for 5 min. The crude mixture was subjected to preparative C18 reverse phase HPLC purification using 0.01% TFA in water and $CH_3CN$ as eluent, and used directly for fluorescence assay. HRMS (ESI) calcd. for $C_{33}H_{32}N_3O_9$ ($[M+H]^+$) 614.2133, found 614.2114.

Example 12. Preparation of 4-azidobenzyl (R)-2-diazo-3-oxo-4-((2R,3S)-4-oxo-3-((R)-1-((triethylsilyl)oxy)ethyl)azetidin-2-yl)pentanoate (38)

Overall Synthesis Scheme:

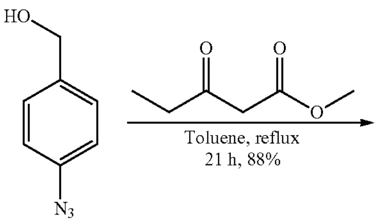

7

-continued

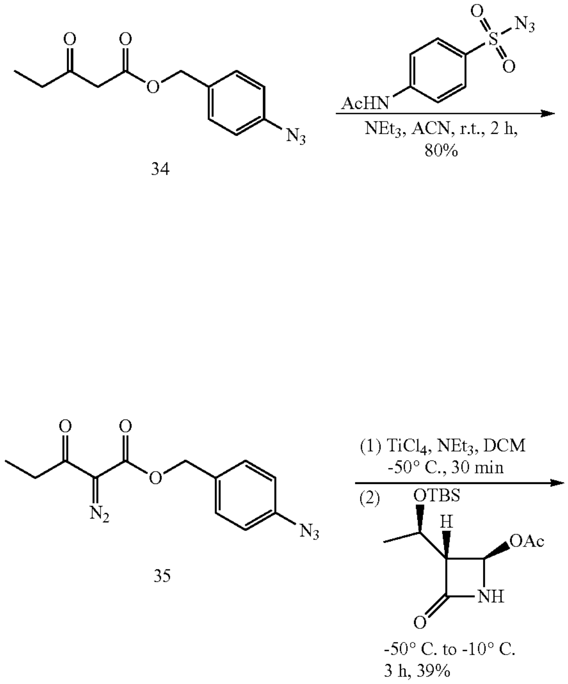

34

35

-continued

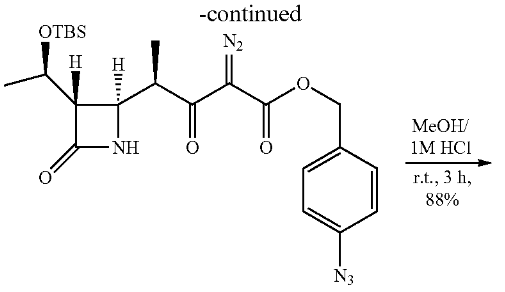

36

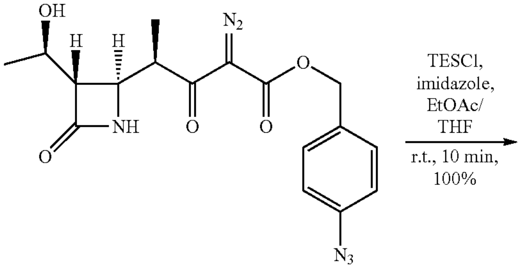

37

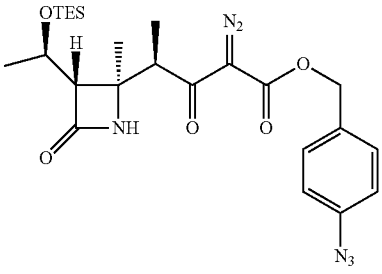

38

Step 1:

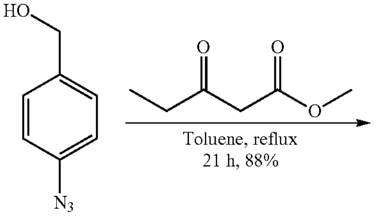

7

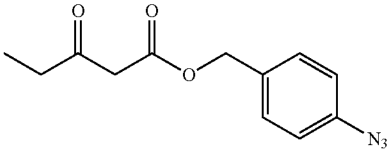

34

To a round bottom flask were added alcohol 7 (1.50 g, 10.1 mmol), toluene (15 mL) and ester 34 (1.20 mL, 9.57 mmol). The reaction mixture was stirred for 21 h under reflux. When TLC indicated the reaction was complete, the reaction mixture was concentrated and purified by flash column chromatography to afford 34 (2.02 g, 88%) as a pale yellow liquid.

Analytical TLC (40% ethyl acetate in n-hexane), $R_f$=0.6; $^1$H NMR (500 MHz, $CDCl_3$) δ 7.35 (d, J=8.5 Hz, 2H), 7.02 (d, J=8.5 Hz, 2H), 5.14 (s, 3H), 3.48 (s, 2H), 2.54 (q, J=7.3 Hz, 2H), 1.07 (t, J=7.3 Hz, 3H); $^{13}$C NMR (125 MHz, $CDCl_3$) δ 203.0, 167.1, 140.3, (132.1), 130.1, 119.2, 66.5, 48.9, 36.4, 7.6; LRMS (EI) 247.1 ([M]$^+$, 5), 219.0 (26), 148.0 (100), 99.0 (25); HRMS (EI) calcd. for $C_{12}H_{13}N_3O_3$ ([M]$^+$) 247.0951, found 247.0951.

Note: the NMR spectra show an equilibrium mixture of keto and enol tautomers in a ratio of 98:2. Observable signals corresponding to the minor species are shown in parentheses.

Step 2:

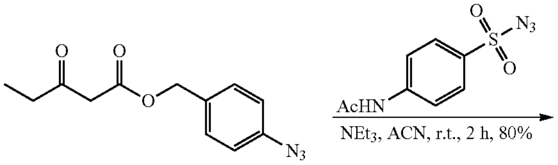

34

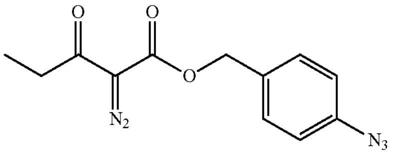

35

To a round bottom flask were added ketone 34 (2.06 g, 8.34 mmol), ACN (20 mL) and 4-acetamidobenzenesulfonyl azide (2.00 g, 8.34 mmol) at room temperature. $NEt_3$ (1.74 mL, 10.8 mmol) was then added and the reaction mixture was stirred for 2 h. When TLC indicated the reaction was complete, the reaction mixture was concentrated and filtered through silica gel. The resulting crude product was concentrated and purified by flash column chromatography to afford 35 (1.82 g, 80%) as a pale yellow liquid.

Analytical TLC (40% ethyl acetate in n-hexane), $R_f$=0.6; $^1$H NMR (500 MHz, $CDCl_3$) δ 7.37 (d, J=8.4 Hz, 2H), 7.04 (d, J=8.4 Hz, 2H), 5.22 (s, 2H), 2.85 (q, J=7.3 Hz, 2H), 1.13 (t, J=7.3 Hz, 3H); $^{13}$C NMR (125 MHz, $CDCl_3$) δ 193.2, 161.2, 140.5, 131.9, 130.1, 119.3, 75.6, 66.3, 33.8, 8.2; LRMS (EI) 273.0 ([M]$^+$, 9), 148.0 (23), 104.0 (100), 97.0 (34); HRMS (EI) calcd. for $C_{12}HN_5O_3$ ([M]$^+$) 273.0856, found 273.0865.

Step 3:

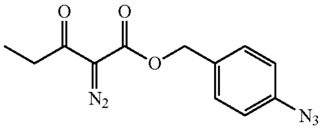

35

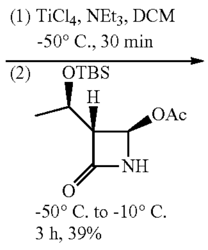

-continued

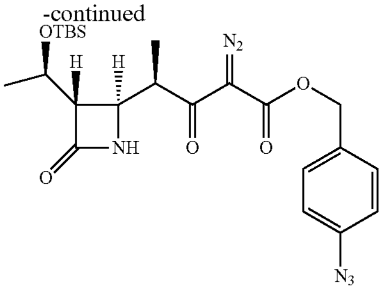

36

To a round bottom flask were added β-ketoester 35 (1.53 g, 5.61 mmol) and DCM (10 mL). $TiCl_4$ (0.54 mL, 4.91 mmol) was added at −50° C. and the resulting mixture was stirred for 15 min. $NEt_3$ (1.50 mL, 9.35 mmol) was then added slowly, and the reaction mixture was stirred for 30 min. The azetidinone (1.34 g, 4.68 mmol) dissolved in DCM (5 mL) was added dropwise at −50° C. This reaction mixture was warmed up to −10° C. over 3 h. The reaction was quenched with water (30 mL). The mixture was partitioned with ethyl acetate (90 mL) and then washed with brine (30 mL). The aqueous layer was further extracted with ethyl acetate (2x30 mL). The combined organic extract was dried over anhydrous sodium sulphate, filtered, and concentrated in vacuo. The crude product was purified by flash column chromatography to afford 36 (916 mg, 39%) as a pale yellow oil.

Analytical TLC (40% ethyl acetate in n-hexane), $R_f$=0.4; $^1$H NMR (500 MHz, $CDCl_3$) δ 7.34 (d, J=8.4 Hz, 2H), 7.01 (d, J=8.4 Hz, 2H), 6.17 (s, 1H), 5.19 (s, 2H), 4.21-4.07 (m, 1H), 3.95-3.75 (m, 2H), 2.92 (dd, J=3.7, 1.7 Hz, 1H), 1.14 (t, J=7.2 Hz, 6H), 0.82 (s, 9H), 0.03 (s, 3H), 0.02 (s, 3H); $^{13}$C NMR (125 MHz, $CDCl_3$) δ 194.4, 168.2, 160.8, 140.6, 131.5, 130.2, 119.2, 76.2, 66.5, 65.0, 61.1, 51.5, 43.2, 25.7, 22.4, 17.8, 12.3, −4.4, −5.1; LRMS (ESI) 501.3 ([M+H]$^+$); HRMS (ESI) calcd. for $C_{23}H_{33}N_6O_5Si$ ([M+H]$^+$) 501.2287, found 501.2258.

Step 4:

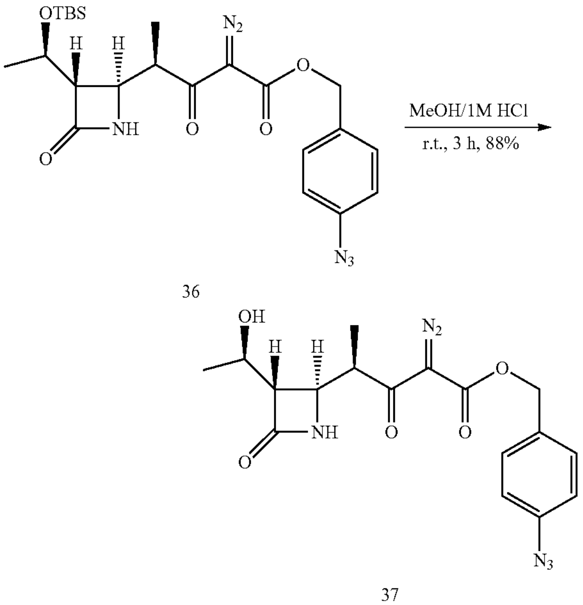

36

37

To a round bottom flask were added azetidinone 36 (908 mg, 1.81 mmol) and MeOH (9 mL). HCl (3 mL, 1 M aq) was then added. The mixture was stirred at room temperature for 3 h. When TLC indicated the reaction was complete, the reaction was quenched with water (30 mL). The resulting mixture was partitioned with ethyl acetate (90 mL) and then washed with saturated $NaHCO_3$ (30 mL) and brine (30 mL). The aqueous layer was further extracted with ethyl acetate (3x30 mL). The combined organic extract was dried over anhydrous sodium sulphate, filtered, and concentrated in vacuo. The crude product was purified by flash column chromatography to afford 37 (615 mg, 88%) as a yellow viscous liquid.

Analytical TLC (60% ethyl acetate in n-hexane), $R_f$=0.3; $^1$H NMR (500 MHz, $CDCl_3$) δ 7.38 (d, J=8.4 Hz, 2H), 7.10 (s, 1H), 7.03 (d, J=8.4 Hz, 2H), 5.24 (s, 2H), 4.11 (dq, J=7.6, 5.2 Hz, 1H), 3.85 (dd, J=6.4, 1.6 Hz, 1H), 3.81 (dq, J=7.4, 6.6 Hz, 1H), 3.73 (s, 1H), 2.91 (d, J=5.5 Hz, 1H), 1.26 (d, J=6.3 Hz, 3H), 1.21 (d, J=6.8 Hz, 3H); $^{13}$C NMR (125 MHz, $CDCl_3$) δ 194.6, 168.4, 160.3, 140.1, 131.2, 129.9, 118.9, 76.1, 66.2, 64.8, 61.4, 52.7, 44.5, 20.7, 12.9; LRMS (EI) 386.0 ([M]$^+$, 1), 358.0 (2), 330.0 (4), 149.0 (30), 104.0 (100); HRMS (EI) calcd. for $C_{17}H_{18}N_6O_5$ ([M]$^+$) 386.1333, found 386.1330.

Step 5:

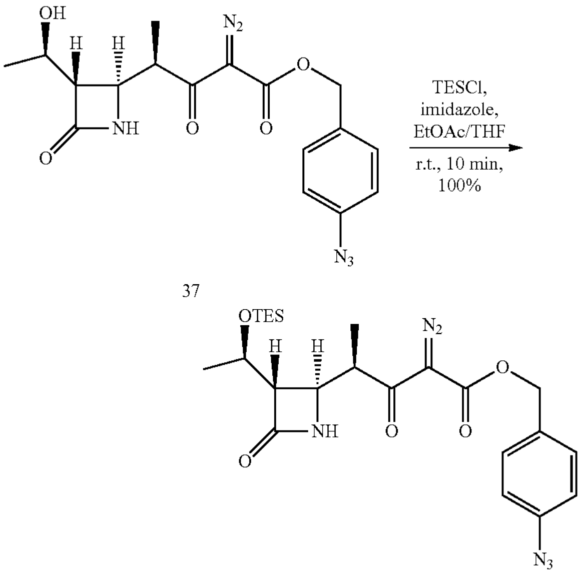

37

38

To a round bottom flask were added azetidinone 37 (559 mg, 1.45 mmol), ethyl acetate (6 mL), and THF (1.5 mL). Imidazole (177 mg, 2.61 mmol) and TESCl (0.34 mL, 2.03 mmol) were added at room temperature and the reaction mixture was stirred for 10 min. The reaction was quenched with water (15 mL). The resulting mixture was partitioned with ethyl acetate (60 mL) and then washed with brine (15 mL). The aqueous layer was further extracted with ethyl acetate (2x15 mL). The combined organic extract was dried over anhydrous sodium sulphate, filtered, and concentrated in vacuo. The crude product was purified by flash column chromatography to afford 38 (863 mg, 100%) as a colorless viscous liquid.

Analytical TLC (60% ethyl acetate in n-hexane), $R_f$=0.7; $^1$H NMR (500 MHz, $CDCl_3$) δ 7.37 (d, J=8.1 Hz, 2H), 7.05

(d, J=7.8 Hz, 2H), 6.11-5.89 (m, 1H), 5.22 (dd, J=13.7, 12.6 Hz, 2H), 4.17 (dq, J=6.4, 5.0 Hz, 1H), 3.90 (dq, J=6.9, 6.4 Hz, 2H), 3.00-2.90 (m, 1H), 1.21 (d, J=6.2 Hz, 3H), 1.16 (d, J=6.9 Hz, 3H), 0.94 (t, J=7.9 Hz, 9H), 0.59 (q, J=8.0 Hz, 6H); $^{13}C$ NMR (125 MHz, $CDCl_3$) δ 194.4, 168.1, 160.9, 140.7, 131.5, 130.2, 119.3, 76.2, 66.6, 65.3, 61.2, 51.9, 43.3, 22.6, 12.2, 6.8, 4.9; LRMS (ESI) 501.3 ($[M+H]^+$); HRMS (ESI) calcd. for $C_{23}H_{33}N_6O_5Si$ ($[M+H]^+$) 501.2287, found 501.2255.
Example 13. Preparation of (4S,5R,6S)-6-((R)-1-hydroxyethyl)-3-((E)-3-(2-methoxy-4-(((3-oxo-3H-phenoxazin-7-yl)oxy)methyl)phenoxy)prop-1-en-1-yl)-4-methyl-7-oxo-1-azabicyclo[3.2.0]hept-2-ene-2-carboxylic acid (MCW-007)
Overall Synthetic Scheme:
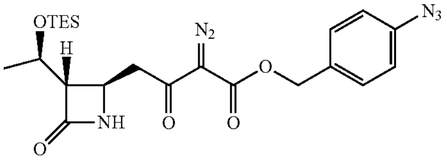
38
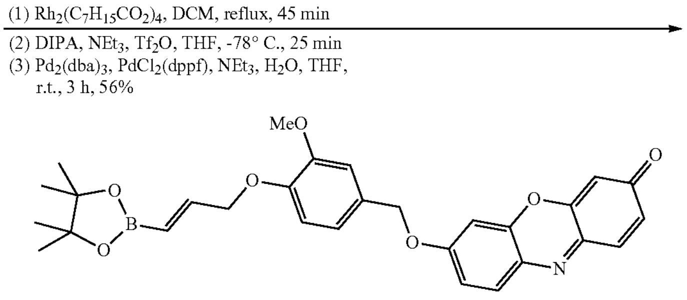
6
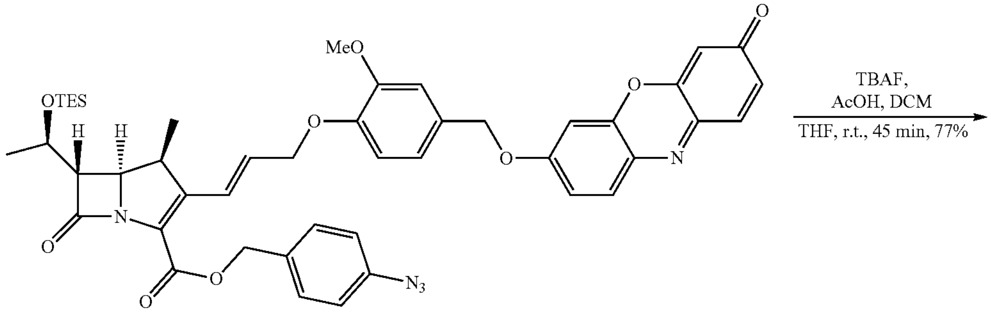
39
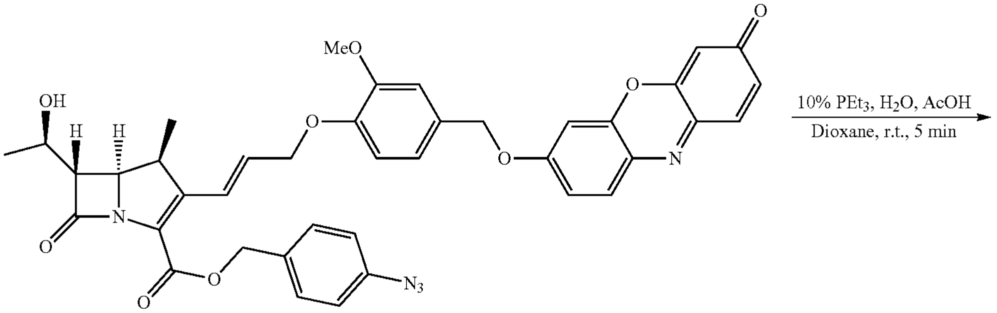
40
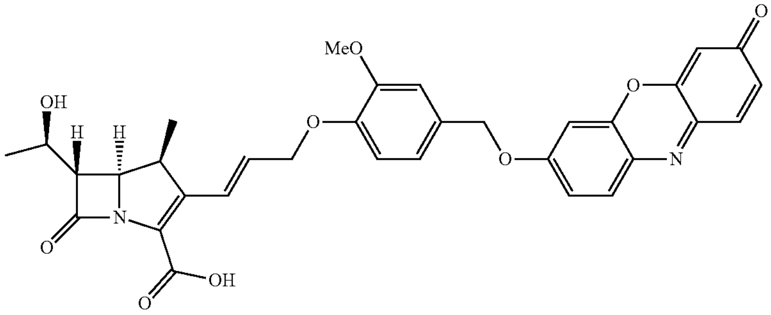
MCW-007

Step 1:

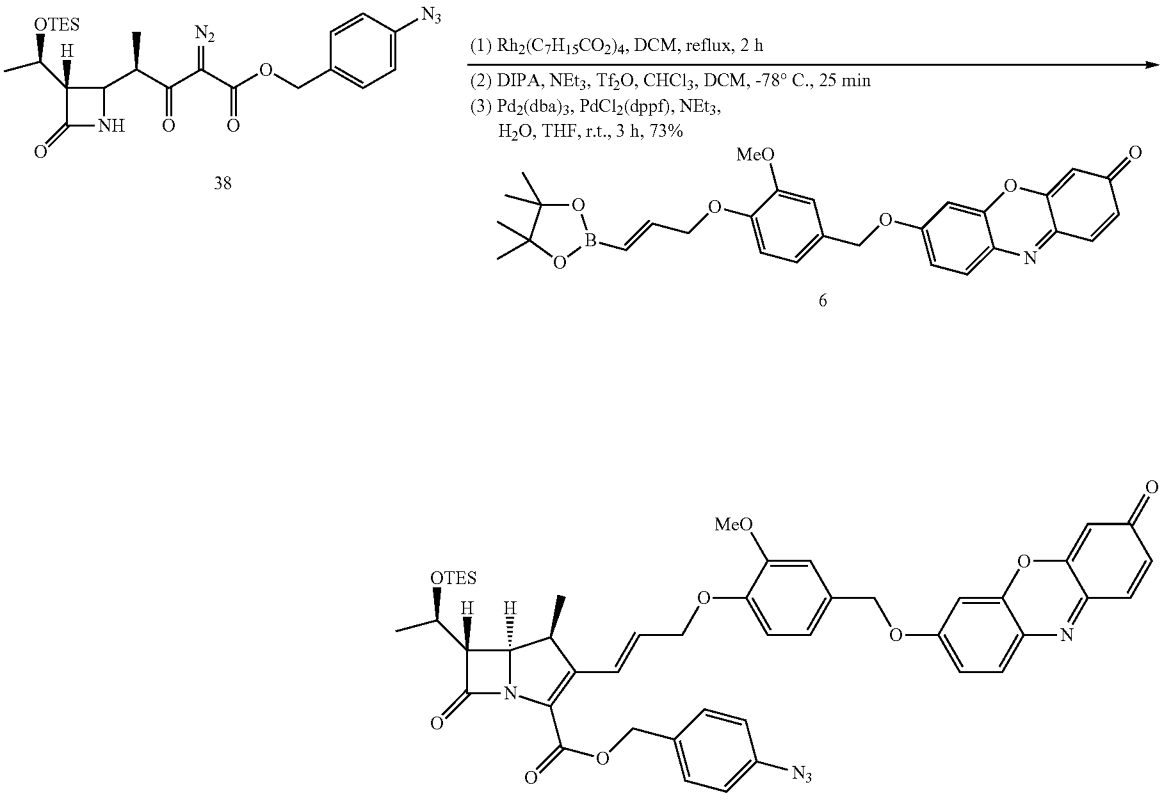

38

6

39

To a round bottom flask were added azetidinone 38 (117 mg, 234 μmol) and DCM (1.5 mL). Rhodium octanoate dimer (2.7 mg, 3 μmol) was then added and the resulting mixture was stirred under reflux for 2 h. When TLC indicated the reaction was complete, the mixture was concentrated and used directly for the next step.

To a round bottom flask were added the crude ketone, $CHCl_3$ (1 mL), and DCM (0.35 mL) at −78° C. DIPA (43 μL, 304 μmol) and $NEt_3$ (15 μL, 93.5 μmol) were then added dropwise and the resulting solution was stirred for 10 min. $Tf_2O$ (51 μL, 304 μmol) was then added dropwise and the reaction mixture was stirred at −78° C. for 15 min. When TLC indicated the reaction was complete, $NEt_3$ (125 μL, 779 μmol), $H_2O$ (13.7 μL, 779 μmol), boronic ester 6 (100 mg, 195 μmol), $Pd_2(dba)_3$ (13.1 mg, 14.3 μmol) and $PdCl_2dppf$ (10.5 mg, 14.3 μmol) were added. The resulting solution was warmed up to room temperature and stirred for 3 h. When TLC indicated the reaction was complete, the reaction was quenched with water (5 mL). The mixture was partitioned with ethyl acetate (15 mL) and then washed with brine (5 mL). The aqueous layer was further extracted with ethyl acetate (3×5 mL). The combined organic extract was dried over anhydrous sodium sulphate, filtered, and concentrated in vacuo. The crude product was purified by flash column chromatography to afford 39 (123 mg, 73%) as an orange solid.

Analytical TLC (40% ethyl acetate in n-hexane), $R_f$=0.2; $^1$H NMR (400 MHz, 10% $C_6D_6$ in $CDCl_3$) δ 7.60 (d, J=8.9 Hz, 1H), 7.44 (d, J=16.3 Hz, 1H), 7.37 (d, J=8.4 Hz, 2H), 7.25 (d, J=9.8 Hz, 1H), 6.93-6.84 (m, 5H), 6.84-6.67 (m, 3H), 6.22 (d, J=1.9 Hz, 1H), 6.11 (dt, J=16.3, 5.9 Hz, 1H), 5.20 (d, J=12.7 Hz, 1H), 5.09 (d, J=12.7 Hz, 1H), 4.91 (s, 2H), 4.66-4.55 (m, 2H), 4.15 (dq, J=6.7, 6.0 Hz, 1H), 4.06 (dd, J=9.3, 2.5 Hz, 1H), 3.77 (s, 3H), 3.23-3.05 (m, 2H), 1.22 (d, J=6.1 Hz, 3H), 1.06 (d, J=7.3 Hz, 3H), 0.94 (t, J=8.0 Hz, 9H), 0.57 (q, J=7.6 Hz, 6H); $^{13}$C NMR (100 MHz, 10% $C_6D_6$ in $CDCl_3$) δ 185.8, 172.2, 162.4, 160.8, 149.7, 149.4, 148.0, 146.7, 145.4, 145.2, 139.6, 134.4, 133.8, 132.2, 132.1, 131.3, 129.4, 128.5, 128.2, 126.4, 125.2, 120.2, 118.8, 113.9, 113.6, 111.3, 106.4, 100.7, 70.6, 69.5, 65.9, 65.9, 59.0, 56.2, 55.6, 39.1, 22.4, 16.4, 6.6, 4.8; LRMS (ESI) 844.3 ([M+H]$^+$); HRMS (ESI) calcd. for $C_{46}H_{50}N_5O_9Si$ ([M+H]$^+$) 844.3383, found 844.3342.

Step 2:

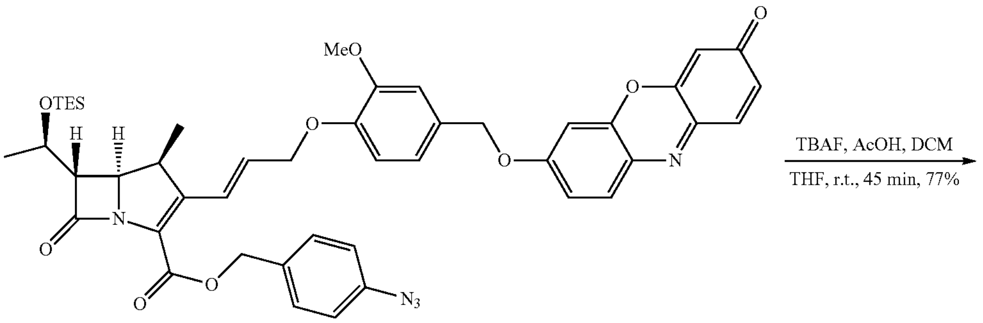

39

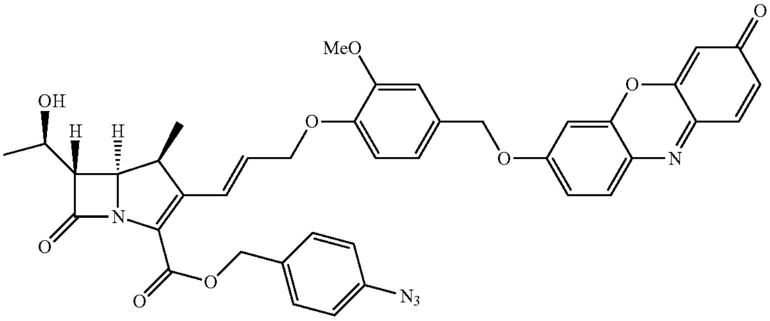

40

To a round bottom flask were added β-lactam 39 (120 mg, 137 μmol), THF (0.75 mL), and $CHCl_3$ (2 mL). AcOH (86.4 μL, 1.51 mmol) and TBAF (1.38 mL, 1.38 mmol, 1 M in THF) were added at room temperature and the reaction mixture was stirred for 45 min. When TLC indicated the reaction was complete, the reaction was quenched with water (5 mL). The resulting mixture was partitioned with ethyl acetate (15 mL) and then washed with brine (5 mL). The aqueous layer was further extracted with ethyl acetate (2×5 mL). The combined organic extract was dried over anhydrous sodium sulphate, filtered, and concentrated in vacuo. The crude product was purified by flash column chromatography to afford 40 (77.6 mg, 77%) as an orange solid.

Analytical TLC (80% ethyl acetate in n-hexane), $R_f$=0.2; $^1H$ NMR (400 MHz, $CDCl_3$) δ 7.72 (d, J=8.9 Hz, 1H), 7.49-7.37 (m, 4H), 7.06-6.94 (m, 5H), 6.92-6.86 (m, 2H), 6.84 (dd, J=9.8, 2.1 Hz, 1H), 6.32 (d, J=2.1 Hz, 1H), 6.23 (dt, J=16.3, 6.0 Hz, 1H), 5.31 (d, J=12.6 Hz, 1H), 5.18 (d, J=12.6 Hz, 1H), 5.11 (s, 2H), 4.76-4.74 (m, 2H), 4.24 (dq, J=7.0, 6.3 Hz, 1H), 4.18 (dd, J=9.2, 2.6 Hz, 1H), 3.90 (s, 3H), 3.41 (dq, J=8.1, 7.6 Hz, 1H), 3.25 (dd, J=6.9, 2.6 Hz, 1H), 2.13 (s, 1H), 1.36 (d, J=6.3 Hz, 3H), 1.20 (d, J=7.3 Hz, 3H); $^{13}C$ NMR (100 MHz, 10% $C_6D_6$ in $CDCl_3$) δ 186.4, 172.4, 162.8, 161.1, 150.1, 149.9, 148.2, 147.3, 145.72, 145.66, 140.1, 134.8, 134.3, 132.7, 132.4, 131.7, 129.9, 128.8, 128.6, 126.7, 125.5, 120.5, 119.2, 114.4, 114.0, 111.5, 106.8, 101.1, 71.0, 69.9, 66.4, 66.0, 58.7, 56.6, 56.1, 39.5, 21.9, 16.7; LRMS (ESI) 730.3 ($[M+H]^+$); HRMS (ESI) calcd. for $C_{40}H_{36}N_5O_9$ ($[M+H]^+$) 730.2519, found 730.2481.

Step 3:

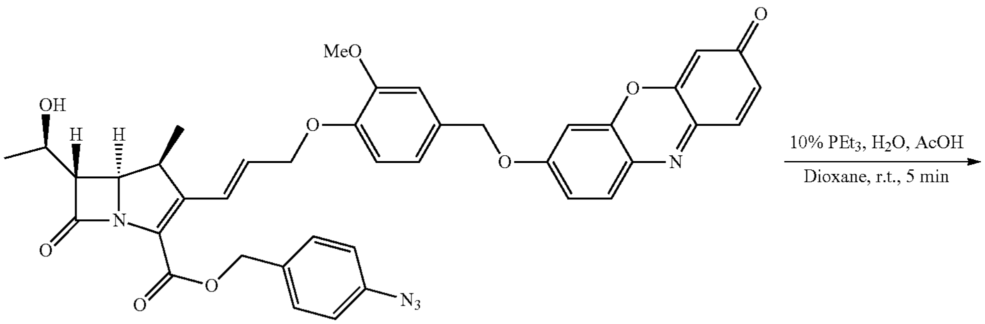

40

-continued

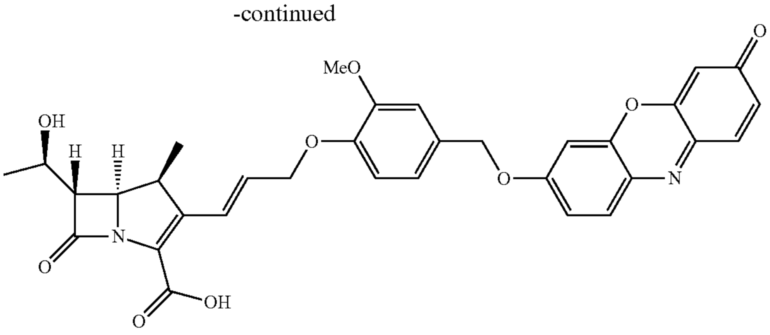

MCW-007

To a round bottom flask were added β-lactam 40 (5.0 mg, 6.8 μmol), dioxane (0.5 mL), and $H_2O$ (50 μL). AcOH (5 μL) and $PEt_3$ (24.5 μL, 13.6 μmol, 10% in n-hexane) at room temperature and the reaction mixture was stirred for 5 min. The crude mixture was subjected to preparative C18 reverse phase HPLC purification using 0.01% TFA in water and $CH_3CN$ as eluent, and used directly for fluorescence assay. Alternatively, the eluent was partitioned between PBS pH 7.4 buffer (2 mL), DCM (50 mL) with AcOH (50 μL). The organic extract was concentrated to afford 40 (3.2 mg, 78%) as a red solid.

$^1H$ NMR (500 MHz, $CDCl_3$) δ 7.72 (d, J=8.9 Hz, 1H), 7.43 (d, J=9.8 Hz, 1H), 7.37 (d, J=16.3 Hz, 1H), 7.02 (dd, J=8.9, 2.7 Hz, 1H), 6.98-6.96 (m, 2H), 6.91 (d, J=8.7 Hz, 1H), 6.87 (d, J=2.7 Hz, 1H), 6.85 (dd, J=9.8, 2.0 Hz, 1H), 6.33 (d, J=2.0 Hz, 1H), 6.25 (dt, J=16.3, 6.0 Hz, 1H), 5.11 (s, 2H), 4.79 (d, J=6.0 Hz, 2H), 4.28 (dq, J=6.8, 5.9 Hz, 1H), 4.24 (dd, J=9.2, 2.7 Hz, 1H), 3.91 (s, 3H), 3.46 (dq, J=7.6, 7.1 Hz, 1H), 3.33 (dd, J=6.4, 2.6 Hz, 1H), 1.37 (d, J=6.2 Hz, 3H), 1.23 (d, J=7.3 Hz, 3H); HRMS (ESI) calcd. for $C_{33}H_{31}N_2O_9$ ([M+H]$^+$) 599.2024, found 599.2010.

The OH peak was not observed in $^1H$ NMR due to rapid exchange with signal from residual water.

Example 14. Preparation of 7-((4-(4,4,5,5-tetramethyl-1,3,2-dioxaborolan-2-yl)benzyl)oxy)-3H-phenoxazin-3-one (43)

Overall Synthesis Scheme:

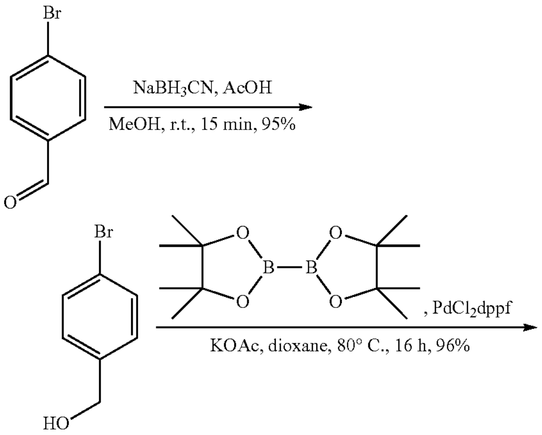

41

-continued

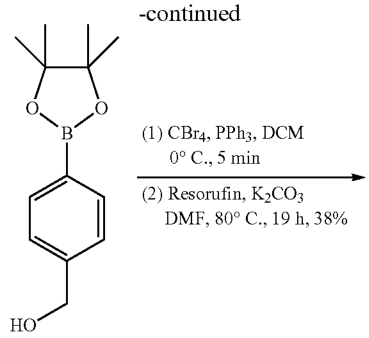

42

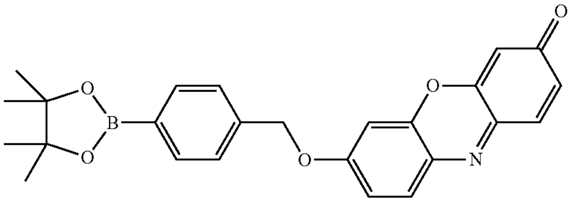

43

Step 1:

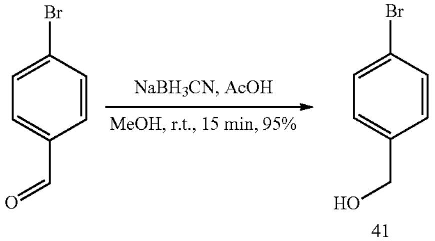 [SMILES: O=Cc1ccc(Br)cc1 ; OCc1ccc(Br)cc1]

41

To a round bottom flask were added p-bromobenzaldehyde (500 mg, 2.70 mmol), MeOH (5 mL), AcOH (773 μL, 13.5 mmol), and $NaBH_3CN$ (339 mg, 5.41 mmol) at room temperature and the resulting solution was stirred for 15 minutes. When TLC indicated the reaction was completed, the reaction was quenched with water (5 mL). The resulting mixture was diluted with ethyl acetate (15 mL) and then washed with brine (1×5 mL). The aqueous layer was further extracted with ethyl acetate (3×5 mL). The organic layer was dried over anhydrous sodium sulphate, filtered, and concentrated in vacuo. The crude product was purified by flash column chromatography to obtain the purified product 41 (479 mg, 95%) as a colorless oil.

Analytical TLC (silica gel 60), 50% ethylacetate in n-hexane, $R_f$=0.5; $^1H$ NMR (300 MHz, $CDCl_3$) δ 7.39 (d, J=8.4 Hz, 2H), 7.08 (d, J=8.3 Hz, 2H), 4.45 (s, 2H), 3.55 (s, 1H); $^{13}C$ NMR (75 MHz, $CDCl_3$) δ 139.5, 131.4, 128.4, 121.2, 63.9; LRMS (EI) 188.0 ([M]$^+$, 52), 186.0 (13), 107.1 (77), 79 (100), 77.0 (86). The characterization data are consistent with the reported data (*Org Lett,* 2007, 9, 5429)

Step 2:

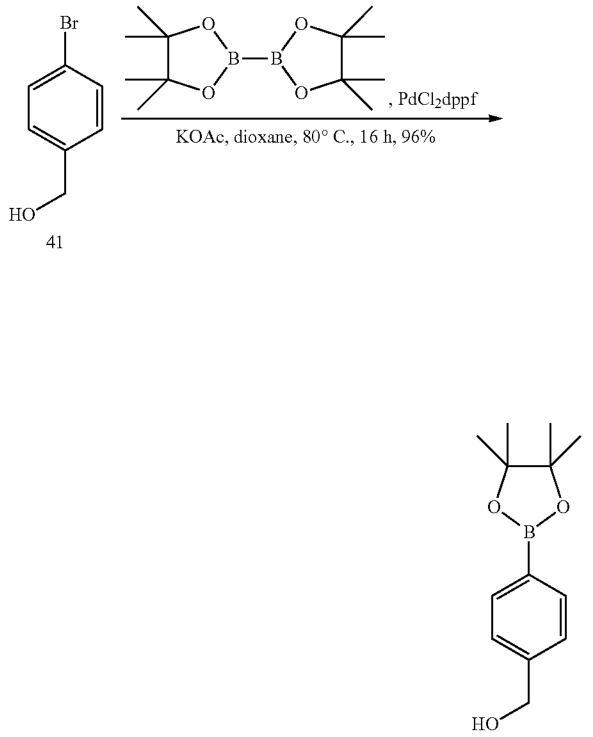

41

42

To a round bottom flask were added the alcohol 41 (250 mg, 1.34 mmol), bis(pinacolato)diboron (512 mg, 2.02 mmol), KOAc (395 mg, 4.03 mmol), Pd(dppf)$Cl_2$ (98.0 mg, 0.134 mmol), and degassed dioxane (4 mL) at 80° C. The resulting solution was stirred for 16 h. When TLC indicated the reaction was complete, the reaction mixture was diluted with ethyl acetate (15 mL) and filtered through silica gel. The organic fraction was washed with water (5 mL) and then brine (1×5 mL). The aqueous layer was further extracted with ethyl acetate (3×5 mL). The organic layer was dried over anhydrous sodium sulphate, filtered, and concentrated. The crude product was purified by flash column chromatography to obtain the purified product 42 (303 mg, 96%) as a colorless oil.

Analytical TLC (silica gel 60), 50% ethyl acetate in n-hexane, $R_f$=0.5; $^1H$ NMR (400 MHz, $CDCl_3$) δ 7.75 (d, J=7.9 Hz, 2H), 7.28 (d, J=7.8 Hz, 2H), 4.59 (s, 2H), 3.36 (s, 1H), 1.31 (s, 12H); $^{13}C$ NMR (100 MHz, $CDCl_3$) δ 144.1, 134.8, 125.9, 83.7, 64.6, 24.7; LRMS (EI) 234.1 ([M]$^+$, 33), 219.1 (44), 148.1 (48), 135.0 (100); HRMS (EI) calcd. for $C_{13}H_{19}BO_3$ ([M]$^+$) 234.1422, found 234.1424.

The $^{13}C$ NMR signal corresponding to the carbon directly attached to the boron atom was not reported due to quadrupolar broadening.

Step 3:

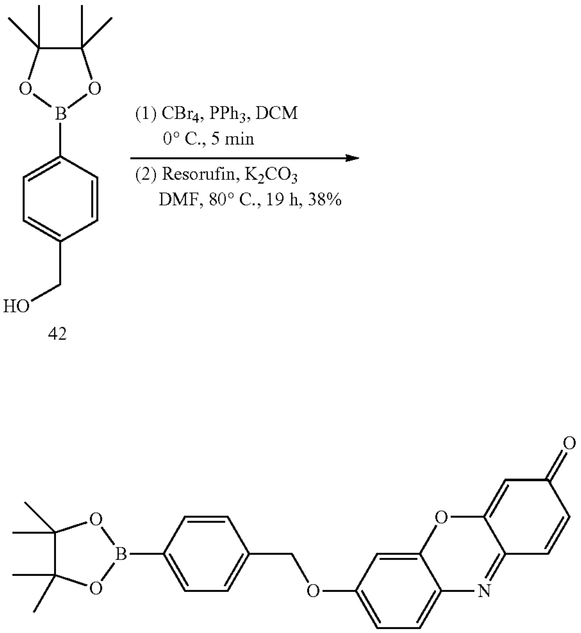

42

43

To a round bottom flask were added alcohol 42 (160 mg, 0.685 mmol), DCM (4 mL), and $PPh_3$ (323 mg, 1.23 mmol) at 0° C. $CBr_4$ (409 mg, 1.23 mmol) was then added and the resulting mixture was stirred for 5 minutes. When TLC indicated the reaction was complete, the reaction was quenched with water (5 mL). The resulting mixture was diluted with ethyl acetate (15 mL) and then washed with brine (1×5 mL). The aqueous layer was further extracted with ethyl acetate (3×5 mL). The organic layer was dried over anhydrous sodium sulphate, filtered, and concentrated. The crude product was quickly purified by flash column chromatography and eluted with 10% ethyl acetate in n-hexane to remove triphenylphosphin oxide.

To a round bottom flask were added the crude product bromide, DMF (1.5 mL), resorufin (292 mg, 1.37 mmol), and $K_2CO_3$ (189 mg, 1.37 mmol) at room temperature, and the reaction mixture was stirred for 19 h. When TLC indicated the reaction was complete, the reaction mixture was dissolved in DCM (40 mL) and the resulting solution was filtered through silica gel. The crude product was purified by flash column chromatography to obtain the purified product 43 (111 mg, 38%) as a red-orange solid.

Analytical TLC (silica gel 60), 50% ethyl acetate in n-hexane, $R_f$=0.5; $^1H$ NMR (400 MHz, $CDCl_3$) δ 7.86 (d, J=7.9 Hz, 2H), 7.70 (d, J=8.9 Hz, 1H), 7.45-7.40 (m, 3H), 7.00 (dd, J=8.9, 2.5 Hz, 1H), 6.89-6.78 (m, 2H), 6.31 (d, J=1.9 Hz, 1H), 5.20 (s, 2H), 1.35 (s, 12H); $^{13}C$ NMR (100 MHz, $CDCl_3$) δ 186.3, 162.6, 149.8, 145.7, 145.6, 138.5, 135.2, 134.7, 134.3, 131.6, 128.5, 126.5, 114.3, 106.8, 101.1, 84.0, 70.8, 24.9; LRMS (EI) 429.1 ([M]$^+$, 9), 217.2 (100); HRMS (EI) calcd. for $C_{25}H_{24}BNO_5$ ([M]$^+$) 429.1742, found 429.1739.

The $^{13}C$ NMR signal corresponding to the carbon directly attached to the boron atom was not reported due to quadrupolar broadening.

Example 15. Preparation of (5R,6S)-6-((R)-1-hydroxyethyl)-7-oxo-3-(4-(((3-oxo-3H-phenoxazin-7-yl)oxy)methyl)phenyl)-1-azabicyclo[3.2.0]hept-2-ene-2-carboxylic acid (MCW-008)
Overall Synthesis Scheme:
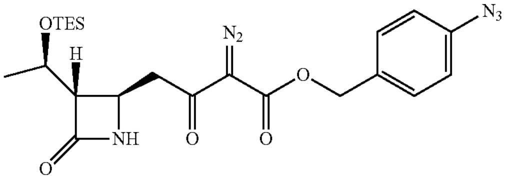
12
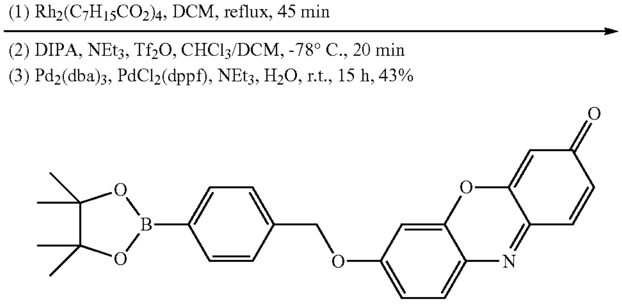
43
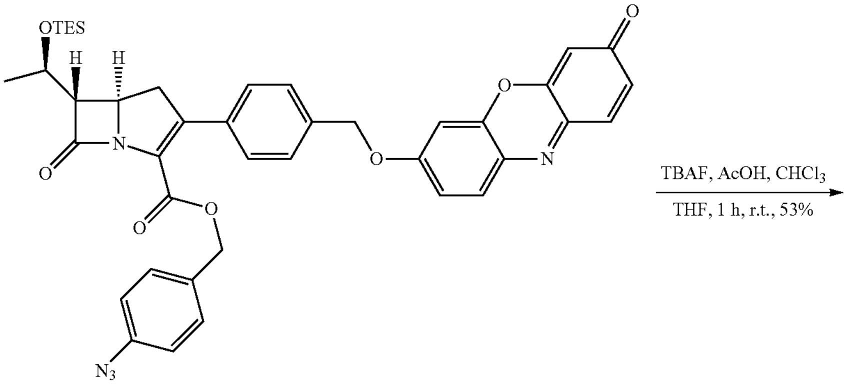
44
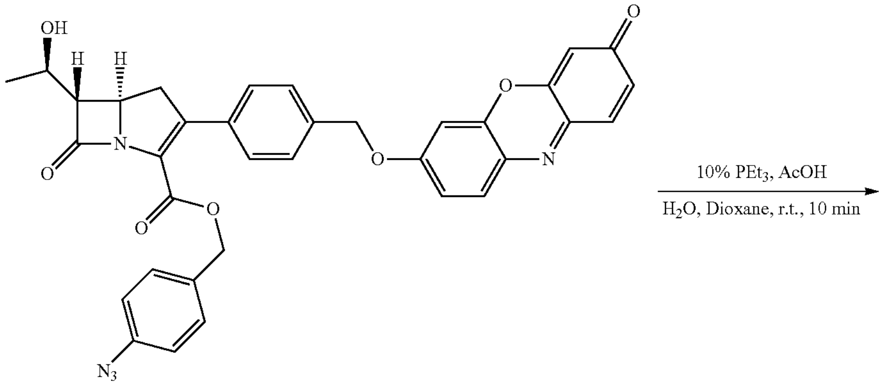
45
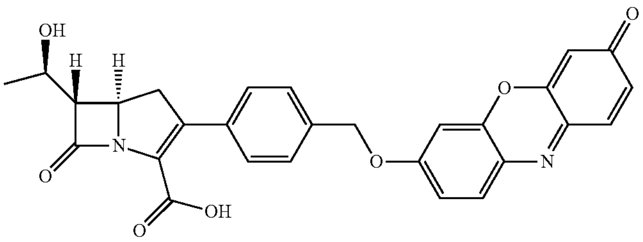
MCW-008

Step 1:

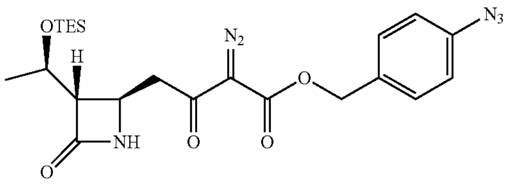

12

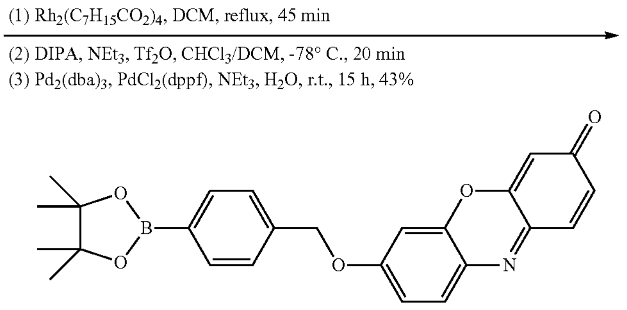

43

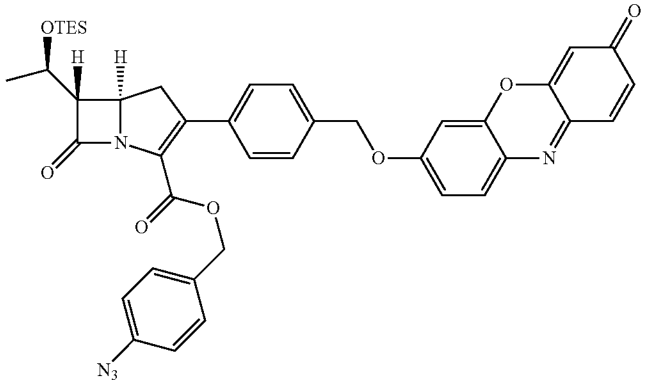

44

To a round bottom flask were added azetidinone 12 (392 mg, 0.806 mmol) and DCM (4 mL). Rhodium octanoate dimer (3.1 mg, 4 μmol) was then added and the reaction mixture was stirred under reflux for 45 minutes. When TLC indicated the reaction was complete, the reaction mixture was concentrated and used directly for the next step. To a round bottom flask were added the crude ketone, $CHCl_3$ (4 mL), and DCM (1.5 mL) at −78° C. DIPA (250 μL, 1.05 mmol) and $NEt_3$ (30 μL, 0.322 mmol) were then added dropwise and the resulting solution was stirred for 10 minutes. $Tf_2O$ (180 μL, 1.05 mmol) was then added dropwise and the resulting mixture was stirred at −78° C. for 15 minutes. When TLC indicated the reaction was complete, $NEt_3$ (195 μL, 2.08 mmol), $H_2O$ (38 μL, 2.08 mmol), boronic ester 43 (223 mg, 0.520 mmol), and $Pd_2(dba)_3$ (47.7 mg, 50 μmol) and $PdCl_2dppf$ (38.0 mg, 50 μmol) were added. The reaction mixture was heated to room temperature and stirred for 15 h. When TLC indicated the reaction was complete, the reaction was quenched with water (5 mL). The final mixture was diluted with ethyl acetate (15 mL) and then washed with brine (1×5 mL). The aqueous layer was further extracted with ethyl acetate (3×5 mL). The organic layer was dried over anhydrous sodium sulphate, filtered, and concentrated. The crude product was purified by flash column chromatography to obtain the purified product (165 mg, 43%) as an orange solid.

Analytical TLC (silica gel 60), 40% ethyl acetate in n-hexane, $R_f$=0.3; $^1H$ NMR (400 MHz, $CDCl_3$) δ 7.70 (d, J=8.9 Hz, 1H), 7.42-7.38 (m, 5H), 7.29 (d, J=8.6 Hz, 2H), 7.00 (dd, J=8.9, 2.6 Hz, 1H), 6.94 (d, J=8.5 Hz, 2H), 6.86 (d, J=2.6 Hz, 1H), 6.81 (dd, J=9.8, 2.0 Hz, 1H), 6.29 (d, J=2.0 Hz, 1H), 5.28-5.03 (m, 4H), 4.3-4.24 (m, 2H), 3.34-3.13 (m, 3H), 1.30 (d, J=6.2 Hz, 3H), 0.96 (t, J=7.9 Hz, 9H), 0.61 (q, J=7.6 Hz, 6H); HRMS (ESI) calcd. for $C_{41}H_{42}BN_5O_7Si$ ($[M+H]^+$) 744.2848, found 744.2816.

Step 2:

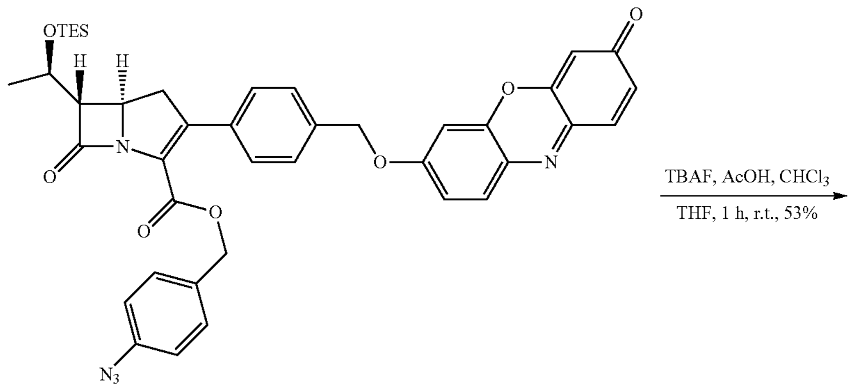

44

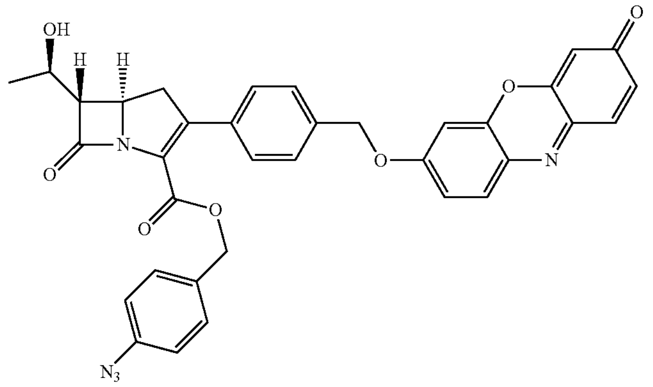

45

To a 10 mL round bottom flask were added the beta-lactam 44 (68.9 mg, 93 μmol), THF (1.4 mL), and DCM (0.7 mL). AcOH (58 μL, 1.02 mmol) and TBAF (926 μL, 0.926 mmol, 1 M in THF) were added at room temperature and the reaction mixture was stirred for 1 h. When TLC indicated the reaction was complete, the reaction was quenched with water (5 mL). The resulting mixture was diluted with ethyl acetate (15 mL) and then washed with brine (1x5 mL). The aqueous layer was further extracted with ethyl acetate (2x5 mL). The organic layer was dried over anhydrous sodium sulphate, filtered, and concentrated. The crude product was purified by flash column chromatography to obtain the purified product 45 (30.8 mg, 53%) as an orange solid.

Analytical TLC (silica gel 60), 80% ethyl acetate in n-hexane, $R_f$=0.5; $^1$H NMR (400 MHz, 10% $CH_3OD$ in $CDCl_3$) δ 7.76 (d, J=8.9 Hz, 1H), 7.47 (d, J=9.8 Hz, 1H), 7.42-7.34 (m, 4H), 7.23 (s, 2H), 7.06 (dd, J=8.9, 2.6 Hz, 1H), 6.97-6.90 (m, 3H), 6.86 (dd, J=9.7, 2.0 Hz, 1H), 6.35 (d, J=2.0 Hz, 1H), 5.26-5.05 (m, 4H), 4.32 (td, J=9.4, 2.7 Hz, 1H), 4.20 (dt, J=10.6, 6.2 Hz, 1H), 3.46-3.18 (m, 3H), 1.34 (d, J=6.3 Hz, 3H); $^{13}$C NMR (100 MHz, $CDCl_3$) δ 186.7, 176.7, 162.7, 160.8, 149.9, 145.5, 145.2, 144.6, 139.8, 135.9, 134.8, 133.9, 133.4, 131.7, 131.6, 129.7, 128.4, 128.3, 127.1, 127.0, 118.8, 114.4, 106.4, 100.9, 70.3, 66.6, 66.2, 65.1, 52.6, 42.3, 21.3; HRMS (ESI) calcd. for $C_{35}H_{28}N_5O_7$ ([M+H]$^+$) 630.1983, found 630.1957.

Step 3:

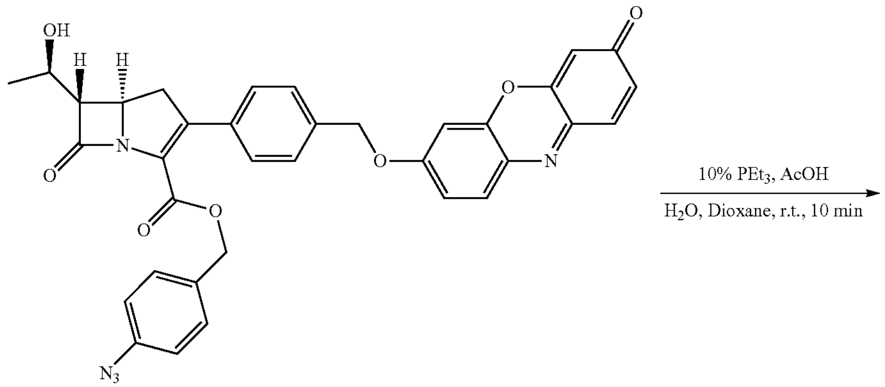

45

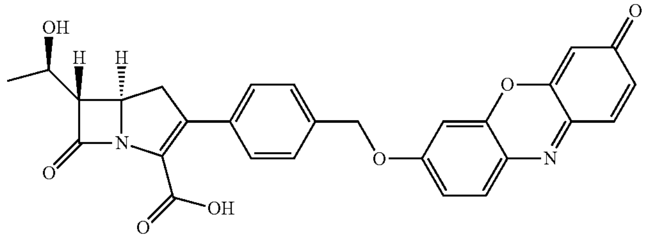

MCW-008

To a 10 mL round bottom flask were added beta-lactam 45 (2.4 mg, 3.8 μmol), dioxane (0.24 mL), and $H_2O$ (24 μL). AcOH (2.4 μL) and $PEt_3$ (13.7 μL, 7.6 μmol, 10% in n-hexane) were added at room temperature and the reaction mixture was stirred for 10 minutes. The crude mixture was subjected to preparative C18 reverse phase HPLC purification using 0.01% TFA in water and $CH_3CN$ as eluent, and used directly for fluorescence assay.

$^1H$ NMR (500 MHz, $CD_3OD$) δ 7.79 (d, J=9.0 Hz, 1H), 7.53 (d, J=9.8 Hz, 1H), 7.49-7.43 (m, 3H), 7.12 (dd, J=8.9, 2.5 Hz, 1H), 7.02 (d, J=2.5 Hz, 1H), 6.88 (d, J=9.9 Hz, 1H), 6.37 (s, 1H), 5.25 (s, 2H), 4.30 (td, J=9.3, 2.4 Hz, 1H), 4.16 (qd, J=13.3, 5.9 Hz, 1H), 3.27 (dd, J=7.1, 2.5 Hz, 1H), 3.21 (dd, J=17.7, 9.9 Hz, 1H), 1.34 (d, J=6.3 Hz, 3H); HRMS (ESI) calcd. for $C_{28}H_{23}N_2O_7$ ($[M+H]^+$) 499.1500, found 499.1483.

Example 16. Preparation of 9-(4-methoxy-2-methylphenyl)-6-((4-(4,4,5,5-tetramethyl-1,3,2-dioxaborolan-2-yl)benzyl)oxy)-3H-xanthen-3-one (46)

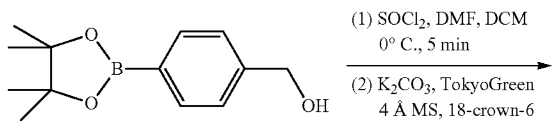

42

-continued

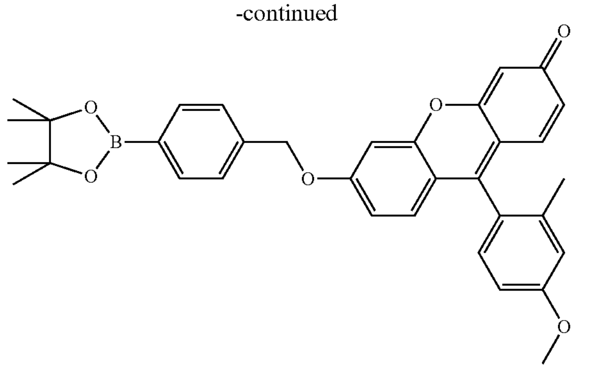

46

To a round bottom flask were added alcohol 42 (100 mg, 0.427 mmol), DCM (2 mL), DMF (66 μL, 0.855 mmol), and $SOCl_2$ (79 μL, 0.769 mmol) at 0° C. and the resulting solution was stirred for 5 minutes. When TLC indicated the reaction was complete, the reaction was quenched with water (5 mL). The resulting mixture was diluted with ethyl acetate (15 mL) and then washed with brine (1×5 mL). The aqueous layer was further extracted with ethyl acetate (3×5 mL). The organic layer was dried over anhydrous sodium sulphate, filtered, and concentrated. The crude product was purified by flash column chromatography and eluted with 10% ethyl acetate in n-hexane.

To a round bottom flask were added the crude product chloride, DMF (1 mL), TokyoGreen (170 mg, 5.13 mmol), $K_2CO_3$ (88 mg, 0.64 mmol), a few crystals of 18-crown-6, and a few granules of 3 Å molecular sieve at 80° C. The resulting mixture was stirred for 19 h. When TLC indicated the reaction was complete, the crude product was dissolved in DCM (40 mL) and filtered by silica gel. The crude product was purified by flash column chromatography to obtain the purified product 46 (88.0 mg, 38%) as a red-orange solid.

Analytical TLC (silica gel 60), 80% ethyl acetate in n-hexane, $R_f$=0.5; $^1$H NMR (500 MHz, $CDCl_3$) δ 7.85 (d, J=7.7 Hz, 2H), 7.43 (d, J=7.7 Hz, 2H), 7.11-6.77 (m, 7H), 6.57 (dd, J=9.7, 1.5 Hz, 1H), 6.44 (d, J=1.5 Hz, 1H), 5.21 (s, 2H), 3.89 (s, 3H), 2.04 (s, 3H), 1.34 (s, 12H); $^{13}$C NMR (125 MHz, $CDCl_3$) δ 185.8, 163.2, 160.4, 159.0, 154.6, 149.6, 138.5, 137.9, 135.2, 130.7, 130.4, 130.0, 129.6, 126.5, 124.6, 118.8, 116.0, 115.0, 114.0, 111.5, 105.7, 101.4, 83.9, 70.6, 55.4, 24.9, 20.0; HRMS (ESI) calcd. for $C_{34}H_{34}BO_6$ ($[M+H]^+$) 549.2449, found 549.2427.

The $^{13}$C NMR signal corresponding to the carbon directly attached to the boron atom was not reported due to quadrupolar broadening.

Example 17. Preparation of (5R,6S)-6-((R)-1-hydroxyethyl)-3-(4-(((9-(4-methoxy-2-methylphenyl)-3-oxo-3H-xanthen-6-yl)oxy)methyl)phenyl)-7-oxo-1-azabicyclo[3.2.0]hept-2-ene-2-carboxylic acid (MCW-009)

Overall Synthesis Scheme:

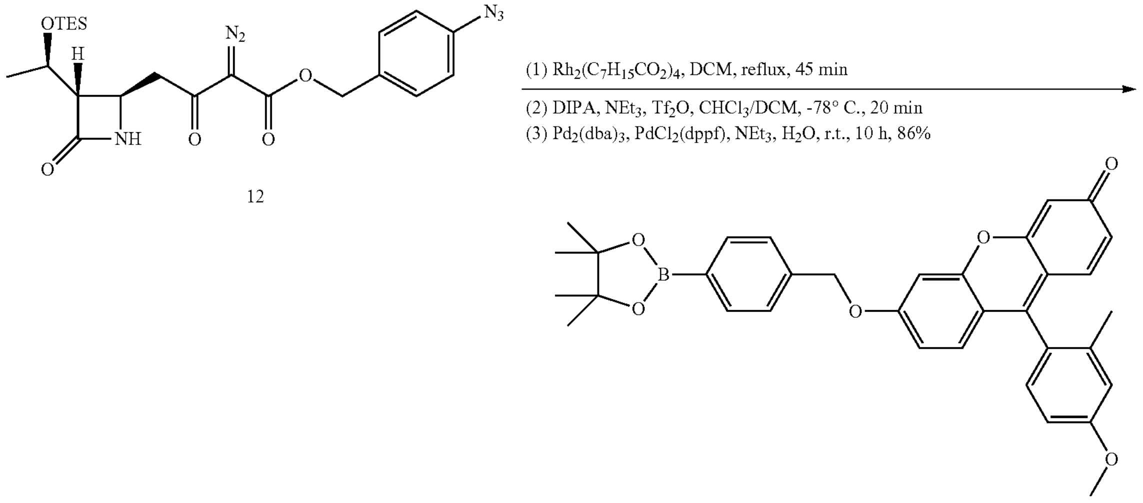

12

46

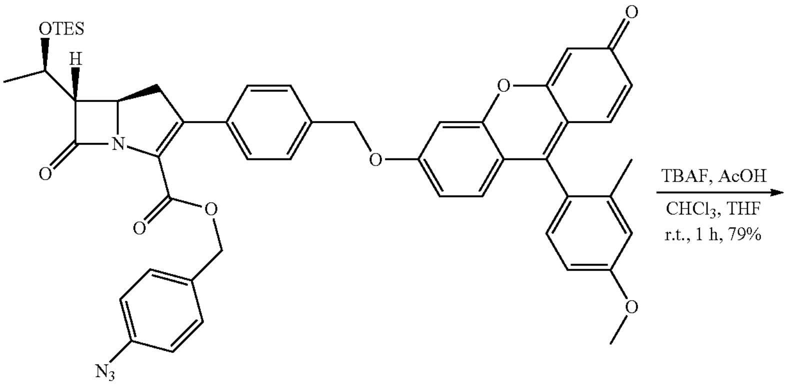

47

-continued
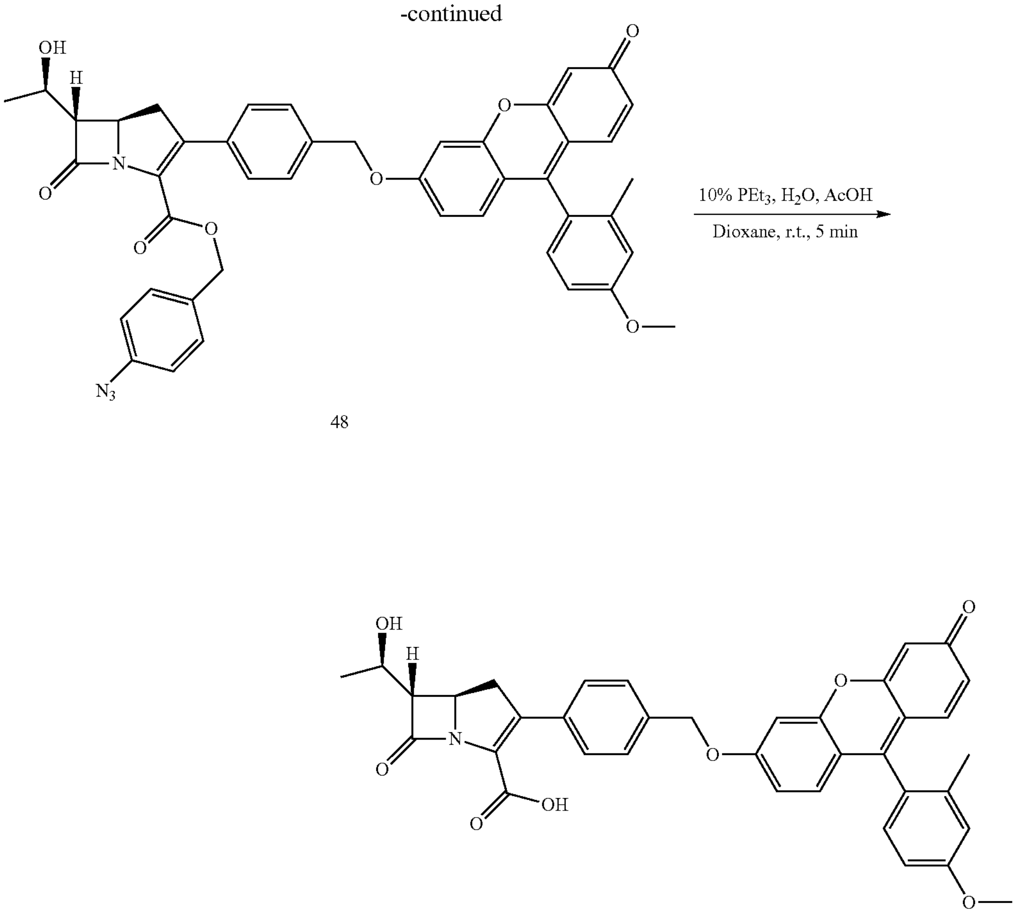
48
MCW-009
Step 1:
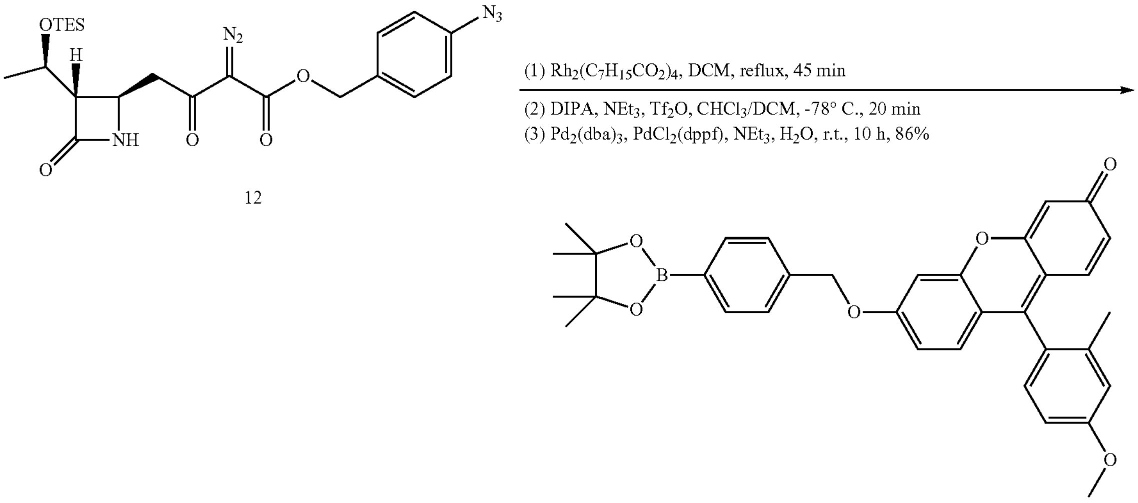
12
46

-continued

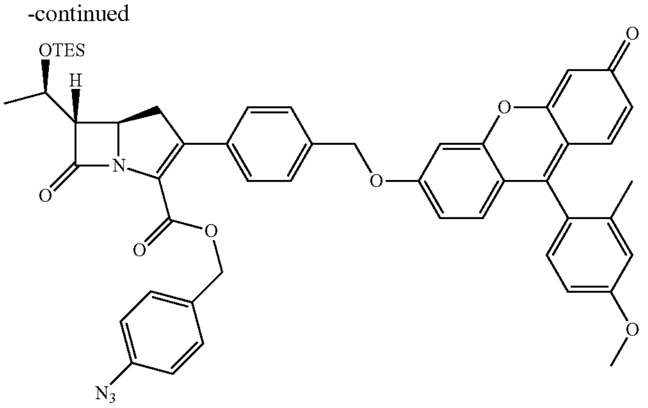

47

To a round bottom flask were added the azetidinone 12 (94.1 mg, 0.182 mmol) and DCM (2 mL). Rhodium octanoate dimer (0.7 mg, 1 μmol) was then added and the reaction mixture was stirred under reflux for 45 min. When TLC indicated the reaction was complete, the reaction mixture was concentrated and used directly for the next step. To a round bottom flask were added the crude product, DCM (0.35 mL), and $CHCl_3$ (1 mL) at −78° C. DIPA (33 μL, 0.237 mmol) and $NEt_3$ (12 μL, 70 μmol) were then added dropwise and the resulting solution was stirred for 10 min. $Tf_2O$ (40 μL, 0.237 mmol) was then added dropwise and the resulting mixture was stirred at −78° C. for 15 min. When TLC indicated the reaction was complete, $NEt_3$ (82 μL, 0.511 mmol), $H_2O$ (9 μL, 0.511 mmol), boronic ester 46 (70.0 mg, 0.128 mmol), and $Pd_2(dba)_3$ (17.5 mg, 20 μmol) and $PdCl_2dppf$ (14.0 mg, 20 μmol) were added. The resulting solution was heated to room temperature and stirred for 10 h. When TLC indicated the reaction was complete, the reaction was quenched with water (5 mL). The final mixture was diluted with ethyl acetate (15 mL) and then washed with brine (1×5 mL). The aqueous layer was further extracted with ethyl acetate (3×5 mL). The organic layer was dried over anhydrous sodium sulphate, filtered, and concentrated. The crude product was purified by flash column chromatography to obtain the purified product 47 (80 mg, 86%) as an orange solid.

Analytical TLC (silica gel 60), 80% ethyl acetate in n-hexane, $R_f$=0.6; $^1H$ NMR (500 MHz, $CDCl_3$) δ 7.38 (s, 4H), 7.30 (d, J=8.2 Hz, 2H), 7.13-7.03 (m, 2H), 7.03-6.80 (m, 7H), 6.58 (d, J=9.6 Hz, 1H), 6.45 (s, 1H), 5.27-5.06 (m, 4H), 4.31-4.19 (m, 2H), 3.89 (s, 3H), 3.29 (dd, J=18.2, 8.8 Hz, 1H), 3.22 (dd, J=6.1, 2.5 Hz, 1H), 3.16 (dd, J=18.1, 10.0 Hz, 1H), 2.05 (s, 3H), 1.30 (d, J=6.1 Hz, 3H), 0.96 (t, J=7.9 Hz, 9H), 0.61 (q, J=7.8 Hz, 6H); $^{13}C$ NMR (125 MHz, $CDCl_3$) δ 185.7, 176.1, 163.1, 160.8, 160.4, 158.9, 154.5, 149.5, 143.8, 139.8, 137.8, 136.1, 133.5, 132.0, 130.7, 130.3, 130.0, 129.7, 129.6, 128.4, 127.4, 127.0, 124.5, 118.9, 118.8, 116.0, 115.0, 113.8, 111.5, 105.7, 101.3, 70.2, 67.3, 66.2, 66.1, 55.3, 52.5, 42.3, 22.6, 19.9, 6.7, 4.9; HRMS (ESI) calcd. for $C_{50}H_{51}N_4O_8Si$ ($[M+H]^+$) 863.3471, found 863.3437.

Step 2:

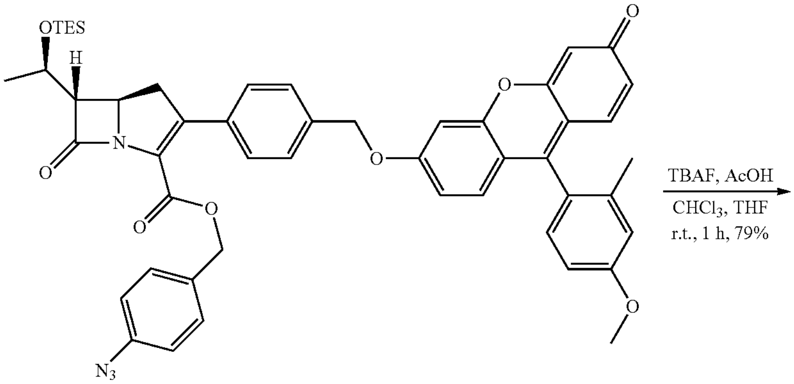

47

-continued

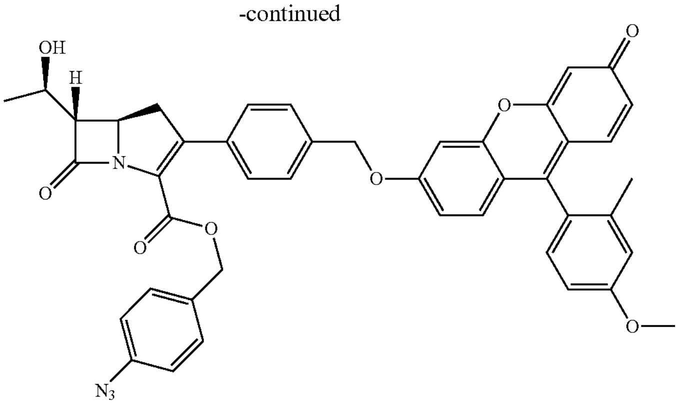

48

To a round bottom flask were added the beta-lactam 47 (22.9 mg, 26.5 μmol), THF (0.15 mL), and $CHCl_3$ (0.4 mL). AcOH (16.7 μL, 0.292 mmol) and TBAF (265 μL, 26.5 μmol, 1 M in THF) were added at room temperature and the reaction mixture was stirred for 1 h. When TLC indicated the reaction was complete, the reaction was quenched with water (5 mL). The resulting mixture was diluted with ethyl acetate (15 mL) and then washed with brine (1×5 mL). The aqueous layer was further extracted with ethyl acetate (2×5 mL). The organic layer was dried over anhydrous sodium sulphate, filtered, and concentrated. The crude product was purified by flash column chromatography to obtain the purified product (12.9 mg, 79%) as an orange solid.

Analytical TLC (silica gel 60), 80% ethyl acetate in n-hexane, $R_f$=0.4; $^1H$ NMR (500 MHz, $CDCl_3$) δ 7.41-7.33 (m, 4H), 7.28 (d, J=8.4 Hz, 2H), 7.06 (t, J=8.5 Hz, 2H), 7.03-6.98 (m, 2H), 6.97-6.88 (m, 4H), 6.85 (dd, J=8.9, 2.4 Hz, 1H), 6.58 (dd, J=9.7, 1.8 Hz, 1H), 6.44 (d, J=1.8 Hz, 1H), 5.28-5.04 (m, 4H), 4.32 (td, J=9.5, 2.6 Hz, 1H), 4.27 (dt, J=13.1, 6.4 Hz, 1H), 3.89 (s, 3H), 3.36-3.25 (m, 2H), 3.21 (dd, J=18.2, 9.9 Hz, 1H), 2.33 (br s, 1H), 2.05 (s, 3H), 1.38 (d, J=6.3 Hz, 3H); $^{13}C$ NMR (125 MHz, $CDCl_3$) δ 185.8, 176.0, 163.1, 160.8, 160.4, 159.0, 154.6, 149.7, 144.2, 139.9, 137.9, 136.2, 133.5, 132.0, 130.8, 130.4, 130.0, 129.8, 129.7, 128.5, 127.4, 127.1, 124.5, 119.0, 118.9, 116.1, 115.1, 113.9, 111.6, 105.7, 101.3, 70.2, 66.7, 66.4, 66.0, 55.4, 52.7, 42.5, 21.9, 20.0; HRMS (ESI) calcd. for $C_{44}H_{37}N_4O_8$ ($[M+H]^+$) 749.2606, found 749.2573.

Step 3:

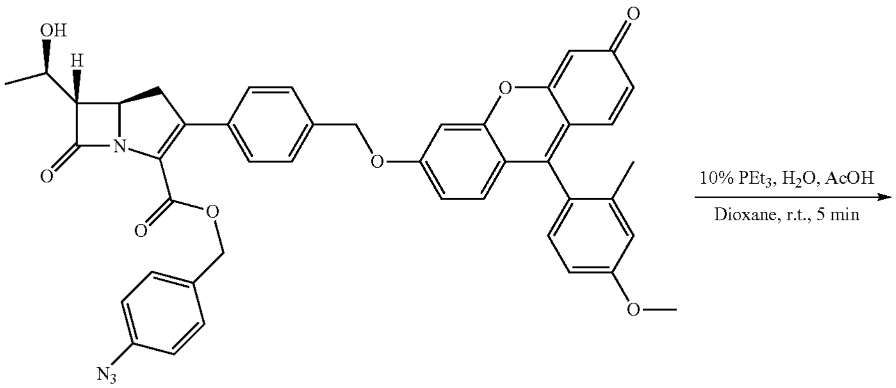

48

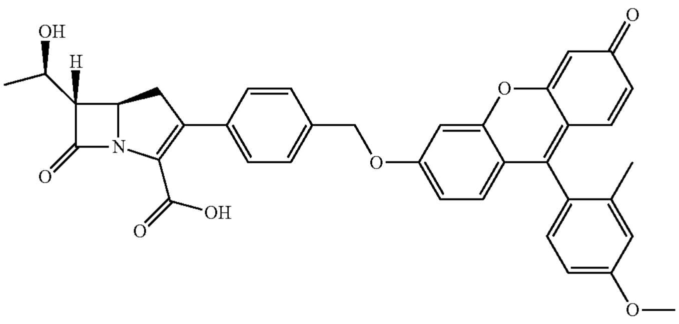

MCW-009

To a round bottom flask were added the beta-lactam 48 (1.0 mg, 1.3 μmol), dioxane (0.1 mL), and $H_2O$ (10 μL). AcOH (1 μL) and $PEt_3$ (13.1 μL, 2.6 μmol, 10% in n-hexane) were added at room temperature and the reaction mixture was stirred for 5 min. The crude mixture was subjected to preparative C18 reverse phase HPLC purification using 0.01% TFA in water and $CH_3CN$ as eluent, and used directly for fluorescence assay. HRMS (ESI) calcd. for $C_{37}H_{32}NO_8$ ($[M+H]^+$) 618.2122, found 618.2109.

Example 18. Preparation of 7-((3-nitro-4-(4,4,5,5-tetramethyl-1,3,2-dioxaborolan-2-yl)benzyl)oxy)-3H-phenoxazin-3-one (52)

Overall Synthesis Scheme:

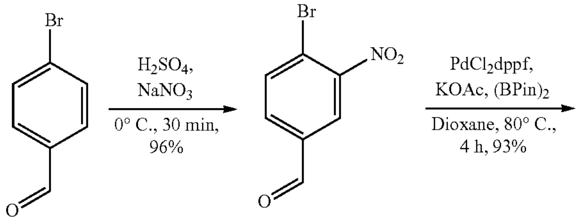

49

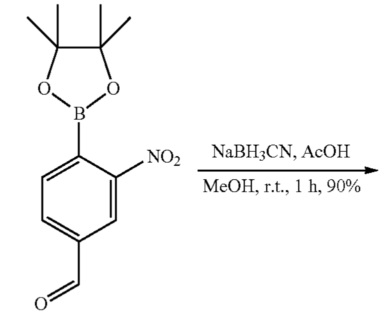

50

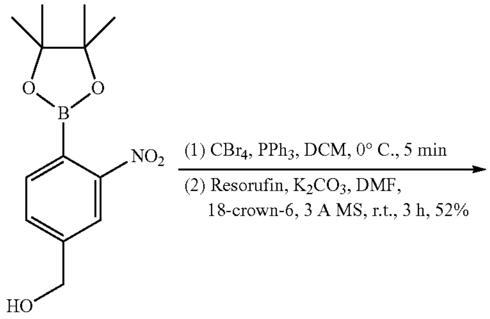

51

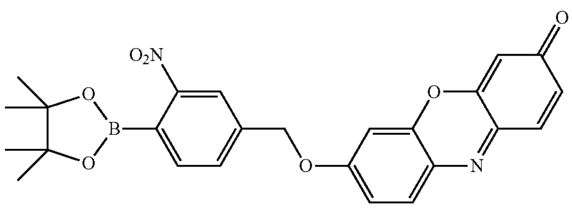

52

Step 1:

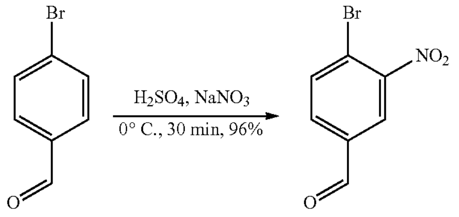

49

To a round bottom flask were added $NaNO_2$ (1.79 g, 21.1 mmol) and $H_2SO_4$ (20 mL). p-Bromobenzaldehyde (3.00 g, 16.2 mmol) was then added at 0° C. slowly and the resulting solution was stirred at room temperature for 30 min. When a homogenous mixture was obtained, water (200 mL) was added to precipitate the product. The resulting white precipitate was washed with water (20 mL) and determined to be pure by NMR (3.57 g, 96%).

Analytical TLC (silica gel 60), 40% ethyl acetate in n-hexane, $R_f$=0.5; $^1$H NMR (500 MHz, $CDCl_3$) δ 10.04 (d, J=2.6 Hz, 1H), 8.31 (dd, J=3.3, 1.4 Hz, 1H), 8.02-7.85 (m, 2H); $^{13}$C NMR (125 MHz, $CDCl_3$) δ 188.7, 150.4, 136.3, 136.1, 132.7, 126.1, 121.1; The characterization data are consistent with the reported data (*J Org Chem,* 2006, 71, 8891.

Step 2:

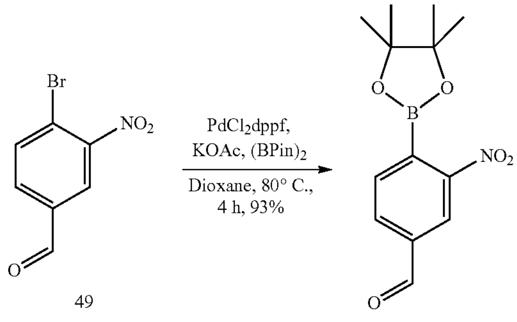

49

50

To a round bottom flask were added the aldehyde 49 (1.00 g, 4.35 mmol), bis(pinacolato)diboron (1.66 g, 6.52 mmol), KOAc (1.28 g, 13.0 mmol), $Pd(dppf)Cl_2$ (64 mg, 87 μmol), and degassed dioxane (5 mL) at 80° C. The resulting solution was stirred for 4 h. When TLC indicated the reaction was complete, the reaction mixture was diluted with DCM (40 mL) and filtered by silica gel. The solution was further washed with 40% ethyl acetate in DCM. The crude product was purified by flash column chromatography to obtain the purified product 50 (1.12 g, 93%) as a pale yellow solid.

Analytical TLC (silica gel 60), 40% ethyl acetate in n-hexane, $R_f$=0.5; $^1$H NMR (500 MHz, $CDCl_3$) δ 10.10 (s, 1H), 8.61 (s, 1H), 8.16 (dd, J=7.5, 1.1 Hz, 1H), 7.73 (d, J=7.5 Hz, 1H), 1.44 (s, 12H); $^{13}$C NMR (125 MHz, $CDCl_3$) δ 189.9, 151.5, 137.7, 133.8, 133.4, 123.6, 85.0, 24.6; HRMS (ESI) calcd. for $C_{13}H_{17}BNO_5$ ($[M+H]^+$) 278.1197, found 278.1183.

The $^{13}$C NMR signal corresponding to the carbon directly attached to the boron atom was not reported due to quadrupolar broadening.

Step 3:

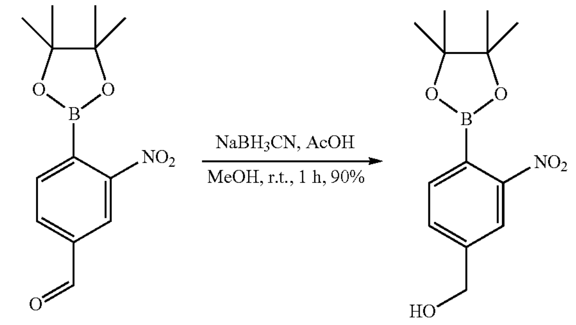

50 51

-continued

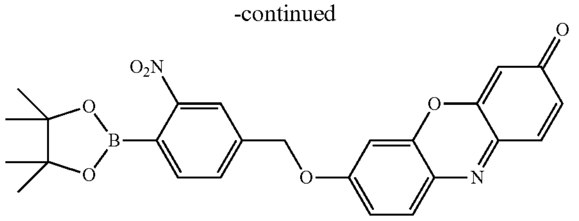

52

To a round bottom flask were added the aldehyde 50 (1.12 g, 4.03 mmol), $^{i}$PrOH (10 mL), AcOH (310 μL, 5.40 mmol), and $NaBH_3CN$ (272 mg, 4.33 mmol) at room temperature and the resulting solution was stirred for 1 h. When TLC indicated the reaction was complete, the reaction was quenched with water (10 mL). The mixture was diluted with ethyl acetate (30 mL) and then washed with brine (1×10 mL). The aqueous layer was further extracted with ethyl acetate (3×10 mL). The organic layer was dried over anhydrous sodium sulphate, filtered, and concentrated. The crude product was purified by flash column chromatography to obtain the purified product 51 (1.01 g, 90%) as colorless oil.

Analytical TLC (silica gel 60), 40% ethyl acetate in n-hexane, $R_f$=0.4; $^1$H NMR (400 MHz, $CDCl_3$) δ 7.96 (s, 1H), 7.49 (d, J=7.5 Hz, 1H), 7.39 (d, J=7.5 Hz, 1H), 4.64 (s, 2H), 1.42 (s, 12H); $^{13}$C NMR (100 MHz, $CDCl_3$) δ 150.8, 144.4, 132.5, 131.2, 120.2, 84.7, 62.9, 24.5; HRMS (ESI) calcd. for $Cl_3H_{19}BNO_5$ ($[M+H]^+$) 280.1354, found 280.1341.

The $^{13}$C NMR signal corresponding to the carbon directly attached to the boron atom was not reported due to quadrupolar broadening.

Step 4:

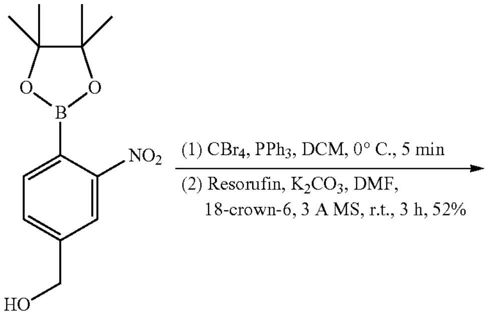

51

To a round bottom flask were added the alcohol 51 (201 mg, 0.720 mmol), DCM (4 mL), and $PPh_3$ (340 mg, 1.30 mmol) at 0° C. $CBr_4$ (430 mg, 1.30 mmol) was then added and the reaction mixture was stirred for 5 min. When TLC indicated the reaction was complete, the reaction was quenched with water (5 mL). The mixture was diluted with ethyl acetate (15 mL) and then washed with brine (1×5 mL). The aqueous layer was further extracted with ethyl acetate (3×5 mL). The organic layer was dried over anhydrous sodium sulphate, filtered, and concentrated. The crude product was purified by flash column chromatography and eluted with 10% ethyl acetate in n-hexane to remove triphenylphosphin oxide.

The crude product was dissolved in anhydrous DMF (2 mL) in a round bottom flask. Resorufin (230 mg, 1.08 mmol), $K_2CO_3$ (149 mg, 1.08 mmol), a few pieces of 3 Å molecular sieve, and a few crystals of 18-crown-6 were then added and the mixture was stirred at room temperature for 3 h. When TLC indicated the reaction was complete, the reaction mixture was diluted with DCM (40 mL), filtered through silica gel to remove unreacted resorufin and $K_2CO_3$, and then concentrated. The crude product was purified by flash column chromatography to obtain the purified product 52 (176 mg, 52%) as an orange solid.

Analytical TLC (silica gel 60), 40% ethyl acetate in n-hexane, $R_f$=0.3; $^1$H NMR (500 MHz, $CDCl_3$) δ 8.25 (s, 1H), 7.73 (t, J=6.9 Hz, 2H), 7.61 (d, J=7.5 Hz, 1H), 7.41 (d, J=9.8 Hz, 1H), 7.00 (dd, J=8.9, 2.6 Hz, 1H), 6.89-6.75 (m, 2H), 6.31 (d, J=2.0 Hz, 1H), 5.26 (s, 2H), 1.43 (s, 12H); $^{13}$C NMR (125 MHz, $CDCl_3$) δ 186.3, 161.7, 151.4, 149.6, 146.1, 145.5, 138.5, 134.7, 134.4, 133.5, 132.0, 131.8, 128.7, 121.5, 114.0, 106.9, 101.3, 84.8, 69.3, 24.7; HRMS (ESI) calcd. for $C_{25}H_{24}BN_2O_7$ ($[M+H]^+$) 475.1676, found 475.1655.

The $^{13}$C NMR signal corresponding to the carbon directly attached to the boron atom was not reported due to quadrupolar broadening.

Example 19. Preparation of (5R,6S)-6-((R)-1-hydroxyethyl)-3-(2-nitro-4-(((3-oxo-3H-henoxazin-7-yl)oxy)methyl)phenyl)-7-oxo-1-azabicyclo[3.2.0]hept-2-ene-2-carboxylic acid (MCW-010)
Overall Synthesis Scheme:
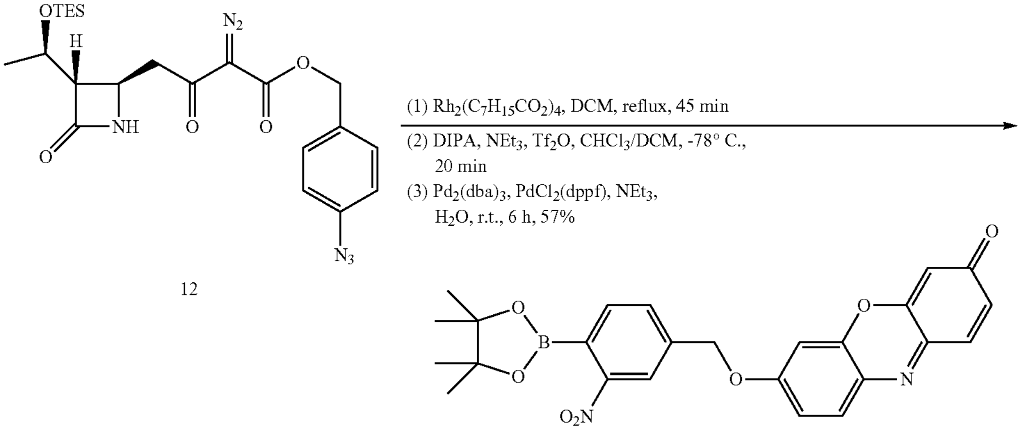
12
52
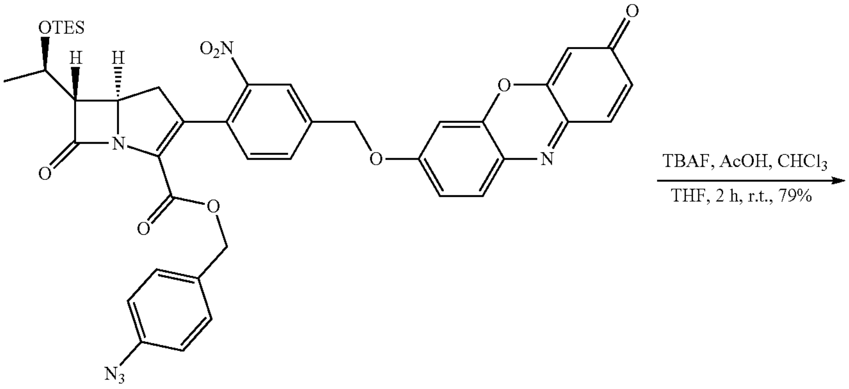
53
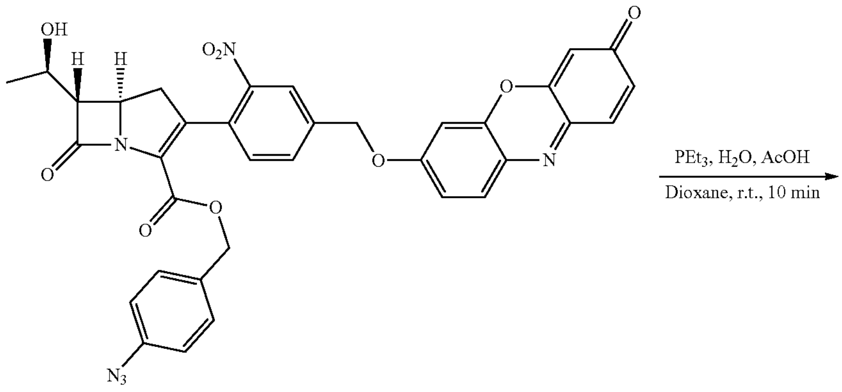
54

-continued

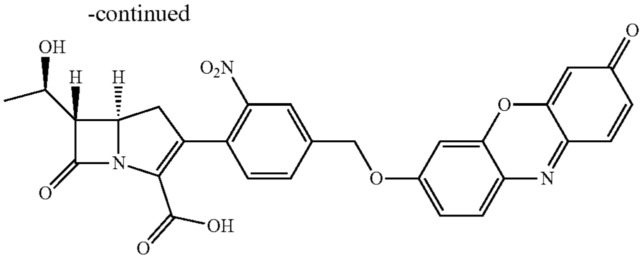

MCW-010

Step 1:

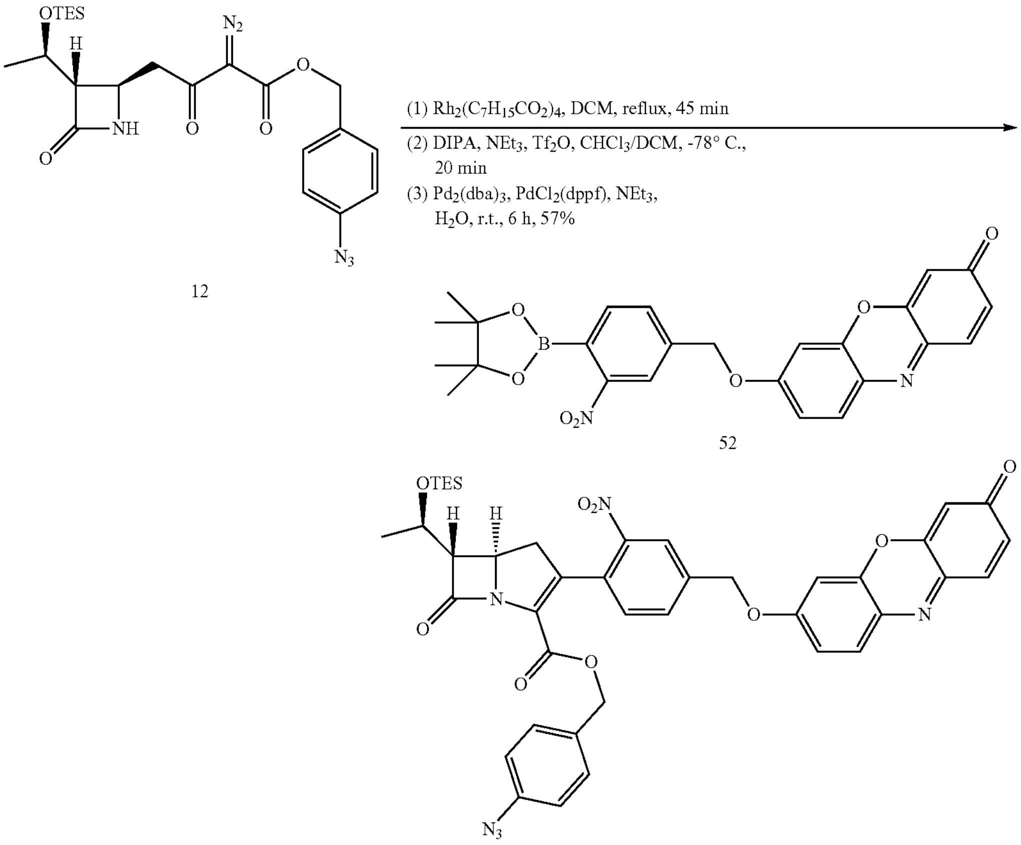

12

52

53

To a round bottom flask were added azetidinone 12 (220 mg, 0.452 mmol) and DCM (3 mL). Rhodium octanoate dimer (1.8 mg, 2 umol) was then added and the reaction mixture was stirred under reflux for 45 min. When TLC indicated the reaction was complete, the reaction mixture was concentrated and used directly for the next step. To a round bottom flask were added the crude ketone, $CHCl_3$ (2.2 mL) and DCM (0.8 mL) at −78° C. DIPA (83 μL, 0.588 mmol) and $NEt_3$ (17 μL, 0.181 mmol) was then added dropwise and the resulting solution was stirred for 10 min. $Tf_2O$ (99 μL, 0.588 mmol) was then added dropwise and the resulting mixture was stirred at −78° C. for 15 min. When TLC indicated the reaction was complete, $NEt_3$ (103 μL, 1.10 mmol), $H_2O$ (20 μL, 1.10 mmol), boronic ester 52 (130 mg, 0.274 mmol), and $Pd_2(dba)_3$ (25 mg, 27 μmol) and $PdCl_2$dppf (20 mg, 27 μmol) were added. The resulting solution was heated to room temperature and stirred for 6 h. When TLC indicated the reaction was complete, the reaction was quenched with water (5 mL). The final mixture was diluted with ethyl acetate (15 mL) and then washed with brine (1×5 mL). The aqueous layer was further extracted with ethyl acetate (3×5 mL). The organic layer was dried over anhydrous sodium sulphate, filtered, and concentrated. The crude product was purified by flash column chromatography to obtain the purified product 53 (113 mg, 57%) as an orange solid.

Analytical TLC (silica gel 60), 40% ethyl acetate in n-hexane, $R_f$=0.2; $^1H$ NMR (500 MHz, $CDCl_3$) δ 8.13 (s, 1H), 7.75 (d, J=8.9 Hz, 1H), 7.67 (d, J=7.9 Hz, 1H), 7.40 (d, J=9.8 Hz, 1H), 7.33 (d, J=7.9 Hz, 1H), 7.15 (d, J=8.4 Hz, 2H), 7.04 (dd, J=8.9, 2.6 Hz, 1H), 6.97-6.85 (m, 3H), 6.81 (dd, J=9.8, 1.9 Hz, 1H), 6.30 (d, J=1.9 Hz, 1H), 5.20 (s, 2H), 5.04 (d, J=12.5 Hz, 1H), 4.93 (d, J=12.5 Hz, 1H), 4.41 (ddd, J=10.9, 8.6, 3.0 Hz, 1H), 4.27 (dt, J=12.1, 6.1 Hz, 1H), 3.36 (dd, J=6.0, 3.0 Hz, 1H), 3.30 (dd, J=18.3, 8.1 Hz, 1H), 3.17 (dd, J=18.3, 10.2 Hz, 1H), 1.31 (d, J=6.2 Hz, 3H), 0.96 (t, J=7.9 Hz, 9H), 0.62 (q, J=7.8 Hz, 6H); $^{13}C$ NMR (125 MHz, $CDCl_3$) δ 186.1, 176.4, 161.6, 159.9, 149.5, 147.4, 145.0, 145.4, 141.0, 139.7, 137.4, 134.6, 134.2, 131.7, 131.6, 131.6, 130.4, 130.1, 129.6, 129.0, 128.7, 123.2, 118.8, 113.7, 106.7, 101.0, 68.9, 67.7, 66.3, 65.9, 53.0, 42.5, 22.5, 6.7, 4.8; HRMS (ESI) calcd. for $C_{41}H_{41}N_6O_9Si$ ([M+H]$^+$) 789.2699, found 789.2664.

Step 2:

mL). The organic layer was dried over anhydrous sodium sulphate, filtered, and concentrated. The crude product was purified by flash column chromatography to obtain the purified product 54 (76.7 mg, 79%) as an orange solid.

Analytical TLC (silica gel 60), 80% ethyl acetate in n-hexane, $R_f$=0.2; $^1H$ NMR (500 MHz, $CDCl_3$) δ 8.10 (s, 1H), 7.81 (d, J=8.9 Hz, 1H), 7.67 (d, J=7.6 Hz, 1H), 7.48 (d, J=9.8 Hz, 1H), 7.35 (d, J=6.0 Hz, 2H), 7.09 (d, J=7.5 Hz, 2H), 6.97 (s, 1H), 6.91 (d, J=8.0 Hz, 2H), 6.87 (d, J=9.6 Hz, 1H), 6.36 (s, 1H), 5.21 (s, 2H), 5.02 (d, J=12.3 Hz, 1H), 4.92 (d, J=12.3 Hz, 1H), 4.44 (t, J=7.9 Hz, 1H), 4.22 (dt, J=12.3, 6.0 Hz, 1H), 3.38 (br s, 1H), 3.33 (dd, J=18.5, 8.0 Hz, 1H),

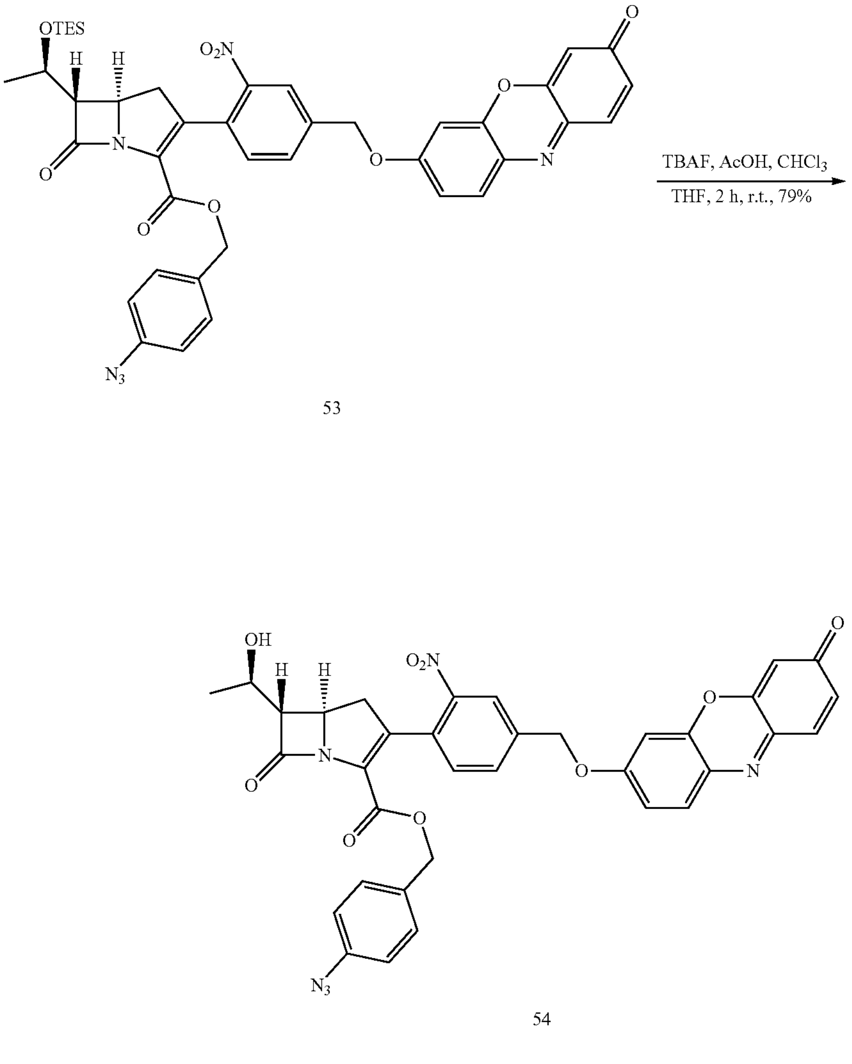

53

54

To a round bottom flask were added the beta-lactam 53 (114 mg, 0.144 mmol), THF (2 mL), and $CHCl_3$ (2 mL). AcOH (91 μL, 1.59 mmol) and TBAF (1.44 mL, 1.44 mmol, 1 M in THF) were added at room temperature and the reaction mixture was stirred for 1 h. When TLC indicated the reaction was complete, the reaction was quenched with water (5 mL). The resulting mixture was diluted with ethyl acetate (15 mL) and then washed with brine (1×5 mL). The aqueous layer was further extracted with ethyl acetate (2×5

3.22 (dd, J=18.3, 10.1 Hz, 1H), 1.35 (d, J=6.0 Hz, 3H); $^{13}C$ NMR (125 MHz, 10% $CD_3OD$ and 10% $C_6D_6$ in $CDCl_3$) δ 186.6, 176.96, 161.8, 159.9, 149.7, 147.3, 145.6, 145.4, 141.7, 139.8, 137.3, 134.7, 134.0, 131.7, 131.5, 131.3, 130.2, 129.9, 129.7, 128.7, 128.7, 123.0, 118.7, 113.9, 106.4, 100.9, 68.7, 67.0, 66.4, 65.0, 53.2, 42.5, 21.2; LRMS (ESI) 675.1 ([M+H]$^+$); HRMS (ESI) calcd. for $C_{35}H_{26}N_6O_9$ ([M+H]$^+$) 675.1845, found 675.1814.

Step 3:

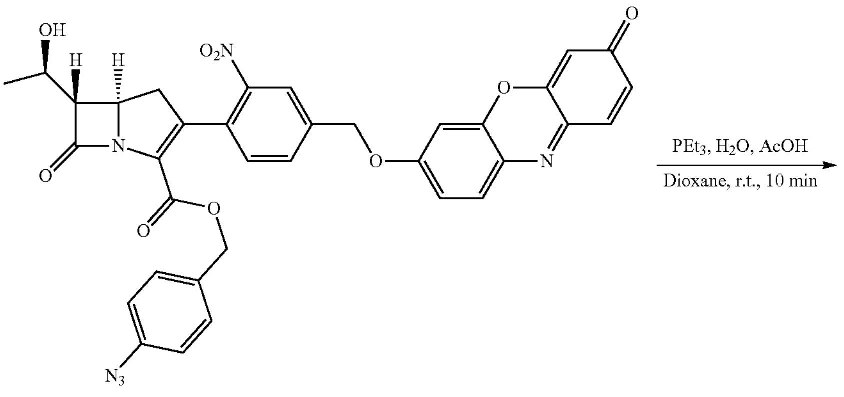

54

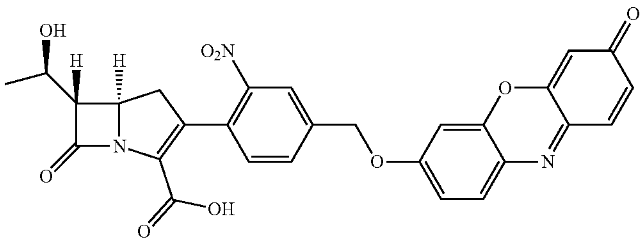

MCW-010

To a round bottom flask were added beta-lactam 54 (4.6 mg, 6.8 μmol), dioxane (0.46 mL), and $H_2O$ (46 μL). AcOH (4.6 μL) and $PEt_3$ (14.6 μL, 8.8 μmol, 10% in n-hexane) were added at room temperature and the reaction mixture was stirred for 5 min. The crude mixture was subjected to preparative C18 reverse phase HPLC purification using 0.01% TFA in water and $CH_3CN$ as eluent, and used directly for fluorescence assay.

$^1H$ NMR (500 MHz, $CDCl_3$ in MeOD) δ 8.15 (s, 1H), 7.78 (d, J=9.0 Hz, 1H), 7.71 (d, J=8.0 Hz, 1H), 7.50 (d, J=9.8 Hz, 1H), 7.42 (d, J=7.9 Hz, 1H), 7.11 (dd, J=8.9, 2.6 Hz, 1H), 7.03 (d, J=2.6 Hz, 1H), 6.84 (dd, J=9.8, 2.0 Hz, 1H), 6.34 (d, J=2.1 Hz, 1H), 5.29 (s, 2H), 4.33 (ddd, J=10.5, 8.4, 2.8 Hz, 1H), 4.15 (dt, J=12.4, 6.2 Hz, 1H), 3.30-3.22 (m, 2H), 3.09 (dd, J=17.6, 10.0 Hz, 1H), 1.29 (d, J=6.2 Hz, 3H); HRMS (ESI) calcd. for $C_{28}H_{22}N_3O_9$ ($[M+H]^+$) 544.1350, found 544.1332.

Example 20. Preparation of (5R,6S)-6-((R)-1-hydroxyethyl)-3-((E)-3-(2-methoxy-4-(((9-(4-methoxy-2-methylphenyl)-3-oxo-3H-xanthen-6-yl)oxy)methyl)phenoxy)prop-1-en-1-yl)-7-oxo-4-thia-1-azabicyclo[3.2.0]hept-2-ene-2-carboxylic acid (MCW-011)

Overall Synthesis Scheme:

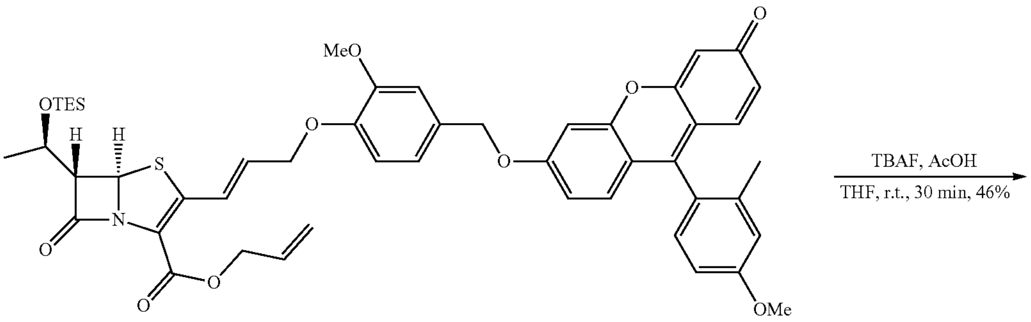

55

-continued

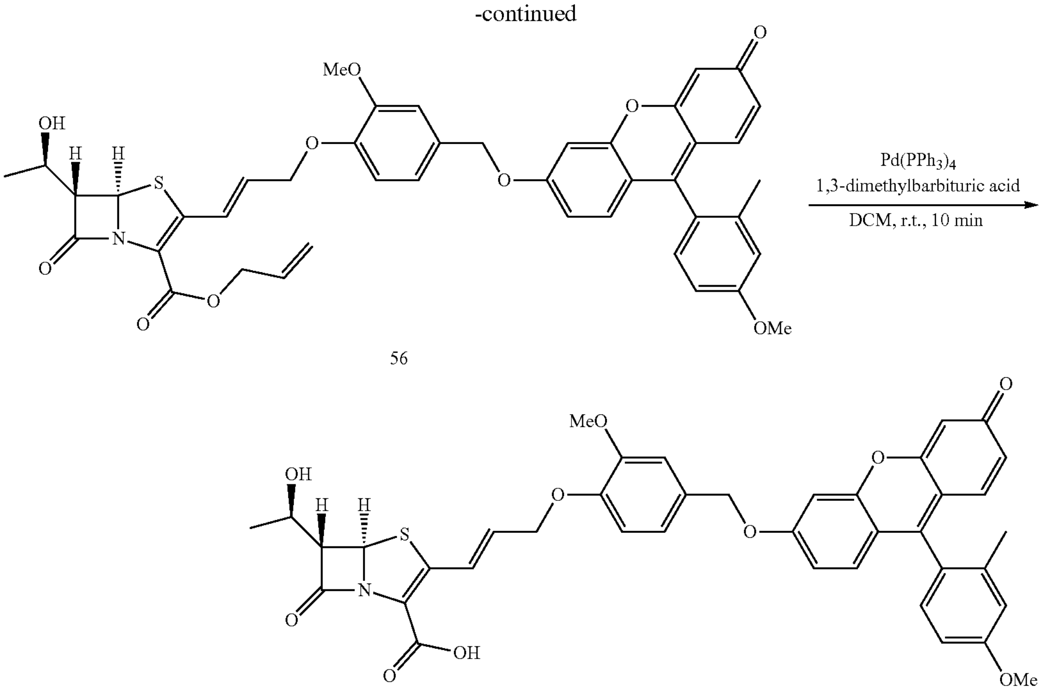

56

MCW-011

Step 1:

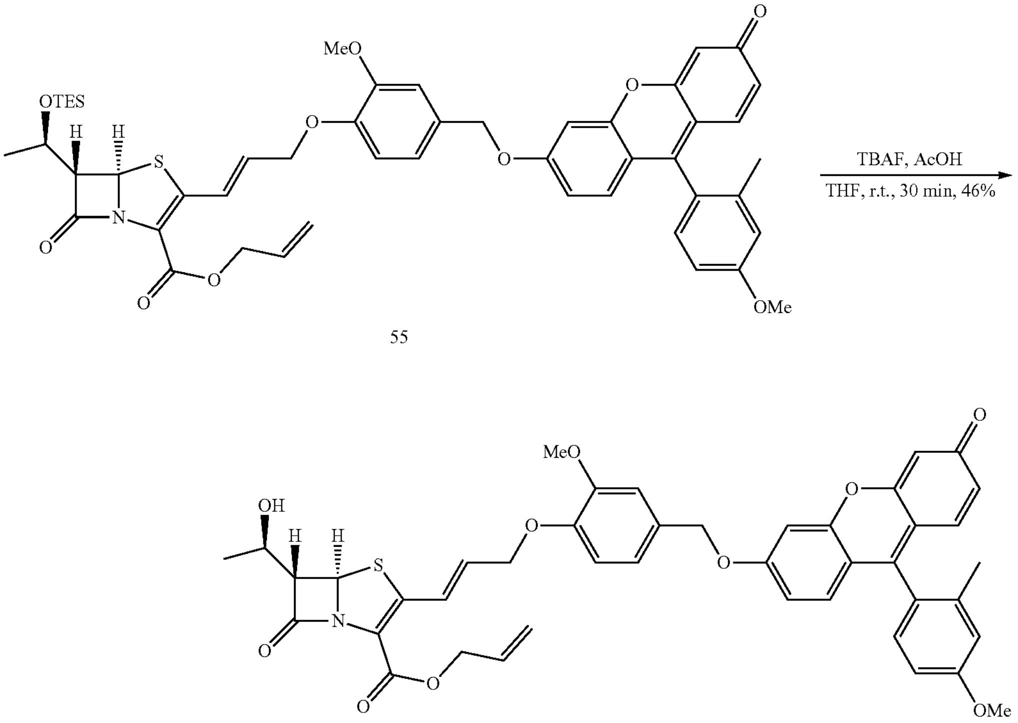

55

56

To a round bottom flask were added the beta-lactam 55 (5.5 mg, 6.3 μmol), THF (0.2 mL). AcOH (7.2 μL, 126 μmol) and TBAF (63 μL, 63 μmol, 1 M in THF) were added at room temperature and the reaction mixture was stirred for 30 min. When TLC indicated the reaction was complete, the reaction was quenched with water (5 mL). The resulting mixture was diluted with ethyl acetate (15 mL) and then washed with brine (1×5 mL). The aqueous layer was further extracted with ethyl acetate (2×5 mL). The organic layer was dried over anhydrous sodium sulphate, filtered, and concentrated. The crude product was purified by flash column chromatography to obtain the purified product 56 (2.0 mg, 46%) as a yellow solid.

Analytical TLC (silica gel 60), 80% ethyl acetate in n-hexane, $R_f$=0.4; $^1$H NMR (500 MHz, $CDCl_3$) δ $^1$H NMR (500 MHz, $CDCl_3$) δ 7.59 (dd, J=15.8, 1.8 Hz, 1H), 7.07 (d, J=8.3 Hz, 1H), 7.04 (d, J=8.8 Hz, 1H), 7.02-6.95 (m, 4H), 6.93-6.89 (m, 3H), 6.85 (dd, J=8.9, 2.4 Hz, 1H), 6.58 (dd, J=9.7, 1.9 Hz, 1H), 6.43 (d, J=2.0 Hz, 1H), 6.21 (dt, J=15.8, 5.6 Hz, 1H), 5.99-5.89 (m, 1H), 5.57 (dd, J=1.6, 1.6 Hz, 1H), 5.40 (d, J=17.6 Hz, 1H), 5.25 (dd, J=10.5, 1.3 Hz, 1H), 5.14 (s, 2H), 4.82-4.75 (m, 3H), 4.70-4.66 (m, 1H), 4.25 (dt, J=13.3, 6.4 Hz, 1H), 3.89 (s, 3H), 3.89 (s, 3H), 3.72 (dt, J=7.2, 1.5 Hz, 1H), 2.04 (s, 3H), 1.39 (d, J=6.3 Hz, 3H); LRMS (ESI) 762.1 ([M+H]$^+$).

Step 2:

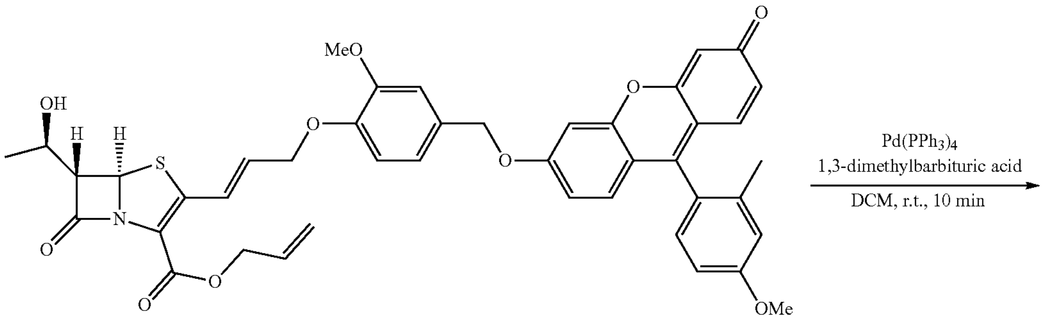

56

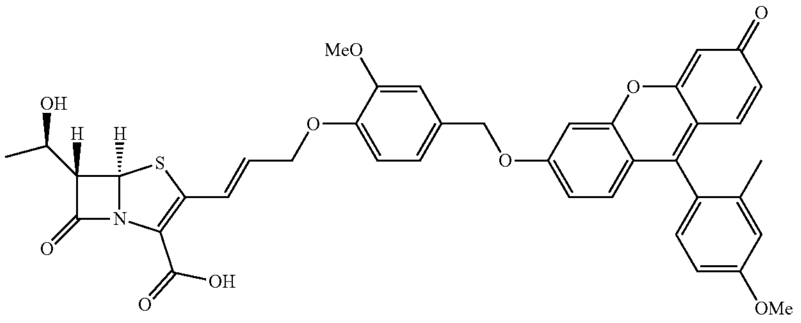

MCW-011

To a vial were added beta-lactam 56 (0.7 mg, 0.92 μmol), $Pd(PPh_3)_4$ (0.5 mg, 0.46 μmol), 1,3-dimethylbarbituric acid (0.6 mg, 3.7 μmol) and DCM (0.1 mL). The crude mixture was subjected to preparative C18 reverse phase HPLC purification using 0.01% TFA in water and $CH_3CN$ as eluent, and used directly for fluorescence assay.

Example 21. Preparation of (5R,6S)-6-((R)-1-hydroxyethyl)-3-((E)-3-(2-methoxy-4-((4-nitrophenoxy)methyl)phenoxy)prop-1-en-1-yl)-7-oxo-4-thia-1-azabicyclo[3.2.0]hept-2-ene-2-carboxylic acid (MCW-012)

Overall Synthesis Scheme:

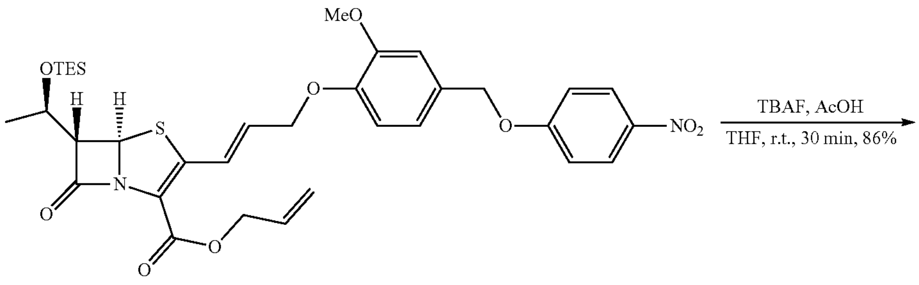

57

-continued

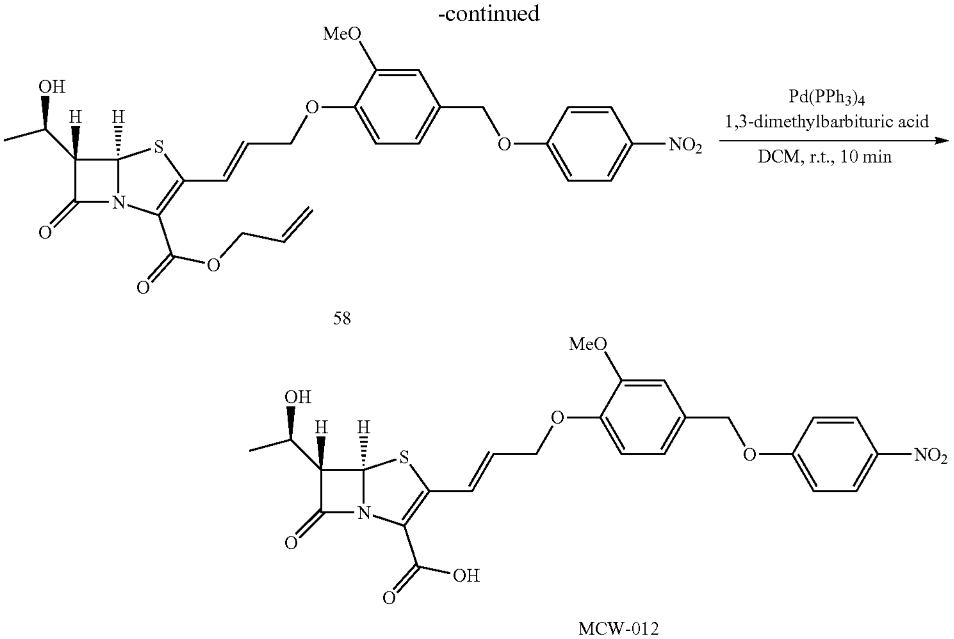

58

MCW-012

Step 1:

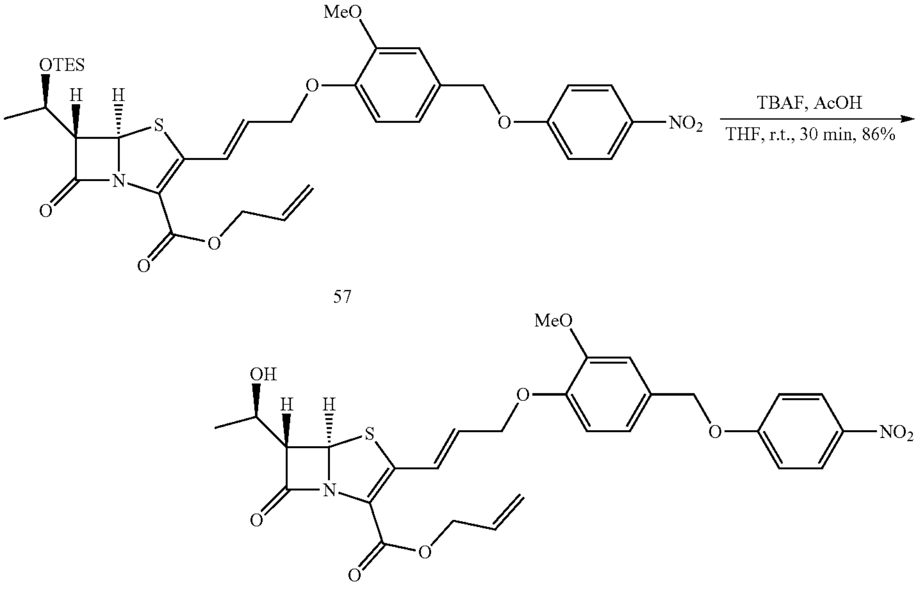

57

58

To a round bottom flask were added the beta-lactam 57 (14.6 mg, 21.4 μmol), THF (0.4 mL). AcOH (29 μL, 513 μmol) and TBAF (257 μL, 214 μmol, 1 M in THF) were added at room temperature and the reaction mixture was stirred for 30 min. When TLC indicated the reaction was complete, the reaction was quenched with water (5 mL). The resulting mixture was diluted with ethyl acetate (15 mL) and then washed with brine (1×5 mL). The aqueous layer was further extracted with ethyl acetate (2×5 mL). The organic layer was dried over anhydrous sodium sulphate, filtered, and concentrated. The crude product was purified by flash column chromatography to obtain the purified product 56 (12 mg, 86%) as a white solid.

Analytical TLC (silica gel 60), 40% ethyl acetate in n-hexane, $R_f$=0.1; $^1$H NMR (500 MHz, $CDCl_3$) δ 8.21 (d, J=9.3 Hz, 2H), 7.59 (d, J=15.9 Hz, 1H), 7.03 (d, J=9.2 Hz, 2H), 7.00-6.92 (m, 2H), 6.88 (d, J=8.1 Hz, 1H), 6.24 (dt, J=15.8, 5.6 Hz, 1H), 5.99-5.88 (m, 1H), 5.56 (d, J=1.6 Hz, 1H), 5.40 (dd, J=17.2, 1.6 Hz, 1H), 5.25 (dd, J=10.5, 1.4 Hz, 1H), 5.08 (s, 2H), 4.82-4.72 (m, 3H), 4.68 (ddt, J=13.4, 5.6, 1.5 Hz, 1H), 4.26 (dt, J=12.8, 6.4 Hz, 1H), 3.90 (s, 3H), 3.72 (dd, J=6.7, 1.7 Hz, 1H), 2.03 (br s, 1H), 1.37 (d, J=6.3 Hz, 3H); $^{13}$C NMR (125 MHz, $CDCl_3$) δ 171.7, 163.7, 159.3, 149.9, 149.4, 148.0, 141.7, 136.7, 131.6, 128.9, 125.9, 123.6, 120.9, 120.4, 118.6, 114.9, 113.9, 111.5, 70.9, 70.7, 69.2, 65.8, 65.5, 62.1, 56.0, 21.9; LRMS (ESI) 569.2 ([M+H]$^+$).

Step 2:

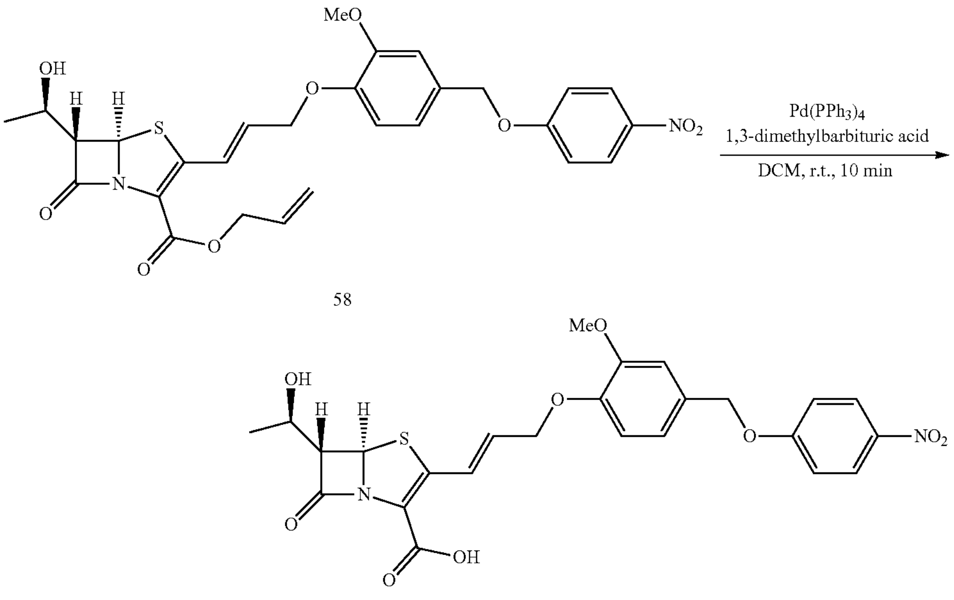

58

MCW-012

To a vial were added beta-lactam 56 (1.6 mg, 2.82 μmol), $Pd(PPh_3)_4$ (1.6 mg, 1.41 μmol), 1,3-dimethylbarbituric acid (1.1 mg, 4.04 μmol) and DCM (0.3 mL). The crude mixture was subjected to preparative C18 reverse phase HPLC purification using 0.01% TFA in water and $CH_3CN$ as eluent, and used directly for enzymatic assay.

Example 22. Preparation of 4-nitrobenzyl (5R,6S)-6-((R)-1-hydroxyethyl)-3-((E)-3-(2-methoxy-4-(((3-oxo-3H-phenoxazin-7-yl)oxy)methyl)phenoxy)prop-1-en-1-yl)-7-oxo-1-azabicyclo[3.2.0]hept-2-ene-2-carboxylate (MCW-013)

The synthesis of MCW-013 was similar to MCW-001 by using commercially available 4-nitrobenzyl (5R,6S)-6-((R)-1-hydroxyethyl)-3,7-dioxo-1-azabicyclo[3.2.0]heptane-2-carboxylate

Example 23. Activity of Beta-Lactamases Towards Compounds MCW-001 to MCW-011

Materials and Methods

Recombinant his-tagged beta-lactamases, including NDM-1, IMP-1, KPC-2, VIM-2 and OXA-48 were overexpressed in *Escherichia coli*. The enzymes were purified using HisTrap Ni-NTA columns. AmpC and TEM were purchased from commercial sources.

The enzymatic activity of these beta-lactamases in hydrolysing beta-lactam compounds was tested using nitrocefin as a probe. Nitrocefin (50 μM) dissolved in phosphate buffer (pH=7.4) was mixed with each purified beta-lactamase. Once hydrolyzed, nitrocefin underwent a rapid color change from yellow to red. The hydrolysis process of nitrocefin was monitored by measuring the absorbance at 485 nm with a Molecular Device SpectraMax® Paradigm® Multi-Mode Microplate Reader.

The activity of the beta-lactamases towards compounds MCW-001 to MCW-011 were then monitored using a Hitachi F7000 fluorescent spectrometer, Molecular Device SpectraMax© Paradigm® Multi-Mode Microplate Reader and Cary 50 UV-Visible spectrometer. The fluorescence-based activity assays were performed in phosphate-buffer saline. The concentration of some of the compounds were determined by boiling the compounds in PBS solution until fluorescence signal was saturated. The amount of released fluorophore was quantified via fluorescence spectroscopy by comparing to a corresponding calibration curve.

The selectivity of some probes were evaluated with clinical isolates. The carbapenemases presence in the bacteria (CPE, i.e., Carbapenemase Producing Enterobacteriaceae) were verified by PCR (Polymerase Chain Reaction). 1 μL loop-full of each test bacterium from overnight-cultured LB agar plate were added to 100 μL PBS buffer with 0.5% CHAPS. The bacteria were vortexed to give a homogenious suspension and incubated for 15 min. To each of the bacteria-lysis buffer mixture (20 μL) were added quick test reagents (Probes (Final concentration=10 μM), CarbaNP solution A and CarbaNP solution B). CarbaNP solutions A and B were freshly prepared according to CLSI protocol, where solution A contains 10 mM zinc sulphate and phenol red buffer at pH=7.8±0.1 and solution B was a mixture of solution A with 3 mg/mL imipenem.

Results

The enzymatic activity of beta-lactamases, including NDM-1, IMP-1, VIM-2, KPC-2, OXA-48, AmpC, and TEM, was examined against the synthesized fluorescence turn-on probes MCW-001 to MCW-011. Among the tested beta-lactamases, NDM-1, IMP-1, VIM-2, KPC-2 and OXA-48 are carbapenemases, whereas AmpC and TEM are not. Nitrocefin was used as a control to test the activity of the beta-lactamases because it can be hydrolyzed by a wide range of beta-lactamases.

FIG. 1 shows that all of the tested beta-lactamases can hydrolyze nitrocefin (50 μM). Except NDM-1, the hydrolysis reactions became complete within about 30 min as the optical absorption at 485 nm plateaued.

Figure 2:
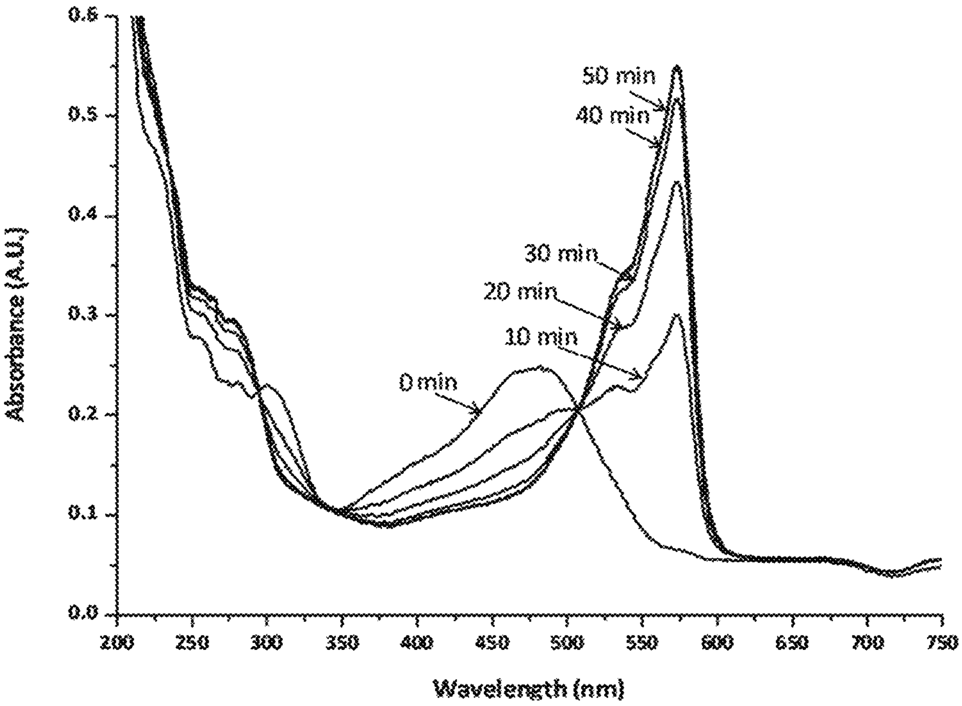
FIG. 2 is a graph showing the absorption change of MCW-001(10 μM) in the presence of IMP-1 (2 μM) over time.

FIG. 2 shows that the reactions of MCW-001 (10 μM) with IMP-1 (2 μM) provided a decreased in absorbance maximum at 480 nm and increase in absorbance maximum at 571 nm, which is the fundamental basis of the colorimetric response. The new absorbance maximum matched with the absorbance maximum of resorufin. Single isosbestic point at around 520 nm suggested no detectable intermediated was formed in the hydrolysis process and the fluorophore release is spontaneous upon beta-lactam hydrolysis.

Figure 3:
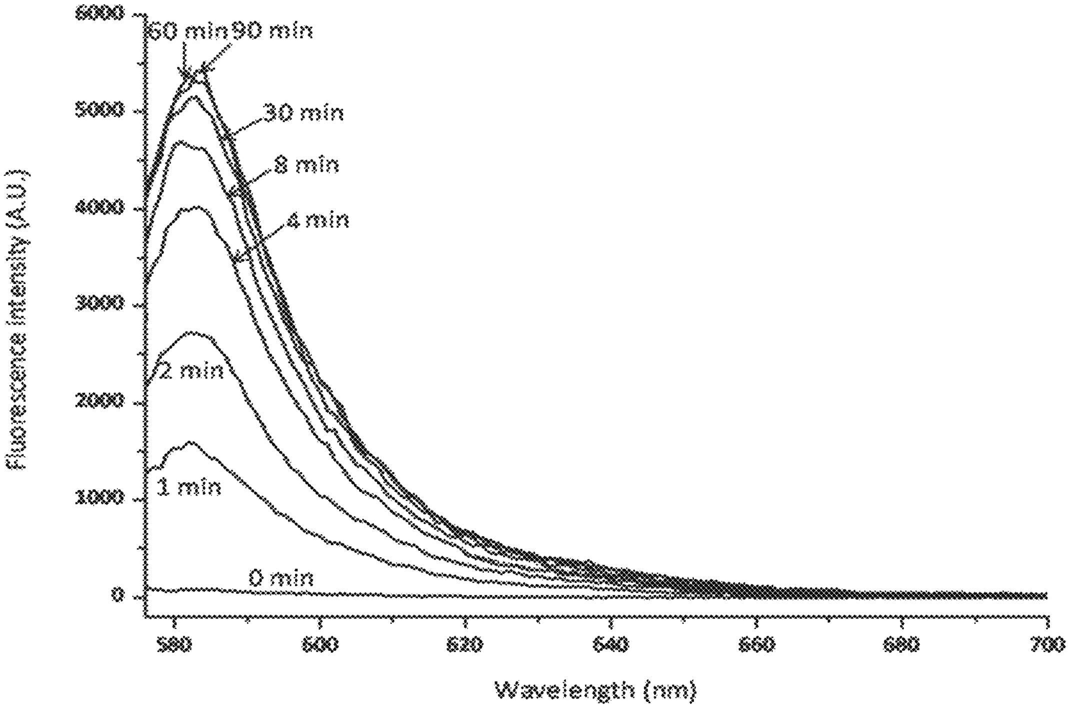
FIG. 3 is a graph showing the fluorescence signal of MCW-001 (1 μM) in the presence of IMP-1 (0.5 μM) over time.

FIG. 3 shows that the reaction of MCW-001 (1 μM) with IMP-1 (0.5 μM) provide more than 60-fold fluorescence turn-on signal upon beta-lactam hydrolysis.

Figure 4:
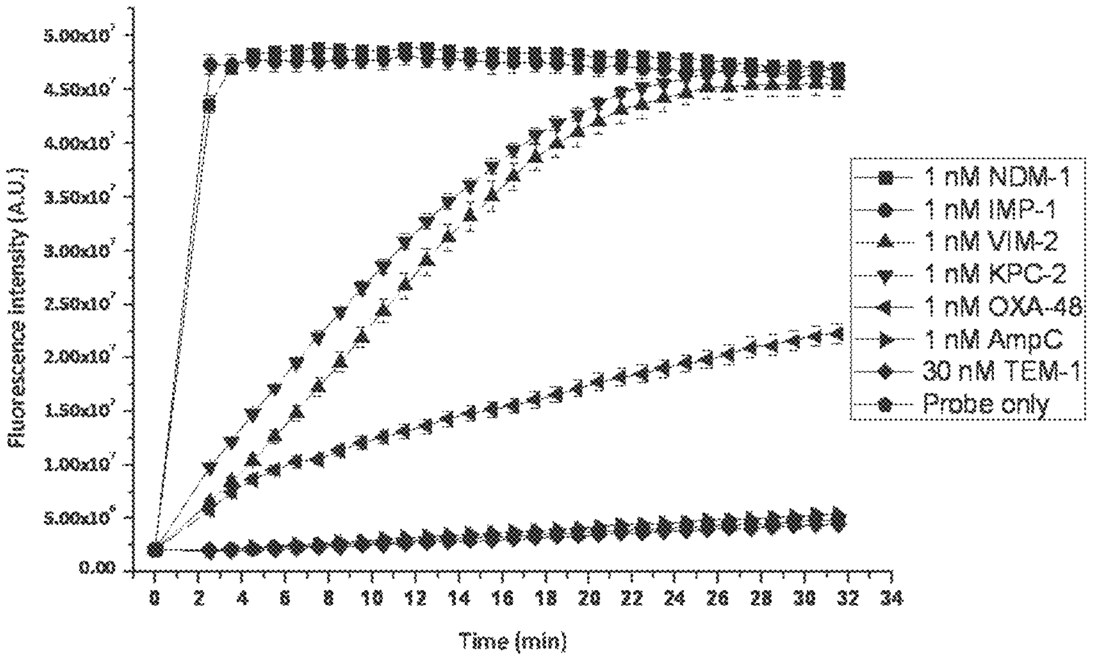
FIG. 4 is a graph showing the fluorescence signal over time (min) in reaction systems containing MCW-001 with various beta-lactamases. [MCW-001]=2.0 μM.

FIG. 4 shows that the reactions of MCW-001 with the carbapenemases, i.e., NDM-1, IMP-1, VIM-2, KPC-2 and OXA-48, resulted in a pronounced increase in the fluorescent signal. The hydrolysis reactions with NDM-1 and IMP-1 became complete within about 2 min as the fluorescent signal plateaued. The hydrolysis reaction with VIM-2 and KPC-2 were slower compared to the reactions with NDM-1 and IMP-1, and became complete at about 25 min. Hydrolysis by OXA-48 provided significant fluorescence signal but did not reach plateau within 30 minutes. The reactions of MCW-001 with AmpC and TEM, however, only caused minimal changes in the fluorescent signal. Therefore, MCW-001 can be readily hydrolyzed by NDM-1, IMP-1, VIM-2, KPC-2 and OXA-48, but not AmpC or TEM, thereby demonstrating that MCW-001 is specific for carbapenemases. The activity of carbapenemases towards MCW-001 was evaluated with Michaelis-Menten kinetics and summarized in Table 2. The detection limit for MCW-001 towards various carbapenemases were determined. All of the carbapenemases could be detected from pico-molar to sub-pico-molar range and the results were summarized in Table 3.

Figure 5:
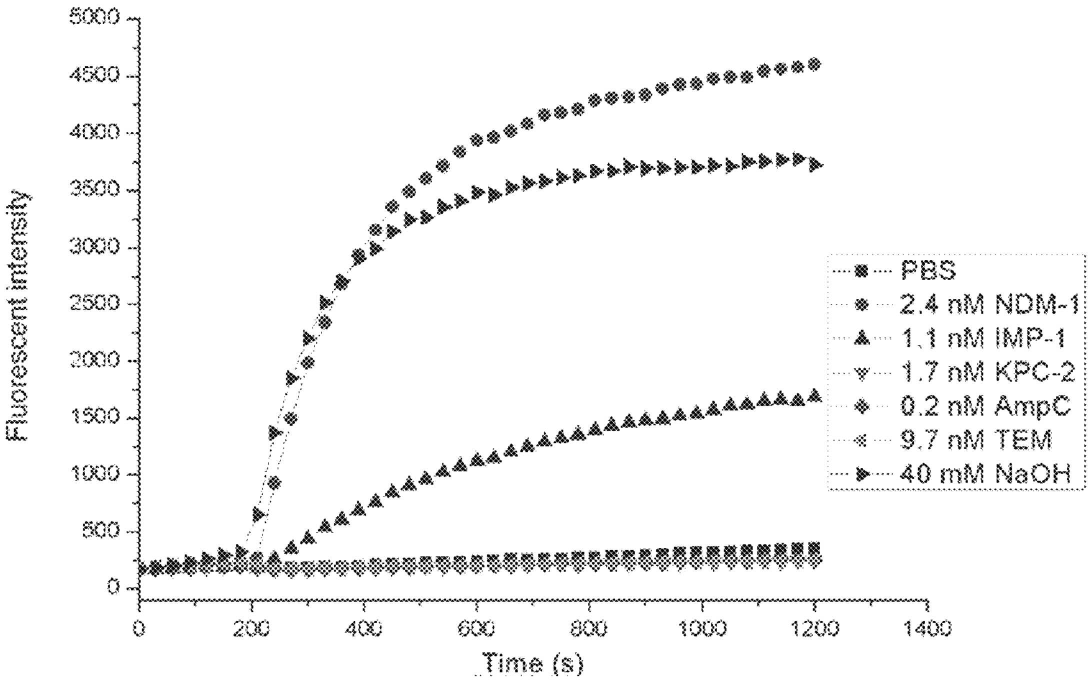
FIG. 5 is a graph showing the fluorescence signal over time (min) in reaction systems containing MCW-002 with various beta-lactamases. [MCW-002]=1.1 μM.

FIG. 5 shows that the reactions of MCW-002 with NDM-1 and IMP-1 resulted in a pronounced increase in the fluorescent signal. The hydrolysis reaction with IMP-1 was slower compared to the reaction with NDM-1. The reactions of MCW-002 with KPC-2, AmpC, and TEM, however, only induced minimal changes in the fluorescent signal. Therefore, MCW-002 can be readily hydrolyzed by NDM-1 and IMP-1, but not KPC-2, AmpC or TEM, demonstrating that MCW-002 is specific for NDM-1 and IMP-1, especially NDM-1.

Figure 6:
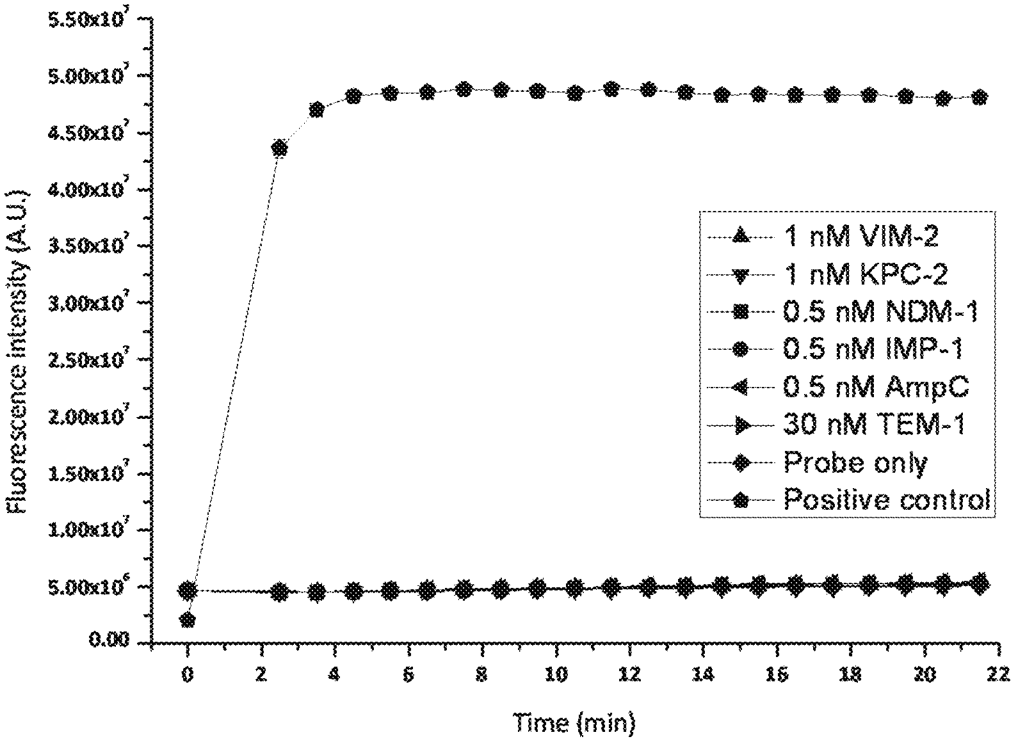
FIG. 6 is a graph showing the fluorescence signal over time (min) in reaction systems containing MCW-003 with various beta-lactamases. [MCW-003]=2.0 μM.

FIG. 6 shows that none of the reactions involving MCW-003 exhibited changes in the fluorescence signal, due to the fact that MCW-003 was unreactive to the tested beta-lactamases. MCW-001 (2 μM) in NDM-1 (1 nM) was used as positive control.

Figure 7:
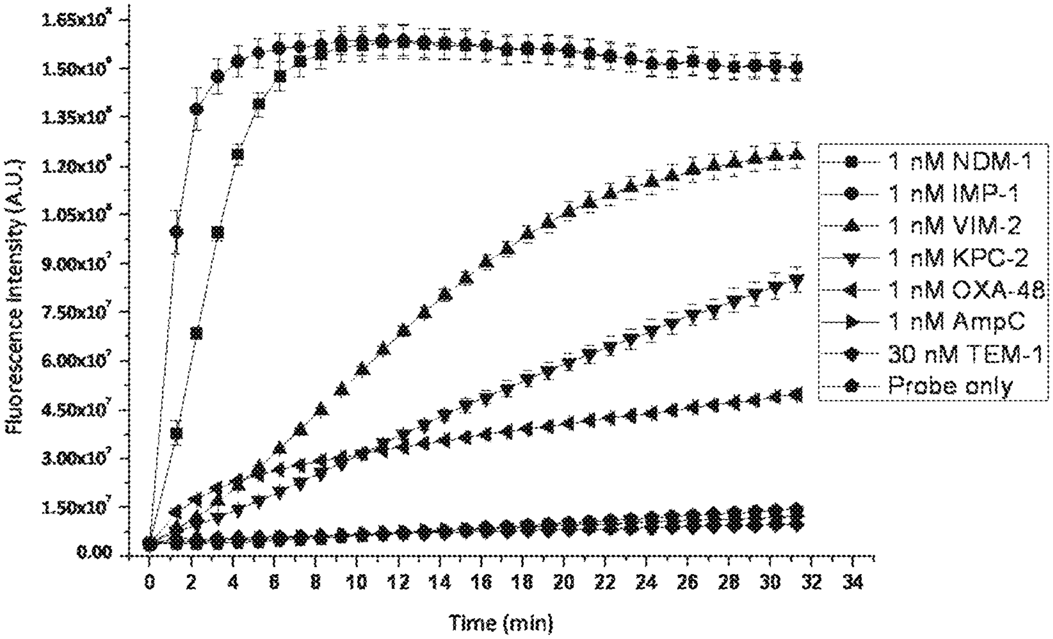
FIG. 7 is a graph showing the fluorescence signal over time (min) in reaction systems containing MCW-004 with various beta-lactamases. [MCW-004]=2.0 μM.

FIG. 7 shows that the performance of MCW-004 in the presence of NDM-1, IMP-1, VIM-2, KPC-2 and OXA-48 are similar to MCW-001. The Michaelis-Menten kinetics data for MCW-004 were summarized in Table 4. The limit of detection for MCW-004 towards selected carbapenemases were summarized in Table 5.

Figure 8:
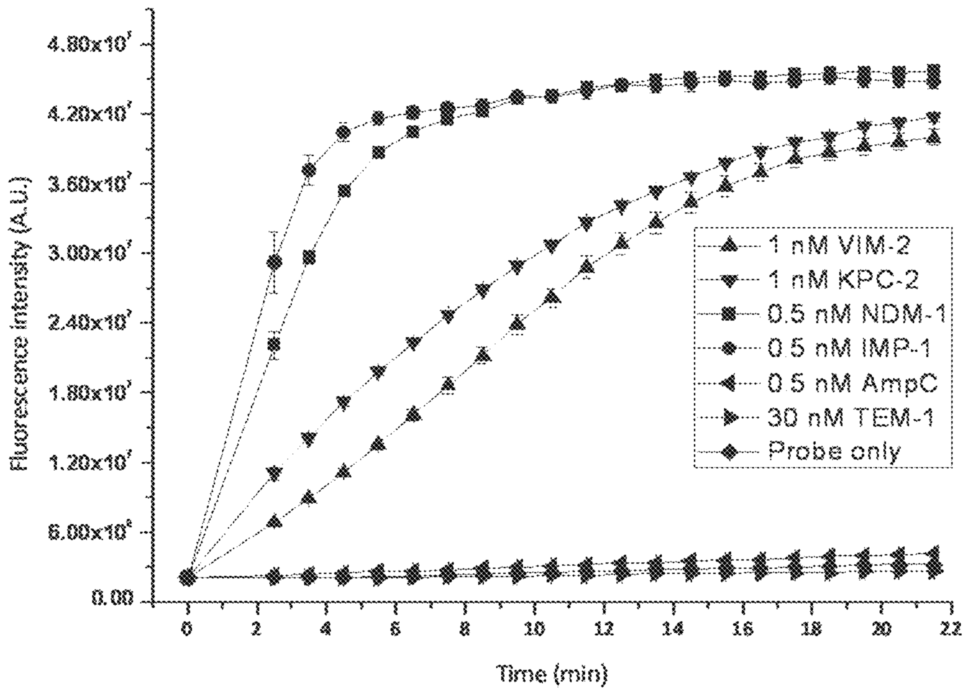
FIG. 8 is a graph showing the fluorescence signal over time (min) in reaction systems containing MCW-005 with various beta-lactamases. [MCW-005]=2.0 μM.

FIG. 8 shows that the performance of MCW-005 in the presence of NDM-1, IMP-1, VIM-2 and KPC-2 are similar to MCW-001.

Figure 9:
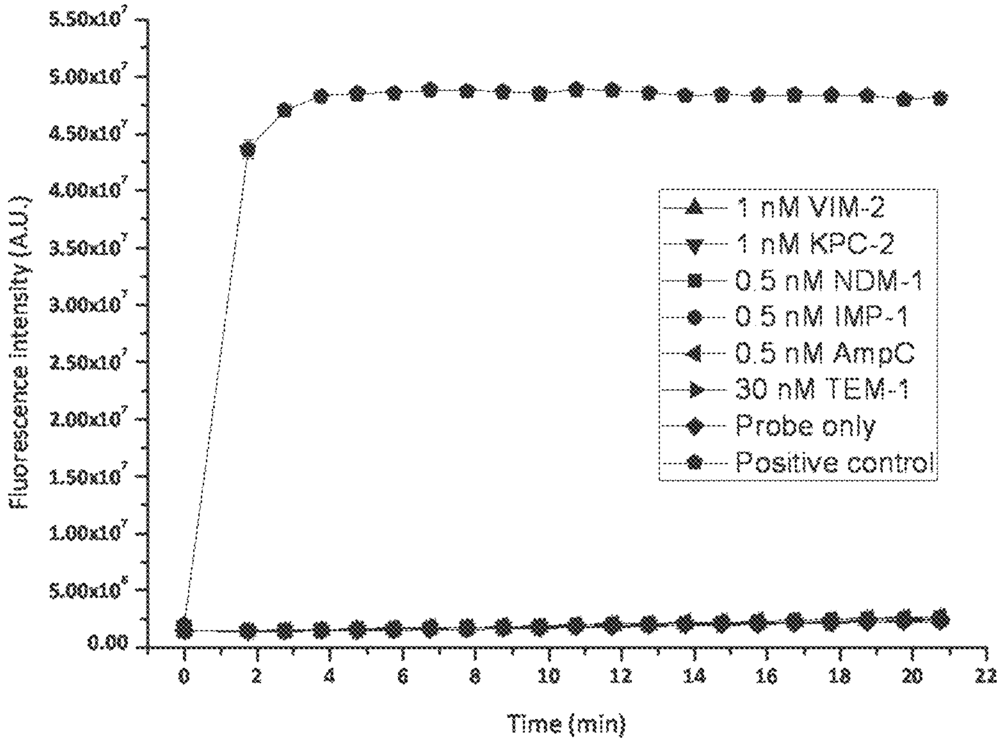
FIG. 9 is a graph showing the fluorescence signal over time (min) in reaction systems containing MCW-006 with various beta-lactamases. [MCW-006]=2.0 μM.

FIG. 9 shows that none of the reactions involving MCW-006 exhibited changes in the fluorescence signal, due to the fact that MCW-006 was unreactive to the tested beta-lactamases. MCW-001 (2 μM) in NDM-1 (1 nM) was used as positive control.

Figure 10:
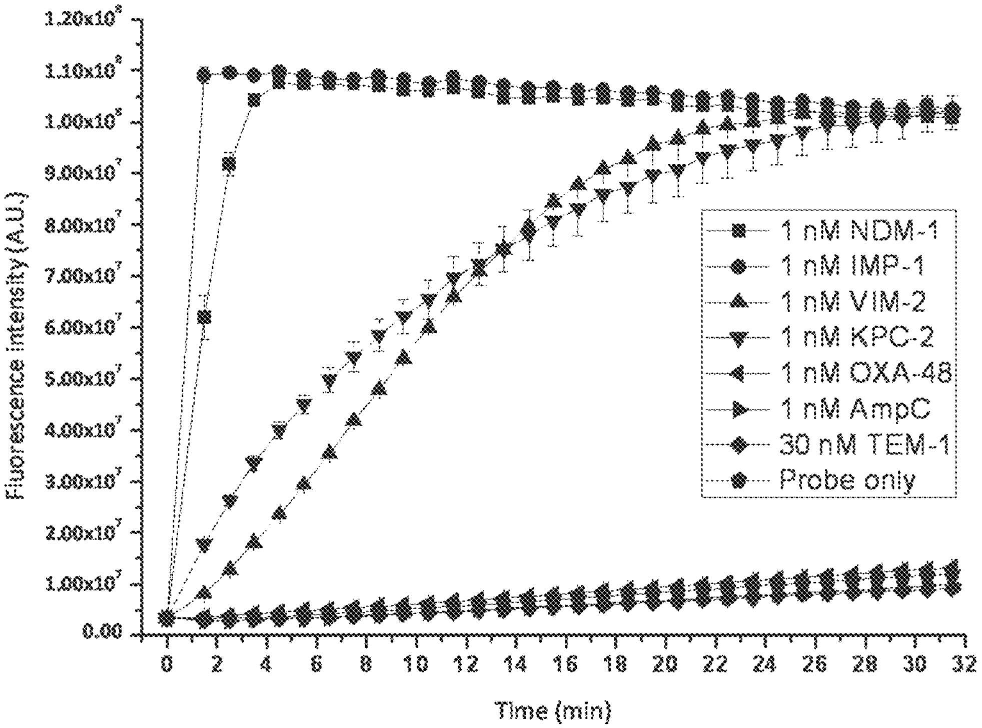
FIG. 10 is a graph showing the fluorescence signal over time (min) in reaction systems containing MCW-007 with various beta-lactamases. [MCW-007]=2.0 μM.

FIG. 10 shows that the reactions of MCW-007 with the carbapenemases, i.e., NDM-1, IMP-1, VIM-2 and KPC-2, resulted in a pronounced increase in the fluorescent signal. The hydrolysis reaction with NDM-1 and IMP-1 became complete within about 5 min as the fluorescent signal plateaued. The hydrolysis reactions with VIM-2 and KPC-2 were slower compared to the reaction with NDM-1 and IMP-1. However, MCW-007 did not provide significant fluorescence response towards OXA-48. The reactions of MCW-007 with AmpC and TEM, only induced minimal changes in the fluorescent signal. This demonstrated that MCW-007 is specific for some carbapenemases. The Michaelis-Menten kinetics data for MCW-007 were summarized in Table 6. The limit of detection for MCW-007 towards selected carbapenemases were summarized in Table 7.

Figure 11:
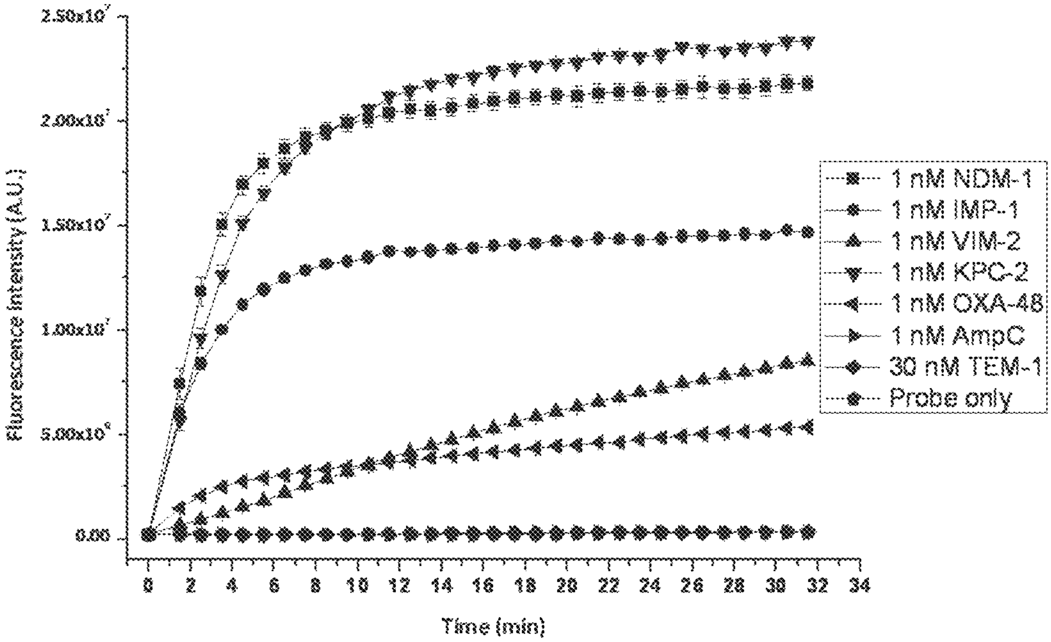
FIG. 11 is a graph showing the fluorescence signal over time (min) in reaction systems containing MCW-008 with various beta-lactamases. [MCW-008]=2.0 μM.

FIG. 11 shows that the reactions of MCW-008 with the carbapenemases, i.e., NDM-1, IMP-1, VIM-2, KPC-2 and OXA-48, resulted in an increase in the fluorescent signal. The reactions of MCW-008 with AmpC and TEM, however, only induced minimal changes in the fluorescent signal. Therefore, MCW-008 can be hydrolyzed by NDM-1, IMP-1, VIM-2, KPC-2 and OXA-48, but not AmpC or TEM, thereby demonstrating that MCW-008 is specific for carbapenemases.

Figure 12:
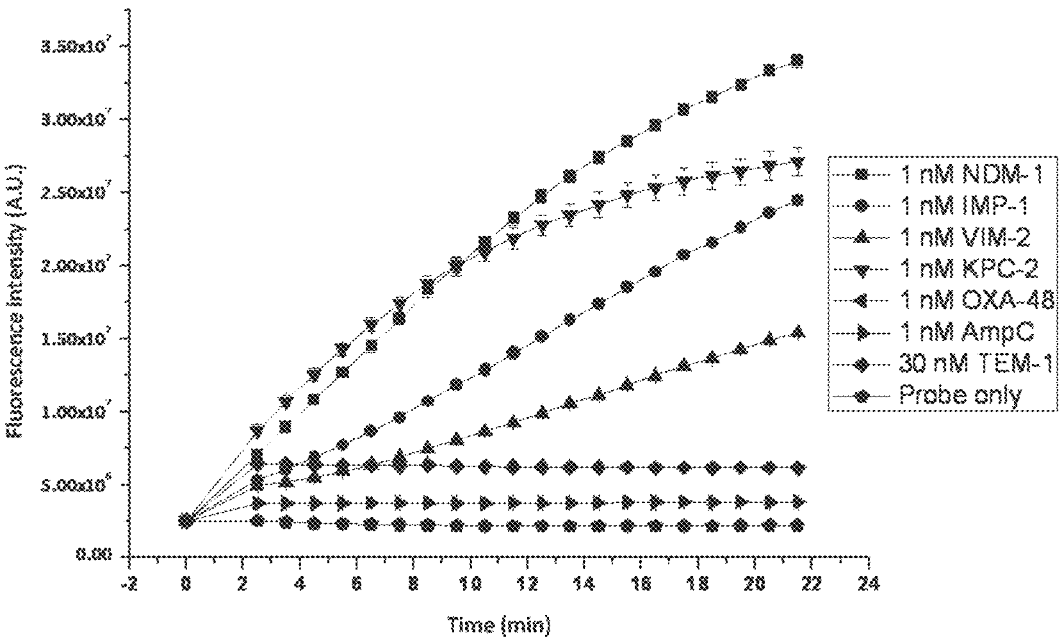
FIG. 12 is a graph showing the fluorescence signal over time (min) in reaction systems containing MCW-009 with various beta-lactamases. [MCW-009]=2.0 μM.

FIG. 12 shows that only the reaction of MCW-009 with NDM-1, IMP-1, VIM-2, and KPC-2 resulted in an increase in the fluorescent signal; the rate and magnitude of the fluorescent signal increase in this reaction were much smaller and did not reach plateau within 20 minutes.

Figure 13:
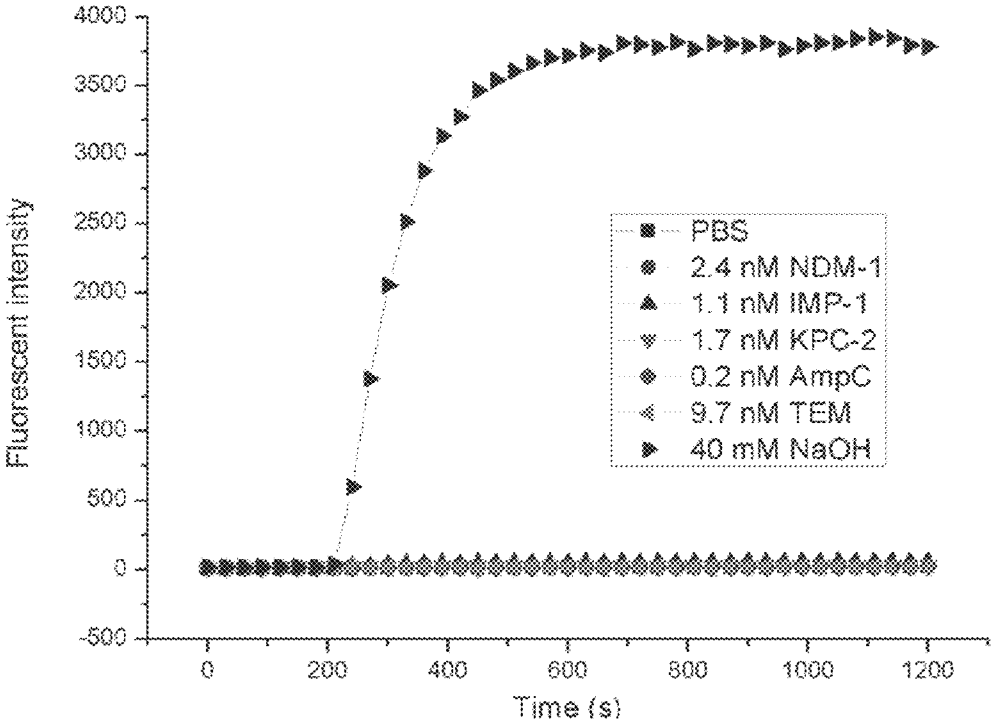
FIG. 13 is a graph showing the fluorescence signal over time (min) in reaction systems containing MCW-010 with various beta-lactamases. [MCW-010]=2.0 μM.

FIG. 13 shows that MCW-010 did not exhibited changes in the fluorescence signal upon incubation with selected beta-lactamases within 20 minutes.

Figure 14:
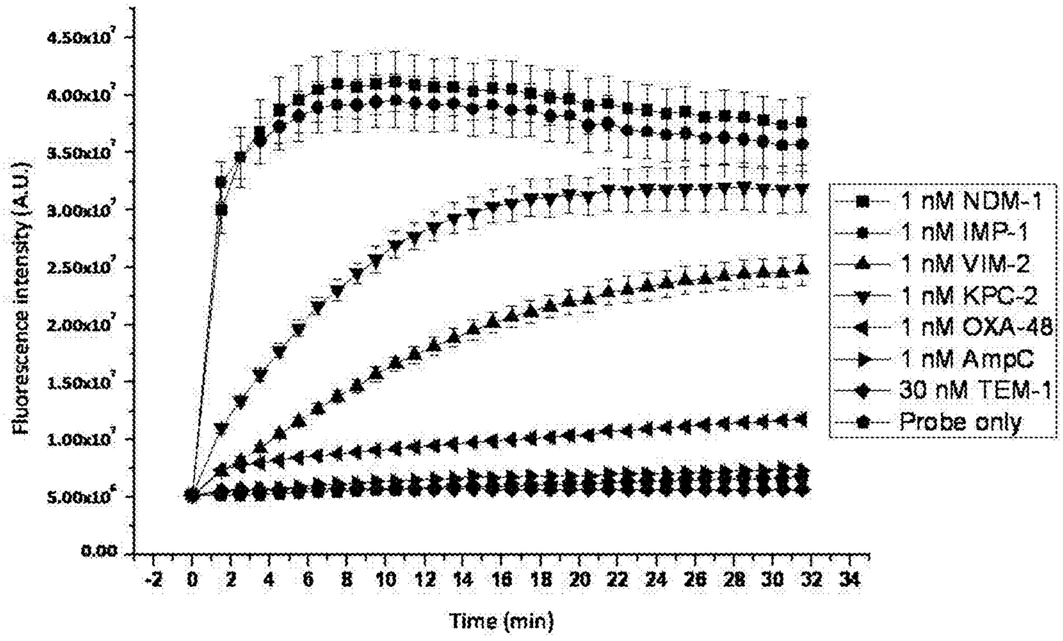
FIG. 14 is a graph showing the fluorescence signal over time (min) in reaction systems containing MCW-011 with various beta-lactamases. [MCW-0011]=0.5 μM.

FIG. 14 shows that the reactions of MCW-011 with the carbapenemases, i.e., NDM-1, IMP-1, VIM-2, KPC-2 and OXA-48, resulted in an increase in the fluorescent signal. The reactions of MCW-011 with AmpC and TEM, however, only induced minimal changes in the fluorescent signal. Therefore, MCW-011 can be hydrolyzed by NDM-1, IMP-1, VIM-2, KPC-2 and OXA-48, but not AmpC or TEM, thereby demonstrating that MCW-011 is specific for carbapenemases.

Figure 15:
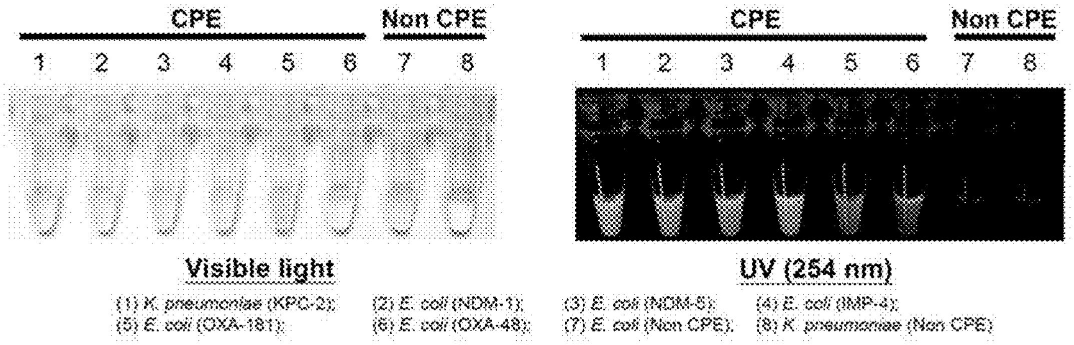
FIG. 15 is a photo taken after MCW-004 incubated with clinical isolates in the presence of lysis buffer after 15 min under visible light and UV light.

FIG. 15 shows that the reaction of MCW-004 against panel of clinical isolates, incubated for 15 min, observed under visible light and UV light. The images of FIG. 15 indicate that MCW-004 provide observable fluorogenic signal in CPE strains but not the Non CPE strains.

Figure 16:
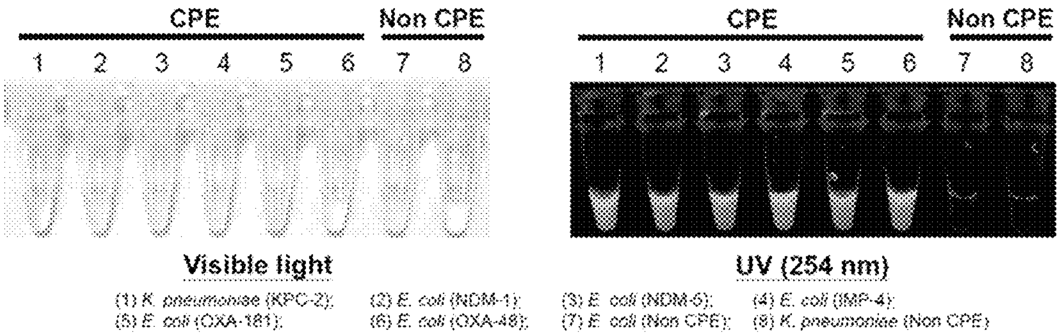
FIG. 16 is a photo taken after MCW-004 incubated with clinical isolates in the presence of lysis buffer after 120 min under visible light and UV light.

FIG. 16 shows that the reaction of MCW-004 against panel of clinical isolates, incubated for 120 min, observed under visible light and UV light. The images of FIG. 16 indicate that MCW-004 provide observable fluorogenic signal in CPE strains but not the Non CPE strains.

Figure 17:
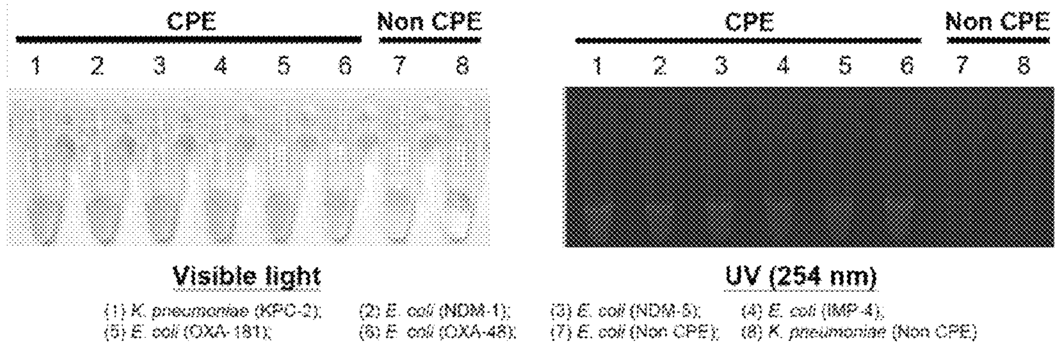
FIG. 17 is a photo taken after MCW-001 incubated with clinical isolates in the presence of lysis buffer after 15 min under visible light and UV light.

FIG. 17 shows that the reaction of MCW-001 against panel of clinical isolates, incubated for 15 min, observed under visible light and UV light. The images of FIG. 17 indicate that MCW-001 provide observable colorimetric and fluorescence signal in CPE strains but not the Non CPE strains.

Figure 18:
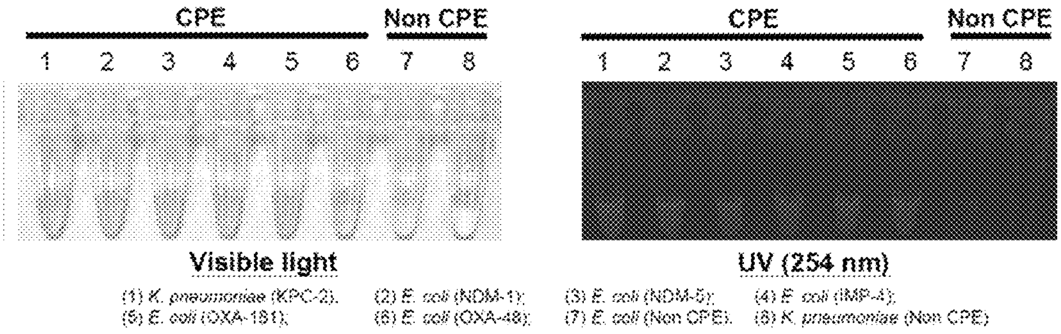
FIG. 18 is a photo taken after MCW-001 incubated with clinical isolates in the presence of lysis buffer after 120 min under visible light and UV light.
Figure 19:
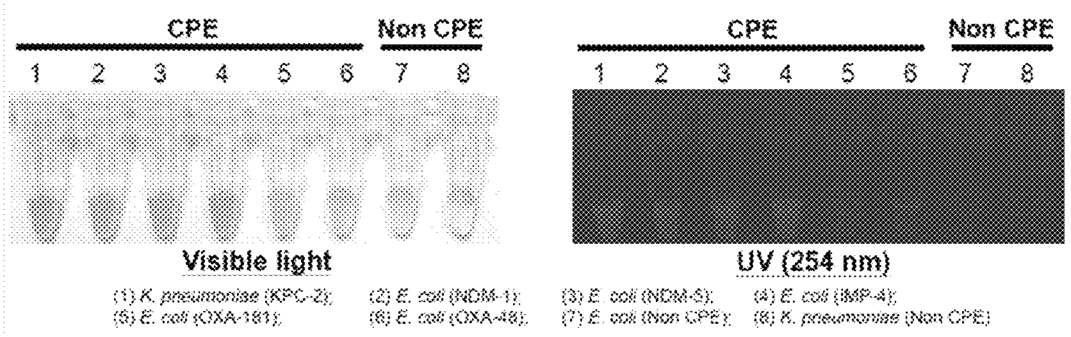
FIG. 19 is a photo taken after MCW-007 incubated with clinical isolates in the presence of lysis buffer after 15 min under visible light and UV light.
Figure 20:
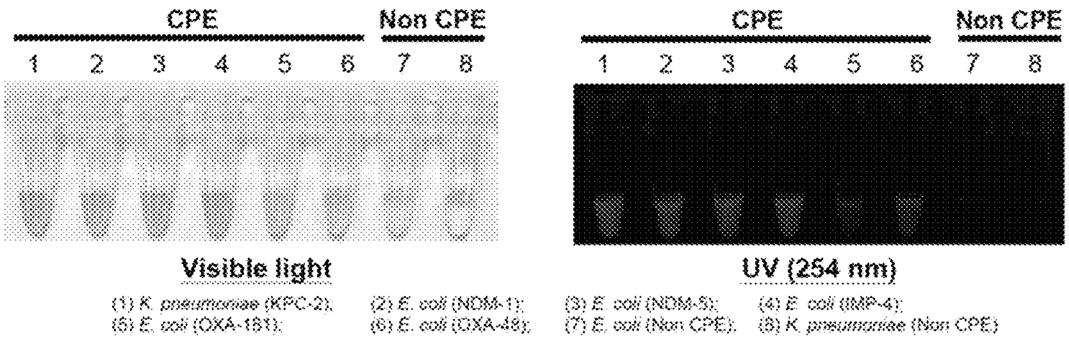
FIG. 20 is a photo taken after MCW-007 incubated with clinical isolates in the presence of lysis buffer after 120 min under visible light and UV light.
Figure 21:
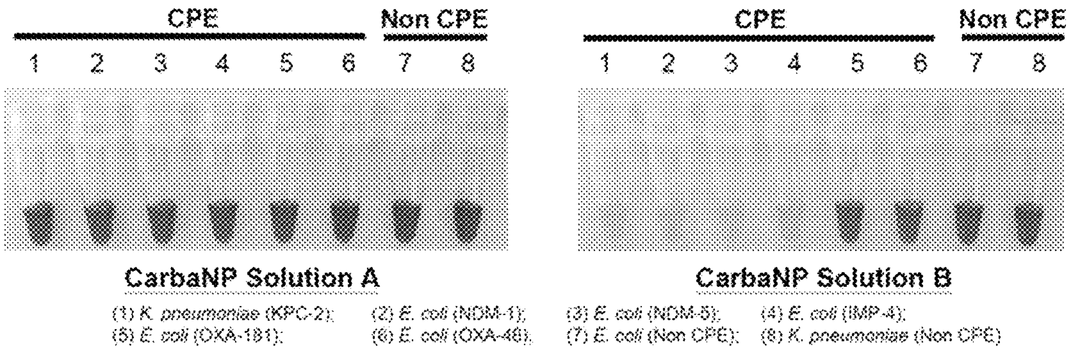
FIG. 21 is a photo taken after CarbaNP solution A and solution B incubated with clinical isolates in the presence of lysis buffer after 15 min under visible light.
Figure 22:
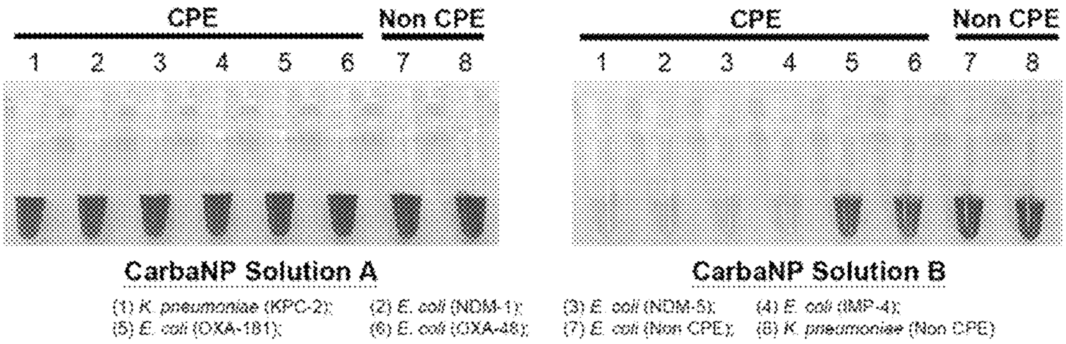
FIG. 22 is a photo taken after CarbaNP solution A and solution B incubated with clinical isolates in the presence of lysis buffer after 120 min under visible light.

FIG. 18 shows that the reaction of MCW-001 against panel of clinical isolates, incubated for 120 min, observed under visible light and UV light. The images of FIG. 18 indicate that MCW-001 provide observable colorimetric and fluorescence signal in CPE strains but not the Non CPE strains FIG. 19 shows that the reaction of MCW-007 against panel of clinical isolates, incubated for 15 min, observed under visible light and UV light. The images of FIG. 19 indicate that MCW-007 provide observable colorimetric and fluorescence signal in some CPE strains but not the Non CPE strains FIG. 20 shows that the reaction of MCW-007 against panel of clinical isolates, incubated for 120 min, observed under visible light and UV light. The images of FIG. 20 indicate that MCW-007 provide observable colorimetric and fluorescence signal in CPE strains but not the Non CPE strains FIG. 21 shows that the reaction of CarbaNP solution A and solution B against panel of clinical isolates, incubated for 15 min, observed under visible light. The images of FIG. 21 indicate that CarbaNP solution provide observable colorimetric signal in non-OXA producing CPE strains but not the Non CPE strains FIG. 22 shows that the reaction of CarbaNP solution A and solution B against panel of clinical isolates, incubated for 120 min, observed under visible light. The images of FIG. 22 indicate that CarbaNP solution provide observable colorimetric signal in non-OXA producing CPE strains but not the Non CPE strains.

TABLE 2

| Enzyme | $k_{cat}$ ($s^{-1}$) | $K_M$ (μM) | $k_{cat}/K_M$ ($M^{-1}s^{-1}$) |
|---|---|---|---|
| NDM-1 | 29.8 ± 0.81 | 1.66 ± 0.13 | $1.80 \times 10^7$ |
| IMP-1 | 33.9 ± 0.71 | 1.20 ± 0.08 | $2.82 \times 10^7$ |
| VIM-2 | 1.96 ± 0.05 | 1.18 ± 0.10 | $1.66 \times 10^6$ |
| KPC-2 | 2.17 ± 0.07 | 0.93 ± 0.11 | $2.32 \times 10^6$ |
| OXA-48 | 2.83 ± 0.18 | 0.66 ± 0.08 | $4.25 \times 10^6$ |

TABLE 3

| Carbapenemases | 3S/k |
|---|---|
| NDM-1 | 0.327 pM |
| IMP-1 | 0.333 pM |
| VIM-2 | 3.28 pM |
| KPC-2 | 4.43 pM |
| OXA-48 | 30.3 pM |

TABLE 4

| Enzyme | $k_{cat}$ ($s^{-1}$) | $K_M$ (μM) | $k_{cat}/K_M$ ($M^{-1}s^{-1}$) |
|---|---|---|---|
| NDM-1 | 23.5 ± 0.98 | 1.57 ± 0.16 | $1.50 \times 10^7$ |
| IMP-1 | 47.3 ± 3.34 | 1.74 ± 0.29 | $2.72 \times 10^7$ |
| VIM-2 | 2.28 ± 0.07 | 1.88 ± 0.13 | $1.21 \times 10^6$ |
| KPC-2 | 2.36 ± 0.22 | 3.41 ± 0.59 | $6.91 \times 10^5$ |
| OXA-48 | 10.2 ± 0.74 | 1.09 ± 0.12 | $9.42 \times 10^6$ |

TABLE 5

| Carbapenemases | 3S/k |
|---|---|
| NDM-1 | 0.546 pM |
| IMP-1 | 0.328 pM |
| VIM-2 | 5.37 pM |
| KPC-2 | 5.28 pM |
| OXA-48 | 24.9 pM |

TABLE 6

| Enzyme | $k_{cat}$ ($s^{-1}$) | $K_M$ (μM) | $k_{cat}/K_M$ ($M^{-1}s^{-1}$) |
|---|---|---|---|
| NDM-1 | 95.1 ± 4.32 | 1.56 ± 0.17 | $6.11 \times 10^7$ |
| IMP-1 | 116 ± 2.81 | 1.33 ± 0.08 | $8.76 \times 10^7$ |
| VIM-2 | 6.87 ± 0.11 | 0.92 ± 0.04 | $7.46 \times 10^6$ |
| KPC-2 | 8.04 ± 1.96 | 0.77 ± 0.06 | $1.05 \times 10^7$ |

TABLE 7

| Carbapenemases | 3S/k |
|---|---|
| NDM-1 | 0.439 pM |
| IMP-1 | 0.379 pM |
| VIM-2 | 5.22 pM |
| KPC-2 | 8.50 pM |
| OXA-48 | 367 pM |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A compound to detect carbapenemases or microbial carbapenemase resistance, wherein the compound have the structure of CP-A-D or salts thereof, wherein CP is an azabicyclo moiety composed of a beta-lactam ring and an unsaturated five-membered hetero-ring having a C—C double bond; A is a conjugated system attached to the unsaturated five-membered hetero-ring at a carbon atom of the double bond and is at meta-position relative to the nitrogen atom; and D is connected to A via a methylene bridge and comprises a chemical probe, wherein the beta-lactam ring of the compound can be hydrolyzed by one or more carbapenemases, thereby triggering intramolecular rearrangement to release D from the compounds, wherein D further comprises a self-immolative linker interposed between the methylene bridge and the rest of D, wherein D comprises a luminescence probe, and the luminescence probe is selected from the group consisting of resorufin, fluorescein, Tokyo Green, coumarin, and luciferin, wherein the self-immolative linker is spontaneously separated from the rest of D following the release of D from the compound, wherein the self-immolative linker is 4-methanediyl-2-methoxyphenoxy, and wherein the phenoxy oxygen of the self-immolative linker is connected to the methylene bridge and the methanediyl group of the self-immolative linker is connected to the rest of D.

2. A compound to detect carbapenemases or microbial carbapenemase resistance, wherein the compound has the structure of Formulas Ia, Ib, Ic, Id or Ie, or salts thereof, Formula Ia

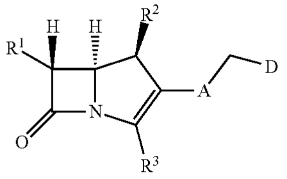

Formula Ib

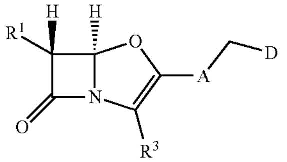

Formula Ic

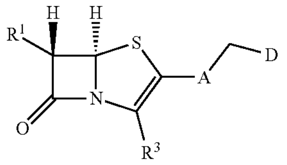

Formula Id

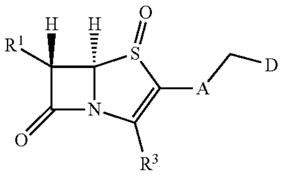

Formula Ie

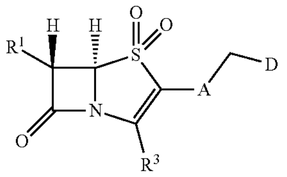

(a) wherein A is a divalent group selected from $-(CR^4=CR^5)_m-$, $-(C\equiv C)_n-$, optionally substituted arylenes, optionally substituted heteroarylenes, and covalent adducts thereof, wherein the covalent adducts are conjugated systems and wherein m and n are positive integers;

(b) wherein D is connected to A via a methylene bridge and comprises a chemical probe, wherein D comprises a luminescence probe, and the luminescence probe is selected from the group consisting of resorufin, fluorescein, Tokyo Green, coumarin, and luciferin;

(c) wherein the beta-lactam ring of the compound can be hydrolyzed by one or more carbapenemases, thereby triggering intramolecular rearrangement to release D from the compound;

(d) wherein $R^1$, $R^2$, $R^4$, and $R^5$ are independently:

a hydrogen atom, a halogen atom, a sulfonic acid, an azide group, a cyanate group, an isocyanate group, a nitrate group, a nitrile group, an isonitrile group, a nitrosooxy group, a nitroso group, a nitro group, an aldehyde group, an acyl halide group, a carboxylic acid group, a carboxylate group, an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, an optionally substituted heteroaryl group;

a hydroxyl group optionally containing one substituent at the hydroxyl oxygen, wherein the substituent is an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

a thiol group optionally containing one substituent at the thiol sulfur, wherein the substituent is an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

a sulfonyl group containing an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

an amino group optionally containing one or two substituents at the amino nitrogen, wherein the substituents are optionally substituted alkyl groups, optionally substituted heteroalkyl groups, optionally substituted alkenyl groups, optionally substituted heteroalkenyl groups, optionally substituted alkynyl groups, optionally substituted heteroalkynyl groups, optionally substituted aryl groups, optionally substituted heteroaryl groups, or combinations thereof;

an amide group optionally containing one or two substituents at the amide nitrogen, wherein the substituents are optionally substituted alkyl groups, optionally substituted heteroalkyl groups, optionally substituted alkenyl groups, optionally substituted heteroalkenyl groups, optionally substituted alkynyl groups, optionally substituted heteroalkynyl groups, optionally substituted aryl groups, optionally substituted heteroaryl groups, or combinations thereof;

an azo group containing an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

an acyl group containing an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

an ester group containing an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

a carbonate ester group containing an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

an ether group containing an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

an aminooxy group optionally containing one or two substituents at the amino nitrogen, wherein the substituents are optionally substituted alkyl groups, optionally substituted heteroalkyl groups, optionally substituted alkenyl groups, optionally substituted heteroalkenyl groups, optionally substituted alkynyl groups, optionally substituted heteroalkynyl groups, optionally substituted aryl groups, optionally substituted heteroaryl groups, or combinations thereof; or a hydroxyamino group optionally containing one or two substituents, wherein the substituents are optionally substituted alkyl groups, optionally substituted heteroalkyl groups, optionally substituted alkenyl groups, optionally substituted heteroalkenyl groups, optionally substituted alkynyl groups, optionally substituted heteroalkynyl groups, optionally substituted aryl groups, optionally substituted heteroaryl groups, or combinations thereof;

(e) wherein $R^3$ is:

a carboxylic acid or carboxylate;

an ester group containing an optionally substituted alkyl group, an optionally substituted heteroalkyl group, an optionally substituted alkenyl group, an optionally substituted heteroalkenyl group, an optionally substituted alkynyl group, an optionally substituted heteroalkynyl group, an optionally substituted aryl group, or an optionally substituted heteroaryl group;

an amide group optionally containing one or two substituents at the amide nitrogen, wherein the substituents are optionally substituted alkyl groups, optionally substituted heteroalkyl groups, optionally substituted alkenyl groups, optionally substituted heteroalkenyl groups, optionally substituted alkynyl groups, optionally substituted heteroalkynyl groups, optionally substituted aryl groups, optionally substituted heteroaryl groups, or combinations thereof; or a hydroxamate group optionally containing one or two substituents, wherein the substituents are optionally substituted alkyl groups, optionally substituted heteroalkyl groups, optionally substituted alkenyl groups, optionally substituted heteroalkenyl groups, optionally substituted alkynyl groups, optionally substituted heteroalkynyl groups, optionally substituted aryl groups, optionally substituted heteroaryl groups, or combinations thereof;

(f) wherein $R^1$, $R^2$, $R^3$, $R^4$, and $R^5$, and their substituents are optionally and independently substituted with one or more chemical groups, wherein each chemical group is independently:

a halogen atom, an alkyl group, a heteroalkyl group, an alkenyl group, a heteroalkenyl group, an alkynyl group, a heteroalkynyl group, an aryl group, a heteroaryl group, —OH, —SH, $—NH_2$, $—N_3$, —OCN, —NCO, $—ONO_2$, —CN, —NC, —ONO, $—CONH_2$, —NO, $—NO_2$, $—ONH_2$, —SCN, —SNCS, $—CF_3$, $—CH_2CF_3$, $—CH_2Cl$, $—CHCl_2$, $—CH_2NH_2$, —NHCOH, —CHO, —OOCl, —COF, —COBr, —COOH, $—SO_3H$, $—CH_2SO_2CH_3$, $—PO_3H_2$, $—OPO_3H_2$, $—P(=O)(OR^{G1})(OR^{G2})$, $—OP(=O)(OR^{G1})(OR^{G2})$, $—BR^{G1}(OR^{G2})$, $—B(OR^{G1})(OR^{G2})$, or $-GR^{G1}$ in which -G is —O—, —S—, $—NR^{G2}—$, —C(=O)—, —S(=O)—, $—SO_2—$, —C(=O)O—, $—C(=O)NR^{G2}—$, —OC(=O)—, $—NR^{G2}C(=O)—$, —OC(=O)O—, $—OC(=O)NR^{G2}—$, $—NR^{G2}C(=O)O—$, $—NR^{G2}C(=O)NR^{G3}—$, —C(=S)—, —C(=S)S—, —SC(=S)—, —SC(=S)S—, $—C(=NR^{G2})—$, $—C(=NR^{G2})O—$, $—C(=NR^{G2})NR^{G3}—$, $—OC(=NR^{G2})—$, $—NR^{G2}C(=NR^{G3})—$, $—NR^{G2}SO_2—$, $—C(=NR^{G2})NR^{G3}—$, $—OC(=NR^{G2})—$, $—NR^{G2}C(=NR^{G3})—$, $—NR^{G2}SO_2—$, $—NR^{G2}SO_2NR^{G3}—$, $—NR^{G2}C(=S)—$, $—SC(=S)NR^{G2}—$, $—NR^{G2}C(=S)S—$, $—NR^{G2}C(=S)NR^{G3}—$, $—SC(=NR^{G2})—$, $—C(=S)NR^{G2}—$, $—OC(=S)NR^{G2}—$, $—NR^{G2}C(=S)O—$, $—SC(=O)NR^{G2}—$, $—NR^{G2}C(=O)S—$, —C(=O)S—, —SC(=O)—, —SC(=O)S—, —C(=S)O—, —OC(=S)—, —OC(=S)O—, $—SO_2NR^{G2}—$, $—BR^{G2}—$, or $—PR^{G2}—$, wherein each occurrence of $R^{G1}$, $R^{G2}$, and $R^{G3}$ is, independently, a hydrogen atom, a halogen atom, an alkyl group, a heteroalkyl group, an alkenyl group, a heteroalkenyl group, an alkynyl group, a heteroalkynyl group, an aryl group, or a heteroaryl group.

3. The compound of claim 1, wherein the luminescence probe remains non-luminescent or luminescence-quenched prior to carbapenemase-catalyzed hydrolysis of the compound and becomes luminescent or luminescence-enhanced after being released from the compound.

4. The compound of claim 1, wherein the beta-lactam ring of the compound can be hydrolyzed by one or more carbapenemases independently selected from the group consisting of Class A carbapenemases, Class B carbapenemases, Class C carbapenemases, and Class D carbapenemases.

5. A method to detect carbapenemases or microbial carbapenem resistance, comprising:

(a) contacting a sample containing one or more populations of bacteria with the compound of claim 1;

(b) detecting the release of D from the compound, wherein detection of the release of D indicates the presence of carbapenemases, wherein the presence of carbapenemases indicates the presence of microbial carbapenem resistance.

6. The method of claim 5, wherein D comprises a luminescence probe that remains non-luminescent or luminescence-quenched prior to carbapenemase-catalyzed hydrolysis of the compound and becomes luminescent or luminescence-enhanced after being released from the compound.

7. The method of claim 6, wherein the release of D is detected by detecting the luminescence signal of the luminescence probe, wherein the luminescence signal of the luminescence probe reaches between about 80 and about 100% of its maximum value within about 5 minutes, about 10 minutes, about 15 minutes, about 20 minutes, about 25 minutes, or about 30 minutes, following the contact of the sample with the compound.

8. The method of claim 7, wherein the luminescence signal of the luminescence probe, detected at about 5 minutes, about 10 minutes, about 15 minutes, about 20 minutes, about 25 minutes, or about 30 minutes following the contact of the sample with the compound, is positively correlated with the total concentration of carbapenemases, the total population of bacteria with carbapenem resistance, or both.

9. The method of claim 5, wherein the one or more populations of bacteria comprise enterobacteriaceae.

10. The method of claim 9, wherein the enterobacteriaceae comprise *Escherichia coli, Enterobacter aerogenes, Enterobacter cloacae, Klebsiella pneumoniae, Klebsiella oxytoca*, or combinations thereof.

11. The method of claim 5, wherein the sample comprises a human or non-human animal bodily fluid, a human or non-human animal tissue, or both.

12. The method of claim 5, further comprising, before step (a), lysing the sample to release carbapenemases from the bacteria.

13. The method of claim 5, further comprising, before, during, or after step (a), contacting the sample with one or more additional compounds that can trigger colorimetric change, luminescence change, or both, of the chemical probe of D after D is released from the compound.

14. The method of claim 13, wherein the one or more additional compounds comprise an enzyme.

15. The method of claim 14, wherein the enzyme is a peroxidase, a luciferase, or a beta-galactosidase.

16. A method to test the efficacy of a carbapenemase inhibitor, comprising:

(a) contacting a solution or suspension comprising an isolated carbapenemase, a bacterial cell lysate, one or more populations of bacteria, or combinations thereof, with the compound of claim 1 in the absence of the carbapenemase inhibitor and, separately, in the presence of the carbapenemase inhibitor;

(b) detecting the release of D from the compound, wherein the magnitude of the difference in the release of D detected in the absence of the carbapenemase inhibitor and in the presence of the carbapenemase inhibitor indicates the efficacy of the carbapenemase inhibitor.

17. The method of claim 16, wherein the compound and the carbapenemase inhibitor are simultaneously added to the solution or suspension.

18. The method of claim 17, wherein the compound and the carbapenemase inhibitor are mixed together before being added to the solution or suspension.

19. The method of claim 16, wherein the compound is added after the addition of the carbapenemase inhibitor to the solution or suspension.

20. The method of claim 16, wherein the carbapenemase inhibitor is added after the addition of the compound to the solution or suspension.

21. The method of claim 16, further comprising, before, during, or after step (a), adding one or more additional compounds that can trigger colorimetric change, luminescence change, or both, of the chemical probe of D after D is released from the compound.

22. The method of claim 21, wherein the one or more additional compounds comprise an enzyme.

23. The method of claim 22, wherein the enzyme is a peroxidase, a luciferase, or a beta-galactosidase.

24. A kit for detecting carbapenemases or microbial carbapenem resistance, comprising, in one or more containers, the compound of claim 1, a carrier, instructions for use, and, optionally, an ionic or non-ionic detergent.

25. The kit of claim 24, wherein the microbial carbapenem resistance is mediated by carbapenemases that are detected by the release of D from the compound.

26. A method to protect a carboxylic acid or carboxylate group of an organic compound during organic synthesis, comprising:

(a) using or forming an ester of the carboxylic acid or carboxylate group of the organic compound, wherein the ester contains a p-azido-benzyl group or a derivative thereof; and (b) deprotecting the carboxylic acid or carboxylate group via hydrolyzing the ester in the presence of triethylphosphine.

27. The compound of claim 2, wherein the luminescence probe remains non-luminescent or luminescence-quenched prior to carbapenemase-catalyzed hydrolysis of the compound and becomes luminescent or luminescence-enhanced after being released from the compound.

28. A method to detect carbapenemases or microbial carbapenem resistance, comprising:

(a) contacting a sample containing one or more populations of bacteria with the compound of claim 2;

(b) detecting the release of D from the compound, wherein detection of the release of D indicates the presence of carbapenemases, wherein the presence of carbapenemases indicates the presence of microbial carbapenem resistance.

29. The method of claim 28, wherein D comprises a luminescence probe that remains non-luminescent or luminescence-quenched prior to carbapenemase-catalyzed hydrolysis of the compound and becomes luminescent or luminescence-enhanced after being released from the compound.

30. The method of claim 29, wherein the release of D is detected by detecting the luminescence signal of the luminescence probe, wherein the luminescence signal of the luminescence probe reaches between about 80 and about 100% of its maximum value within about 5 minutes, about 10 minutes, about 15 minutes, about 20 minutes, about 25 minutes, or about 30 minutes, following the contact of the sample with the compound.

31. The method of claim 30, wherein the luminescence signal of the luminescence probe, detected at about 5 minutes, about 10 minutes, about 15 minutes, about 20 minutes, about 25 minutes, or about 30 minutes following the contact of the sample with the compound, is positively correlated with the total concentration of carbapenemases, the total population of bacteria with carbapenem resistance, or both.

32. The method of claim 28, wherein the one or more populations of bacteria comprise enterobacteriaceae.

33. The method of claim 32, wherein the enterobacteriaceae comprise *Escherichia coli, Enterobacter aerogenes, Enterobacter cloacae, Klebsiella pneumoniae, Klebsiella oxytoca*, or combinations thereof.

34. The method of claim 28, wherein the sample comprises a human or non-human animal bodily fluid, a human or non-human animal tissue, or both.

35. The method of claim 28, further comprising, before step (a), lysing the sample to release carbapenemases from the bacteria.

36. The method of claim 28, further comprising, before, during, or after step (a), contacting the sample with one or more additional compounds that can trigger colorimetric change, luminescence change, or both, of the chemical probe of D after D is released from the compound.

37. A method to test the efficacy of a carbapenemase inhibitor, comprising:

(a) contacting a solution or suspension comprising an isolated carbapenemase, a bacterial cell lysate, one or more populations of bacteria, or combinations thereof, with the compound of claim 2 in the absence of the carbapenemase inhibitor and, separately, in the presence of the carbapenemase inhibitor;

(b) detecting the release of D from the compound, wherein the magnitude of the difference in the release of D detected in the absence of the carbapenemase inhibitor and in the presence of the carbapenemase inhibitor indicates the efficacy of the carbapenemase inhibitor.

38. The method of claim 37, wherein the compound and the carbapenemase inhibitor are simultaneously added to the solution or suspension.

39. The method of claim 38, wherein the compound and the carbapenemase inhibitor are mixed together before being added to the solution or suspension.

40. The method of claim 37, wherein the compound is added after the addition of the carbapenemase inhibitor to the solution or suspension.

41. The method of claim 37, wherein the carbapenemase inhibitor is added after the addition of the compound to the solution or suspension.

42. The method of claim 37, further comprising, before, during, or after step (a), adding one or more additional compounds that can trigger colorimetric change, luminescence change, or both, of the chemical probe of D after D is released from the compound.

43. A kit for detecting carbapenemases or microbial carbapenem resistance, comprising, in one or more containers, the compound of claim 2, a carrier, instructions for use, and, optionally, an ionic or non-ionic detergent.

44. The kit of claim 43, wherein the microbial carbapenem resistance is mediated by carbapenemases that are detected by the release of D from the compound.

* * * * *